United States Patent [19]
Lahn et al.

[11] Patent Number: 6,103,886
[45] Date of Patent: Aug. 15, 2000

[54] GENES IN THE NON-RECOMBINING REGION OF THE Y CHROMOSOME

[75] Inventors: Bruce T. Lahn, Cambridge; David C. Page, Winchester, both of Mass.

[73] Assignee: Whitehead Institute for Biomedical Research, Cambridge, Mass.

[21] Appl. No.: 09/058,489

[22] Filed: Apr. 10, 1998

Related U.S. Application Data

[60] Provisional application No. 60/041,877, Apr. 11, 1997.

[51] Int. Cl.$^7$ ..................................................... C07H 21/04
[52] U.S. Cl. ........................................ 536/23.1; 536/24.31
[58] Field of Search ................................. 536/23.1, 24.31

[56] References Cited

FOREIGN PATENT DOCUMENTS

WO 92 00375  1/1992  WIPO.
WO 95 11300  4/1995  WIPO.
WO 96 41007  12/1996  WIPO.
WO 97 10267  3/1997  WIPO.

OTHER PUBLICATIONS

Hawkins et al., GenEmbl., Accession # AC002531, Oct. 1997.

Ma, K. et al., "A Y Chromosome Gene Family with Rna–binding Protein Homology: Candidates for the Azoospermia Factor Azf Controlling Human Spermatogenesis" *Cell*, 75: 1287–1295 (Dec. 31, 1993).

Page, D. et al., "The Sex–determining Region of the Human Y Chromosome Encodes a Finger Protein" *Cell*, 51:1091–1104 (Dec. 24, 1987).

Foote, S. et al., "The Human Y Chromosome: Overlapping Dna Clones Spanning the Euchromatic Region" *Science*, 258:60–66 (Oct. 2, 1992).

Lahn, B. and Page, D., "Functional Coherence of the Human Y Chromosome" *Science*, 278:675–680 (Oct. 24, 1997).

Zhang J. et al., "Molecular Isolation and Characterization of an Expressed Gene from the Human Y Chromosome" *Human Molecular Genetics*, 1(9):717–726 (Dec. 1992).

Delbridge, Margaret L., et al., "A human candidate spermatogenesis gene, RBM1, is conserved and amplified on the marsupial Y chromosome," *Nature Genetics*, 15:131–136 (Feb. 1997).

Reijo, Renee, et al., "Diverse spermatogenic defects in humans caused by Y chromosome deletions encompassing a novel RNA–binding protein gene," *Nature Genetics*, 10:383–393 (Aug. 1995).

Vogt, P.H., et al., "Human Y chromosome azoospermia factors (AZF) mapped to different subregions in Yq11," *Human Molecular Genetics*, 5(7):933–943 (1996).

Sinclair, Andrew H., et al., "A gene from the human sex–determining region encodes a protein with homology to a conserved DNA–binding motif," *Nature*, 346:240–244 (Jul. 19, 1990).

Vollrath, Douglas, et al., "The Human Y Chromosome: A 43–Interval Map based on Naturally Occurring Deletions," *Science*, 258:52–59 (Oct. 2, 1992).

*Primary Examiner*—John S. Brusca
*Assistant Examiner*—Andrew Wang
*Attorney, Agent, or Firm*—Hamilton, Brook, Smith & Reynolds, P.C.

[57] ABSTRACT

Genes of the non-recombining region of the human Y chromosome, which fall into two classes: X-homologous DNA which is expressed in many organs and has functional X homologs and testis-specific DNA.

4 Claims, 51 Drawing Sheets

FIG. 2A

Human CDY protein

Chromodomain

| | | |
|---|---|---|
| CDY (Human) | 1 | MASQEFEVEAIVDKRQD-KNGNTQYLVRWRGY |
| HP1 (*Drosophila*) | 19 | EEEEYAVEKIIDRRVR-K-GKVEYYLKWKGY |
| Polycomb (*Drosophila*) | 21 | PVDLVYAAEKIIQKSVK-K-GVVEYRVKWKGW |
| CHD1 (*Drosophila*) | 346 | NGFDPHAGFDEKQTPDA-E-TEAQFLIKWKGW |
| Su(var)3-9 (*Drosophila*) | 214 | PPKGEYVVERIECVEMD-Q-YQPVFFVKWLGY |
| PDD1 (*Tetrahymena*) | 44 | EEEDQYEVFKILCSRFNPKTKQKEYLVKWENW |

FIG. 2C

```
                                    ┌─── Covalent Modification Domain ───
CDY protein, cont  ⎫
                   ⎭

CDY (Human)                          246  SVPRVKGGQRNITDDSRDQPFIKKMHFTIRLT
Enoyl-CoA Hydratase (Human)            1  MAALRVLLSCARGPLRPPVRCPAWRPFASG
4-CBA-CoA dehalogenase (Arthrobacter)  1
Carnitine Racemase (E. coli)           1  MKRQGTTLPANNHALKQYAFFAGMLSSLKKQK
Crotonase (C. acetobutylicum)          1
Naphthoate Synthase (E. coli)          1  MIYPDEAMLYAPVEWHD
```

```
                                             ┌──────── Linker ────────┐
CDY (Human)                          349  YFVKHLRNNRNTASLEMVDTIKNFVNTFIQFK
Enoyl-CoA Hydratase                  102  EM----QNLSFQDCYSSKFLKHWGHL TQVK
4-CBA-CoA dehalogenase                72  EVPMGPASEIQSHFRLKALYYHAVIHM ARIE
Carnitine Racemase                   105  AA----AEGEAPDADFGPGGFAGLTEIFNLD
Crotonase                             70  EM----KEMNTIEGRKFGILGNKVFRR ELLE
Naphthoate Synthase                   90  VR  GDYGGYKDDSGVHHLNVLDFQRQIRTCP
```

```
CDY (Human)                          454  REA CAK GLVSQ V FLTGTFTQ E VMIQIKE LAS Y
Enoyl-CoA Hydratase                  201  QD AKQAGLVSK ICP VET L VEE A IQC A EKI ASN
4-CBA-CoA dehalogenase               177  DEA VEWG VVN RV FSE A DFQSRVG E IARQ LAA A
Carnitine Racemase                   205  EEAL RW GI VN R VVSQ A E LMDN A RELAQQ L VNS
Crotonase                            171  DEALRI GL VNK VV EPSE L MNT AKE I ANK IV SN
Naphthoate Synthase                  193  KQ AL DM GLVNT VV PLA D L EK E TVRWCREMLQ N
```

CDY protein, cont.

Covalent Modification Domain

```
ESASTYRDIVVK[KEDGFTQ[IVL[STR]STEKI[NAL]NTEVI[KEI
ANFEYIIAEKRGI[KNNT]VGLIIQ[L]-[MRPKA[L]NAL]CDGLIDE[L
MSSNSDHHISVEHT[DGVAT[IRF-[TRP[SKHNA]ASGQLLL[E]T
WRKGMSESLHLTRNGSILEITL-[DRPKA]-[NA[IDAKI[I]SF[EM
         MELNNVILE[KEGK[VAVVI[T] [NRPKA[L[NAI]NSDIL[KEM
CSEGFEDIRYEKST[DG[IA[KIT[I]-[NRPQVR[NA]FRPLI[VKEM
```

```
KP[IVVS]VNG[PA]IG[L]GASILPL[CDL]VW[A]NEK[A]W[FQT]PYTTF
KPVIAAVNGYPFGGG[C[E]LAMM]CDI[I]YA[GEKA[QFA]QPEILI
KPTL]AA[I]NG[PA]VGGG[LGMSLA]CDI[AVCT]DR[A]TF[LPAWMSI
KPVIAAVNGYAFGGG[FE[L]ALAA]DFIVCA[DNASFA[LPE]AKL
KPVIAAVNG[FA]LGGG[CE[I]AMS]CD[IRI]A[SSNARFG]QPEVGL
KPVIAAVNG[FA]LGGG[CE[I]AMS]CD[IRI]A[SSNARFG]QPEVGL
KPV[VA[M]V[A]GYSIGGGHVL[H]MM]CDL[TIA[A]DNAI]FG[Q]TGPKV
```

```
N[P]IVLEEC[KA]LVRCNIKLE[L]E[QANERE]CEVLRKIWSSARG
SKIVVAMA[KESV[N]AAFEMT[L[T]EGSKLE[KKLFYSTFATDDR
PTHLQGLV[KNRIQEGSSETL[E]SCTEHE[VQNVIASVGHPHF
AP[L[A]IAALKEIYRTTSEMPVE[EAYRYIRSGVLKHYPSVLH
APVA[VKLSKQAIN[RGMQCDIDTALAFE]SEAFGECFSTEDQ
SP[M[A]LRCLL[K]AAL[N]ADCDGQAGLQELAGNATMLFYMTEEGQ
```

FI

DBX & DBY
long and short transcripts

TPRY
short, medium and long transcripts

```
-1005                                                                             gctcatcgtttgttg
 -990  tttagataatatcatgaactgataaatgcagttgccacgttgattccctagggcctgctgagtcttaccgactgaggtcataagatattatgcct
 -900  tctctttagacttggtcagtggagtggagaggaaatgggcaaaaccagcctatggaggtgacaaggccttaggcgcaaaagtcttgagggtga
 -810  aggtttagggcctgcgcagctccctgccatggtctcgcattcgccccgtgggtgatgccccttccatgccgctctctctcccttcaagcg
 -720  cctaaagtccatggtgtcctctttcgcattgcgccgtgggtgatgccccatttctatcttaatgcattaactagcacaacctagttgttccatccag
 -630  tatcgcaactgcaaaaacaccccagcacacagacactccatttctccatagacgtgaccatccaaccagcggtcagaatcagtcgcctgtcatgtt cctgtcctggcgaac
 -540  agactaccctttctcctcatagacgtgaccatccaaccagcggtcagaatcagtcgcctgtcatgtcctgagacgaatcagtcgcct
 -450  tggctgggcgggggtcccagcagctaggagtgggaggtggagcaatgcctgcggtcgtggggttcgccgtgcgagcttcgcactgccgagcttgc
 -360  agattggctacaactaagtggttgggaggaaattctgctgtgctctccagcactcgcctcaatatcttttccctgtagtttcccagatgtgatccag
 -270  ctggcaaagtttgtgattttaagaaattctgcgctgcgtgctgtgctctccagcactcgcctcaatatcttttccctgtagtttcccagatgtgatccag
 -180  gtagccgagttccgctgccccgtgcctgcctagctttaagtctttgcctcagcttttccctgcctcagcttttgctccagcttttccctgaggaggcgataaaattggc
 -90   gtcacagtctcaagcagcgattgaaggcgtcttttcaactactcgattaaggttgggtatcgtcgtgggacttgtcgtgggacttggaatttgtgttttcc 1    ATGAAATCCTGCGCAGTGTCGCTCACTACCGCCGCTGTTGCCTTCGGTGATGAGGCAAAGAAAATGGCGGAAGGAAAAGCGAGCCGCGAG
  1    M  K  S  C  A  V  S  L  T  T  A  A  V  A  F  G  D  E  A  K  K  M  A  E  G  K  A  S  R  E 91   AGTGAAGAGGAGTCTGTTAGCCTGACAGTCGAAGGGAGGCGCTTGGTGGCATGGACAGCCGTCTCTTCGGGTTCGTGAGGCTTCAT
  31   S  E  E  E  S  V  S  L  T  V  E  E  R  E  A  L  G  G  M  D  S  R  L  F  G  F  V  R  L  H 181  GAAGATGGCGCCAGAACGAAGACCCTACTAGGCAAGGCTGTTCGCTGCTACGAATCTTTAATCTTTAAAGCTGAAGGAAAGTGGAGTCT
  61   E  D  G  A  R  T  K  T  L  L  G  K  A  V  R  C  Y  E  S  L  I  L  K  A  E  G  K  V  E  S
```

```
              T  K  L  P  A  F  A  R  V  V  S  A  G  N  L  L  T  H  V  G  H  T  I  L  G  M  N  T  V  Q
Medium  1051  ACTAAAACTTCCTGCTTTTGCGCGTGTGGTCAGCAGGAAATCTTCTAACCATGTTGGGCATACCATTCTGGGCATGAATACAGTACAA
Short   3151  GCTTGTCTTGAACTCCTGACTTCAGGTGGTCTGCTTGCCTCAGCATCCCAAAGTGCTGGATTACAGTGTGAGCCACATGCCCGGTAA  1079
        1051  A  C  L  E  L  L  T  S  G  G  L  L  A  S  Q  S  A  G  I  T  G  V  S  H  H  A  R  *

L  Y  M  K  V  P  G  S  R  T  P  G  H  Q  E  N  N  F  C  S  V  N  I  N  I  G  P  G  D
Medium  1081  CTGTATATGAAAGTTCCAGGAGTCGGACACCAGTCCACCAAGAAATAACAACTTCTGCTCTGTTAACATAAATATTGGTCCAGGAGAT
Short   3241  actttaaaaatgtaagcaaaattacacagtatgtaaaacacacattgctaatggagaaatagctaagttcctactttacatctaaaaaaaaaa  3330

C  E  W  F  V  V  P  E  D  Y  W  G  V  L  N  D  F  C  E  K  N  N  L  N  F  L  M  S  S  W
Medium  1111  TGTGAATGGTTTGTTGTACCTGAAGATTATTGGGGTGTTCTGAATGACTTCTGTGAAAAAAATAATTTGAATTTTTTAATGAGTTCTTGG W  P  N  L  E  D  L  Y  E  A  N  V  P  V  Y  R  F  I  Q  R  P  G  D  L  V  W  I  N  A  G
Medium  1141  TGGCCCAAACCTTGAAGATCTTTATGAAGCAAATGTCCCTGTGTATAGATTTATTCAGCGACCTGGAGATTTGGTCTGGATAAATGCAGGC T  V  H  W  V  Q  T  V  G  W  C  N  N  I  A  W  N  V  G  P  L  T  A  C  Q  Y  K  L  A  V
Medium  1171  ACTGTGCATTGGGTTCAAACTGTTGGCTGGTGCAATAACATTGCCTGGAATGTTGGTCCACTTACAGCCTGCCAGTATAAATTGGCAGTG E  R  Y  E  W  N  K  L  K  S  V  K  S  P  V  P  M  V  H  L  S  W  N  M  A  R  N  I  K  V
Medium  1201  GAACGGTATGAATGGAACAAATTGAAAAGTGTGAAGTCACCAGTACCCATGGTGCATCTTTCCTGAATATGGCACGAAATATCAAAGTC
```

```
Long  4051  tccatgaatatttaaatgagattatttctgctcttcaggaaatttctgcaccactggttttgtagctgtttcataaaactgttgactaaaa
Long  4141  gctatgtctatgcaaccttcaagaatagtatgtcgacacagtgctgcctctgcttcaggacttaacatgctgatccagct
Long  4231  gtacttcagaaaaataatcatatgttttgtgtacgtatgacaaactgtcaaagtgacacagaatgacacagaatacctgatttgaagatagcctt
Long  4321  tttatgttctctatttctggctgataatattcattgtatttaaccctgcagaatttcctagttaaaacactttccta
Long  4411  gctggtcatttctccattcataagatagcaaatttaaatctctccgatcagcttgtactatctgaggaagtttttttac
Long  4501  tgcttatgttttgtgtgttttgaggccatgatgattacattgtgttgattttgttctaaactgatacagattttataaaata
Long  4591  gataatggattgcacatagacaaagaaataaacttcagatttgtgaatgttgtttttccagacgtaactgccattaaatactaaggagttctgtagttta
Long  4681  cgtatttattgcctgaaaatatttgtatatgttagtaataaaactgcttagtatatacagaaatttttattaaaattgttaaatgtttaaaggg
Long  4771  aacactactcctattacatttttgagttttaaaaaagactttctgaaaaatccacttttgttcattttcaaacctaatgattatatgttttttatatgt
Long  4861  ttcccaatgtttgagttgtacacacatgccatattataaaatatttacggaagtttgctgtgtttttatagtctttttgattattaagttgtagtca
Long  4951  gtgtgtttgaggtgtcagcccataaaataaattgctggaaaattgtattttataacagtagaaaacatatagtcagtgaatgataacctctttagagaacaaat
Long  5041  tagttttttgaggtgcctatttcataaaataaattgctggaaaattgtttataattaagagttcttataagagtctataactgtcctgctatactgt
Long  5131  ccatagtgatagcccatatttgataaatgttgtttaaagctagatgactttgaaatgctagtgtcctgctgtacaacatggtttgggtgaaggggaggaagta
Long  5221  acattatagatttttttaaagctagtaaattgtaataagttctattaaaacttgtattctcatatgaaaaaaaaaa  5471
Long  5311  aagtgactttattttttaaagctagtaaattgtaataagttctattaaaacttgtattctcatatgaaaaaaaaaa
Long  5401  ttaaaaatctatatcgctagtaaattgtaataagttctattaaaacttgtattctcatatgaaaaaaaaaa  5471
```

EIF1AX & EIF1AY

```
                                                         ggcacgaggcgccatttgctgccgccgagcg
eIF-1AX  -207 eIF-1AX  -130  tggacgcaggcggatctctgaagagctgggtcgccagcctctcccgcgcac...gcctg.cctc.agcaccta.ttgg..ccgc....t.
eIF-1AY  -176                                                 agtttatgagagagctctgtagccagccctctctgccgcac eIF-1AX   -86  ..t.g..tc..cc..cg.ag...ca.c.g.cgc.gtcgccgctac..g......a.-----.a.g.cgcga.tc.c.gc...
eIF-1AY   -90  ccacctgctgcatcttagttcagtcggctcttagagtagtaaccgccagaaaggagtcggaagaggtctcacgaggctgtcatcaccgcc . A .              .  .  .  A.  C
eIF-1AX    1   ATGCCCAAGAATAAAGGAGGTAAAAAACAGGCGCAGGGTAAATGAGAATGAATCTGAAAAAAGAGAGTTGGTGTTTAAAGAG
eIF-1AY    1   M  P  K  N  K  G  G  K  N  R  R  G  K  N  E  N  E  S  E  K  R  E  L  V  F  K  E
           1

. G. G                      . A                         . C. A. C
eIF-1AX   31   GATGGACAAGAGTATGCTCAGGGTAATCAAAATGTTGGGAATGGACGATTGTGTTTTGATGGTGTAAAGAGGTTATGCCAT
eIF-1AY   91   D  G  Q  E  Y  A  Q  G  N  Q  N  V  G  N  G  R  L  C  F  D  G  V  K  R  L  C  H
          31

. C. G                         . T                         . C. A. C
eIF-1AX   61   ATCAGAGGGAAATTGAGAAAAAAGGTTTGGATAAATACAGACATTATTGGTTGGTCTACGGGACTATCAGGATAACAAAGCTGAT
eIF-1AY  181   I  R  G  K  L  R  K  K  V  W  I  N  T  S  D  I  I  L  V  G  L  R  D  Y  Q  D  N  K  A  D
          61

. A                         . C                         . G
eIF-1AX   91   GTAATTTTAAAGTACAATGCAGATGAAGCCTGAAGGCATATGGCGGGCTTCCAGAACATGCTAAAATCAATGAAACAGACACA
eIF-1AY  271   V  I  L  K  Y  N  A  D  E  A  R  S  L  K  A  Y  G  G  L  P  E  H  A  K  I  N  E  T  D  T
          91

. T                                    . T
eIF-1AX  121   TTTGGTCCTGGAGATGATGATGACGATATTGGAGATGATGATGAAGACATTGATGATATCTAAattgaaccaagtgtt
eIF-1AY  361   F  G  P  G  D  D  D  D  D  I  G  D  D  D  E  D  I  D  D  I  *   144
         121                                                              *  144
```

DFFRX & DFFRY

```
DFFRY -1664                                                              gaagtgacatgttggcatgggcccaattctgctgtcctttagt
DFFRY -1620  atacaaaaaaaataaaggtttaccagtatgtcactacatgcagatttatgattgtacagaaaattggtgattcccaaattcactgtgc
DFFRY -1530  atcaaaataatcgatggaacttaaagactaaagattctagaccccaggcccgatgattgagaatatctagagggaccaaga
DFFRY -1440  atccatatattaagtgcccaccacaatgaccttaagcagtagttgcatttggaaccactgctacaggttactagtgggac
DFFRY -1350  aaccagttaggagcataagtttgaacatttacagtttgtcacctgtatagcttatcacctgtgatataaccagaaatccaattaagat
DFFRY -1260  tgctatctctctgtaatctgtttgcaattaggtgtgttaattttttgaaagttcagaaagtagacaaaacagaaaaatcaagta
DFFRY -1170  caactacataatgacaaaaaacgtattacacttgtattaaacttcagagaataaggtgcaatacatgaaaataattaaat
DFFRY -1080  gctaagtgaaataatcaaatgtagttgacccctgaagaaaatgcagtagtgagggatccctaacctgtgggccctccaggaattactgt
DFFRY -990   tgaatggtcttgagaatccactgaaaacaattgttacctgaataattgaactttgtttatttctccatatttttgcagtggta
DFFRY -900   attccattatataaaacctaatgactgaggagtgttatagatggtgtggaaagacttttctgggctcagagtgaaactgacccttgtat
DFFRY -810   cagcagcattctgactgactgtagtgattaacagagttgtgatgttgatgttagttaagaaactttagaaaactagattgccattgcttc
DFFRY -720   taccaattagcagattgtttaactcactgaaattgtaaagtggtagacgtggactttagtcattactgggcagcttatgaattgtattcat
DFFRY -630   ttactcatgatgtaaaaatggttagtctccacttttaaggctctagtggctaaataggtacttatttatacagtatgataactg
DFFRY -540   ctgtattaaaatacatgtctcaaatgtggaatagtagaaaggtagaacatagtttgagtagaatactccactgggaaacagtttaaagatactaagtttgctggtcttaaa
DFFRY -450   aactgtggtatttggtgattccataaattaggaggggaattagcgagcttgaaactgtttgaatgagactgggtcataagtgattc
DFFRY -360   aatgaggaagacacaccagatatttaggagggaattagcagcactgaagtcagattttttccttttaaaagaaaggattcatgatgaaatctgc
DFFRY -270   aagtaccagattaaggcactgagattttattttaagcactgaagtcagatttttcctttaaattcacagtattataaggca
DFFRY -180   ttttgttttgcagagagcttggagataattctggtggctggtgtgtggaggtattgtttgaggtattaaattcacagtatatataaggca DFFRX -59    c.tttct..ag.ca.ctac.t..gc...c...tt......g..
DFFRY -90    gcaattgataggcctttcacagattctcttctgataactacataaagagacaaaactacataaagagagcaaagatctgtgctgtcaagt
```

BPY1

```
     -72                                                                gagaggggtatacacaggaggaggccaggcagcctggagttagtcgaccgttgcgagacgttgagctgcggcag
      1  ATGAGTCCAAAGCCGAGAGCCGAGAGCCTCGGACCCTCCGGCCCAAGGCCAAGGAGACAGGAAGTCCTCCTCTCCAGCCTCCTCAGCCCCAGTGGC
      1   M  S  P  K  P  R  A  S  G  P  P  A  K  E  T  G  K  R  K  S  S  S  Q  P  S  Q  P  S  G
     91  CCGAAGAAGAAGACTACCAAGGTGGCCGAGAAGGGAGAAGCAGTTCGTGGCGGGAGAGGCCGGAGGGGCAAGAAAGGGCTGCAGAAAGATGGCG
     31   P  K  K  K  T  T  K  V  A  E  K  G  E  A  V  R  G  G  R  R  G  K  K  G  A  A  T  K  M  A
    181  GCCGTGACGGCACCTGAGGCGGGGAGAGCGGGCCCAGCCCCCCCAGGGCCCCAGGAGCTCCCTCCAGCACGAGCTGCCG
     61   A  V  T  A  P  E  A  E  S  G  P  A  A  P  G  P  S  D  Q  P  S  Q  E  L  P  Q  H  E  L  P
    271  CCGGAGGAGCCAGTGAGCGAGGGGACACCCAGCAGCACGACCCCCTGAGTCAGGAGAGCGAGCTGGAGGAACCACTGAGTTAAGGGGCCCATCT
     91   P  E  E  P  V  S  E  G  T  Q  H  D  P  L  S  Q  E  S  E  L  E  E  P  L  S  K  G  R  P  S
    361  ACTCCCCTATCTCCCTGAgcagcaactaagttaggccagctgccagctgccagacctcagagatcttcaccagcagggtgcttcccatgttgatga
    121   T  P  L  S  P  *
                        125
    451  caataaaatgaatgtgttgcaaaaaaaa  480
                    94
```

FIG. 9

BPY2

```
     -332 aatatctcaggaccaggaccatgtgatatgggcccaacacctggatgatgttactcttctg
     -270 cctaggtcatgcgtaaagagggaattaggcatattgcttggcccgtaatgatgatcctcctgcttgtgccagagccacaga
     -180 agtgtgcttggtgacataatcttgaggcgtgtcacatccaccagattatgtatcactgaccagcataaagctgacacttctgacta
      -90 tgcccagccttcaaataataccactgtataattggctcaacaccaggtgatattgttccattacctgagaccagataaaaagccta
        1 ATGATGACGCTTGTCCCCAGAGCCAGGACACGTGCAGGACAGGATCATTACTCTCATCCCTGCCCTGCCCAGATTTCACAGGTGCTGCTTACA
        1  M  M  T  L  V  P  R  A  R  T  R  A  G  Q  D  H  Y  S  H  P  C  P  R  F  S  Q  V  L  L  T
       91 GAGGGCATCATGACATATTGCTTGACAAAGAACCTAAGTGATGTTAATATTCTGATGTTAATATTCTGTAAAAAATGGGAATGTGAGAAATACC
       31  E  G  I  M  T  Y  C  L  T  K  N  L  S  D  V  N  I  L  H  R  L  L  K  N  G  N  V  R  N  T
      181 TTGCTTCAGTCCAAAGTGGGCTTGCTTGACATATTATGTGAAACTGTACCCGGGTGAAGTGACTCTTCTGACTAGGCCCAGCATACAAATG
       61  L  L  Q  S  K  V  G  L  L  T  Y  Y  V  K  L  Y  P  G  E  V  T  L  L  T  R  P  S  I  Q  M
      271 AGATTATGCTGTATCACTGGCTCAGTGTCCAGCCCCAGATGTCGAAGCCCAGAAGCCCAGAAGTCACAGAAGTAATTgtgccatatgtggaacaagcagctaagcaatagataa
       91  R  L  C  C  I  T  G  S  V  S  K  P  P  R  S  Q  K  *  106
      361 catccatcgtggctctgcctgcaaaggaaattttacatatgtcactgggaccatcaccagatgatgtcctgccactaaaagaattgt
      451 gacataacgctgactgcaaaaactgggtaatgcaactctcctcttattctggagtctgccaaaacaaggattatcacatattgcggag
      541 tccagcaccaggtaaaatttgtcatatacccagcttcagatacaatgataacatcatacctggaccaaagaggagagat
      631 attttgattctcattgccattccttatgcaagcaatgttctcatagtggttataaagttcacacagtattatgacactccca
      721 gcgtatcatagaaaatgtgagtagtacaatgagttgtataacaggaacagcaaaccaatgctattgtgattgattggattcacacccagc
      811 tgacgcgactatcattcctctctcacaagaaccctgcaaataagtactaaatctcaccaaaaaaaa   880
```

FIG. 10

XKRY

```
-663                                                              attaaaaacttctgataaattacctaagtaca
-630  cacaaacaaaaacatgcccacacaaatcacttaatttctaaaacttttatttttctgctctctagtacccttgtattccatccacacagc
-540  aaaatctggcagctccactcccagaattTacttgaactccacagcttattccgattccTgttatcaccagagtctaaaacacagttta
-450  tattgcattcacctcctatttTacaccgtaattcctactttacacTcttatataaaagaaactaccTTtcaagatctaatT
-360  cacgcaatttattTgttctTaaTtgagacTtcTttctaggtgctgtcacacccTtgtTgtatatgtctctaTccaattTca
-270  tgagttccagttattTtattttaagggaatgtgTataCattTataaTttgtgtatgttatTcacTcattctTtTatatgt
-180  tTTgcatgcaTataTTcacTaaatccctgataaTagaaagataacaaaTcTTTTcTTTTtgTatgTaaatTaTTTccga
-90   aggaggTggTtgggagaaaTaTaTcTTaacTtggcaagTTaaaagagaaagTTggccaTTacTaaTgaaaaTTaTTcTcTagcaTTTTc 1 ATGTTTTATCTTTAATAGCATTGCTGATGACATATTCCCTCTTATCAGTTGTGTAGGTGCCATTCACTGCAATATACTGGCAATCCGCACT
    1  M  F  I  F  N  S  I  A  D  D  I  F  P  L  I  S  C  V  G  A  I  H  C  N  I  L  A  I  R  T 91 GGCAACGACTTTGCCATTAAGCTACAGGTGATAAAATTGATCTATCTCATGATATGGCATTCGTTGGTGATTATCTCACCTGAGTG
   31  G  N  D  F  A  I  K  L  Q  V  I  K  L  I  Y  L  M  I  W  H  S  L  V  I  I  S  P  V  V 181 ACTCTGGCATTCTTCCCTGCATCTCTGAAACAGGGAGCTTACACTTTCTATTAATTAATCCAGCAACAACAAATAATTCCAGCTTGGATTATTGTATTATTGTTGACACCATGGCTG
   61  T  L  A  F  F  P  A  S  L  K  Q  G  S  L  H  F  L  L  I  Y  F  V  L  L  T  P  W  L 271 GAGTTTTCGAAAAGTCGGGAACTCATCTTCCTAGCAACAACAAATAATTCCAGCATGGTGGGTAAGTATGGATGCTTATCTTAATCATGCT
   91  E  F  S  K  S  G  T  H  L  P  S  N  T  K  I  I  P  A  W  W  V  S  M  D  A  Y  L  N  H  A 361 AGTATATGCTGCCATCAATTCTCCTGCTTGTCAGCAGTGAAACTGCAGTGTCAAATGAGGAATTGATAAGAGACACGAGGTGGACATA
  121  S  I  C  C  H  Q  F  S  C  L  S  A  V  K  L  Q  L  S  N  E  E  L  I  R  D  T  R  W  D  I 451 CAATCCTACACTACAGATTTCAGTTTTTAGaaaatgtgataatattgatatttagttTcttTgagggaacgttTtaccgaagtgtT
  151  Q  S  Y  T  T  D  F  S  F  *  159

541 gtgactcaataattgccgtgagtTcaTcaaaacctacaTatTagccTttggcttTaagcTccgcTtcTgtcagTaTttgcaaccaaggT
  631 ggtcgggcaaagTaTtgccaggagaaTTgccaggagaaTcaTccagaagcacTgTgaTaTtgtTaagcaTcTggagaaaTTcagTtaaaaga
  721 aTaaaagTaagcagcTgaggaaTTcacTcaTgagagaagggTaggaTaTtTtcaaTaagTgagTaTgcaaTaTccaTaTaTacTtT
  811 cacagaacaaagagTaaagaggcTgagTgTgacTtTaTaaagaTacTcaTgaaaaaTaTaaaacaacaaaccTtggaagTagtttcTaaT
  901 aaaaTtgaTtTTtcTaaaaaaaaa  925
```

FIG. 11

PTPRY

```
         gaagaggagcacaccaccagaaacagacatcttgcagtgttcactgtctcaacttatctgcacagtccgaggtcagtctgagagag  aa
   -182  cttctgagagaccaggatgaaggatgcagtgaggtcaagacccaacctcttcactgacaccacttcttaaggactcagaagagac
   -180
    -90

1  ATGAATAAAATGGGCCTCAACAATCCCAAGAAGAAGAACCACTCCAAGGAGCCACTGGGGAGCCACTGGCTTCCTACTTCCCTGGAAACAA
      1   M  N  K  M  G  L  N  N  P  K  K  K  N  H  S  R  T  M  G  A  T  G  L  L  P  W  K  Q

91  GACAATTTGAATGGCCACTGACTGCCCAGGGATGCAATGCTTATATTTATACTTCTCTGAGACTTCTGAGACTACGGGAGCATGTGTTCTGAACTTTCCCTGAAC
     31   D  N  L  N  G  T  D  C  Q  G  C  N  I  L  Y  F  S  E  T  T  G  S  M  C  S  E  L  S  L  N

181  AGAGGTCTTGAGGCCAGGAAGAAGGATCTTAAAGACTTCATTTTCCAGAGATATGGCAAGGTTGGCTGTATCTCCACTTCGT
     61   R  G  L  E  A  R  R  K  K  D  L  K  D  S  F  L  W  R  Y  G  K  V  G  C  I  S  L  P  L  R

271  GAGATGACCGCCTGGATTAACCCACCCCAAATTTCAGAGATTTTCCAAGGCTACCACCAGAGGGTGCACGGAGCTGATGCACTGAGCCTG
     91   E  M  T  A  W  I  N  P  P  Q  I  S  E  I  F  Q  G  Y  H  Q  R  V  H  G  A  D  A  L  S  L

361  CAAACCAACTCTCTGAGAAGCAGGTTATCTTCCCAGTGCCCTCGGACAGAGCTGCCTTCCATCTCAGGACCCTGAGAGGACCACTCCCCAAGAGTGGCGGGCTTTGGGACA
    121   Q  T  N  S  L  R  S  S  R  L  S  S  Q  C  L  G  Q  S  F  L  L  R  T  L  E  R  A  V  S  G

451  CACTTGGGGACATCTGTGGCCACGTTCATGAAGAAGACTAAGCCTACTTCATCTCAGGACCCGCCCAAGAGTGGCCGGTTTGGGACA
    151   H  L  G  T  S  V  A  T  F  M  K  K  T  K  P  T  S  S  Q  D  P  P  K  S  G  R  G  F  G  T

541  CCTGCGGTCGGGTCCAGGTCCACCATGAGAATAAAACCTCCTCTCTTCTGGACATGTCCAGGAGTGGCCGTTGCTACAAGTCACCTGGTGCTACG
    181   P  A  V  G  S  T  M  R  R  I  K  P  P  S  L  L  D  M  S  R  S  G  R  C  Y  K  S  P  G  A  T

631  ACCAGGGTGAGAATAAAGACGTCTCCTCCCAGGAGTACATGGCATTGAGACTAGTTCATGGCATTGAGACCACATCTGGCGGCCAAGTGAGGAAGAAAGACAC
    211   T  R  V  R  I  K  T  S  P  Q  D  P  P  R  R  V  H  G  I  E  T  S  G  G  Q  V  R  K  R  H

721  CCTGTCTGCAGCACCCAGAACTGAggagggcactgcactgtcacagctgtcacagatggtttgcagatgatctgggcttgttctgcagagatctgta
    241   P  V  C  S  T  Q  N  *
                             247
    811  ccttgagtgaggcagtgaccacgcattgtcacagctgtcacagatggtttgcagatgatctgggcttgttctgcagagatctggta
    901  cagagaaaggagaggccgttgagtgaacccacgatgggctgaggccaggggagacatcacacctccaacaacacttttcatgcttta
    991  ataaatcattttcttagagaactaaaagtagtgaaacaatatagaaaacattttaagtaggcataaaaaaaaa  1066
```

FIG. 12

TTY1 tgtctgtcagagctgtcagctgctcagccctgcttaagcagagtgctgcagccctggtagcgagaaaaaaggctgcctgtgaaatc
ccactgtgggaccataagtgtggggacctcagggcccttcatgcatctccatgtcatgccatgtcatgctggagaaggaggcgtttcaagaatg
tgagctgatcgctggaaactgctcatctgactctgtcaagaaggctatgtgcaagaatcgggtgaagttgtgagacccatccacc
cctcacaagattgtatcccacctgtctgactatctgtccaaggatgaaactatctgtggatttcacagagacagagagagtaa
cccctcatgatgtgaagcacgtgttcacctgtcacctgtgaatataacctgaatatcatgagatcatgcagatatctgtaatcctgtgaatcatgagactatt
gacaccgctgacacttctccacggaggtctcctttccaccaagatgcagatgcttcttgccaagctccaagcctcctgccatgatcatgagactatt
gacaggtgtgtggtttccaatgccggtgcacctccaaggtacagcatggcatccacccctcaccagaggtatcccccctatccgacctattacc
gtggatttcacagagaagatagttgaaggtgaaagctcccagactgaaatcccaagacaatgagaagttccccctgatgatgtgaagcaccaactcctctgg
ttattgctgttcaaagtctctatcccagactgaaatcccaagacaatgagaagttccccctgatgatgtgaagcaccaactcctctgg
aatcaaattcgaggtaaatttaataggcccggtagagatgaatgatagtgtctctcccttggattggctgaaagacaattaaacactggta
tatttctgttaaaaaaaaa

FIG. 13

TTY2

```
aggcttgccatcaccacagatggcctctgagacactgtttgaaccacatctgccacctgtgagaggccagtttgaggtatgagaacactgt
ttcaatttggactttgccttgtcttgtctttgtcctgcttctgcttcccagatgcacctaccccaaccaccagatgaatgagtgcagagaggtcaagtg
ccaggccatcttttgctgacaccctttctgtattcaggtataagtccatcatccaaagactgctcaacatctccaccagaatactattt
caatcctcatgggcatgatcttttcacaaaaccctttcaggaatggagtccctaagtttgagactttaggtactgcaatgcgttatcac
acggctctgcctcccatgtctgatctgaccatggagatgcctctgcctgtaccatttccctctgcttaggcaggctgacagccctgacaccctgtgctcc
aggcagcctttatcctgataccaagccagctctgctgagtctggatgtgctagtgtgcttgggcaatggacctgagctgtgagctgtagctagtgtcacaatgaatgccagctt
gctagtcactatatgtggatgtgctagtctggcttggtagagagaggtagatgtgagcctgcactgtggtgcactgtcacctgtctctctgtgga t
ccaggdacagttccatgatcctcttgctcctaggagagtagatgtgagccagctgagctgcctgaggtacaatggtggtgcaagcagagcccagaatgtccaagcacaaat
cactacagatccaaaggatctgcagaattgtcaggcctttctctctcccagtggggcttctgcagacacagcctcattgaaatgtccactgtaatt
tccaacttcagcctttcctgtcttgttccagcagttcctcgattgattcagcatgttgatgtcagcatgtgtgttggcgacccgtttgtgtgtcgttggctgtcggcgccctgcccaaagaatt
gtgtgttactgtggagtgttgcgagtgatcagcaattcatcagtagttaagctgtctgtgaccgactatcccagtgttgcattataaagcagcacacctcacactacagacat caaagcaccctccccatacctccgcatgtcttgcattatataaagcagcacaaccgactatcccagctacactcct c
cagtactctctctagaaagaagaggagcaccacaacagaacagatctccagaattaacctagaattcagttctctagtatgttgcattgaacagccccagaatgtgccaatcctgaaaaatc
ctagcactctgagattccataagtctctgcattgaagacaacagagatgctgacagctactgacagtgtgtacatcccacattcccacccacaattggaccaattgcaaat t
catcatcttgagattctaacctgctgacaacagctggcttcagagtcattacctagatggcaaaacctgggagatcgtgtggccctcacacactcttgtcctcttt
ggtccgtacctcaccaacatggcctgtgttaatacctgtcgtacagagtgtgacagcaacagaaagggtgaaatagatgaggagtactcaaactcttcctgccaatctgaaaactc
cagtcaacaacatgcctttaatacctgtcgtaggtgttaaggcaggtgacagtactccaacctgcagagtggaatagatgaagtcttcctgggcacattgtggccacatttgcttattgtcctcttt
ctggtttgagggtttccattgtcctcattggtctagggctcaaggacccctgcaaggatctgaaggagaccagtgaggtcaagaagccatctcttcctgttcacagaagacc
tactgacttccattgcattgtagaccatgcagagtctgagctgcaaggacccagccatcccaaagagttctgatgtatggcgctc a
atcataaaaatgcattgtcttcaggctgttctcaggctgttcctgacagtcctgacagccccatcgacagccatcacaaggactgagctatgggctcca
cttctgggttctcaggctgctgacaatgaaggccaccatcaggtagagcatactctttgtggataagaactccgtggagcaatccaagggagaga
gctagcatcacaggaaggccaccatcaggtctagggataagtccctgaatttgattcccagaggagttggtgcttcacatcatcaggggaacttc
cactatcattcatctctaccggcctattaaatttacctggactttgaacagcaatcattttcaacatcatctacatgagtagagacccgttcgaca
tccattgtcttggattctgagtctgggatagagactttgaccctgcctttgtcgtgttcctgctttctcatagatccctgccagccaggatgataggagc
cccagtcatcatgaaatgatcctcatgtgcagaatgctcatttgaattaacctgaatctctgggtataatttccatcacataaatccctcaacaactca
aaaatcaacactaccagtcatgttgcagagctcattgaacctgattcttgcacacagcctccttcaggaatggagtcagaagagcagtcttcagagaccacc
gcaatcctccatcatcctggattcattccgcagacctctggaacacagagtttgagcagcaataaggctggtcccctcaacagcatttag
tggacatgatgtcagactgcaatttccgcagacacctctgtgaacatcatcatctacagtgagtgagacccgttcgaca
tgtaagaatactgcttgaatcttgacctttgacctctgtgttgtcttcctgctttgaaagctgactctgggtgtctcggtatatccatccacataaatccctcaacaactca
aatgaagtcaaggcgagccgagccatttcattgaaccacagatgctcttgcacacagcctctttcaggaatgagtcagaagagcagtcttcagagaccacc
ccagactatattccaatctccatgtttcagtgaacctgattcttgcacacagcctccttcaggaatggagtcagaagagcagtcttcagagaccacc
ttggttatcacagacagactttttcggcaaatgtcatgatgcatcatgtcgtctatagcatcatttcctctgcttaggcaggctgacaactctgacag
gccaggggcccgaatctctaccctgctctactctcagtgcactagtgtcacaataaat
gccgccattgcctagtgaaaaaaaaa
```

FIG. 14

Human CDYL (CDY Like)

```
ggagagaggacctatttctactaaggacattcccggaaggcaatgggtttcaaacaatatcct
gaagactcatctcggggaactaagcaggtggtaatcagagaacacagagcccccggaagaat
tttATGGCATTTCAGGCAAGCCACAGGCCAGCCTGGGAAAAAGCAGGAAGAGAAAACTGGCAAT
ACGAGGGCCCAACCCAAAGTTATTCCTGAAGAGAAACAACGTGTCAGCACCAGATGGGCCTTC
AGACCCCAGCCATCTCCCGCAGCAGTGAGCAAAGCGGGCACAGCCCTCCCGGTTTACAGGTT
GAAAGGATTGTTGACAAAAGGAAAAATAAAAAGGAAGACAGAGTATTTGGTTCGGTGGAAAG
GCTATGACAGCGAGGACGACACTTGGGCCGGAACAGCCACCTCGTGAACTGTGAGGAATACAT
CCACGACTTCAACAGACGCCACGGAGAAGCAGAAGGAGCACATTGACCAGAACAAACAGG
ACCTCTCCCAACAATGCTAGGAACAAATCTCCAGATCCAACACCAGCCAGCTTTCTAAGACCT
CTCCTAAGGCACTCGTGATTGGGAAAGACACAGCTCCATCTCTCCAGCCGAAGAACATGACCTAGCGAAG
CCAGAAGTTCAGGAACAACACAGTCCTAAAAGCCCCGTTAAGAGCAGGACCGCCAGTGGACGGCTTTC
TCAGGTATCAAGATCCTCGTGCCTAAAACTGGACAAACCGGTCGGACCCCCGTCGAGCAGGGCCACCCGA
AGAGCGAGAGCCCTGAGAAAGCCCTGGAGCTTTATTGGCCCCCGGTGCCGAGGACAGTGGCACCGGAGATGGGG
AGTGGCAGCGGGAAAAAGCCGGTCGGAGCTTTATTGCCCTCAGGTGCCCTGTGACTGCTGCCAGGAT
AGCAGGCCCAGGATACACCCACTAGTGCCTCAGGTGCCCTGTGACTGCTGCCAGCCA
```

FIG. 15A

CAGGCTTAGCTGTGTTAACGGGAAAGGTACATCTCCGTTCATGGATGCATTAACAGCCAATGGAC
AACCAACATACAGACATCTGTTACAGGAGTGACTGCCAGCAGTGACTGCCAGCAGAAATTTATTGACGACAGA
AGAGACCAGCCCTTTTGACAAGCGATTGCCGTTCAGGCGTGAGGCAAACAGAAAGTGCCTACAGAT
ACAGAGATATTGTGGTCAGGAAGCAGGATGGCTTCACCCACATCTGTTATCCACAAAGTCCTC
AGAGAATAACTCACTAAATCCAGAGAGTAATGAGAGAAGTCCAGAAGTGCTCTGAGCACGGCCGCT
GCCGATGACAGCAAGCTGGTACTGCTCGACAGATGACACAGGAGCCCGTTGGACGCGTCTTCTGTTGGACTTGACT
TTATTTATTTTATACGACGTCGTGAATACTTTCATTCAATTAAGAAGCACTAAATGGCAGAAGC
TATCAGAAACTTCGTGAATACTTTCATTCAATTAAGAAGCCCATTATTGTAGCAGTCAATGGC
CCAGCCATTGGTCTCTAGGAGCATCTATATTGCCCTCTTTGCCTGATGTGGTTTGGGCTGTTGAAAAGG
CTTGGTTTCAAACACCCTGGTCAAGGCCTGGTCTCCCCAGTTGTCTTCTACCGTTATGTT
TCCCAAGATAATGGGAGGAGCATCTGCAAACGAGATGCTGCTCAGTGGACGAAGCTGACAGCG
CAGGAGGCGTGTGGCAAGCTTGCCTGCCTGTGGAGCTTGTGCTTGAGGAATCCAAAGCCCT
TGATGGTTCGCATTAAGGAGCTTGAGGCTGGAGCTGGAGCTGGAGGAGTGTGAGGTGCTGAAG
CGTGCGCTGCAACATGAAGATGGACTCCAGGGATGGACTCCAGGGATGGACTTAAGTACTTGCAGAGGAAGATCGATG
AAAATCTGGGGCTCGGCCCAGGGGATG

FIG. 15B

AGTTCTGAgtgtgtcggctgcgccactggtgacaccgggatcgggctgagcgaggagaacatcaccg
gctccagttccctgatccattctcacagcctgaaacaagctcacccgtagcttacgcttgaa
gcaggactgggaacatccagctcttattatcgaggagtttaaagtactgtaacttaaaat
aaataactacaaagcttctttgtcvaaacgtcattatttatacttatacacgcaggtgtaa
aagtataaagtgagcactagactgctcttagaagctcttaatttttgttttcttttgctagtac
tgtataaaaacagaattgtgttttattggtttttggatgacagaaaagtctgaataatgtttg
ttttcctcattctccttctagaacacagaatctaaggggtgttagccagcctcgcctcct
gccccacgtagagacacagagtgatgtgaggcgttggcttttctccaagaagtacagatacc
tcagattcgggaaactcaaaatcaaaagactgcttctaggatataacttctgatgaaaaat
ccgctgaggagcatacccaaaccagacatatgcttaccagtcctgagattcatgctgagatatcaattggtt
tccccttctttaaaatacgtccagttcttaccagttaacatgaagaaaccactgtctctag
aagaaagcttgttttgcagtagtgaatcactgaatagctatgactatctaagttat
aagttagtctttagtggtttaaatagtttctgacctctgaaaataactacataagtg
cttcttgttgctgggtgagaaatactacttttataagacagtttggttttctgtttgcagatatg
attgatgtattcaccaaaatattttatgttttataagtgtaattttaggttcactt
agaatatatttattaataagtaaaattcttttggcacactattaaatgcaaaactccttt
c

FIG. 15C

Mouse Cdyl (CDY like)

```
ctttgaggtggtttagcatcccacttgttcctgaggacatctgttcctaagagcactcacc
tgagatgctcaaaggtccagagaaacacttctcggtgacaaagcaggtggtgaccagaacag
aggcccccaaaatttatggcattcaaggcaaagcacagccaacccgagggaaagcaagagtc
cagcctggaaatacatagcccaacccgaaggttatctctgaaggaaacaATGGGCATAGGCAATA
GCCAGCCTAATTCACAGGAAGCCTCTGCACACTTCCAGAGAAAGCTGAACAACCTACTGATG
ATAACACCTGCCAGCAGCAAAATAATGTGGTTCCTGCAAACAGTCTCAGAAAAGGAAGAAGGAAGA
CAATTCAAGACGCGGAGACTCAGTGGAAAGCTATGACAGTGAGGATGACACGTGGGAGCCTGAGCAGCACC
CAGAATATCTGGTGCCGTGGAGAATACATCCATGACTTCAACCGCGCCACAACCCGAGAGGCAAAAGGAAGGTA
TGGTGAACTGTGAGGAATACATCCATGACTTCAACCGCGCCACAACCCGAGAGGCAAAAGGAAGGTA
GCCTGGCTCGTGCCAGCAGACCCCCCAGCAAGCCCGGAAGCAGATTCCAGTTCCACCACA
GCACTCTCTCCAAGACCAACTCCAAAGCACTTGTTGGTAGGCAAAGATCATGAGTCCAAAAGCAGCC
AGCTGTTGGCCTGCCAGCAGCCCAGCCAGAAGTTCAGGAAAACCCAGCCCCATCTCTTGCAAACCGCAAGAACA
TGGACCTCGCCAAGTCAGGGATCAAAATTCTGCTTAAGAGCCCGTTAAGGCAGGACCTCGG
TTGATGGCTTTCAGGGGAGAGCCCTGTGGATCAGGGTGCCGAGGACACTG
TAGCCCCAGAGGTGACTGCAGAGAAGCCCACTGGGGCTTTGCTGGGCCTGGTGCCGAGCCAGCCA
```

FIG. 16A

```
GGATGGGGAGCAGGCCCCGAATACATCCACTAGTGCCTCAGGTTTCTGGCCCCGTGACTGCTGCCA
TGGCCACAGGCTTAGCTGTTAATGGAAAAGGTACATCTCCATTCCATTCATGGATGCGCTAGCAGCCAACG
GAACAGTCACCATACAGACATCCGTAACAGGAGTGACAGCCGGAAAAGGAAATTTATTGACGACA
GAAGAGACCAACCTTTGACAAGCGGTTGCGTTTCAGTGTGAGGCAGACAGAGAGTGCCTACAGAT
ACAGAGATATTGTCGTCAGGAAGCAAGATGGCTTCACCCACATCTGTTATCCACAAATCGTCAG
AGAATAACTCACTAAACCCAGAGGTGATGAAAGAAGTRCAGAGCGCCCTGAGCACAGCTGCAGCCG
ACGACAGCAAGCTGGTTCTGCTCAGCGCCGTGGGCAGCGTCTTCTGCTGGACTTTATTT
ATTTATTCGGCGCCTCACAGATGACCGAAAAGAGACCTAAAAATGGCAGACGCTATCAGAA
ACTTCGTGAATACTTTCATTCAGTTAAGAAGCCTATTATTGTAGCTGTGTTAATGGCCCAGCCATTG
GACTAGGAGCATCCATATGCCTCTTTGTGATGCTAACGAAAAGGCTTGGTTTCAAA
CACCCTATACCACCTTCGACAGAGTCGTTCAGTGGGCGAAGTTGACGGCACAGGAGGCCTGTGCA
GAGGAGCATCTGCGAATGAAATGTCCCAGGTGTTTGGCCAGGAACCTTCACACAGGAAGTCATGGTTCGAATCAAGG
AGGGTCTGGTCTCCCAGGTGTAACCCAGTTGTCCTGGAGGAATCCAAAGCCCCTGCCTGGTTGCGCTGCAATATGAAGA
AGCTGGCTTCATGTAACCCAGTTGTCCTGGAGGAATCCAAAGCCCCTGGTTGCGCTGCAATATGAAGA
```

FIG. 16B

```
TGGAGCTAGAGAGCCAGGCCAATGAGAGAGAATGTGAAGTGCTGAAGAAGATCTGGGCTCCGCCCAGG
GCATGGACTCCATGTTTAAAGTACTTACAGAGGAAAATCGATGAGTTCTGAtgggcaggctgagcag
gacatcggtggctcccactgctctacgtcgtcctgcagtggctcgtgcttggaggcagaactggaaa
catccgagctatttattgccgcggagttttaagtactgtaactttaaaataacaaagcttct
ttgtctaagcgtctttatttatactcatgtatacaagtataaaatgtaattgagcactaggc
tgctcttggaagctctaattttcttgtaagctagttgtggatttgttttgttttgtttttaaa
aggaattatgttttcattttgggtgacagaagagtttgaaataatgtttgtttactcttttttt
tttccttaaatctagatcacagaccctcaaaattactagccagcctctcccctcccctactga
aacatgtagaaatactaaacatgttcctgcctctaggggggaggggaggtgtgagtacctcaat
gctgaaacagttctgatcaaacttaagaccaacctggtaaaaagcatcactgatggaaaatcc
caccacggggcgtgggtttctgctgaaatgccccgcctctacctttctactgtccattctt
accagccaccgagtcgagtgtcgagtgtcgagtgtcgagtgtcgagtgtcgagtgtcactc
cgtagctcgagtgttacttgctaagttatgaattagcattagtggtttaaatagttttctgacc
ctttttgaaaaataactacatagtactccttgtgctggtgagaaatactactttgcatagttt
tgtttgtctatctcgagatatgattgctgtattacaccaaagtatttttatgttttataaagtgt
aattttaggttcacttagaatatatttttattaattctcttggcacactattaaatac
gtaaactcctttc
```

FIG. 16C

VCP2r (VCP with 2 repeats)

```
gttgcgagacgttgagctgcgcggaagaATGAGTCCAAAGCCGAGAGCCTCGGGACCTCCGGCCAAGGCCAC
GGAGGCAGGAAAAGAGGAAGTCCTCCTCAGCCGAGCCCAGTGACCCGAAGAAGAAGACTACCAAGGT
GGCCCGAGAAGGGAAAAGCAGTTCGTAGAGGGAGACGCGGGAAGAGAAAGGGGCTGCCGACAAAGATGGCGGC
CGTGACGGCCACCTGAGGCGGGCACCCGGCCACCGGGCCACCGCAGCCCAGCCCAGCCAGGAGCT
CCCTCAGCACGAGCTGCCCGGAGGAGCCAGTGAGGGAGCCAGTCAGGAGAGCACCCCGAGTCAGGA
GGCCGAGCTGGAGGAACCACTGAGTCAGGAGAGCGAGGTGAAGAACCACTGACTGTGTGGATGGCCAG
CTTTCCCCTGTCTCCGAGAGCGACTAAgttcaggcccagcccgccagcccgccagacctcagagatctcaccag
cggggtgcttgccattctgaagataataaaatgaatgtgttgcaaattgaaaaaaaaa
```

FIG. 17A

VCP8r (VCP with 8 repeats)

```
cggaagATGGAGTCCAAAGCCGAGAGCCTCGGGACCTCCGGCCAAGGCCACGGAGGCAGGAAAGAGGAAG
TCCTCCTCAGCCGAGCCCCAGTGACCCGAAGAAGACTACCAAGGTGGCCAAGAAGGGAAAAGCA
GTTCGTAGAGGGAGACCGGGAAGAAAGGGCTGCGACAAAGATGGCGGCCGTGACGGCACCTGAGGCG
GAGAGCGGGCCAGCGGGCCACCCGCCCCCAGCGACCCCAGCCCCTCAGCGAGCTCCCTCAGCGAGCTGCCG
CCGGAGGAGCCAGTGAGCGGAGTCAGGAGAGCAGGGACCACGAGCCCCTGAGTCAGGAGCCGAGCTGGAGAACCA
CTGAGTCAGGAGAGCGAGGTGGAAGAACCACTGAGTCAGGAGAGCCAGGTGGAGGAACCACTGAGTCAG
GAGAGCCAGGTGGAGGAACCGCTGAGTCAGGAGAGCCAGGTGGAGGAACCACTGAGTCAGGAGAGCGAG
GTGGAGGAACCACTGAGTGTGTAGACGGCCAGTCGAGTCCCCTATCTCCCGAGACCAGCGAGATGGAAGAA
GTACCGAGTGTGTAGACGGCCAGCAGTCCCCTATCTCCCGAGACCAGCGACTAAgttcaggcccagccg
ccagacctcagagatctcaccagcggggtgcttgccattctgaagataataaaatgaatgtgttgcaaa
ttgaaaaaaaaa
```

FIG. 17B

VCP10r (VCP with 10 repeats)

```
cgttgcgagacgttgagctgcggaagATGAGTCCAAAGCCGAGACCCTCGGGACCTCCGGCCAAGGCCA
CGGAGGCAGGAAAGAGGAAGTCCTCTCAGCCGAGCCCCAGTGACCCGAAGAAGACTACCAAGG
TGGCCAAGACGGAAAAGCAGTTCGTAGAGAGCGGGAAGAAAGGGCTGCGACAAAGATGGCGG
CCGTGACGGCCACCTGAGCGGGAGAGCCCAGCGCCCAGCCACCCGGCCACCCGGCCAGCCCCAGCCAGGAGC
TCCCTCAGCACGAGCTGCCGGAGAGCCAGTGAGCGAGGAGGGCCAGCACGACCCCTGAGTCAGG
AGCCGAGCTGGAGGAACCACTGAGTCAGGAGAGCGAGGTGGAAGAACCACTGAGTCAGGAGAGCCAGG
TGGAGGAACCACTGAGTCAGGAGAGCGAGGTGGAAGAACCACTGAGTCAGGAGAGCCAGGAAC
CACTGAGTCAGGAGAGCCAGGTGGAGGAACCACTGAGTCAGGAGAGCCAGGTGGAGGAACCACTGAGTC
AGGAGAGCGAGATGGAAGAACCACCAGGTGGAGGAACCACTGAGTCAGGAGAGCG
AGATGGAAGAACTACCGAGTGTGTAGACGGCCAAGTACTCCCCTATCTCCGAGCAGCAGCAGGACTAAgttc
aggcccagcgccagactcagagatctcaccagcggggtgcttgccattctgaagataataaaatgaa
tgtgttgcaaattgaaaaaaaaa
```

FIG. 17C

SEQUENCE LISTING

<160> NUMBER OF SEQ ID NOS: 91

<210> SEQ ID NO 1
<211> LENGTH: 61
<212> TYPE: PRT
<213> ORGANISM: Human

<400> SEQUENCE: 1

Met Ala Ser Gln Glu Phe Glu Val Glu Ala Ile Val Asp Lys Arg Gln
1               5                   10                  15

Asp Lys Asn Gly Asn Thr Gln Tyr Leu Val Arg Trp Arg Gly Tyr Asp
            20                  25                  30

Lys Gln Asp Asp Thr Trp Glu Pro Glu Gln His Leu Met Asn Cys Glu
        35                  40                  45

Lys Cys Val His Asp Phe Asn Arg Arg Gln Thr Glu Lys
    50                  55                  60

<210> SEQ ID NO 2
<211> LENGTH: 60
<212> TYPE: PRT
<213> ORGANISM: Drosophila

<400> SEQUENCE: 2

Glu Glu Glu Glu Glu Tyr Ala Val Glu Lys Ile Ile Asp Arg Arg Val
1               5                   10                  15

Arg Lys Gly Lys Val Glu Tyr Tyr Leu Lys Trp Lys Gly Tyr Pro Glu
            20                  25                  30

Thr Glu Asn Thr Trp Glu Pro Glu Asn Asn Leu Asp Cys Gln Asp Leu
        35                  40                  45

Ile Gln Gln Tyr Glu Ala Ser Arg Lys Asp Glu Glu
    50                  55                  60

<210> SEQ ID NO 3
<211> LENGTH: 60
<212> TYPE: PRT
<213> ORGANISM: Drosofophila

<400> SEQUENCE: 3

Pro Val Asp Leu Val Tyr Ala Ala Glu Lys Ile Ile Gln Lys Arg Val
1               5                   10                  15

Lys Lys Gly Val Val Glu Tyr Arg Val Lys Trp Lys Gly Trp Asn Gln
            20                  25                  30

Arg Tyr Asn Thr Trp Glu Pro Glu Val Asn Ile Leu Asp Arg Arg Leu
        35                  40                  45

Ile Asp Ile Tyr Glu Gln Thr Asn Lys Ser Ser Gly
    50                  55                  60

<210> SEQ ID NO 4
<211> LENGTH: 60
<212> TYPE: PRT
<213> ORGANISM: Drosofophila

<400> SEQUENCE: 4

Asn Gly Phe Asp Pro His Ala Gly Phe Asp Glu Lys Gln Thr Pro Asp
1               5                   10                  15

Ala Glu Thr Glu Ala Gln Phe Leu Ile Lys Trp Lys Gly Trp Ser Tyr
            20                  25                  30

Ile His Asn Thr Trp Glu Ser Glu Ala Thr Leu Arg Asp Met Lys Ala

```
                    35                  40                  45

Lys Gly Met Lys Lys Leu Asp Asn Phe Ile Lys Lys
         50                  55                  60

<210> SEQ ID NO 5
<211> LENGTH: 60
<212> TYPE: PRT
<213> ORGANISM: Drosofophila

<400> SEQUENCE: 5

Pro Pro Lys Gly Glu Tyr Val Val Glu Arg Ile Glu Cys Val Glu Met
1               5                   10                  15

Asp Gln Tyr Gln Pro Val Phe Phe Val Lys Trp Leu Gly Tyr His Asp
            20                  25                  30

Ser Glu Asn Thr Trp Glu Ser Leu Ala Asn Val Ala Asp Cys Ala Glu
        35                  40                  45

Met Glu Lys Phe Val Glu Arg His Gln Gln Leu Tyr
         50                  55                  60

<210> SEQ ID NO 6
<211> LENGTH: 62
<212> TYPE: PRT
<213> ORGANISM: Tetrahymena

<400> SEQUENCE: 6

Glu Glu Glu Asp Gln Tyr Glu Val Glu Lys Ile Leu Asp Ser Arg Phe
1               5                   10                  15

Asn Pro Lys Thr Lys Gln Lys Glu Tyr Leu Val Lys Trp Glu Asn Trp
            20                  25                  30

Pro Ile Glu Asp Ser Thr Trp Glu Pro Tyr Glu His Leu Ser Asn Val
        35                  40                  45

Lys Glu Ile Val Gln Ala Phe Glu Lys Lys Gln Lys Ala Asn
         50                  55                  60

<210> SEQ ID NO 7
<211> LENGTH: 309
<212> TYPE: PRT
<213> ORGANISM: Human

<400> SEQUENCE: 7

Ser Val Pro Arg Val Lys Gly Gly Gln Arg Asn Ile Thr Asp Asp Ser
1               5                   10                  15

Arg Asp Gln Pro Phe Ile Lys Lys Met His Phe Thr Ile Arg Leu Thr
            20                  25                  30

Glu Ser Ala Ser Thr Tyr Arg Asp Ile Val Val Lys Lys Glu Asp Gly
        35                  40                  45

Phe Thr Gln Ile Val Leu Ser Thr Arg Ser Thr Glu Lys Asn Ala Leu
         50                  55                  60

Asn Thr Glu Val Ile Lys Glu Ile Val Asn Ala Leu Asn Ser Ala Ala
65                  70                  75                  80

Ala Asp Asp Ser Lys Leu Val Leu Phe Ser Ala Ala Gly Ser Val Phe
                85                  90                  95

Cys Cys Gly Leu Asp Phe Gly Tyr Phe Val Lys His Leu Arg Asn Asn
                100                 105                 110

Arg Asn Thr Ala Ser Leu Glu Met Val Asp Thr Ile Lys Asn Phe Val
            115                 120                 125

Asn Thr Phe Ile Gln Phe Lys Lys Pro Ile Val Val Ser Val Asn Gly
         130                 135                 140
```

```
Pro Ala Ile Gly Leu Gly Ala Ser Ile Leu Pro Leu Cys Asp Leu Val
145                 150                 155                 160

Trp Ala Asn Glu Lys Ala Trp Phe Gln Thr Pro Tyr Thr Thr Phe Gly
                165                 170                 175

Gln Ser Pro Asp Gly Cys Ser Ser Ile Thr Phe Pro Ile Met Met Gly
            180                 185                 190

Lys Ala Ser Ala Asn Glu Met Leu Ile Ala Gly Arg Lys Leu Thr Ala
        195                 200                 205

Arg Glu Ala Cys Ala Lys Gly Leu Val Ser Gln Val Phe Leu Thr Gly
210                 215                 220

Thr Phe Thr Gln Glu Val Met Ile Gln Ile Lys Glu Leu Ala Ser Tyr
225                 230                 235                 240

Asn Pro Ile Val Leu Glu Glu Cys Lys Ala Leu Val Arg Cys Asn Ile
                245                 250                 255

Lys Leu Glu Leu Glu Gln Ala Asn Glu Arg Glu Cys Glu Val Leu Arg
            260                 265                 270

Lys Ile Trp Ser Ser Ala Arg Gly Ile Glu Ser Met Leu Lys Ile Pro
        275                 280                 285

Leu Leu Gly Tyr Lys Ala Ala Phe Pro Pro Arg Lys Thr Gln Asn Asp
    290                 295                 300

Gln Arg Trp Cys Pro
305

<210> SEQ ID NO 8
<211> LENGTH: 290
<212> TYPE: PRT
<213> ORGANISM: Human

<400> SEQUENCE: 8

Met Ala Ala Leu Arg Val Leu Leu Ser Cys Ala Arg Gly Pro Leu Arg
1               5                   10                  15

Pro Pro Val Arg Cys Pro Ala Trp Arg Pro Phe Ala Ser Gly Ala Asn
                20                  25                  30

Phe Glu Tyr Ile Ile Ala Glu Lys Arg Gly Lys Asn Asn Thr Val Gly
            35                  40                  45

Leu Ile Gln Leu Asn Arg Pro Lys Ala Leu Asn Ala Leu Cys Asp Gly
50                  55                  60

Leu Ile Asp Glu Leu Asn Gln Ala Leu Lys Ile Phe Glu Glu Asp Pro
65                  70                  75                  80

Ala Val Gly Gly Ile Val Leu Thr Gly Gly Asp Lys Ala Phe Ala Ala
                85                  90                  95

Gly Ala Asp Ile Lys Glu Met Gln Asn Leu Ser Phe Gln Asp Cys Tyr
            100                 105                 110

Ser Ser Lys Phe Leu Lys His Trp Gly His Leu Thr Gln Val Lys Lys
        115                 120                 125

Pro Val Ile Ala Ala Val Asn Gly Tyr Pro Phe Gly Gly Gly Cys Glu
130                 135                 140

Leu Ala Met Met Cys Asp Ile Ile Tyr Ala Gly Glu Lys Ala Gln Phe
145                 150                 155                 160

Ala Gln Pro Glu Ile Leu Ile Gly Thr Ile Pro Gly Ala Gly Gly Thr
                165                 170                 175

Gln Arg Leu Thr Arg Ala Val Gly Lys Ser Leu Glu Leu Glu Met Val
            180                 185                 190

Leu Thr Gly Asp Ala Ile Ser Ala Gln Asp Ala Lys Gln Ala Gly Leu
```

-continued

```
                195                 200                 205
Val Ser Lys Ile Cys Pro Val Glu Thr Leu Val Glu Glu Ala Ile Gln
    210                 215                 220

Cys Ala Glu Lys Ile Ala Ser Asn Ser Lys Ile Val Ala Met Ala
225                 230                 235                 240

Lys Glu Ser Val Asn Ala Ala Phe Glu Met Thr Leu Thr Glu Gly Ser
                245                 250                 255

Lys Leu Glu Lys Lys Leu Phe Tyr Ser Thr Phe Ala Thr Asp Asp Arg
                260                 265                 270

Lys Glu Gly Met Thr Ala Phe Val Glu Lys Arg Lys Ala Asn Phe Lys
                275                 280                 285

Asp Gln
    290

<210> SEQ ID NO 9
<211> LENGTH: 276
<212> TYPE: PRT
<213> ORGANISM: Arthrobacter

<400> SEQUENCE: 9

Met Ser Ser Asn Ser Asp His His Ile Ser Val Glu His Thr Asp Gly
1               5                   10                  15

Val Ala Thr Ile Arg Phe Thr Arg Pro Ser Lys His Asn Ala Ala Ser
                20                  25                  30

Gly Gln Leu Leu Leu Glu Thr Leu Glu Ala Leu Tyr Arg Leu Glu Ser
            35                  40                  45

Asp Asp Ser Val Gly Ala Ile Val Leu Thr Gly Glu Gly Ala Val Phe
    50                  55                  60

Ser Ala Gly Phe Asp Leu Glu Glu Val Pro Met Gly Pro Ala Ser Glu
65                  70                  75                  80

Ile Gln Ser His Phe Arg Leu Lys Ala Leu Tyr Tyr His Ala Val Ile
                85                  90                  95

His Met Leu Ala Arg Ile Glu Lys Pro Thr Leu Ala Ala Ile Asn Gly
                100                 105                 110

Pro Ala Val Gly Gly Gly Leu Gly Met Ser Leu Ala Cys Asp Leu Ala
            115                 120                 125

Val Cys Thr Asp Arg Ala Thr Phe Leu Pro Ala Trp Met Ser Ile Gly
    130                 135                 140

Ile Ala Asn Asp Ala Ser Ser Phe Tyr Leu Pro Arg Ile Val Gly
145                 150                 155                 160

Tyr Arg Arg Ala Met Glu Trp Leu Leu Ile Asn Arg Thr Leu Gly Ala
                165                 170                 175

Asp Glu Ala Val Glu Trp Gly Val Val Asn Arg Val Phe Ser Glu Ala
            180                 185                 190

Asp Phe Gln Ser Arg Val Gly Glu Ile Ala Arg Gln Leu Ala Ala Ala
    195                 200                 205

Pro Thr His Leu Gln Gly Leu Val Lys Asn Arg Ile Gln Glu Gly Ser
            210                 215                 220

Ser Glu Thr Leu Glu Ser Cys Thr Glu His Glu Val Gln Asn Val Ile
225                 230                 235                 240

Ala Ser Val Gly His Pro His Phe Ala Glu Arg Leu Ala Met Phe Arg
                245                 250                 255

Ser Lys Glu Met Arg Ser Ser Ala Leu Ala Val Asp Leu Asp Ala Val
                260                 265                 270
```

```
Cys Gly Gly His
        275

<210> SEQ ID NO 10
<211> LENGTH: 297
<212> TYPE: PRT
<213> ORGANISM: E. Coli

<400> SEQUENCE: 10

Met Lys Arg Gln Gly Thr Thr Leu Pro Ala Asn Asn His Ala Leu Lys
 1               5                  10                  15

Gln Tyr Ala Phe Phe Ala Gly Met Leu Ser Ser Leu Lys Lys Gln Lys
             20                  25                  30

Trp Arg Lys Gly Met Ser Glu Ser Leu His Leu Thr Arg Asn Gly Ser
         35                  40                  45

Ile Leu Glu Ile Thr Leu Asp Arg Pro Lys Ala Asn Ala Ile Asp Ala
     50                  55                  60

Lys Ile Ser Phe Glu Met Gly Glu Val Phe Leu Asn Phe Arg Asp Asp
 65                  70                  75                  80

Pro Gln Leu Arg Val Ala Ile Ile Thr Gly Ala Gly Glu Lys Phe Phe
                 85                  90                  95

Ser Ala Gly Trp Asp Leu Lys Ala Ala Ala Glu Gly Glu Ala Pro Asp
            100                 105                 110

Ala Asp Phe Gly Pro Gly Gly Phe Ala Gly Leu Thr Glu Ile Phe Asn
        115                 120                 125

Leu Asp Lys Pro Val Ile Ala Ala Val Asn Gly Tyr Ala Phe Gly Gly
130                 135                 140

Gly Phe Glu Leu Ala Leu Ala Ala Asp Phe Ile Val Cys Ala Asp Asn
145                 150                 155                 160

Ala Ser Phe Ala Leu Pro Glu Ala Lys Leu Gly Ile Val Pro Asp Ser
                165                 170                 175

Gly Gly Val Leu Arg Leu Pro Lys Ile Leu Pro Pro Ala Ile Val Asn
            180                 185                 190

Glu Met Val Met Thr Gly Arg Arg Met Gly Ala Glu Glu Ala Leu Arg
        195                 200                 205

Trp Gly Ile Val Asn Arg Val Val Ser Gln Ala Glu Leu Met Asp Asn
    210                 215                 220

Ala Arg Glu Leu Ala Gln Gln Leu Val Asn Ser Ala Pro Leu Ala Ile
225                 230                 235                 240

Ala Ala Leu Lys Glu Ile Tyr Arg Thr Thr Ser Glu Met Pro Val Glu
                245                 250                 255

Glu Ala Tyr Arg Tyr Ile Arg Ser Gly Val Leu Lys His Tyr Pro Ser
            260                 265                 270

Val Leu His Ser Glu Asp Ala Ile Glu Gly Leu Leu Ala Phe Ala Glu
        275                 280                 285

Lys Arg Asp Pro Val Trp Lys Gly Arg
    290                 295

<210> SEQ ID NO 11
<211> LENGTH: 261
<212> TYPE: PRT
<213> ORGANISM: C. acctobotylieum

<400> SEQUENCE: 11

Met Glu Leu Asn Asn Val Ile Leu Glu Lys Glu Gly Lys Val Ala Val
 1               5                  10                  15
```

```
Val Ile Ile Asn Arg Pro Lys Ala Leu Asn Ala Leu Asn Ser Asp Ile
            20                  25                  30

Leu Lys Glu Met Asp Tyr Val Ile Gly Glu Ile Glu Asn Asp Ser Glu
        35                  40                  45

Val Leu Ala Val Ile Leu Thr Gly Ala Gly Glu Lys Ser Phe Val Ala
 50                  55                  60

Gly Ala Asp Ile Ser Glu Met Lys Glu Met Asn Thr Ile Glu Gly Arg
 65                  70                  75                  80

Lys Phe Gly Ile Leu Gly Asn Lys Val Phe Arg Arg Leu Glu Leu Leu
                85                  90                  95

Glu Lys Pro Val Ile Ala Ala Val Asn Gly Phe Ala Leu Gly Gly Gly
            100                 105                 110

Cys Glu Ile Ala Met Ser Cys Asp Ile Arg Ile Ala Ser Ser Asn Ala
            115                 120                 125

Arg Phe Gly Gln Pro Glu Val Gly Leu Gly Ile Thr Pro Gly Phe Gly
        130                 135                 140

Gly Thr Gln Arg Leu Ser Arg Ile Val Gly Met Gly Met Ala Lys Gln
145                 150                 155                 160

Leu Ile Phe Ile Ala Gln Asn Ile Lys Ala Asp Glu Ala Leu Arg Ile
                165                 170                 175

Gly Leu Val Asn Lys Val Val Glu Pro Ser Glu Leu Met Asn Thr Ala
            180                 185                 190

Lys Glu Ile Ala Asn Lys Ile Val Ser Asn Ala Pro Val Ala Val Lys
        195                 200                 205

Leu Ser Lys Cys Ala Ile Asn Arg Gly Met Gln Cys Asp Ile Asp Thr
        210                 215                 220

Ala Leu Ala Phe Glu Ser Glu Ala Phe Gly Glu Cys Phe Ser Thr Glu
225                 230                 235                 240

Asp Gln Lys Asp Ala Met Thr Ala Phe Ile Glu Lys Arg Lys Ile Glu
                245                 250                 255

Gly Phe Lys Asn Arg
            260

<210> SEQ ID NO 12
<211> LENGTH: 285
<212> TYPE: PRT
<213> ORGANISM: E. Coli

<400> SEQUENCE: 12

Met Ile Tyr Pro Asp Glu Ala Met Leu Tyr Ala Pro Val Glu Trp His
 1               5                  10                  15

Asp Cys Ser Glu Gly Phe Glu Asp Ile Arg Tyr Glu Lys Ser Thr Asp
            20                  25                  30

Gly Ile Ala Lys Ile Thr Ile Asn Arg Pro Gln Val Arg Asn Ala Phe
        35                  40                  45

Arg Pro Leu Thr Val Lys Glu Met Ile Gln Ala Leu Ala Asp Ala Arg
 50                  55                  60

Tyr Asp Asp Asn Ile Gly Val Ile Ile Leu Thr Gly Ala Gly Asp Lys
 65                  70                  75                  80

Ala Phe Cys Ser Gly Gly Asp Gln Lys Val Arg Gly Asp Tyr Gly Gly
                85                  90                  95

Tyr Lys Asp Asp Ser Gly Val His His Leu Asn Val Leu Asp Phe Gln
            100                 105                 110

Arg Gln Ile Arg Thr Cys Pro Lys Pro Val Val Ala Met Val Ala Gly
        115                 120                 125
```

Tyr Ser Ile Gly Gly His Val Leu His Met Met Cys Asp Ile Thr
    130                 135                 140

Ile Ala Ala Asp Asn Ala Ile Phe Gly Gln Thr Gly Pro Lys Val Gly
145                 150                 155                 160

Ser Phe Asp Gly Gly Trp Gly Ala Ser Tyr Met Ala Arg Ile Val Gly
                165                 170                 175

Gln Lys Lys Ala Arg Glu Ile Trp Phe Leu Cys Arg Gln Tyr Asp Ala
            180                 185                 190

Lys Gln Ala Leu Asp Met Gly Leu Val Asn Thr Val Val Pro Leu Ala
        195                 200                 205

Asp Leu Glu Lys Glu Thr Val Arg Trp Cys Arg Glu Met Leu Gln Asn
    210                 215                 220

Ser Pro Met Ala Leu Arg Cys Leu Lys Ala Ala Leu Asn Ala Asp Cys
225                 230                 235                 240

Asp Gly Gln Ala Gly Leu Gln Glu Leu Ala Gly Asn Ala Thr Met Leu
                245                 250                 255

Phe Tyr Met Thr Glu Glu Gly Gln Glu Gly Arg Asn Ala Phe Asn Gln
            260                 265                 270

Lys Arg Gln Pro Asp Phe Gly Lys Phe Lys Arg Asn Pro
        275                 280                 285

<210> SEQ ID NO 13
<211> LENGTH: 5322
<212> TYPE: DNA
<213> ORGANISM: Human

<400> SEQUENCE: 13
ctttcccctt actccgctcc cctcttttcc ctccctctcc tccccttccc tctgttctct      60
cctcctcttc ccctccctc cccgtccgg ggcactctat attcaagcca ccgtttcctg      120
cttcacaaaa tggccaccgc acgcgacacc tacggtcacg tggcctgccg ccctctcagt      180
ttcgggaatc tgcctagctc ccactaaggg gaggctaccc gcggaagagc gagggcagat      240
tagaccggag aaatcccacc acatctccaa gcccgggaac tgagagagga agaagagtga      300
aggccagtgt taggaaaaaa aaaaacaaaa acaaaaaaaa cgaaaaacga aagctgagtg      360
catagagttg gaaagggggag cgaatgcgta aggttggaaa gggggggcgaa gaggcctagg      420
ttaacatttt caggcgtctt agccggtgga aagcgggaga cgcaagttct cgcgagatct      480
cgagaactcc gaggctgaga ctagggtttt agcggagagc acgggaagtg tagctcgaga      540
gaactgggac agcatttcgc accctaagct ccaaggcagg actgctaggg gcgacaggac      600
taagtaggaa atcccttgag cttagacctg agggagcgcg cagtagccgg gcagaagtcg      660
ccgcgacagg gaattgcggt gtgagaggga gggcacacgt tgtacgtgct gacgtagccg      720
gctttccagc gggtatatta gatccgtggc cgcgcggtgc gctccagagc cgcagttctc      780
ccgtgagagg gccttcgcgg tggaacaaac actcgcttag cagcggaaga ctccgagttc      840
tcggtactct tcagggatga gtcatgtggc agtggaaaat gcgctcgggc tggaccagca      900
gtttgctggc ctagacctga actcttcaga taatcagagt ggaggaagta cagccagcaa      960
agggcgctat attcctcctc atttaaggaa ccgagaagct actagaggtt tctacgataa     1020
agacagttca gggtggagtt ctagcaaaga taaggatgcg tatagcagtt ttggatctcg     1080
tagtgattca agaggggaagt ctagcttctt cagtgatcgt ggaagtggat caaggggaag     1140
gtttgatgat cgtggacgga gtgattacga tggcattggc agccgtggtg acagaagtgg     1200

```
ctttggcaaa tttgaacgtg gtggaaacag tcgctggtgt gacaaatcag atgaagatga    1260
ttggtcaaaa ccactcccac caagtgaacg cttggaacag gaactctttt ctggaggcaa    1320
cactgggatt aattttgaga aatacgatga cattccagtt gaggcaacag gcaacaactg    1380
tcctccacat attgaaagtt tcagtgatgt tgagatggga gaaattatca tgggaaacat    1440
tgagcttact cgttatactc gcccaactcc agtgcaaaag catgctattc ctattatcaa    1500
agagaaaaga gacttgatgg cttgtgccca acagggtct ggaaaaactg cagcatttct     1560
gttgcccatc ttgagtcaga tttattcaga tggtccaggc gaggctttga gggccatgaa    1620
ggaaaatgga aggtatgggc gccgcaaaca atacccaatc tccttggtat tagcaccaac    1680
gagagagttg gcagtacaga tctacgaaga agccagaaaa ttttcatacc gatctagagt    1740
tcgtccttgc gtggtttatg gtggtgccga tattggtcag cagattcgag acttggaacg    1800
tggatgccat ttgttagtag ccactccagg acgtctagtg gatatgatgg aaagaggaaa    1860
gattggatta gacttttgca aatacttggt gttagatgaa gctgatcgga tgttggatat    1920 gggggtttgag cctcagattc gtagaatagt cgaacaagat actatgcctc caaagggtgt    1980
ccgccacact atgatgttta gtgctacttt tcctaaggaa atacagatgc tggctcgtga    2040
tttcttagat gaatatatct tcttggctgt aggaagagtt ggctctacct ctgaaaacat    2100
cacacagaaa gtagtttggg tggaagaatc agacaaacgg tcatttctgc ttgacctcct    2160
aaatgcaaca ggcaaggatt cactgacctt agtgtttgtg gagaccaaaa agggtgcaga    2220
ttctctggag gatttcttat accatgaagg atacgcatgt accagcatcc atggagaccg    2280
ttctcagagg gatagagaag aggcccttca ccagttccgc tcaggaaaaa gcccaatttt    2340
agtggctaca gcagtagcag caagaggact ggacatttca aatgtgaaac atgttatcaa    2400
ttttgacttg ccaagtgata ttgaagaata tgtacatcgt attggtcgta cgggacgtgt    2460
aggaaacctt ggcctggcaa cctcattctt taacgagagg aacataaata ttactaagga    2520
tttgttggat cttcttgttg aagctaaaca agaagtgccg tcttggttag aaaacatggc    2580
ttatgaacac cactcaagg gtagcagtcg tggacgttct aagagtagca gatttagtgg     2640
agggtttggt gccagagact accgacaaag tagcggtgcc agcagttcca gcttcagcag    2700
cagccgcgca agcagcagcc gcagtggcgg aggtggccac ggtagcagca gaggatttgg    2760
tggaggtggc tatggaggct tttacaacag tgatggatat ggaggaaatt ataactccca    2820
gggggttgac tggtggggta actgagcctg ctttgcagta ggtcaccctg ccaaacaagc    2880
taatatggaa accacatgta acttagccag actatacctt gtgtagtttc aagaactcgc    2940
agtacattac cagctgtgat tctccactga aattttttt ttaagggagc tcaaggtcac     3000
aagaagaaat gaaaggaaca atcagcagcc ctgttcagaa ggtggtttga agacttcatt    3060
gctgtagttt ggattaactc ccctcccgcc taccccatc ccaaactgca tttataattt     3120
tgtgactgag gatcatttgt ttgttaatgt actgtgcctt taactataga caacttttta    3180
ttttgatgtc ctgttggctc agtaatgctc aagatatcaa ttgttttgac aaaataaatt    3240
tactgaactt gggctaaaat caaaccttgg cacacaggtg tgatacaact taacaggaat    3300
catcgattca tccataaata atataaggaa aaacttatgc ggtagcctgc attagggctt    3360
tttgatactt gcagattggg ggaaaacaac aaatgtcttg aagcatatta atggaattag    3420
tttctaatgt ggcaaactgt attaagttaa agttctgatt tgctcactct atcctggata    3480
ggtatttaga acctgatagt cttaagcca ttccagtcat gatgaggtga tgtatgaata     3540
catgcataca ttcaaagcac tgttttcaaa gttaatgcaa gtaaatacag caattcctct    3600
```

```
ttcaacgttt aggcagatca ttaattatga gctagccaaa tgtgggcata ctattacagg    3660
gaaagtttaa aggtctgata acttgaaaat aggttttag gagaattcat ctacttagac    3720
tttttaagtg cctgccataa atgaaattga atggtagaa tggctgacca cagcaatgac    3780
cagccctcat tagggccctg gatgattttt ggtctaataa cgcatgctag tgttgatgtt    3840
ttttggtcag agggtatgaa caggaagaat taaatgcagc aggctttatt ttaaatgccg    3900
attcacatta ctctgttcaa gctgcgttga gatgttaaac tggcttacta tagacttcgt    3960
aaaaatggct ccagaaaagt aacaaactga atctttgag atcacacagg ttggaaatat    4020
gtacataact gcacaaggtg tcaattctgc tctacagtgc agttttagtc agttttagtt    4080
gcataggttt ccattgtatt tatagtctgt ttatgctaaa tctggccaaa gatgaacatt    4140
gtccaccact aaaatgcctc tgccactttg aattctgtgc taattttgtg gccagaatgc    4200
ggtgatcaaa acgctccatc ttttacagt ggcataggaa gacggcaaaa atttcctaaa    4260
gtgcaataga ttttcaagtg tattgtgcct tgttctaaaa cttttattaa gtaggtgcac    4320
ttgacagtat tgaggtcatt tgttatggtg ctatttcaat tagtctaggt ttaggccctt    4380
gtacattttg cccataactt tttacaaagt acttctttta ttgcacattc agagaattt     4440 atatatatgt cttgtgtgcg tgtccttaaa cttccaatct tactttgtct cttggagatt    4500
gttgaacgca gcttgtctag aagggatg ggactagatt ctaaaattta tttgggacca     4560
tgggaatgat agttgggaag aaaactattt gcacacgaca gatttctaga acttttttgc    4620
tgctagcttt atgtaatatt tattgaacat tttgacaaat atttatttt gtaagcctaa    4680 aagtgattct tgaaagttt aaagaaactt gaccaaaaga cagtacaaaa acactggcac    4740
ttgaatgttg aatgtcaccg tatgcgtgaa attatatt tcgggtagt gtgagctttt      4800 aatgtttaag tcatattaaa ctcttaagtc aaattaagca gacccggcgt tggcagtgta    4860
gccataactt tctgatgtta gtaaaaacaa aattggcgac ttgaaattaa attatgccaa    4920
ggttttgata cacttgtctt aagatattaa tgaaacactt caaaacactg atgtgaagtg    4980
tccagattct cagatgttg ttgtgtggat tttgttagt tgtgtgtttt ttttttttc       5040 agtgaatgtc tggcacattg caatcctcaa acatgtggtt atctttgttg tattggcata    5100
atcagtgact tgtacattca gcaatagcat ttgagcaagt tttatcagca agcaatattt    5160
tcagttaata aggtttcaaa aatcatgtaa ggatttaaac ttgctgaatg taaagattga    5220
acctcaagtc actgtagctt tagtaattgc ttattgtatt agtttagatg ctagcactgc    5280
atgtgctgtg catattctga ttttattaaa ataaaaaaaa aa                      5322

<210> SEQ ID NO 14
<211> LENGTH: 3408
<212> TYPE: DNA
<213> ORGANISM: Human

<400> SEQUENCE: 14 ctttccccctt actccgctcc cctctttttcc ctccctctcc tccccttccc tctgttctct   60
cctcctcttc ccctccctc cccgtccgg ggcactctat attcaagcca ccgtttcctg     120
cttcacaaaa tggccaccgc acgcgacacc tacggtcacg tggcctgccg ccctctcagt    180
ttcgggaatc tgcctagctc ccactaaggg gaggctaccc gcggaagagc gagggcagat    240
tagaccggag aaatcccacc acatctccaa gcccgggaac tgagagagga agaagagtga    300
aggccagtgt taggaaaaaa aaaacaaaa acaaaaaaaa cgaaaaacga aagctgagtg     360
```

-continued

```
catagagttg gaaagggag cgaatgcgta aggttggaaa ggggggcgaa gaggcctagg      420
ttaacatttt caggcgtctt agccggtgga aagcgggaga cgcaagttct cgcgagatct      480
cgagaactcc gaggctgaga ctagggtttt agcggagagc acgggaagtg tagctcgaga      540
gaactgggac agcatttcgc accctaagct ccaaggcagg actgctaggg gcgacaggac      600
taagtaggaa atcccttgag cttagacctg agggagcgcg cagtagccgg gcagaagtcg      660
ccgcgacagg gaattgcggt gtgagaggga gggcacacgt tgtacgtgct gacgtagccg      720
gctttccagc gggtatatta gatccgtggc cgcgcggtgc gctccagagc cgcagttctc      780
ccgtgagagg gccttcgcgg tggaacaaac actcgcttag cagcggaaga ctccgagttc      840
tcggtactct tcagggatga gtcatgtggc agtggaaaat cgctcgggc tggaccagca      900 gtttgctggc ctagacctga actcttcaga taatcagagt ggaggaagta cagccagcaa      960
agggcgctat attcctcctc atttaaggaa ccgagaagct actagaggtt tctacgataa     1020
agacagttca gggtggagtt ctagcaaaga taaggatgcg tatagcagtt ttggatctcg     1080
tagtgattca agaggaagt ctagcttctt cagtgatcgt ggaagtggat caaggggaag     1140
gtttgatgat cgtggacgga gtgattacga tggcattggc agccgtggtg acagaagtgg     1200
ctttggcaaa tttgaacgtg gtggaaacag tcgctggtgt gacaaatcag atgaagatga     1260
ttggtcaaaa ccactcccac caagtgaacg cttggaacag gaactctttt ctggaggcaa     1320
cactgggatt aattttgaga aatacgatga cattccagtt gaggcaacag gcaacaactg     1380
tcctccacat attgaaagtt tcagtgatgt tgagatggga gaaattatca tgggaaacat     1440
tgagcttact cgttatactc gcccaactcc agtgcaaaag catgctattc ctattatcaa     1500
agagaaaaga gacttgatgg cttgtgccca acagggtct ggaaaaactg cagcatttct     1560
gttgcccatc ttgagtcaga tttattcaga tggtccaggc gaggctttga gggccatgaa     1620
ggaaaatgga aggtatgggc gccgcaaaca atacccaatc tccttggtat tagcaccaac     1680
gagagagttg gcagtacaga tctacgaaga agccagaaaa ttttcatacc gatctagagt     1740
tcgtccttgc gtggtttatg gtggtgccga tattggtcag cagattcgag acttggaacg     1800
tggatgccat ttgttagtag ccactccagg acgtctagtg gatatgatgg aaagaggaaa     1860
gattggatta gacttttgca aatacttggt gttagatgaa gctgatcgga tgttggatat     1920
ggggtttgag cctcagattc gtagaatagt cgaacaagat actatgcctc caaagggtgt     1980
ccgccacact atgatgttta gtgctacttt tcctaaggaa atacagatgc tggctcgtga     2040
tttcttagat gaatatatct tcttggctgt aggaagagtt ggctctacct ctgaaaacat     2100
cacacagaaa gtagtttggg tggaagaatc agacaaacgg tcatttctgc ttgacctcct     2160
aaatgcaaca ggcaaggatt cactgacctt agtgtttgtg gagaccaaaa agggtgcaga     2220
ttctctggag gatttcttat accatgaagg atacgcatgt accagcatcc atggagaccg     2280
ttctcagagg gatagagaag aggcccttca ccagttccgc tcaggaaaaa gcccaattt     2340 agtggctaca gcagtagcag caagaggact ggacatttca aatgtgaaac atgttatcaa     2400
ttttgacttg ccaagtgata ttgaagaata tgtacatcgt attggtcgta cgggacgtgt     2460
aggaaacctt ggcctggcaa cctcattctt taacgagagg aacataaata ttactaagga     2520
tttgttggat cttcttgttg aagctaaaca agaagtgccg tcttggttag aaaacatggc     2580
ttatgaacac cactacaagg gtagcagtcg tggacgttct aagagtagca gatttagtgg     2640
agggtttggt gccagagact accgacaaag tagcggtgcc agcagttcca gcttcagcag     2700
cagccgcgca agcagcagcc gcagtggcgg aggtggccac ggtagcagca gaggatttgg     2760
```

-continued

```
tggaggtggc tatggaggct tttacaacag tgatggatat ggaggaaatt ataactccca    2820
gggggttgac tggtggggta actgagcctg ctttgcagta ggtcaccctg ccaaacaagc    2880
taatatggaa accacatgta acttagccag actatacctt gtgtagtttc aagaactcgc    2940
agtacattac cagctgtgat tctccactga aatttttttt ttaagggagc tcaaggtcac    3000
aagaagaaat gaaggaaca atcagcagcc ctgttcagaa ggatcatgct catctgtgga    3060
gcaagtgccc ccatgaaatg ccatattttg tgaagaaagt gcatgcagga atattcaggg    3120
agtccagcat gtagtcatgg cagccttagg tatttgagac cgaccaaccc tcctgatgaa    3180
gacaaccata actcatgcag aacttggagc gtgatgccca gaagtgtgtg aactggtctg    3240
tgaccacaaa gatgagaacc gcatgctgag attggtggaa tggagatttc agtgagccta    3300
catgcagatg acatggtgac acccgtgccc agcctgagct gttttcttct ggccctctta    3360
ttacatgaga aaataaaca cctatgcacc ttggcctcaa aaaaaaaa                  3408
```

<210> SEQ ID NO 15
<211> LENGTH: 662
<212> TYPE: PRT
<213> ORGANISM: Human

<400> SEQUENCE: 15

```
Met Ser His Val Ala Val Glu Asn Ala Leu Gly Leu Asp Gln Gln Phe
  1               5                  10                  15

Ala Gly Leu Asp Leu Asn Ser Ser Asp Asn Gln Ser Gly Gly Ser Thr
             20                  25                  30

Ala Ser Lys Gly Arg Tyr Ile Pro Pro His Leu Arg Asn Arg Glu Ala
         35                  40                  45

Thr Arg Gly Phe Tyr Asp Lys Asp Ser Ser Gly Trp Ser Ser Ser Lys
     50                  55                  60

Asp Lys Asp Ala Tyr Ser Ser Phe Gly Ser Arg Ser Asp Ser Arg Gly
 65                  70                  75                  80

Lys Ser Ser Phe Phe Ser Asp Arg Gly Ser Gly Ser Arg Gly Arg Phe
                 85                  90                  95

Asp Asp Arg Gly Arg Ser Asp Tyr Asp Gly Ile Gly Ser Arg Gly Asp
            100                 105                 110

Arg Ser Gly Phe Gly Lys Phe Glu Arg Gly Gly Asn Ser Arg Trp Cys
        115                 120                 125

Asp Lys Ser Asp Glu Asp Asp Trp Ser Lys Pro Leu Pro Pro Ser Glu
    130                 135                 140

Arg Leu Glu Gln Glu Leu Phe Ser Gly Gly Asn Thr Gly Ile Asn Phe
145                 150                 155                 160

Glu Lys Tyr Asp Asp Ile Pro Val Glu Ala Thr Gly Asn Asn Cys Pro
                165                 170                 175

Pro His Ile Glu Ser Phe Ser Asp Val Glu Met Gly Glu Ile Ile Met
            180                 185                 190

Gly Asn Ile Glu Leu Thr Arg Tyr Thr Arg Pro Thr Pro Val Gln Lys
        195                 200                 205

His Ala Ile Pro Ile Ile Lys Glu Lys Arg Asp Leu Met Ala Cys Ala
    210                 215                 220

Gln Thr Gly Ser Gly Lys Thr Ala Ala Phe Leu Leu Pro Ile Leu Ser
225                 230                 235                 240

Gln Ile Tyr Ser Asp Gly Pro Gly Glu Ala Leu Arg Ala Met Lys Glu
                245                 250                 255
```

-continued

```
Asn Gly Arg Tyr Gly Arg Arg Lys Gln Tyr Pro Ile Ser Leu Val Leu
            260                 265                 270

Ala Pro Thr Arg Glu Leu Ala Val Gln Ile Tyr Glu Glu Ala Arg Lys
            275                 280                 285

Phe Ser Tyr Arg Ser Arg Val Arg Pro Cys Val Val Tyr Gly Gly Ala
            290                 295                 300

Asp Ile Gly Gln Gln Ile Arg Asp Leu Glu Arg Gly Cys His Leu Leu
305                 310                 315                 320

Val Ala Thr Pro Gly Arg Leu Val Asp Met Met Glu Arg Gly Lys Ile
            325                 330                 335

Gly Leu Asp Phe Cys Lys Tyr Leu Val Leu Asp Glu Ala Asp Arg Met
            340                 345                 350

Leu Asp Met Gly Phe Glu Pro Gln Ile Arg Arg Ile Val Glu Gln Asp
            355                 360                 365

Thr Met Pro Pro Lys Gly Val Arg His Thr Met Met Phe Ser Ala Thr
            370                 375                 380

Phe Pro Lys Glu Ile Gln Met Leu Ala Arg Asp Phe Leu Asp Glu Tyr
385                 390                 395                 400

Ile Phe Leu Ala Val Gly Arg Val Gly Ser Thr Ser Glu Asn Ile Thr
            405                 410                 415

Gln Lys Val Val Trp Val Glu Glu Ser Asp Lys Arg Ser Phe Leu Leu
            420                 425                 430

Asp Leu Leu Asn Ala Thr Gly Lys Asp Ser Leu Thr Leu Val Phe Val
            435                 440                 445

Glu Thr Lys Lys Gly Ala Asp Ser Leu Glu Asp Phe Leu Tyr His Glu
            450                 455                 460

Gly Tyr Ala Cys Thr Ser Ile His Gly Asp Arg Ser Gln Arg Asp Arg
465                 470                 475                 480

Glu Glu Ala Leu His Gln Phe Arg Ser Gly Lys Ser Pro Ile Leu Val
            485                 490                 495

Ala Thr Ala Val Ala Ala Arg Gly Leu Asp Ile Ser Asn Val Lys His
            500                 505                 510

Val Ile Asn Phe Asp Leu Pro Ser Asp Ile Glu Glu Tyr Val His Arg
            515                 520                 525

Ile Gly Arg Thr Gly Arg Val Gly Asn Leu Gly Leu Ala Thr Ser Phe
            530                 535                 540

Phe Asn Glu Arg Asn Ile Asn Ile Thr Lys Asp Leu Leu Asp Leu Leu
545                 550                 555                 560

Val Glu Ala Lys Gln Glu Val Pro Ser Trp Leu Glu Asn Met Ala Tyr
            565                 570                 575

Glu His His Tyr Lys Gly Ser Ser Arg Gly Arg Ser Lys Ser Ser Arg
            580                 585                 590

Phe Ser Gly Gly Phe Gly Ala Arg Asp Tyr Arg Gln Ser Ser Gly Ala
            595                 600                 605

Ser Ser Ser Ser Phe Ser Ser Ser Arg Ala Ser Ser Ser Arg Ser Gly
            610                 615                 620

Gly Gly Gly His Gly Ser Ser Arg Gly Phe Gly Gly Gly Tyr Gly
625                 630                 635                 640

Gly Phe Tyr Asn Ser Asp Gly Tyr Gly Asn Tyr Asn Ser Gln Gly
            645                 650                 655

Val Asp Trp Trp Gly Asn
            660
```

-continued

```
<210> SEQ ID NO 16
<211> LENGTH: 662
<212> TYPE: PRT
<213> ORGANISM: Human

<400> SEQUENCE: 16
```

| | | | | | | | | | | | | | | |
|---|---|---|---|---|---|---|---|---|---|---|---|---|---|---|
| Met | Ser | His | Val | Ala | Val | Glu | Asn | Ala | Leu | Gly | Leu | Asp | Gln | Gln | Phe |
| 1 | | | | 5 | | | | | 10 | | | | | 15 | |

| Ala | Gly | Leu | Asp | Leu | Asn | Ser | Ser | Asp | Asn | Gln | Ser | Gly | Gly | Ser | Thr |
| --- | --- | --- | --- | --- | --- | --- | --- | --- | --- | --- | --- | --- | --- | --- | --- |
| | | | 20 | | | | | 25 | | | | | 30 | | |

| Ala | Ser | Lys | Gly | Arg | Tyr | Ile | Pro | Pro | His | Leu | Arg | Asn | Arg | Glu | Ala |
| --- | --- | --- | --- | --- | --- | --- | --- | --- | --- | --- | --- | --- | --- | --- | --- |
| | | 35 | | | | | 40 | | | | | 45 | | | |

| Thr | Arg | Gly | Phe | Tyr | Asp | Lys | Asp | Ser | Ser | Gly | Trp | Ser | Ser | Ser | Lys |
| --- | --- | --- | --- | --- | --- | --- | --- | --- | --- | --- | --- | --- | --- | --- | --- |
| | 50 | | | | | 55 | | | | | 60 | | | | |

| Asp | Lys | Asp | Ala | Tyr | Ser | Ser | Phe | Gly | Ser | Arg | Ser | Asp | Ser | Arg | Gly |
| --- | --- | --- | --- | --- | --- | --- | --- | --- | --- | --- | --- | --- | --- | --- | --- |
| 65 | | | | | 70 | | | | | 75 | | | | | 80 |

| Lys | Ser | Ser | Phe | Phe | Ser | Asp | Arg | Gly | Ser | Gly | Ser | Arg | Gly | Arg | Phe |
| --- | --- | --- | --- | --- | --- | --- | --- | --- | --- | --- | --- | --- | --- | --- | --- |
| | | | | 85 | | | | | 90 | | | | | 95 | |

| Asp | Asp | Arg | Gly | Arg | Ser | Asp | Tyr | Asp | Gly | Ile | Gly | Ser | Arg | Gly | Asp |
| --- | --- | --- | --- | --- | --- | --- | --- | --- | --- | --- | --- | --- | --- | --- | --- |
| | | | 100 | | | | | 105 | | | | | 110 | | |

| Arg | Ser | Gly | Phe | Gly | Lys | Phe | Glu | Arg | Gly | Gly | Asn | Ser | Arg | Trp | Cys |
| --- | --- | --- | --- | --- | --- | --- | --- | --- | --- | --- | --- | --- | --- | --- | --- |
| | | 115 | | | | | 120 | | | | | 125 | | | |

| Asp | Lys | Ser | Asp | Glu | Asp | Asp | Trp | Ser | Lys | Pro | Leu | Pro | Pro | Ser | Glu |
| --- | --- | --- | --- | --- | --- | --- | --- | --- | --- | --- | --- | --- | --- | --- | --- |
| | 130 | | | | | 135 | | | | | 140 | | | | |

| Arg | Leu | Glu | Gln | Glu | Leu | Phe | Ser | Gly | Gly | Asn | Thr | Gly | Ile | Asn | Phe |
| --- | --- | --- | --- | --- | --- | --- | --- | --- | --- | --- | --- | --- | --- | --- | --- |
| 145 | | | | | 150 | | | | | 155 | | | | | 160 |

| Glu | Lys | Tyr | Asp | Asp | Ile | Pro | Val | Glu | Ala | Thr | Gly | Asn | Asn | Cys | Pro |
| --- | --- | --- | --- | --- | --- | --- | --- | --- | --- | --- | --- | --- | --- | --- | --- |
| | | | | 165 | | | | | 170 | | | | | 175 | |

| Pro | His | Ile | Glu | Ser | Phe | Ser | Asp | Val | Glu | Met | Gly | Glu | Ile | Ile | Met |
| --- | --- | --- | --- | --- | --- | --- | --- | --- | --- | --- | --- | --- | --- | --- | --- |
| | | | 180 | | | | | 185 | | | | | 190 | | |

| Gly | Asn | Ile | Glu | Leu | Thr | Arg | Tyr | Thr | Arg | Pro | Thr | Pro | Val | Gln | Lys |
| --- | --- | --- | --- | --- | --- | --- | --- | --- | --- | --- | --- | --- | --- | --- | --- |
| | | 195 | | | | | 200 | | | | | 205 | | | |

| His | Ala | Ile | Pro | Ile | Ile | Lys | Glu | Lys | Arg | Asp | Leu | Met | Ala | Cys | Ala |
| --- | --- | --- | --- | --- | --- | --- | --- | --- | --- | --- | --- | --- | --- | --- | --- |
| | 210 | | | | | 215 | | | | | 220 | | | | |

| Gln | Thr | Gly | Ser | Gly | Lys | Thr | Ala | Ala | Phe | Leu | Leu | Pro | Ile | Leu | Ser |
| --- | --- | --- | --- | --- | --- | --- | --- | --- | --- | --- | --- | --- | --- | --- | --- |
| 225 | | | | | 230 | | | | | 235 | | | | | 240 |

| Gln | Ile | Tyr | Ser | Asp | Gly | Pro | Gly | Glu | Ala | Leu | Arg | Ala | Met | Lys | Glu |
| --- | --- | --- | --- | --- | --- | --- | --- | --- | --- | --- | --- | --- | --- | --- | --- |
| | | | | 245 | | | | | 250 | | | | | 255 | |

| Asn | Gly | Arg | Tyr | Gly | Arg | Arg | Lys | Gln | Tyr | Pro | Ile | Ser | Leu | Val | Leu |
| --- | --- | --- | --- | --- | --- | --- | --- | --- | --- | --- | --- | --- | --- | --- | --- |
| | | | 260 | | | | | 265 | | | | | 270 | | |

| Ala | Pro | Thr | Arg | Glu | Leu | Ala | Val | Gln | Ile | Tyr | Glu | Glu | Ala | Arg | Lys |
| --- | --- | --- | --- | --- | --- | --- | --- | --- | --- | --- | --- | --- | --- | --- | --- |
| | | 275 | | | | | 280 | | | | | 285 | | | |

| Phe | Ser | Tyr | Arg | Ser | Arg | Val | Arg | Pro | Cys | Val | Val | Tyr | Gly | Gly | Ala |
| --- | --- | --- | --- | --- | --- | --- | --- | --- | --- | --- | --- | --- | --- | --- | --- |
| | 290 | | | | | 295 | | | | | 300 | | | | |

| Asp | Ile | Gly | Gln | Gln | Ile | Arg | Asp | Leu | Glu | Arg | Gly | Cys | His | Leu | Leu |
| --- | --- | --- | --- | --- | --- | --- | --- | --- | --- | --- | --- | --- | --- | --- | --- |
| 305 | | | | | 310 | | | | | 315 | | | | | 320 |

| Val | Ala | Thr | Pro | Gly | Arg | Leu | Val | Asp | Met | Met | Glu | Arg | Gly | Lys | Ile |
| --- | --- | --- | --- | --- | --- | --- | --- | --- | --- | --- | --- | --- | --- | --- | --- |
| | | | | 325 | | | | | 330 | | | | | 335 | |

| Gly | Leu | Asp | Phe | Cys | Lys | Tyr | Leu | Val | Leu | Asp | Glu | Ala | Asp | Arg | Met |
| --- | --- | --- | --- | --- | --- | --- | --- | --- | --- | --- | --- | --- | --- | --- | --- |
| | | | 340 | | | | | 345 | | | | | 350 | | |

| Leu | Asp | Met | Gly | Phe | Glu | Pro | Gln | Ile | Arg | Arg | Ile | Val | Glu | Gln | Asp |
| --- | --- | --- | --- | --- | --- | --- | --- | --- | --- | --- | --- | --- | --- | --- | --- |
| | | 355 | | | | | 360 | | | | | 365 | | | |

| Thr | Met | Pro | Pro | Lys | Gly | Val | Arg | His | Thr | Met | Met | Phe | Ser | Ala | Thr |
| --- | --- | --- | --- | --- | --- | --- | --- | --- | --- | --- | --- | --- | --- | --- | --- |
| | 370 | | | | | 375 | | | | | 380 | | | | |

```
Phe Pro Lys Glu Ile Gln Met Leu Ala Arg Asp Phe Leu Asp Glu Tyr
385                 390                 395                 400

Ile Phe Leu Ala Val Gly Arg Val Gly Ser Thr Ser Glu Asn Ile Thr
                405                 410                 415

Gln Lys Val Val Trp Val Glu Glu Ser Asp Lys Arg Ser Phe Leu Leu
            420                 425                 430

Asp Leu Leu Asn Ala Thr Gly Lys Asp Ser Leu Thr Leu Val Phe Val
        435                 440                 445

Glu Thr Lys Lys Gly Ala Asp Ser Leu Glu Asp Phe Leu Tyr His Glu
    450                 455                 460

Gly Tyr Ala Cys Thr Ser Ile His Gly Asp Arg Ser Gln Arg Asp Arg
465                 470                 475                 480

Glu Glu Ala Leu His Gln Phe Arg Ser Gly Lys Ser Pro Ile Leu Val
                485                 490                 495

Ala Thr Ala Val Ala Ala Arg Gly Leu Asp Ile Ser Asn Val Lys His
            500                 505                 510

Val Ile Asn Phe Asp Leu Pro Ser Asp Ile Glu Glu Tyr Val His Arg
        515                 520                 525

Ile Gly Arg Thr Gly Arg Val Gly Asn Leu Gly Leu Ala Thr Ser Phe
    530                 535                 540

Phe Asn Glu Arg Asn Ile Asn Ile Thr Lys Asp Leu Leu Asp Leu Leu
545                 550                 555                 560

Val Glu Ala Lys Gln Glu Val Pro Ser Trp Leu Glu Asn Met Ala Tyr
                565                 570                 575

Glu His His Tyr Lys Gly Ser Ser Arg Gly Arg Ser Lys Ser Ser Arg
            580                 585                 590

Phe Ser Gly Gly Phe Gly Ala Arg Asp Tyr Arg Gln Ser Ser Gly Ala
        595                 600                 605

Ser Ser Ser Ser Phe Ser Ser Arg Ala Ser Ser Arg Ser Gly
    610                 615                 620

Gly Gly Gly His Gly Ser Ser Arg Gly Phe Gly Gly Gly Tyr Gly
625                 630                 635                 640

Gly Phe Tyr Asn Ser Asp Gly Tyr Gly Asn Tyr Asn Ser Gln Gly
                645                 650                 655

Val Asp Trp Trp Gly Asn
            660

<210> SEQ ID NO 17
<211> LENGTH: 4416
<212> TYPE: DNA
<213> ORGANISM: Human

<400> SEQUENCE: 17
ccagtgtaag agttccgcta ttcggtctca cacctacagt ggactacccg attttcgct      60 tctcttcagg gatgagtcat gtggtggtga aaaatgaccc tgaactggac cagcagcttg    120
ctaatctgga cctgaactct gaaaaacaga gtggaggagc aagtacagcg agcaaagggc    180
gctatatacc tcctcactta aggaacaaag aagcatctaa aggattccat gataaagaca    240
gttcaggttg gagttgcagc aaagataagg atgcatatag cagttttggg tctcgagatt    300
ctagaggaaa gcctggttat ttcagtgaac gtggaagtgg atcaagggga agatttgatg    360
atcgtggacg gagtgactat gatggtattg gcaatcgtga agacctggct tttggcagat    420 tgaacggag tggacatagt cgttggtgtg acaagtcagt tgaagatgat tggtcaaaac    480
cacttccacc aagtgaacgc ttggagcaag aactgttttc tggaggaaac acggggatta    540
```

```
actttgagaa atatgatgat ataccagtag aggcaaccgg cagtaactgt cctccacata      600
ttgagaattt tagcgatatt gacatgggag aaattatcat ggggaacatt gaacttactc      660
gctatactcg tcctactcca gtgcaaaaac atgccattcc tattattaag ggaaaaagag      720
acttagtggc ttgtgcccaa acaggatctg ggaaaactgc agcatttctt ttacccatac      780
tgagtcagat atatacagat ggtccaggag aagctttgaa ggctgtgaag gaaaatggaa      840
ggtatgggcg ccgcaaacaa tatccaatat ccttggtttt agccccaaca agagaattgg      900
ctgtacagat ctatgaggaa gccagaaaat tttcctaccg atctagagtt cgtccttgtg      960
tagtttatgg tggtgctgat attggtcagc agattcggga cttagaacgt ggatgccact     1020
tgttagtagc cactccagga cgtctagtgg atatgatgga agaggaaag attggattag      1080 acttctgcaa gtacttagtg ttggatgaag ctgataggat gctggatatg ggatttgaac     1140
ctcagatacg tcgtatagtt gaacaagata ctatgccacc aaagggcgtt cgtcacacca     1200
tgatgtttag tgctactttt cctaaggaaa tacagatgct tgctcgtgac tttttggatg     1260
aatatatctt tttggctgta ggcagagtag gctctacctc tgagaacatc acacagaaag     1320
tagtttgggt ggaagactta gataaacggt catttctact ggacatttta ggtgcaacag     1380
ggagtgattc acttactta gtgtttgtgg agaccaaaaa gggagcagat tccctggagg      1440
atttcttata ccatgaagga tatgcttgta ctagtattca tggagaccgg tcacagagag     1500
atcgagagga ggcccttcac cagtttcgct caggaaaaag cccaattcta gtggctacag     1560
ctgtggcagc acgaggacta gacatttcaa atgtgagaca tgttatcaat tttgatttgc     1620
caagtgatat tgaagaatat gtgcatcgta ttggccgtac aggacgtgta ggaaacctgg     1680
gccttgccac ctcattcttt aatgaaaaaa atatgaatat tacaaaggat ttgttggatc     1740
ttcttgtaga agctaaacaa gaagtgcctt cttggttgga aaatatggct tatgaacacc     1800
actacaaggg tggcagtcgt ggacgatcta aaagtaatag attcagtgga ggatttggtg     1860
ccagagacta tcgacaaagt agtggttcca gcagttccgg cttttggtgct agtcgcggaa     1920 gcagcagccg cagtggtgga ggtggttacg gcgacacgcag aggatttggt ggaggtggct     1980
atggaggctt ctacaatagt gatggatatg gaggaaatta taactcccag ggggttgact     2040
ggtggggcaa ctgaatctgc tttgcagcaa agtcacccctt acaaagaagc taatatggaa     2100
accacatgta acttagccag actatattgt gtagcttcaa gaacttgcag tacattacca     2160
gctgtgattc tcctgataat tcaagggagc tcaaagtcac aagaagaaaa atgaaaggaa     2220
aaaacagcag ccctattcag aaattggttt gaagatgtaa ttgctctagt ttggattaaa     2280
ctcttcccct cctgctttag tgccacccca aactgcattt ataattttgt gactgaggat     2340
cgtttgtttg ttaacgtact gtgactttaa ctttagacaa cttactactt tgatgtcctg     2400
ttggctcagt aatgctcacg ataccaattg ttttgacaaa ataaatttac taaacttggc     2460
ctaaaatcaa accttggcac agaggtatga tacaacttta acaggagtca tcaattcatc     2520
cataaatata aaagggaaaa aaacttaag gcagtagtct gcattaggac tgtttgagtt      2580
ttgcagactt ggggttggga aacatcttaa agcattaaaa gcatagtttt ttgtatggcc     2640
aaccttacta aattaagttc tgacttgctc actctatcct ggataggcac ttgggaactt     2700 acactctttta agccattcca gtcatgatga ggtggaatgt atcagtatac caattaatat     2760
ttttgaaaga gttcttttag gttaaatttaa gtacagcaat ttctcatgta atgtttaggg     2820
agtttattct aacctaggca aacggcatgc tatcacaaga aaggttaaa gctttgataa      2880
```

-continued

```
aatgggggag atttaatcag ttttttaat gcctgctata aaaatttgaa atattagaat     2940
ggccgaccat ggcagtgacc aggcctcact acaggcctgg ttggattctg gtctttaatg   3000
catgctagtg ttgatgtttt ttggtcaaga acggtttaaa caggaaggat tgtgcagcag   3060
gctttaattt aatgtagatt catactgctc tgttaaagct gcattgaaat gttaaaatgg   3120
cttacacttg cagactttgc aaatcttaag actaacaaaa ccttgaaatc acacagcttg   3180
caaatacgta ctaaactgca caaggtgtgt gttctatatg tgcagtttta gcgtatttta   3240
gttgcatagg tttccatggt atttatagtc tcttgtgcta aatttggcca agatgattg    3300
tccaccacta aaaatgcctc tcccacttgg aattctgtac tgattttgtg gccagatgca   3360
atgatcttta aaaacaaatc ttttcaatgg cataagaagt tgacaaaaat ttcttaaagt   3420
gcaatagatt ttcaagttat tgtgccttgt tctaaaattt taagtagggc acttgacagt   3480
attgaggtca tttgttaagg tgctatttca attagtgtag gtttagactc ttgtacattt   3540
ctcccataac tttttacaaa gtattttgtt gcacattcag agaattttat atatatatgt   3600
cttgtgtggg tgtcctcgac cttccaatct tatttcgtct cttggagatt gttgaatgca   3660
gccagtgaag aagtagattc ctaaatttta ttggggacca tggaatggta gttgagaaga   3720
aaactatttg cacacaacag attttagata cttttttgctg ctagttgtgt aatatttatt  3780
gaacattttg acaaatattt atttttgtaa gcctaaaaat gattctttga aagtttaaag   3840
aaacttgacc aaaagacagt acaaaaaaca ctggcacttg aatgttgaat gtcaccgtat   3900
gtgaaataat atattttggg gtagtgtgag cttttaatgt taagtctgtt aaacttgagt   3960
caaattaagc agacccggca ttggcaatgt agctgtaatt ttctgacaaa atttaagaca   4020
aaattgtcaa cttgaaacta aaacatgcca aggttttgat atacttgtct taagatatta   4080
atgaaacaat tttgaacact gataggaagg tccacatcca caaagtttct cttgagtttt   4140
gttatgtgtt ttgctgtgtt tgattttcag tgattgtctg gtatatttac agtcctcaaa   4200
catggttatt tctgtcagtg acttaacatt cggttttacc agccagcagt attcttcagt   4260
aaataaagaa tggaattgct gaatgtaatc attgaacctc gagtcactgt aaaagttcag   4320
taattgctta ttgtattagt tttagatgct ggcaccgcat gtgctctgtt tattctgatt   4380
ttactaaaat aaaaagttca aaagtcaaaa aaaaaa                             4416
```

<210> SEQ ID NO 18
<211> LENGTH: 660
<212> TYPE: PRT
<213> ORGANISM: Human

<400> SEQUENCE: 18

```
Met Ser His Val Val Lys Asn Asp Pro Glu Leu Asp Gln Gln Leu
 1               5                  10                  15

Ala Asn Leu Asp Leu Asn Ser Glu Lys Gln Ser Gly Gly Ala Ser Thr
            20                  25                  30

Ala Ser Lys Gly Arg Tyr Ile Pro Pro His Leu Arg Asn Lys Glu Ala
        35                  40                  45

Ser Lys Gly Phe His Asp Lys Asp Ser Ser Gly Trp Ser Cys Ser Lys
    50                  55                  60

Asp Lys Asp Ala Tyr Ser Ser Phe Gly Ser Arg Asp Ser Arg Gly Lys
65                  70                  75                  80

Pro Gly Tyr Phe Ser Glu Arg Gly Ser Gly Ser Arg Gly Arg Phe Asp
                85                  90                  95

Asp Arg Gly Arg Ser Asp Tyr Asp Gly Ile Gly Asn Arg Glu Arg Pro
```

-continued

```
                100                 105                 110
Gly Phe Gly Arg Phe Glu Arg Ser Gly His Ser Arg Trp Cys Asp Lys
            115                 120                 125

Ser Val Glu Asp Asp Trp Ser Lys Pro Leu Pro Pro Ser Glu Arg Leu
130                 135                 140

Glu Gln Glu Leu Phe Ser Gly Gly Asn Thr Gly Ile Asn Phe Glu Lys
145                 150                 155                 160

Tyr Asp Asp Ile Pro Val Glu Ala Thr Gly Ser Asn Cys Pro Pro His
                165                 170                 175

Ile Glu Asn Phe Ser Asp Ile Asp Met Gly Glu Ile Ile Met Gly Asn
            180                 185                 190

Ile Glu Leu Thr Arg Tyr Thr Arg Pro Thr Pro Val Gln Lys His Ala
            195                 200                 205

Ile Pro Ile Ile Lys Gly Lys Arg Asp Leu Val Ala Cys Ala Gln Thr
210                 215                 220

Gly Ser Gly Lys Thr Ala Ala Phe Leu Leu Pro Ile Leu Ser Gln Ile
225                 230                 235                 240

Tyr Thr Asp Gly Pro Gly Glu Ala Leu Lys Ala Val Lys Glu Asn Gly
                245                 250                 255

Arg Tyr Gly Arg Arg Lys Gln Tyr Pro Ile Ser Leu Val Leu Ala Pro
            260                 265                 270

Thr Arg Glu Leu Ala Val Gln Ile Tyr Glu Glu Ala Arg Lys Phe Ser
            275                 280                 285

Tyr Arg Ser Arg Val Arg Pro Cys Val Val Tyr Gly Gly Ala Asp Ile
            290                 295                 300

Gly Gln Gln Ile Arg Asp Leu Glu Arg Gly Cys His Leu Leu Val Ala
305                 310                 315                 320

Thr Pro Gly Arg Leu Val Asp Met Met Glu Arg Gly Lys Ile Gly Leu
                325                 330                 335

Asp Phe Cys Lys Tyr Leu Val Leu Asp Glu Ala Asp Arg Met Leu Asp
            340                 345                 350

Met Gly Phe Glu Pro Gln Ile Arg Arg Ile Val Glu Gln Asp Thr Met
            355                 360                 365

Pro Pro Lys Gly Val Arg His Thr Met Met Phe Ser Ala Thr Phe Pro
370                 375                 380

Lys Glu Ile Gln Met Leu Ala Arg Asp Phe Leu Asp Glu Tyr Ile Phe
385                 390                 395                 400

Leu Ala Val Gly Arg Val Gly Ser Thr Ser Glu Asn Ile Thr Gln Lys
                405                 410                 415

Val Val Trp Val Glu Asp Leu Asp Lys Arg Ser Phe Leu Leu Asp Ile
            420                 425                 430

Leu Gly Ala Thr Gly Ser Asp Ser Leu Thr Leu Val Phe Val Glu Thr
            435                 440                 445

Lys Lys Gly Ala Asp Ser Leu Glu Asp Phe Leu Tyr His Glu Gly Tyr
450                 455                 460

Ala Cys Thr Ser Ile His Gly Asp Arg Ser Gln Arg Asp Arg Glu Glu
465                 470                 475                 480

Ala Leu His Gln Phe Arg Ser Gly Lys Ser Pro Ile Leu Val Ala Thr
                485                 490                 495

Ala Val Ala Ala Arg Gly Leu Asp Ile Ser Asn Val Arg His Val Ile
            500                 505                 510

Asn Phe Asp Leu Pro Ser Asp Ile Glu Glu Tyr Val His Arg Ile Gly
            515                 520                 525
```

-continued

```
Arg Thr Gly Arg Val Gly Asn Leu Gly Leu Ala Thr Ser Phe Phe Asn
        530                 535                 540

Glu Lys Asn Met Asn Ile Thr Lys Asp Leu Leu Asp Leu Leu Val Glu
545                 550                 555                 560

Ala Lys Gln Glu Val Pro Ser Trp Leu Glu Asn Met Ala Tyr Glu His
                565                 570                 575

His Tyr Lys Gly Gly Ser Arg Gly Arg Ser Lys Ser Asn Arg Phe Ser
            580                 585                 590

Gly Gly Phe Gly Ala Arg Asp Tyr Arg Gln Ser Ser Gly Ser Ser Ser
            595                 600                 605

Ser Gly Phe Gly Ala Ser Arg Gly Ser Ser Arg Ser Gly Gly Gly
            610                 615                 620

Gly Tyr Gly Asp Ser Arg Gly Phe Gly Gly Gly Tyr Gly Gly Phe
625                 630                 635                 640

Tyr Asn Ser Asp Gly Tyr Gly Asn Tyr Asn Ser Gln Gly Val Asp
                645                 650                 655

Trp Trp Gly Asn
            660
```

<210> SEQ ID NO 19
<211> LENGTH: 4335
<212> TYPE: DNA
<213> ORGANISM: Human

<400> SEQUENCE: 19

```
gctcatcgtt tgttgtttag ataatatcat gaactgataa atgcagttgc cacgttgatt     60
ccctagggcc tggcttaccg actgaggtca aagatatta tgccttctct ttagacttgg    120
tcagtggaga ggaaatgggc aaagaaccag cctatggagg tgacaaggcc ttagggccaa    180
aagtcttgag ggtgaaggtt tagggcctgc gcagcttccc tgccatgccc cgcaaggtct    240
cgcattcgca aggcttgtga cagtgggagc ctcattacgg actctcctaa agtccatggt    300
gtcctctttt cgcatttgcg cccgtgggt gatgcccgat gccgccctc ccatcgctct    360
cttcccttc aagcgtatcg caactgcaaa acacccagc acagacactc catttctat    420
cttaatgcat ttaactagca caacctacag gttgttccat cccagagact acccttttct    480
ccatagacgt gaccatcaac caaccagcgg tcagaatcag tcagcctctg tcatgttcct    540
aggtccttgg cgaactggct gggcggggtc ccagcagcct aggagtacag tggagcaatg    600
cctgacgtaa gtcaacaaag atcacgtgag acgaatcagt cgcctagatt ggctacaact    660
aagtggttgg gagcggggag gtcgcggcgg ctgcgtgggg ttcgcccgtg acacaattac    720
aactttgtgc tggtgctggc aaagtttgtg atttttaagaa attctgctgt gctctccagc    780
actgcgagct tctgccttcc ctgtagtttc ccagatgtga tccaggtagc cgagttccgc    840
tgcccgtgct tcggtagctt aagtctttgc ctcagctttt ttccttgcag ccgctgagga    900
ggcgataaaa ttggcgtcac agtctcaagc agcgattgaa ggcgtctttt caactactcg    960
attaaggttg ggtatcgtcg tgggacttgg aaatttgttg tttccatgaa atcctgcgca   1020
gtgtcgctca ctaccgccgc tgttgccttc ggtgatgagg caaagaaaat ggcggaagga   1080
aaagcgagcc gcgagagtga agaggagtct gttagcctga cagtcgagga aagggaggcg   1140
cttggtggca tggacagccg tctcttcggg ttcgtgaggc ttcatgaaga tggcgccaga   1200
acgaagaccc tactaggcaa ggctgttcgc tgctacgaat ctttaatctt aaaagctgaa   1260
ggaaaagtgg agtctgactt cttttgccaa ttaggtcact tcaacctctt gttggaagat   1320
```

```
tattcaaaag cattatctgc atatcagaga tattacagtt tacaggctga ctactggaag    1380
aatgctgcgt ttttatatgg ccttggtttg gtctacttct actacaatgc atttcattgg    1440
gcaattaaag catttcaaga tgtcctttat gttgacccca gcttttgtcg agccaaggaa    1500
attcatttac gacttgggct catgttcaaa gtgaacacag actacaagtc tagtttaaag    1560
cattttcagt tagccttgat tgactgtaat ccatgtactt tgtccaatgc tgaaattcaa    1620
tttcatattg cccatttgta tgaaacccag aggaagtatc attctgcaaa ggaggcatat    1680
gaacaacttt tgcagacaga aaaccttcct gcacaagtaa aagcaactgt attgcaacag    1740
ttaggttgga tgcatcataa tatggatcta gtaggagaca aagccacaaa ggaaagctat    1800
gctattcagt atctccaaaa gtctttggag gcagatccta attctggcca atcgtggtat    1860
tttcttggaa ggtgttattc aagtattggg aaagttcagg atgcctttat atcttacagg    1920
caatctattg ataaatcaga agcaagtgca gatacatggt gttcaatagg tgtgttgtat    1980
cagcagcaaa atcagcctat ggatgcttta caggcatata tttgtgctgt acaattggac    2040
catgggcatg ccgcagcctg gatggaccta ggtactctct atgaatcctg caatcaacct    2100
caagatgcca ttaaatgcta cctaaatgca gctagaagca aacgttgtag taatacctct    2160
acgcttgctg caagaattaa atttctacag aatggttctg ataactggaa tggtggccag    2220 agtcttttcac atcatccagt acagcaagtt tattcgttgt gtttgacacc acagaaatta    2280
cagcacttgg aacaactgcg agcaaataga gataatttaa atccagcaca gaagcatcag    2340
ctggaacagt tagaaagtca gtttgtctta atgcagcaaa tgagacacaa agaagttgct    2400
caggtacgaa ctactggaat tcataacggg gccataactg attcatcact gcctacaaac    2460
tctgtctcta atcgacaacc acatggtgct ctgaccagag tatctagcgt ctctcagcct    2520
ggagttcgcc ctgcttgtgt tgaaaaactt ttgtccagtg gagcttttc tgcaggctgt    2580 attccttgtg gcacatcaaa aattctagga agtacagaca ctatcttgct aggcagtaat    2640
tgtatagcag gaagtgaaag taatggaaat gtgccttacc tgcagcaaaa tacacacact    2700
ctacctcata atcatacaga cctgaacagc agcacagaag agccatggag aaaacagcta    2760
tctaactccg ctcagggggct tcataaaagt cagagttcat gtttgtcagg acctaatgaa    2820
gaacaacctc tgttttccac tgggtcagcc cagtatcacc aggcaactag cactggtatt    2880
aagaaggcga atgaacatct cactctgcct agtaattcag taccacaggg ggatgctgac    2940
agtcacctct cctgtcatac tgctacctca ggtggacaac aaggcattat gtttaccaaa    3000
gagagcaagc cttcaaaaaa tagatccttg gtgcctgaaa caagcaggca tactggagac    3060
acatctaatg gctgtgctga tgtcaaggga ctttctaatc atgttcatca gttgatagca    3120
gatgctgttt ccagtcctaa ccatggagat tcaccaaatt tattaattgc agacaatcct    3180
cagctctctg ctttgttgat tggaaaagcc aatggcaatg tgggtactgg aacctgcgac    3240
aaagtgaata atattcaccc agctgttcat acaaagactg atcattctgt tgcctcttca    3300
ccctcttcag ccatttccac agcaacacct tctcctaaat ccactgagca gagaagcata    3360
aacagtgtta ccagccttaa cagtcctcac agtggattac acacagtcaa tggagagggg    3420
ctggggaagt cacagagctc tacaaaagta gacctgcctt tagctagcca cagatctact    3480
tctcagatct taccatcaat gtcagtgtct atatgcccca gttcaacaga agttctgaaa    3540
gcatgcagga atccaggtaa aaatggcttg tctaatagct gcattttgtt agataaatgt    3600
ccacctccaa gaccaccaac ttcaccatac ccacccttgc caaggacaa gttgaatcca    3660
```

| | |
|---|---|
| cccacaccta gtatttactt ggaaaataaa cgtgatgctt tctttcctcc attacatcaa | 3720 |
| ttttgtacaa atccaaaaaa ccctgttaca gtaatacgtg gccttgctgg agctcttaaa | 3780 |
| ttagatcttg acttttctc taccaaaact ttggtagaag ctaacaatga acatatggta | 3840 |
| gaagtgagga cacagttgct gcaaccagca gatgaaaact gggatcccac tggaacaaag | 3900 |
| aaaatctggc gttgtgaaag caatagatct catactacaa ttgccaaata cgcacaatac | 3960 |
| caggcttcct ccttccagga atcattgaga gctggaatgc aatggtgtga tctcagctca | 4020 |
| ctgcagcctc cgcctcctgg gttcaagcga ttctcccacc tcagcctccc gaatagctgg | 4080 |
| aattacaggc acctgccatc atgcccaact aattttgta tttttgtaga cagggttt | 4140 |
| caccatgttg gccaggcttg tcttgaactc ctgacctcag gtggtctgct tgcctcagca | 4200 |
| tcccaaagtg ctgggattac aggtgtgagc caccatgccc ggtaaacttt taaaaatgta | 4260 |
| agcaaaatta cagtatgtaa aacacacatt gctaatggag aaataaagtt cctactttta | 4320 |
| catctaaaaa aaaaa | 4335 |

<210> SEQ ID NO 20
<211> LENGTH: 4931
<212> TYPE: DNA
<213> ORGANISM: Human

<400> SEQUENCE: 20

| | |
|---|---|
| gctcatcgtt tgttgtttag ataatatcat gaactgataa atgcagttgc cacgttgatt | 60 |
| ccctagggcc tggcttaccg actgaggtca taagatatta tgccttctct ttagacttgg | 120 |
| tcagtggaga ggaaatgggc aaagaaccag cctatggagg tgacaaggcc ttagggccaa | 180 |
| aagtcttgag ggtgaaggtt tagggcctgc gcagcttccc tgccatgccc cgcaaggtct | 240 |
| cgcattcgca aggcttgtga cagtgggagc ctcattacgg actctcctaa agtccatggt | 300 |
| gtcctctttt cgcatttgcg ccccgtgggt gatgcccgat gccgcccttc ccatcgctct | 360 |
| cttccccttc aagcgtatcg caactgcaaa acacccagc acagacactc cattttctat | 420 |
| cttaatgcat ttaactagca caacctacag gttgttccat cccagagact acccttttct | 480 |
| ccatagacgt gaccatcaac caaccagcgg tcagaatcag tcagcctctg tcatgttcct | 540 |
| aggtccttgg cgaactggct gggcggggtc ccagcagcct aggagtacag tggagcaatg | 600 |
| cctgacgtaa gtcaacaaag atcacgtgag acgaatcagt cgcctagatt ggctacaact | 660 |
| aagtggttgg gagcggggag gtcgcggcgg ctgcgtgggg ttcgcccgtg acacaattac | 720 |
| aactttgtgc tggtgctggc aaagtttgtg attttaagaa attctgctgt gctctccagc | 780 |
| actgcgagct tctgccttcc ctgtagtttc ccagatgtga tccaggtagc cgagttccgc | 840 |
| tgcccgtgct tcggtagctt aagtctttgc ctcagctttt ttccttgcag ccgctgagga | 900 |
| ggcgataaaa ttggcgtcac agtctcaagc agcgattgaa ggcgtctttt caactactcg | 960 |
| attaaggttg ggtatcgtcg tgggacttgg aaatttgttg tttccatgaa atcctgcgca | 1020 |
| gtgtcgctca ctaccgccgc tgttgccttc ggtgatgagg caaagaaaat ggcggaagga | 1080 |
| aaagcgagcc gcgagagtga agaggagtct gttagcctga cagtcgagga aagggaggcg | 1140 |
| cttggtggca tggacagccg tctcttcggg ttcgtgaggc ttcatgaaga tggcgccaga | 1200 |
| acgaagaccc tactaggcaa ggctgttcgc tgctacgaat ctttaatctt aaaagctgaa | 1260 |
| ggaaaagtgg agtctgactt cttttgccaa ttaggtcact tcaacctctt gttggaagat | 1320 |
| tattcaaaag cattatctgc atatcagaga tattacagtt tacaggctga ctactggaag | 1380 |
| aatgctgcgt ttttatatgg ccttggtttg gtctacttct actacaatgc atttcattgg | 1440 |

-continued

```
gcaattaaag catttcaaga tgtcctttat gttgacccca gcttttgtcg agccaaggaa      1500
attcatttac gacttgggct catgttcaaa gtgaacacag actacaagtc tagtttaaag      1560
cattttcagt tagccttgat tgactgtaat ccatgtactt tgtccaatgc tgaaattcaa      1620
tttcatattg cccatttgta tgaaacccag aggaagtatc attctgcaaa ggaggcatat      1680
gaacaacttt tgcagacaga aaaccttcct gcacaagtaa aagcaactgt attgcaacag      1740
ttaggttgga tgcatcataa tatggatcta gtaggagaca aagccacaaa ggaaagctat      1800
gctattcagt atctccaaaa gtctttggag gcagatccta attctggcca atcgtggtat      1860
tttcttggaa ggtgttattc aagtattggg aaagttcagg atgcctttat atcttacagg      1920
caatctattg ataaatcaga agcaagtgca gatacatggt gttcaatagg tgtgttgtat      1980
cagcagcaaa atcagcctat ggatgcttta caggcatata tttgtgctgt acaattggac      2040
catgggcatg ccgcagcctg gatggaccta ggtactctct atgaatcctg caatcaacct      2100
caagatgcca ttaaatgcta cctaaatgca gctagaagca aacgttgtag taatacctct      2160
acgcttgctg caagaattaa atttctacag aatggttctg ataactggaa tggtggccag      2220
agtctttcac atcatccagt acagcaagtt tattcgttgt gtttgacacc acagaaatta      2280
cagcacttgg aacaactgcg agcaaataga gataatttaa atccagcaca gaagcatcag      2340
ctggaacagt tagaaagtca gtttgtctta atgcagcaaa tgagacacaa agaagttgct      2400
caggtacgaa ctactggaat tcataacggg gccataactg attcatcact gcctacaaac      2460
tctgtctcta atcgacaacc acatggtgct ctgaccagag tatctagcgt ctctcagcct      2520
ggagttcgcc ctgcttgtgt tgaaaaactt ttgtccagtg gagcttttc tgcaggctgt      2580 attccttgtg gcacatcaaa aattctagga agtacagaca ctatcttgct aggcagtaat      2640
tgtatagcag gaagtgaaag taatggaaat gtgccttacc tgcagcaaaa tacacacact      2700
ctacctcata atcatacaga cctgaacagc agcacagaag agccatggag aaaacagcta      2760
tctaactccg ctcaggggct tcataaaagt cagagttcat gtttgtcagg acctaatgaa      2820
gaacaacctc tgttttccac tgggtcagcc cagtatcacc aggcaactag cactggtatt      2880
aagaaggcga atgaacatct cactctgcct agtaattcag taccacaggg ggatgctgac      2940
agtcacctct cctgtcatac tgctacctca ggtggacaac aaggcattat gtttaccaaa      3000
gagagcaagc cttcaaaaaa tagatccttg gtgcctgaaa caagcaggca tactggagac      3060
acatctaatg gctgtgctga tgtcaaggga ctttctaatc atgttcatca gttgatagca      3120
gatgctgttt ccagtcctaa ccatggagat tcaccaaatt tattaattgc agacaatcct      3180
cagctctctg ctttgttgat tggaaaagcc aatggcaatg tgggtactgg aacctgcgac      3240
aaagtgaata atattcaccc agctgttcat acaaagactg atcattctgt tgcctcttca      3300
ccctcttcag ccatttccac agcaacacct tctcctaaat ccactgagca gagaagcata      3360
aacagtgtta ccagccttaa cagtcctcac agtggattac acacagtcaa tggagagggg      3420
ctggggaagt cacagagctc tacaaaagta gacctgcctt tagctagcca cagatctact      3480
tctcagatct taccatcaat gtcagtgtct atatgcccca gttcaacaga agttctgaaa      3540
gcatgcagga atccaggtaa aaatggcttg tctaatagct gcattttgtt agataaatgt      3600
ccacctccaa gaccaccaac ttcaccatac ccacccttgc caaggacaa gttgaatcca      3660 cccacaccta gtatttactt ggaaaataaa cgtgatgctt tctttcctcc attacatcaa      3720
ttttgtacaa atccaaaaaa ccctgttaca gtaatacgtg gccttgctgg agctcttaaa      3780
```

-continued

| | |
|---|---|
| ttagatcttg gacttttctc taccaaaact ttggtagaag ctaacaatga acatatggta | 3840 |
| gaagtgagga cacagttgct gcaaccagca gatgaaaact gggatcccac tggaacaaag | 3900 |
| aaaatctggc gttgtgaaag caatagatct catactacaa ttgccaaata cgcacaatac | 3960 |
| caggcttcct ccttccagga atcattgaga aagaaaatg agaaagaac acaacacaaa | 4020 |
| gatcattcag ataacgaatc cacatcttca gagaattctg gaaggagaag gaaaggacct | 4080 |
| tttaaaacca taaaatttgg gaccaacatt gacctctctg ataacaaaaa gtggaagttg | 4140 |
| cagttacatg aactgactaa acttcctgct tttgcgcgtg tggtgtcagc aggaaatctt | 4200 |
| ctaacccatg ttgggcatac cattctgggc atgaatacag tacaactgta tatgaaagtt | 4260 |
| ccagggagtc ggacaccagg tcaccaagaa ataacaact tctgctctgt taacataaat | 4320 |
| attggtccag agattgtga atggtttgtt gtacctgaag attattgggg tgttctgaat | 4380 |
| gacttctgtg aaaaaaataa tttgaatttt ttaatgagtt cttggtggcc caaccttgaa | 4440 |
| gatctttatg aagcaaatgt ccctgtgtat agatttattc agcgacctgg agatttggtc | 4500 |
| tggataaatg caggcactgt gcattgggtt caaactgttg gctggtgcaa taacattgcc | 4560 |
| tggaatgttg gtccacttac agcctgccag tataaattgg cagtggaacg gtatgaatgg | 4620 |
| aacaaattga aaagtgtgaa gtcaccagta cccatggtgc atctttcctg gaatatggca | 4680 |
| cgaaatatca aagtctcaga tccaaagctt tttgaaatga ttaagtaagt gccttctgaa | 4740 |
| actgctgcag tttctctttg ggggtattgg tagccattca gtattttttt caaaagaatt | 4800 |
| ctgttgacat taaatgatat cagcagtcca gaagtcttgc caaaatgtaa taagatgtaa | 4860 |
| ataatcttat atattcataa gtgttataaa atctcataag attaaaatat tgccttccct | 4920 |
| taaaaaaaaa a | 4931 |

<210> SEQ ID NO 21
<211> LENGTH: 6476
<212> TYPE: DNA
<213> ORGANISM: Human

<400> SEQUENCE: 21

| | |
|---|---|
| gctcatcgtt tgttgtttag ataatatcat gaactgataa atgcagttgc cacgttgatt | 60 |
| ccctagggcc tggcttaccg actgaggtca taagatatta tgccttctct ttagacttgg | 120 |
| tcagtggaga ggaaatgggc aaagaaccag cctatggagg tgacaaggcc ttagggccaa | 180 |
| aagtcttgag ggtgaaggtt tagggcctgc gcagcttccc tgccatgccc cgcaaggtct | 240 |
| cgcattcgca aggcttgtga cagtgggagc ctcattacgg actctcctaa agtccatggt | 300 |
| gtcctctttt cgcatttgcg ccccgtgggt gatgcccgat gccgccccttc ccatcgctct | 360 |
| cttccccttc aagcgtatcg caactgcaaa acacccagc acagacactc catttttctat | 420 |
| cttaatgcat ttaactagca caacctacag gttgttccat cccagagact accctttttct | 480 |
| ccatagacgt gaccatcaac caaccagcgg tcagaatcag tcagcctctg tcatgttcct | 540 |
| aggtccttgg cgaactggct gggcggggtc ccagcagcct aggagtacag tggagcaatg | 600 |
| cctgacgtaa gtcaacaaag atcacgtgag acgaatcagt cgcctagatt ggctacaact | 660 |
| aagtggttgg gagcggggag gtcgcggcgg ctgcgtgggg ttcgcccgtg acacaattac | 720 |
| aactttgtgc tggtgctggc aaagtttgtg atttttaagaa atttctgctgt gctctccagc | 780 |
| actgcgagct tctgccttcc ctgtagtttc ccagatgtga tccaggtagc cgagttccgc | 840 |
| tgcccgtgct tcggtagctt aagtctttgc ctcagcttt ttccttgcag ccgctgagga | 900 |
| ggcgataaaa ttggcgtcac agtctcaagc agcgattgaa ggcgtctttt caactactcg | 960 |

-continued

```
attaaggttg ggtatcgtcg tgggacttgg aaatttgttg tttccatgaa atcctgcgca    1020
gtgtcgctca ctaccgccgc tgttgccttc ggtgatgagg caaagaaaat ggcggaagga    1080
aaagcgagcc gcgagagtga agaggagtct gttagcctga cagtcgagga aagggaggcg    1140
cttggtggca tggacagccg tctcttcggg ttcgtgaggc ttcatgaaga tggcgccaga    1200
acgaagaccc tactaggcaa ggctgttcgc tgctacgaat ctttaatctt aaaagctgaa    1260
ggaaaagtgg agtctgactt cttttgccaa ttaggtcact tcaacctctt gttggaagat    1320
tattcaaaag cattatctgc atatcagaga tattacagtt tacaggctga ctactggaag    1380
aatgctgcgt ttttatatgg ccttggtttg gtctacttct actacaatgc atttcattgg    1440
gcaattaaag catttcaaga tgtcctttat gttgaccccca gcttttgtcg agccaaggaa    1500
attcatttac gacttgggct catgttcaaa gtgaacacag actacaagtc tagtttaaag    1560
cattttcagt tagccttgat tgactgtaat ccatgtactt tgtccaatgc tgaaattcaa    1620
tttcatattg cccatttgta tgaaacccag aggaagtatc attctgcaaa ggaggcatat    1680
gaacaacttt tgcagacaga aaaccttcct gcacaagtaa aagcaactgt attgcaacag    1740
ttaggttgga tgcatcataa tatggatcta gtaggagaca aagccacaaa ggaaagctat    1800
gctattcagt atctccaaaa gtctttggag gcagatccta attctggcca atcgtggtat    1860
tttcttggaa ggtgttattc aagtattggg aaagttcagg atgcctttat atcttacagg    1920
caatctattg ataaatcaga agcaagtgca gatacatggt gttcaatagg tgtgttgtat    1980
cagcagcaaa atcagcctat ggatgcttta caggcatata tttgtgctgt acaattggac    2040
catgggcatg ccgcagcctg gatggaccta ggtactctct atgaatcctg caatcaacct    2100
caagatgcca ttaaatgcta cctaaatgca gctagaagca aacgttgtag taatacctct    2160
acgcttgctg caagaattaa atttctacag aatggttctg ataactgaaa tggtggccag    2220
agtctttcac atcatccagt acagcaagtt tattcgttgt gtttgacacc acagaaatta    2280
cagcacttgg aacaactgcg agcaaataga gataatttaa atccagcaca gaagcatcag    2340
ctggaacagt tagaaagtca gtttgtctta atgcagcaaa tgagacacaa agaagttgct    2400
caggtacgaa ctactggaat tcataacggg gccataactg attcatcact gcctacaaac    2460
tctgtctcta atcgacaacc acatggtgct ctgaccagag tatctagcgt ctctcagcct    2520
ggagttcgcc ctgcttgtgt tgaaaaactt ttgtccagtg gagcttttttc tgcaggctgt    2580 attccttgtg gcacatcaaa aattctagga agtacagaca ctatcttgct aggcagtaat    2640
tgtatagcag gaagtgaaag taatggaaat gtgccttacc tgcagcaaaa tacacacact    2700
ctacctcata atcatacaga cctgaacagc agcacagaag agccatggag aaaacagcta    2760
tctaactccg ctcagggggct tcataaaagt cagagttcat gtttgtcagg acctaatgaa    2820
gaacaacctc tgttttccac tgggtcagcc cagtatcacc aggcaactag cactggtatt    2880
aagaaggcga atgaacatct cactctgcct agtaattcag taccacaggg ggatgctgac    2940
agtcacctct cctgtcatac tgctacctca ggtggacaac aaggcattat gtttaccaaa    3000
gagagcaagc cttcaaaaaa tagatccttg gtgcctgaaa caagcaggca tactggagac    3060
acatctaatg gctgtgctga tgtcaaggga ctttctaatc atgttcatca gttgatagca    3120
gatgctgttt ccagtcctaa ccatggagat tcaccaaatt tattaattgc agacaatcct    3180
cagctctctg ctttgttgat tggaaaagcc aatggcaatg tgggtactgg aacctgcgac    3240
aaagtgaata atattcaccc agctgttcat acaaagactg atcattctgt tgcctcttca    3300
```

-continued

```
ccctcttcag ccatttccac agcaacacct tctcctaaat ccactgagca gagaagcata    3360
aacagtgtta ccagccttaa cagtcctcac agtggattac acacagtcaa tggagagggg    3420
ctggggaagt cacagagctc tacaaaagta gacctgcctt tagctagcca cagatctact    3480
tctcagatct taccatcaat gtcagtgtct atatgcccca gttcaacaga agttctgaaa    3540
gcatgcagga atccaggtaa aaatggcttg tctaatagct gcattttgtt agataaatgt    3600
ccacctccaa gaccaccaac ttcaccatac ccaccttgc caaggacaa gttgaatcca     3660 cccacaccta gtatttactt ggaaaataaa cgtgatgctt tctttcctcc attacatcaa    3720
ttttgtacaa atccaaaaaa ccctgttaca gtaatacgtg gccttgctgg agctcttaaa    3780
ttagatcttg acttttctc taccaaaact ttggtagaag ctaacaatga acatatggta    3840
gaagtgagga cacagttgct gcaaccagca gatgaaaact gggatcccac tggaacaaag    3900
aaaatctggc gttgtgaaag caatagatct catactacaa ttgccaaata cgcacaatac    3960
caggcttcct ccttccagga atcattgaga gaagaaaatg agaaagaac acaacacaaa     4020 gatcattcag ataacgaatc cacatcttca gagaattctg gaaggagaag gaaaggacct    4080
tttaaaacca taaaatttgg gaccaacatt gacctctctg ataacaaaaa gtggaagttg    4140
cagttacatg aactgactaa acttcctgct tttgcgcgtg tggtgtcagc aggaaatctt    4200
ctaacccatg ttgggcatac cattctgggc atgaatacag tacaactgta tatgaaagtt    4260
ccagggagtc ggacaccagg tcaccaagaa aataacaact tctgctctgt taacataaat    4320
attggtccag gagattgtga atggtttgtt gtacctgaag attattgggg tgttctgaat    4380
gacttctgtg aaaaaaataa tttgaatttt ttaatgagtt cttggtggcc caaccttgaa    4440
gatctttatg aagcaaatgt ccctgtgtat agatttattc agcgacctgg agatttggtc    4500
tggataaatg caggcactgt gcattgggtt caaactgttg gctggtgcaa taacattgcc    4560
tggaatgttg gtccacttac agcctgccag tataaattgg cagtggaacg gtatgaatgg    4620
aacaaattga aaagtgtgaa gtcaccagta cccatggtgc atctttcctg gaatatggca    4680
cgaaatatca aagtctcaga tccaaagctt tttgaaatga ttaagtattg tcttttgaaa    4740
attctgaagc aatatcagac attgagagaa gctcttgttg cagcaggaaa agaggttata    4800
tggcatgggc ggacaaatga tgaaccagct cattactgta gcatttgtga ggtggaggtt    4860
tttaatctgc tttttgtcac taatgaaagc aatactcaaa aaacctacat agtacattgc    4920
catgattgtg cacgaaaaac aagcaaaagt ttggaaaatt ttgtggtgct cgaacagtac    4980
aaaatggagg acctaatcca gtttatgat caatttacac tagctctttc attatcatcc     5040
tcatcttgat atagttccat gaatattaaa tgagattatt tctgctcttc aggaaatttc    5100
tgcaccactg gttttgtagc tgtttcataa aactgttgac taaaagctat gtctatgcaa    5160
ccttccaaga atagtatgtc aagcaactgg acacagtgct gcctctgctt caggacttaa    5220
catgctgatc cagctgtact tcagaaaaat aatattaatc atatgttttg tgtacgtatg    5280
acaaactgtc aaagtgacac agaatactga tttgaagata gcctttttta tgtttctcta    5340
tttctgggct gatgaattaa tattcatttg tattttaacc ctgcagaatt ttccttagtt    5400
aaaaacactt tcctagctgg tcatttcttc ataagatagc aaatttaaat ctctcctcga    5460
tcagctttta aaaaatgtgt actattatct gaggaagttt tttactgctt tatgtttttg    5520
tgtgttttga ggccatgatg attacatttg tggttccaaa ataattttt taaatattaa     5580 tagcccatat acaaagataa tggattgcac atagacaaag aaataaactt cagatttgtg    5640 attttttgttt ctaaacttga tacagattta cactatttat aaatacgtat ttattgcctg    5700
```

-continued

```
aaaatatttg tgaatggaat gttgttttt tccagacgta actgccatta aatactaagg      5760
agttctgtag ttttaaacac tactcctatt acattttata tgtgtagata aaactgctta      5820
gtattataca gaaattttta ttaaaattgt taaatgttta aagggtttcc caatgtttga      5880
gtttaaaaaa gactttctga aaaaatccac ttttttgttca ttttcaaacc taatgattat      5940
atgtatttta tatgtgtgtg tatgtgtaca cacatgtata atatatacag aaacctcgat      6000
atataattgt atagatttta aaagtttat ttttacatc tatggtagtt tttgaggtgc        6060
ctattataaa gtattacgga agtttgctgt ttttaaagta aatgtcttt agtgtgattt       6120 attaagttgt agtcaccata gtgatagccc ataataatt gctggaaaat tgtattttat       6180
aacagtagaa aacatatagt cagtgaagta aatattttaa aggaaacatt atatagattt     6240
gataaatgtt gtttataatt aagagtttct tatggaaaag agattcagaa tgataacctc     6300
ttttagagaa caaataagtg acttattttt ttaaagctag atgactttga aatgctatac     6360
tgtcctgctt gtacaacatg gtttggggtg aaggggagga aagtattaaa aaatctatat    6420
cgctagtaaa ttgtaataag ttctattaaa acttgtattt catatgaaaa aaaaaa         6476
```

<210> SEQ ID NO 22
<211> LENGTH: 1079
<212> TYPE: PRT
<213> ORGANISM: Human

<400> SEQUENCE: 22

```
Met Lys Ser Cys Ala Val Ser Leu Thr Thr Ala Ala Val Ala Phe Gly
  1               5                  10                  15
Asp Glu Ala Lys Lys Met Ala Glu Gly Lys Ala Ser Arg Glu Ser Glu
                 20                  25                  30
Glu Glu Ser Val Ser Leu Thr Val Glu Glu Arg Glu Ala Leu Gly Gly
             35                  40                  45
Met Asp Ser Arg Leu Phe Gly Phe Val Arg Leu His Glu Asp Gly Ala
         50                  55                  60
Arg Thr Lys Thr Leu Leu Gly Lys Ala Val Arg Cys Tyr Glu Ser Leu
 65                  70                  75                  80
Ile Leu Lys Ala Glu Gly Lys Val Glu Ser Asp Phe Cys Gln Leu
                 85                  90                  95
Gly His Phe Asn Leu Leu Glu Asp Tyr Ser Lys Ala Leu Ser Ala
                100                 105                 110
Tyr Gln Arg Tyr Tyr Ser Leu Gln Ala Asp Tyr Trp Lys Asn Ala Ala
            115                 120                 125
Phe Leu Tyr Gly Leu Gly Leu Val Tyr Phe Tyr Asn Ala Phe His
        130                 135                 140
Trp Ala Ile Lys Ala Phe Gln Asp Val Leu Tyr Val Asp Pro Ser Phe
145                 150                 155                 160
Cys Arg Ala Lys Glu Ile His Leu Arg Leu Gly Leu Met Phe Lys Val
                165                 170                 175
Asn Thr Asp Tyr Lys Ser Ser Leu Lys His Phe Gln Leu Ala Leu Ile
            180                 185                 190
Asp Cys Asn Pro Cys Thr Leu Ser Asn Ala Glu Ile Gln Phe His Ile
        195                 200                 205
Ala His Leu Tyr Glu Thr Gln Arg Lys Tyr His Ser Ala Lys Glu Ala
    210                 215                 220
Tyr Glu Gln Leu Leu Gln Thr Glu Asn Leu Pro Ala Gln Val Lys Ala
225                 230                 235                 240
Thr Val Leu Gln Gln Leu Gly Trp Met His His Asn Met Asp Leu Val
                245                 250                 255
Gly Asp Lys Ala Thr Lys Glu Ser Tyr Ala Ile Gln Tyr Leu Gln Lys
            260                 265                 270
Ser Leu Glu Ala Asp Pro Asn Ser Gly Gln Ser Trp Tyr Phe Leu Gly
        275                 280                 285
Arg Cys Tyr Ser Ser Ile Gly Lys Val Gln Asp Ala Phe Ile Ser Tyr
    290                 295                 300
Arg Gln Ser Ile Asp Lys Ser Glu Ala Ser Ala Asp Thr Trp Cys Ser
305                 310                 315                 320
Ile Gly Val Leu Tyr Gln Gln Asn Gln Pro Met Asp Ala Leu Gln
                325                 330                 335
Ala Tyr Ile Cys Ala Val Gln Leu Asp His Gly His Ala Ala Ala Trp
            340                 345                 350
```

```
Met Asp Leu Gly Thr Leu Tyr Glu Ser Cys Asn Gln Pro Gln Asp Ala
            355                 360                 365
Ile Lys Cys Tyr Leu Asn Ala Ala Arg Ser Lys Arg Cys Ser Asn Thr
        370                 375                 380
Ser Thr Leu Ala Ala Arg Ile Lys Phe Leu Gln Asn Gly Ser Asp Asn
385                 390                 395                 400
Trp Asn Gly Gly Gln Ser Leu Ser His His Pro Val Gln Gln Val Tyr
                405                 410                 415
Ser Leu Cys Leu Thr Pro Gln Lys Leu Gln His Leu Glu Gln Leu Arg
            420                 425                 430
Ala Asn Arg Asp Asn Leu Asn Pro Ala Gln Lys His Gln Leu Glu Gln
        435                 440                 445
Leu Glu Ser Gln Phe Val Leu Met Gln Gln Met Arg His Lys Glu Val
    450                 455                 460
Ala Gln Val Arg Thr Thr Gly Ile His Asn Gly Ala Ile Thr Asp Ser
465                 470                 475                 480
Ser Leu Pro Thr Asn Ser Val Ser Asn Arg Gln Pro His Gly Ala Leu
                485                 490                 495
Thr Arg Val Ser Ser Val Ser Gln Pro Gly Val Arg Pro Ala Cys Val
            500                 505                 510
Glu Lys Leu Leu Ser Ser Gly Ala Phe Ser Ala Gly Cys Ile Pro Cys
        515                 520                 525
Gly Thr Ser Lys Ile Leu Gly Ser Thr Asp Thr Ile Leu Leu Gly Ser
    530                 535                 540
Asn Cys Ile Ala Gly Ser Glu Ser Asn Gly Asn Val Pro Tyr Leu Gln
545                 550                 555                 560
Gln Asn Thr His Thr Leu Pro His Asn His Thr Asp Leu Asn Ser Ser
                565                 570                 575
Thr Glu Glu Pro Trp Arg Lys Gln Leu Ser Asn Ser Ala Gln Gly Leu
            580                 585                 590
His Lys Ser Gln Ser Ser Cys Leu Ser Gly Pro Asn Glu Glu Gln Pro
        595                 600                 605
Leu Phe Ser Thr Gly Ser Ala Gln Tyr His Gln Ala Thr Ser Thr Gly
    610                 615                 620
Ile Lys Lys Ala Asn Glu His Leu Thr Leu Pro Ser Asn Ser Val Pro
625                 630                 635                 640
Gln Gly Asp Ala Asp Ser His Leu Ser Cys His Thr Ala Thr Ser Gly
                645                 650                 655
Gly Gln Gln Gly Ile Met Phe Thr Lys Glu Ser Lys Pro Ser Lys Asn
            660                 665                 670
Arg Ser Leu Val Pro Glu Thr Ser Arg His Thr Gly Asp Thr Ser Asn
        675                 680                 685
Gly Cys Ala Asp Val Lys Gly Leu Ser Asn His Val His Gln Leu Ile
    690                 695                 700
Ala Asp Ala Val Ser Ser Pro Asn His Gly Asp Ser Pro Asn Leu Leu
705                 710                 715                 720
Ile Ala Asp Asn Pro Gln Leu Ser Ala Leu Leu Ile Gly Lys Ala Asn
                725                 730                 735
Gly Asn Val Gly Thr Gly Thr Cys Asp Lys Val Asn Asn Ile His Pro
            740                 745                 750
Ala Val His Thr Lys Thr Asp His Ser Val Ala Ser Ser Pro Ser Ser
        755                 760                 765
Ala Ile Ser Thr Ala Thr Pro Ser Pro Lys Ser Thr Glu Gln Arg Ser
    770                 775                 780
Ile Asn Ser Val Thr Ser Leu Asn Ser Pro His Ser Gly Leu His Thr
785                 790                 795                 800
Val Asn Gly Glu Gly Leu Gly Lys Ser Gln Ser Ser Thr Lys Val Asp
                805                 810                 815
Leu Pro Leu Ala Ser His Arg Ser Thr Ser Gln Ile Leu Pro Ser Met
            820                 825                 830
Ser Val Ser Ile Cys Pro Ser Ser Thr Glu Val Leu Lys Ala Cys Arg
        835                 840                 845
Asn Pro Gly Lys Asn Gly Leu Ser Asn Ser Cys Ile Leu Leu Asp Lys
    850                 855                 860
Cys Pro Pro Pro Arg Pro Pro Thr Ser Pro Tyr Pro Pro Leu Pro Lys
865                 870                 875                 880
Asp Lys Leu Asn Pro Pro Thr Pro Ser Ile Tyr Leu Glu Asn Lys Arg
                885                 890                 895
Asp Ala Phe Phe Pro Pro Leu His Gln Phe Cys Thr Asn Pro Lys Asn
            900                 905                 910
Pro Val Thr Val Ile Arg Gly Leu Ala Gly Ala Leu Lys Leu Asp Leu
        915                 920                 925
Gly Leu Phe Ser Thr Lys Thr Leu Val Glu Ala Asn Asn Glu His Met
    930                 935                 940
Val Glu Val Arg Thr Gln Leu Leu Gln Pro Ala Asp Glu Asn Trp Asp
945                 950                 955                 960
Pro Thr Gly Thr Lys Lys Ile Trp Arg Cys Glu Ser Asn Arg Ser His
                965                 970                 975
Thr Thr Ile Ala Lys Tyr Ala Gln Tyr Gln Ala Ser Ser Phe Gln Glu
```

```
              980                 985                 990
Ser Leu Arg Ala Gly Met Gln Trp Cys Asp Leu Ser Ser Leu Gln Pro
         995                1000                1005
Pro Pro Pro Gly Phe Lys Arg Phe Ser His Leu Ser Leu Pro Asn Ser
    1010                1015                1020
Trp Asn Tyr Arg His Leu Pro Ser Cys Pro Thr Asn Phe Cys Ile Phe
1025                1030                1035                1040
Val Glu Thr Gly Phe His His Val Gly Gln Ala Cys Leu Glu Leu Leu
                1045                1050                1055
Thr Ser Gly Gly Leu Leu Ala Ser Ala Ser Gln Ser Ala Gly Ile Thr
            1060                1065                1070
Gly Val Ser His His Ala Arg
            1075

<210> SEQ ID NO 23
<211> LENGTH: 1240
<212> TYPE: PRT
<213> ORGANISM: Human

<400> SEQUENCE: 23

Met Lys Ser Cys Ala Val Ser Leu Thr Thr Ala Ala Val Ala Phe Gly
  1               5                  10                  15

Asp Glu Ala Lys Lys Met Ala Glu Gly Lys Ala Ser Arg Glu Ser Glu
             20                  25                  30

Glu Glu Ser Val Ser Leu Thr Val Glu Glu Arg Glu Ala Leu Gly Gly
         35                  40                  45

Met Asp Ser Arg Leu Phe Gly Phe Val Arg Leu His Glu Asp Gly Ala
 50                  55                  60

Arg Thr Lys Thr Leu Leu Gly Lys Ala Val Arg Cys Tyr Glu Ser Leu
 65                  70                  75                  80

Ile Leu Lys Ala Glu Gly Lys Val Glu Ser Asp Phe Phe Cys Gln Leu
                 85                  90                  95

Gly His Phe Asn Leu Leu Leu Glu Asp Tyr Ser Lys Ala Leu Ser Ala
            100                 105                 110

Tyr Gln Arg Tyr Tyr Ser Leu Gln Ala Asp Tyr Trp Lys Asn Ala Ala
            115                 120                 125

Phe Leu Tyr Gly Leu Gly Leu Val Tyr Phe Tyr Asn Ala Phe His
130                 135                 140

Trp Ala Ile Lys Ala Phe Gln Asp Val Leu Tyr Val Asp Pro Ser Phe
145                 150                 155                 160

Cys Arg Ala Lys Glu Ile His Leu Arg Leu Gly Leu Met Phe Lys Val
                165                 170                 175

Asn Thr Asp Tyr Lys Ser Ser Leu Lys His Phe Gln Leu Ala Leu Ile
            180                 185                 190

Asp Cys Asn Pro Cys Thr Leu Ser Asn Ala Glu Ile Gln Phe His Ile
            195                 200                 205

Ala His Leu Tyr Glu Thr Gln Arg Lys Tyr His Ser Ala Lys Glu Ala
        210                 215                 220

Tyr Glu Gln Leu Leu Gln Thr Glu Asn Leu Pro Ala Gln Val Lys Ala
225                 230                 235                 240

Thr Val Leu Gln Gln Leu Gly Trp Met His His Asn Met Asp Leu Val
                245                 250                 255

Gly Asp Lys Ala Thr Lys Glu Ser Tyr Ala Ile Gln Tyr Leu Gln Lys
            260                 265                 270

Ser Leu Glu Ala Asp Pro Asn Ser Gly Gln Ser Trp Tyr Phe Leu Gly
        275                 280                 285

Arg Cys Tyr Ser Ser Ile Gly Lys Val Gln Asp Ala Phe Ile Ser Tyr
        290                 295                 300
```

-continued

```
Arg Gln Ser Ile Asp Lys Ser Glu Ala Ser Ala Asp Thr Trp Cys Ser
305                 310                 315                 320

Ile Gly Val Leu Tyr Gln Gln Asn Gln Pro Met Asp Ala Leu Gln
            325                 330                 335

Ala Tyr Ile Cys Ala Val Gln Leu Asp His Gly His Ala Ala Ala Trp
            340                 345                 350

Met Asp Leu Gly Thr Leu Tyr Glu Ser Cys Asn Gln Pro Gln Asp Ala
            355                 360                 365

Ile Lys Cys Tyr Leu Asn Ala Ala Arg Ser Lys Arg Cys Ser Asn Thr
    370                 375                 380

Ser Thr Leu Ala Ala Arg Ile Lys Phe Leu Gln Asn Gly Ser Asp Asn
385                 390                 395                 400

Trp Asn Gly Gly Gln Ser Leu Ser His His Pro Val Gln Gln Val Tyr
                405                 410                 415

Ser Leu Cys Leu Thr Pro Gln Lys Leu Gln His Leu Glu Gln Leu Arg
            420                 425                 430

Ala Asn Arg Asp Asn Leu Asn Pro Ala Gln Lys His Gln Leu Glu Gln
        435                 440                 445

Leu Glu Ser Gln Phe Val Leu Met Gln Gln Met Arg His Lys Glu Val
    450                 455                 460

Ala Gln Val Arg Thr Thr Gly Ile His Asn Gly Ala Ile Thr Asp Ser
465                 470                 475                 480

Ser Leu Pro Thr Asn Ser Val Ser Asn Arg Gln Pro His Gly Ala Leu
                485                 490                 495

Thr Arg Val Ser Ser Val Ser Gln Pro Gly Val Arg Pro Ala Cys Val
            500                 505                 510

Glu Lys Leu Leu Ser Ser Gly Ala Phe Ser Ala Gly Cys Ile Pro Cys
        515                 520                 525

Gly Thr Ser Lys Ile Leu Gly Ser Thr Asp Thr Ile Leu Leu Gly Ser
        530                 535                 540

Asn Cys Ile Ala Gly Ser Glu Ser Asn Gly Asn Val Pro Tyr Leu Gln
545                 550                 555                 560

Gln Asn Thr His Thr Leu Pro His Asn His Thr Asp Leu Asn Ser Ser
                565                 570                 575

Thr Glu Glu Pro Trp Arg Lys Gln Leu Ser Asn Ser Ala Gln Gly Leu
            580                 585                 590

His Lys Ser Gln Ser Ser Cys Leu Ser Gly Pro Asn Glu Glu Gln Pro
    595                 600                 605

Leu Phe Ser Thr Gly Ser Ala Gln Tyr His Gln Ala Thr Ser Thr Gly
    610                 615                 620

Ile Lys Lys Ala Asn Glu His Leu Thr Leu Pro Ser Asn Ser Val Pro
625                 630                 635                 640

Gln Gly Asp Ala Asp Ser His Leu Ser Cys His Thr Ala Thr Ser Gly
                645                 650                 655

Gly Gln Gln Gly Ile Met Phe Thr Lys Glu Ser Lys Pro Ser Lys Asn
            660                 665                 670

Arg Ser Leu Val Pro Glu Thr Ser Arg His Thr Gly Asp Thr Ser Asn
    675                 680                 685

Gly Cys Ala Asp Val Lys Gly Leu Ser Asn His Val His Gln Leu Ile
    690                 695                 700

Ala Asp Ala Val Ser Ser Pro Asn His Gly Asp Ser Pro Asn Leu Leu
705                 710                 715                 720

Ile Ala Asp Asn Pro Gln Leu Ser Ala Leu Leu Ile Gly Lys Ala Asn
```

-continued

```
                725                 730                 735
Gly Asn Val Gly Thr Gly Thr Cys Asp Lys Val Asn Asn Ile His Pro
                740                 745                 750

Ala Val His Thr Lys Thr Asp His Ser Val Ala Ser Ser Pro Ser Ser
                755                 760                 765

Ala Ile Ser Thr Ala Thr Pro Ser Pro Lys Ser Thr Glu Gln Arg Ser
                770                 775                 780

Ile Asn Ser Val Thr Ser Leu Asn Ser Pro His Ser Gly Leu His Thr
785                 790                 795                 800

Val Asn Gly Glu Gly Leu Gly Lys Ser Gln Ser Ser Thr Lys Val Asp
                805                 810                 815

Leu Pro Leu Ala Ser His Arg Ser Thr Ser Gln Ile Leu Pro Ser Met
                820                 825                 830

Ser Val Ser Ile Cys Pro Ser Ser Thr Glu Val Leu Lys Ala Cys Arg
                835                 840                 845

Asn Pro Gly Lys Asn Gly Leu Ser Asn Ser Cys Ile Leu Leu Asp Lys
                850                 855                 860

Cys Pro Pro Arg Pro Pro Thr Ser Pro Tyr Pro Pro Leu Pro Lys
865                 870                 875                 880

Asp Lys Leu Asn Pro Pro Thr Pro Ser Ile Tyr Leu Glu Asn Lys Arg
                885                 890                 895

Asp Ala Phe Phe Pro Leu His Gln Phe Cys Thr Asn Pro Lys Asn
                900                 905                 910

Pro Val Thr Val Ile Arg Gly Leu Ala Gly Ala Leu Lys Leu Asp Leu
                915                 920                 925

Gly Leu Phe Ser Thr Lys Thr Leu Val Glu Ala Asn Asn Glu His Met
                930                 935                 940

Val Glu Val Arg Thr Gln Leu Leu Gln Pro Ala Asp Glu Asn Trp Asp
945                 950                 955                 960

Pro Thr Gly Thr Lys Lys Ile Trp Arg Cys Glu Ser Asn Arg Ser His
                965                 970                 975

Thr Thr Ile Ala Lys Tyr Ala Gln Tyr Gln Ala Ser Ser Phe Gln Glu
                980                 985                 990

Ser Leu Arg Glu Glu Asn Glu Lys Arg Thr Gln His Lys Asp His Ser
                995                 1000                1005

Asp Asn Glu Ser Thr Ser Ser Glu Asn Ser Gly Arg Arg Arg Lys Gly
                1010                1015                1020

Pro Phe Lys Thr Ile Lys Phe Gly Thr Asn Ile Asp Leu Ser Asp Asn
1025                1030                1035                1040

Lys Lys Trp Lys Leu Gln Leu His Glu Leu Thr Lys Leu Pro Ala Phe
                1045                1050                1055

Ala Arg Val Val Ser Ala Gly Asn Leu Leu Thr His Val Gly His Thr
                1060                1065                1070

Ile Leu Gly Met Asn Thr Val Gln Leu Tyr Met Lys Val Pro Gly Ser
                1075                1080                1085

Arg Thr Pro Gly His Gln Glu Asn Asn Asn Phe Cys Ser Val Asn Ile
                1090                1095                1100

Asn Ile Gly Pro Gly Asp Cys Glu Trp Phe Val Val Pro Glu Asp Tyr
1105                1110                1115                1120

Trp Gly Val Leu Asn Asp Phe Cys Glu Lys Asn Asn Leu Asn Phe Leu
                1125                1130                1135

Met Ser Ser Trp Trp Pro Asn Leu Glu Asp Leu Tyr Glu Ala Asn Val
                1140                1145                1150
```

-continued

```
Pro Val Tyr Arg Phe Ile Gln Arg Pro Gly Asp Leu Val Trp Ile Asn
        1155                1160                1165
Ala Gly Thr Val His Trp Val Gln Thr Val Gly Trp Cys Asn Asn Ile
        1170                1175                1180
Ala Trp Asn Val Gly Pro Leu Thr Ala Cys Gln Tyr Lys Leu Ala Val
1185                1190                1195                1200
Glu Arg Tyr Glu Trp Asn Lys Leu Lys Ser Val Lys Ser Pro Val Pro
                1205                1210                1215
Met Val His Leu Ser Trp Asn Met Ala Arg Asn Ile Lys Val Ser Asp
                1220                1225                1230
Pro Lys Leu Phe Glu Met Ile Lys
        1235                1240

<210> SEQ ID NO 24
<211> LENGTH: 1347
<212> TYPE: PRT
<213> ORGANISM: Human

<400> SEQUENCE: 24

Met Lys Ser Cys Ala Val Ser Leu Thr Thr Ala Ala Val Ala Phe Gly
1               5                   10                  15
Asp Glu Ala Lys Lys Met Ala Glu Gly Lys Ala Ser Arg Glu Ser Glu
            20                  25                  30
Glu Glu Ser Val Ser Leu Thr Val Glu Glu Arg Glu Ala Leu Gly Gly
        35                  40                  45
Met Asp Ser Arg Leu Phe Gly Phe Val Arg Leu His Glu Asp Gly Ala
    50                  55                  60
Arg Thr Lys Thr Leu Leu Gly Lys Ala Val Arg Cys Tyr Glu Ser Leu
65                  70                  75                  80
Ile Leu Lys Ala Glu Gly Lys Val Glu Ser Asp Phe Phe Cys Gln Leu
                85                  90                  95
Gly His Phe Asn Leu Leu Leu Glu Asp Tyr Ser Lys Ala Leu Ser Ala
            100                 105                 110
Tyr Gln Arg Tyr Tyr Ser Leu Gln Ala Asp Tyr Trp Lys Asn Ala Ala
        115                 120                 125
Phe Leu Tyr Gly Leu Gly Leu Val Tyr Phe Tyr Tyr Asn Ala Phe His
    130                 135                 140
Trp Ala Ile Lys Ala Phe Gln Asp Val Leu Tyr Val Asp Pro Ser Phe
145                 150                 155                 160
Cys Arg Ala Lys Glu Ile His Leu Arg Leu Gly Leu Met Phe Lys Val
                165                 170                 175
Asn Thr Asp Tyr Lys Ser Ser Leu Lys His Phe Gln Leu Ala Leu Ile
            180                 185                 190
Asp Cys Asn Pro Cys Thr Leu Ser Asn Ala Glu Ile Gln Phe His Ile
        195                 200                 205
Ala His Leu Tyr Glu Thr Gln Arg Lys Tyr His Ser Ala Lys Glu Ala
    210                 215                 220
Tyr Glu Gln Leu Leu Gln Thr Glu Asn Leu Pro Ala Gln Val Lys Ala
225                 230                 235                 240
Thr Val Leu Gln Gln Leu Gly Trp Met His His Asn Met Asp Leu Val
                245                 250                 255
Gly Asp Lys Ala Thr Lys Glu Ser Tyr Ala Ile Gln Tyr Leu Gln Lys
            260                 265                 270
Ser Leu Glu Ala Asp Pro Asn Ser Gly Gln Ser Trp Tyr Phe Leu Gly
```

-continued

```
            275                 280                 285
Arg Cys Tyr Ser Ser Ile Gly Lys Val Gln Asp Ala Phe Ile Ser Tyr
290                 295                 300

Arg Gln Ser Ile Asp Lys Ser Glu Ala Ser Ala Asp Thr Trp Cys Ser
305                 310                 315                 320

Ile Gly Val Leu Tyr Gln Gln Gln Asn Gln Pro Met Asp Ala Leu Gln
                    325                 330                 335

Ala Tyr Ile Cys Ala Val Gln Leu Asp His Gly His Ala Ala Ala Trp
                340                 345                 350

Met Asp Leu Gly Thr Leu Tyr Glu Ser Cys Asn Gln Pro Gln Asp Ala
            355                 360                 365

Ile Lys Cys Tyr Leu Asn Ala Ala Arg Ser Lys Arg Cys Ser Asn Thr
        370                 375                 380

Ser Thr Leu Ala Ala Arg Ile Lys Phe Leu Gln Asn Gly Ser Asp Asn
385                 390                 395                 400

Trp Asn Gly Gly Gln Ser Leu Ser His His Pro Val Gln Gln Val Tyr
                    405                 410                 415

Ser Leu Cys Leu Thr Pro Gln Lys Leu Gln His Leu Glu Gln Leu Arg
                420                 425                 430

Ala Asn Arg Asp Asn Leu Asn Pro Ala Gln Lys His Gln Leu Glu Gln
            435                 440                 445

Leu Glu Ser Gln Phe Val Leu Met Gln Gln Met Arg His Lys Glu Val
        450                 455                 460

Ala Gln Val Arg Thr Thr Gly Ile His Asn Gly Ala Ile Thr Asp Ser
465                 470                 475                 480

Ser Leu Pro Thr Asn Ser Val Ser Asn Arg Gln Pro His Gly Ala Leu
                    485                 490                 495

Thr Arg Val Ser Ser Val Ser Gln Pro Gly Val Arg Pro Ala Cys Val
                500                 505                 510

Glu Lys Leu Leu Ser Ser Gly Ala Phe Ser Ala Gly Cys Ile Pro Cys
            515                 520                 525

Gly Thr Ser Lys Ile Leu Gly Ser Thr Asp Thr Ile Leu Leu Gly Ser
        530                 535                 540

Asn Cys Ile Ala Gly Ser Glu Ser Asn Gly Asn Val Pro Tyr Leu Gln
545                 550                 555                 560

Gln Asn Thr His Thr Leu Pro His Asn His Thr Asp Leu Asn Ser Ser
                    565                 570                 575

Thr Glu Glu Pro Trp Arg Lys Gln Leu Ser Asn Ser Ala Gln Gly Leu
                580                 585                 590

His Lys Ser Gln Ser Ser Cys Leu Ser Gly Pro Asn Glu Glu Gln Pro
            595                 600                 605

Leu Phe Ser Thr Gly Ser Ala Gln Tyr His Gln Ala Thr Ser Thr Gly
        610                 615                 620

Ile Lys Lys Ala Asn Glu His Leu Thr Leu Pro Ser Asn Ser Val Pro
625                 630                 635                 640

Gln Gly Asp Ala Asp Ser His Leu Ser Cys His Thr Ala Thr Ser Gly
                    645                 650                 655

Gly Gln Gln Gly Ile Met Phe Thr Lys Glu Ser Lys Pro Ser Lys Asn
                660                 665                 670

Arg Ser Leu Val Pro Glu Thr Ser Arg His Thr Gly Asp Thr Ser Asn
            675                 680                 685

Gly Cys Ala Asp Val Lys Gly Leu Ser Asn His Val His Gln Leu Ile
        690                 695                 700
```

-continued

```
Ala Asp Ala Val Ser Ser Pro Asn His Gly Asp Ser Pro Asn Leu Leu
705                 710                 715                 720

Ile Ala Asp Asn Pro Gln Leu Ser Ala Leu Leu Ile Gly Lys Ala Asn
                725                 730                 735

Gly Asn Val Gly Thr Gly Thr Cys Asp Lys Val Asn Asn Ile His Pro
            740                 745                 750

Ala Val His Thr Lys Thr Asp His Ser Val Ala Ser Ser Pro Ser Ser
        755                 760                 765

Ala Ile Ser Thr Ala Thr Pro Ser Pro Lys Ser Thr Glu Gln Arg Ser
    770                 775                 780

Ile Asn Ser Val Thr Ser Leu Asn Ser Pro His Ser Gly Leu His Thr
785                 790                 795                 800

Val Asn Gly Glu Gly Leu Gly Lys Ser Gln Ser Ser Thr Lys Val Asp
                805                 810                 815

Leu Pro Leu Ala Ser His Arg Ser Thr Ser Gln Ile Leu Pro Ser Met
                820                 825                 830

Ser Val Ser Ile Cys Pro Ser Ser Thr Glu Val Leu Lys Ala Cys Arg
            835                 840                 845

Asn Pro Gly Lys Asn Gly Leu Ser Asn Ser Cys Ile Leu Leu Asp Lys
        850                 855                 860

Cys Pro Pro Arg Pro Pro Thr Ser Pro Tyr Pro Pro Leu Pro Lys
865                 870                 875                 880

Asp Lys Leu Asn Pro Pro Thr Pro Ser Ile Tyr Leu Glu Asn Lys Arg
                885                 890                 895

Asp Ala Phe Phe Pro Pro Leu His Gln Phe Cys Thr Asn Pro Lys Asn
            900                 905                 910

Pro Val Thr Val Ile Arg Gly Leu Ala Gly Ala Leu Lys Leu Asp Leu
        915                 920                 925

Gly Leu Phe Ser Thr Lys Thr Leu Val Glu Ala Asn Asn Glu His Met
    930                 935                 940

Val Glu Val Arg Thr Gln Leu Leu Gln Pro Ala Asp Glu Asn Trp Asp
945                 950                 955                 960

Pro Thr Gly Thr Lys Lys Ile Trp Arg Cys Glu Ser Asn Arg Ser His
                965                 970                 975

Thr Thr Ile Ala Lys Tyr Ala Gln Tyr Gln Ala Ser Ser Phe Gln Glu
            980                 985                 990

Ser Leu Arg Glu Glu Asn Glu Lys Arg Thr Gln His Lys Asp His Ser
        995                 1000                1005

Asp Asn Glu Ser Thr Ser Ser Glu Asn Ser Gly Arg Arg Arg Lys Gly
    1010                1015                1020

Pro Phe Lys Thr Ile Lys Phe Gly Thr Asn Ile Asp Leu Ser Asp Asn
1025                1030                1035                1040

Lys Lys Trp Lys Leu Gln Leu His Glu Leu Thr Lys Leu Pro Ala Phe
                1045                1050                1055

Ala Arg Val Val Ser Ala Gly Asn Leu Leu Thr His Val Gly His Thr
            1060                1065                1070

Ile Leu Gly Met Asn Thr Val Gln Leu Tyr Met Lys Val Pro Gly Ser
        1075                1080                1085

Arg Thr Pro Gly His Gln Glu Asn Asn Asn Phe Cys Ser Val Asn Ile
    1090                1095                1100

Asn Ile Gly Pro Gly Asp Cys Glu Trp Phe Val Val Pro Glu Asp Tyr
1105                1110                1115                1120
```

```
Trp Gly Val Leu Asn Asp Phe Cys Glu Lys Asn Asn Leu Asn Phe Leu
            1125                1130                1135

Met Ser Ser Trp Trp Pro Asn Leu Glu Asp Leu Tyr Glu Ala Asn Val
        1140                1145                1150

Pro Val Tyr Arg Phe Ile Gln Arg Pro Gly Asp Leu Val Trp Ile Asn
            1155                1160                1165

Ala Gly Thr Val His Trp Val Gln Thr Val Gly Trp Cys Asn Asn Ile
        1170                1175                1180

Ala Trp Asn Val Gly Pro Leu Thr Ala Cys Gln Tyr Lys Leu Ala Val
1185                1190                1195                1200

Glu Arg Tyr Glu Trp Asn Lys Leu Lys Ser Val Lys Ser Pro Val Pro
            1205                1210                1215

Met Val His Leu Ser Trp Asn Met Ala Arg Asn Ile Lys Val Ser Asp
        1220                1225                1230

Pro Lys Leu Phe Glu Met Ile Lys Tyr Cys Leu Leu Lys Ile Leu Lys
            1235                1240                1245

Gln Tyr Gln Thr Leu Arg Glu Ala Leu Val Ala Ala Gly Lys Glu Val
    1250                1255                1260

Ile Trp His Gly Arg Thr Asn Asp Glu Pro Ala His Tyr Cys Ser Ile
1265                1270                1275                1280

Cys Glu Val Glu Val Phe Asn Leu Leu Phe Val Thr Asn Glu Ser Asn
            1285                1290                1295

Thr Gln Lys Thr Tyr Ile Val Cys His Asp Cys Ala Arg Lys Thr
        1300                1305                1310

Ser Lys Ser Leu Glu Asn Phe Val Val Leu Glu Gln Tyr Lys Met Glu
            1315                1320                1325

Asp Leu Ile Gln Val Tyr Asp Gln Phe Thr Leu Ala Leu Ser Leu Ser
        1330                1335                1340

Ser Ser Ser
1345

<210> SEQ ID NO 25
<211> LENGTH: 556
<212> TYPE: DNA
<213> ORGANISM: Human

<400> SEQUENCE: 25
acaactcggt ggtggccact gcgcagacca gacttcgctc gtactcgtgc gcctcgcttc      60
gcttttcctc cgcaaccatg tctgacaaac ccgatatggc tgagatcgag aaattcgata     120
agtcgaaact gaagaagaca gagacgcaag agaaaaatcc actgccttcc aaagaaacga     180
ttgaacagga gaagcaagca ggcgaatcgt aatgaggcgt cgccgccaa tatgcactgt      240 acattccaca agcattgcct tcttatttta cttcttttag ctgtttaact ttgtaagatg     300
caaagaggtt ggatcaagtt taaatgactg tgctgcccct ttcacatcaa agaactactg     360
acaacgaagg ccgcgctgcc tttcccatct gtctatctat ctggctggca gggaaggaaa     420
gaacttgcat gttggtgaag gaagaagtgg ggtggaagaa gtggggtggg acgacagtga     480
aatctagagt aaaaccaagc tggcccaagt gtcctgcagg ctgtaatgca gtttaatcag     540
agtgccattt tttttt                                                    556

<210> SEQ ID NO 26
<211> LENGTH: 1161
<212> TYPE: DNA
<213> ORGANISM: Human
```

```
<400> SEQUENCE: 26
tgggaacaga cagatccttt gttctgaggc tcactcatct cccgagcccc gagccgtctc      60
ccagcctcag acggctctgc gggctgcatc tgtgcagcct ggcagcggcg gcgctgcgct     120
gtgacatttt cacagcccct cttgcagagg catgtgtgct agggatgccg aaatgccgag     180
agcgccggca ggactagctt ccgggccgcg ctttgtgtgc tgggctgcag tgtggcgcgg     240
gcgaagaact ggtagggcgg ttgtcgcaag ctccagctgc agcctccgcc tacgtgagaa     300
gactagaaag cgggcgcagg acaggcctgc gttgtttgca gaaaagccgt ggctacaaaa     360
tggaagtgct tttgcgacct gggctccatt ttaggaattc ttgcccgatt taaccactt      420 gaacgcggaa gtggctttcc tattctcttc caagccagcc tttaatttta aacgctgtaa     480
ttaacagttc acagggtca aattcctttta ttccggaaca ttccactttg agagggatct     540
gtcctctttg gtccctgcg ttttcaaata tttgaggaaa ggtgtcgcct cttttctgt      600 ggaaagagga agctcatgag cgcgaaacag caggggacgg agggcgagaa gggctttctc     660
aggttgcggg tcggagggca gaagcacagt tcccagtaca gagacccgga caggtggctg     720
tttctcacgc tcactttgga ttgctcccta cggcttcctc cgcagccatg tctgacaaac     780
ctggtatggc tgagatcgag aaattcgata agtcgaaact gaagaagaca gaaacgcaag     840
agaagaatcc attgtcttcc aaagaaacta tcgaacagga gaggcaagca ggcgaatctt     900
aaacaggcat gtgccaccaa tatctactgt acattctaca agcattgctt cttattttta    960 cttctttttac ttgtttaact tggttagatg caaaacacgtt ggatgagttt gaaaggacta   1020 tgctgcccttt ttgacatcaa agacctgctg acaatggagg ccacgcctgc ttctcccatc    1080
gcctgtctgg ctggcaggga aggaaaatag cttgaatgtt ggtgaaagac ttagcggagt    1140
gggagggcag tgaaatctag a                                             1161

<210> SEQ ID NO 27
<211> LENGTH: 44
<212> TYPE: PRT
<213> ORGANISM: Human

<400> SEQUENCE: 27

Met Ser Asp Lys Pro Asp Met Ala Glu Ile Glu Lys Phe Asp Lys Ser
 1               5                  10                  15

Lys Leu Lys Lys Thr Glu Thr Gln Glu Lys Asn Pro Leu Pro Ser Lys
            20                  25                  30

Glu Thr Ile Glu Gln Glu Lys Gln Ala Gly Glu Ser
        35                  40

<210> SEQ ID NO 28
<211> LENGTH: 44
<212> TYPE: PRT
<213> ORGANISM: Human

<400> SEQUENCE: 28

Met Ser Asp Lys Pro Gly Met Ala Glu Ile Glu Lys Phe Asp Lys Ser
 1               5                  10                  15

Lys Leu Lys Lys Thr Glu Thr Gln Glu Lys Asn Pro Leu Ser Ser Lys
            20                  25                  30

Glu Thr Ile Glu Gln Glu Arg Gln Ala Gly Glu Ser
        35                  40

<210> SEQ ID NO 29
<211> LENGTH: 1202
```

```
<212> TYPE: DNA
<213> ORGANISM: Human

<400> SEQUENCE: 29
ggcacgaggc gccatttgct gccgccgagc gtggacgcag gcggatctct gaagagctgg      60
gtcgccagcc tctcccgcgc acgttgcctg gcctccagca cctacttggt cccgcgcgct     120
ccctcgtgtc gcccctcgga gcagcagccg ccgcggtcgc cgctacccgg aaagaagtca     180
gagacgccgc gagtcgccgc caccgccatg cccaagaata aggtaaagg aggtaaaaac      240 agacgcaggg gtaagaatga gaatgaatct gaaaaaagag aactggtatt caaagaggat     300
gggcaggagt atgctcaggt aatcaaaatg ttgggaaatg gacggctaga agcaatgtgt     360
ttcgatggtg taaagaggtt atgtcacatc agaggaaaat tgagaaaaaa ggtttggata     420
aatacctcgg acattatttt ggttggtctc cgagactacc aggataacaa agctgatgta     480
attttaaaat acaatgcaga cgaagctaga agtctgaagg catacggcga gcttccagag     540
catgctaaaa tcaatgaaac tgatacattt ggtcctggag atgatgatga aattcagttt     600
gatgacattg gagatgatga tgaagatatt gatgacatct aaattgaact caacatttta     660
cattccatct tttctgaaga ttgtcctaca atttggattt tgatcatgac aaagaagatt     720
aaaatttcat tagcatgaat gcaatttgtt aaagcagact gatttgtttc taagatattt     780
ttggtttttt taaaactgat aataatgctg aattatctta agtgagatgt taagcccact     840
ttgttctttt aatgtaatgg agcttatggg tagaagacca tgtctactaa ttacaaaaaa     900
aaaaaaaaac catgattgct gcttttccta ccacttccag taagaaaatg ggtgtttttga    960 agaaatcatt tgccttgtct cacggaatct gattaagccc tggcctcttg atgtatagag    1020
tcatggatat tccagttacc tagatattcc cttgagattt tgatacaatt tgagggaggc    1080
agaagtctgc agttgaagaa aaaaaataag tctgtttgtc atatttaagt agcctgtgcg    1140 tattttata ctgattttga tatcatgttc ttttcatagt cgtattttgc caccgtaaac     1200
at                                                                   1202

<210> SEQ ID NO 30
<211> LENGTH: 1384
<212> TYPE: DNA
<213> ORGANISM: Human

<400> SEQUENCE: 30
gcagtttatg agagagctct gtagccagcc tcttctgcgc acccacctgc tgcatcttag      60
ttcagtcggc tcttagagta gtaaccgcca gaaaggagtc ggaagaggtc tcacgaggct     120
gtcatcaccg ccatgcccaa gaataaaggt aaaggaggta aaaacaggcg cagggtaaa     180 aatgagaatg aatctgaaaa agagagttg gtgtttaaag aggatggaca agagtatgct     240
caggtaatca aaatgttggg aaatggacga ttggaagcat tgtgttttga tggtgtaaag     300
aggttatgcc atatcagagg gaaattgaga aaaaggttt ggataaatac atcagacatt     360
atattggttg gtctacggga ctatcaggat aacaaagctg atgtaatttt aaagtacaat     420
gcagatgaag ctagaagcct gaaggcatat ggcgggcttc cagaacatgc taaaatcaat     480
gaaacagaca catttggtcc tggagatgat gatgaaatcc agtttgacga tattggagat     540
gatgatgaag acattgatga tatctaaatt gaaccaagtg ttttacatg acaagttctc     600 tgaggatggt tctacagttg ggattttggc catcatcaac caagaagaga aattcattta     660
gtgtgtagtt tctgaaagca aactgattta ttttcattgt tttaaagtat ttatttcttt    720
```

-continued

```
aaaagctgag gacattgaat taccttaatt taaatgttaa tactttattg ttttgatgta        780
atggaactta aggataaaag accataatat ttgctgttaa aataaataaa cgagtgcctt        840
tcctactgtg ataacgtcaa gtaattggat attttgaata catttctgcc tgataatcat        900
gctgagttct aataagccct acttccacct aatctgttta cagtcttttg gtatgtttca        960
gttacttaga tggtctcata aggtttctga tacaatttga agacagaaat ctgcatttag       1020
aatcagaaaa catggacata tttttcatat ttatctagtc atatgtaatt ttatgctaac       1080
attgatagtt tataaatcct tttcatcctt tgtgcctcgg ttattaagga aaaaaaatg        1140 tccaacatac agttttaaa gtgtggcagt tttgagtagt aacttagaat gtataagatt        1200
aagagttaaa gaaaccgaac aataagtggc aaccaattat cttaacattg gaaatactgg       1260
ggtgccattt tgttttcaaa agttattcat tgtaatccac tgttttggct ttcatgaaca       1320
agtaaattac agtgtataaa tgaaaagcaa tttcataata aattctataa actgaaaaaa       1380
aaaa                                                                    1384
```

<210> SEQ ID NO 31
<211> LENGTH: 144
<212> TYPE: PRT
<213> ORGANISM: Human

<400> SEQUENCE: 31

```
Met Pro Lys Asn Lys Gly Lys Gly Gly Lys Asn Arg Arg Arg Gly Lys
 1               5                  10                  15

Asn Glu Asn Glu Ser Glu Lys Arg Glu Leu Val Phe Lys Glu Asp Gly
            20                  25                  30

Gln Glu Tyr Ala Gln Val Ile Lys Met Leu Gly Asn Gly Arg Leu Glu
        35                  40                  45

Ala Met Cys Phe Asp Gly Val Lys Arg Leu Cys His Ile Arg Gly Lys
    50                  55                  60

Leu Arg Lys Lys Val Trp Ile Asn Thr Ser Asp Ile Ile Leu Val Gly
65                  70                  75                  80

Leu Arg Asp Tyr Gln Asp Asn Lys Ala Asp Val Ile Leu Lys Tyr Asn
                85                  90                  95

Ala Asp Glu Ala Arg Ser Leu Lys Ala Tyr Gly Glu Leu Pro Glu His
            100                 105                 110

Ala Lys Ile Asn Glu Thr Asp Thr Phe Gly Pro Gly Asp Asp Asp Glu
        115                 120                 125

Ile Gln Phe Asp Asp Ile Gly Asp Asp Asp Glu Asp Ile Asp Asp Ile
    130                 135                 140
```

<210> SEQ ID NO 32
<211> LENGTH: 144
<212> TYPE: PRT
<213> ORGANISM: Human

<400> SEQUENCE: 32

```
Met Pro Lys Asn Lys Gly Lys Gly Gly Lys Asn Arg Arg Arg Gly Lys
 1               5                  10                  15

Asn Glu Asn Glu Ser Glu Lys Arg Glu Leu Val Phe Lys Glu Asp Gly
            20                  25                  30

Gln Glu Tyr Ala Gln Val Ile Lys Met Leu Gly Asn Gly Arg Leu Glu
        35                  40                  45

Ala Leu Cys Phe Asp Gly Val Lys Arg Leu Cys His Ile Arg Gly Lys
    50                  55                  60
```

```
Leu Arg Lys Lys Val Trp Ile Asn Thr Ser Asp Ile Ile Leu Val Gly
 65                  70                  75                  80

Leu Arg Asp Tyr Gln Asp Asn Lys Ala Asp Val Ile Leu Lys Tyr Asn
                 85                  90                  95

Ala Asp Glu Ala Arg Ser Leu Lys Ala Tyr Gly Gly Leu Pro Glu His
            100                 105                 110

Ala Lys Ile Asn Glu Thr Asp Thr Phe Gly Pro Gly Asp Asp Asp Glu
            115                 120                 125

Ile Gln Phe Asp Asp Ile Gly Asp Asp Asp Glu Asp Ile Asp Asp Ile
130                 135                 140

<210> SEQ ID NO 33
<211> LENGTH: 8096
<212> TYPE: DNA
<213> ORGANISM: Human

<400> SEQUENCE: 33
```

| | | | | |
|---|---|---|---|---|
| cttttctcaa gacaactaca taagcagaca aaattgcaaa gatctgccct gtgtcgagta | 60 |
| tgacagccac gactcgtggc tctccggtcg gagggaatga caaccagggc caggctcctg | 120 |
| atggacagtc tctgccccc ctccaacaga atcagacttc atcgcctgat tcttccaatg | 180 |
| aaaattcccc ggcaactccc ccagatgagc aaggtcaagg tgatgcccca ccacagcttg | 240 |
| aagatgagga acctgcattt ccacatactg acttggccaa gttggatgac atgatcaaca | 300 |
| ggcctcgatg ggtggttcca gttttgccga aggggaatt agaagtgctt ttagaagctg | 360 |
| ctattgatct tagtaaaaag ggccttgatg ttaaaagtga agcatgtcag cgattttcc | 420 |
| gtgatgggct aacaatatca ttcactaaaa ttcttacaga tgaagcagtg agtggctgga | 480 |
| agtttgaaat tcataggtgt ctggtggagc tatgtgtggc caagttgtcc caagactggt | 540 |
| ttccactttt agaacttctt gccatggcct taaatcctca ttgcaaattc catatctaca | 600 |
| atggtacacg tccatgtgaa tcagtttcct caagtgttca gttgcctgaa gatgaactct | 660 |
| ttgctcgttc tccagatcct cgatcaccaa agggttggct agtggatctt ctcaacaaat | 720 |
| ttggcacttt aaatgggttc cagattttgc atgatcgttt tattaatgga tcagcattaa | 780 |
| acgttcaaat aattgcagcc cttattaaac catttgggca atgctatgag tttctcactc | 840 |
| ttcatacagt gaaaaagtac tttcttccaa taatagaaat ggttccacag ttttagaaa | 900 |
| acttaactga tgaagaactg aaaaaagaag caaagaatga agccaaaaat gatgctcttt | 960 |
| caatgattat taaatctttg aagaatttag cttcaagggt tccaggacaa gaagaaactg | 1020 |
| ttaaaaactt agaatatttt aggttaaaaa tgatacttag attattgcaa atttcttctt | 1080 |
| tcaatggaaa gatgaatgca ctgaatgaag ttaataaggt gatatctagt gtatcatact | 1140 |
| atactcatcg acatggtaat cctgaggagg aagagtggct cacagctgaa cgaatggcag | 1200 |
| aatggataca gcagaacaat atcttatcca tagtgttgcg agatagtctt catcagccac | 1260 |
| agtatgtaga aagttagag aagattcttc gttttgtcat caaagaaaaa gctctgacct | 1320 |
| tacaggatct tgataatatc tgggcagcac aggcagggaa acatgaagcc attgtgaaga | 1380 |
| atgtacatga tctcctggca aaattggcat gggatttttc tcctgaacaa cttgatcatc | 1440 |
| cttttgattg ttttaaggcc agtcggacaa atgcgagtaa aaagcaacgt gaaaagctac | 1500 |
| ttgagctgat acgtcgtctt gcagaagatg ataaagatgg tgtgatggca cacagagtgt | 1560 |
| tgaaccttct gtggaatctg gctcacagtg atgatgtgcc tgtagatatc atggacctgg | 1620 |
| ctctcagtgc ccacataaaa atactagatt acagttgctc ccaggaccgt gatacacaaa | 1680 |

-continued

```
agatccaatg gatagatcgc tttatagaag aacttcgcac aaatgacaaa tgggttattc     1740
ccgcactgaa acaaattaga gaaatttgta gtttgtttgg tgaagcgcct caaaatttga     1800
gtcaaactca gcgaagtccc catgtgtttt atcgccatga cttaatcaat caacttcaac     1860
acaatcatgc cctagttact ttggtagcag aaaaccttgt aacttacatg gaaagcatga     1920
gactatatgc tagagaccat gaagattatg acccacaaac tgtgaggctg ggaagtagat     1980
atagtcatgt tcaagaagtt caagaacggc ttaacttcct tagattttta ttgaaggatg     2040
gtcagctgtg gctatgtgct cctcaggcaa acaaatatg gaaatgctta gctgagaatg      2100
cagtttacct ttgtgatcgt gaagcctgtt ttaagtggta ttccaagttg atggggatg      2160 aaccagactt agatcctgat attaataagg acttctttga agtaatgtg cttcagcttg      2220 atccttctct gttaactgaa aatggaatga agtgttttga gcgattcttc aaagctgtga     2280
attgtcgaga aggaaaacta gtagcaaaaa ggagagccta tatgatggat gacttggagt     2340
taataggatt agattacctt tggagggtcg tgattcagag taatgatgat attgccagca     2400
gagctataga tctcctcaaa gagatataca cgaaccttgg tccaagacta caagtcaatc     2460
aggtggtgat ccatgaagac ttcattcagt cttgttttga tcgtctgaag gcttcctatg     2520
acacattgtg tgttttggat ggtgacaaag acagtgttaa ttgtgcaaga caggaagctg     2580
ttcgaatggt tcgagtatta actgttttaa gggaatatat aaatgaatgt gacagtgatt     2640
atcatgagga aagaacaatt ctccctatgt cgagagcatt ccgcggtaaa cacctctctt     2700
ttgtagttcg atttccaaac cagggcagac aggttgatga cttggaggta tggtctcata     2760
caaatgatac aattggttca gtacgacgat gtattctcaa tcgtattaaa gccaacgtag     2820
cccatacaaa aattgagctc tttgtgggcg gtgagctgat agatcctgca gatgatagaa     2880
agttgattgg acaattaaac ttaaaagata aatcgcttat tacagccaaa cttacacaga     2940
taagttccaa tatgccttca agccctgata gctcttctga ttcctccact ggatctcctg     3000
gaaaccatgg taatcattac agtgatggtc ccaatccaga agtggaaagc tgtttgcctg     3060
gagtgataat gtcactgcat cccagataca tctcttttct ttggcaagtt gcagacttag     3120
gtagcagcct aaatatgcca ccccttagag atggagcaag agtacttatg aaacttatgc     3180
cgccagatag cacaacgata gaaaaattaa gagctatttg tttagaccat gccaaacttg     3240
gagaaagcag ccttagtcca tctcttgact cacttttctt tggtccttca gcctcacaag     3300
tgctatatct aacagaggta gtctatgcct tgttaatgcc tgctggtgca cctctggctg     3360
atgattcctc tgattttcag tttcacttct tgaaaagtgg tggcctaccc cttgtactga     3420
gtatgctaac cagaaataac ttcctaccga atgcagatat ggaaactcga aggggtgcct     3480
acctcaatgc tcttaaaata gccaagcttt tgctaactgc cattggctat ggtcatgttc     3540
gagctgtggc agaagcttgt cagccaggtg tagaaggtgt gaatcccatg acacagatca     3600
accaagttac ccatgatcaa gcagtggtgc tacaaagtgc ccttcagagc attcctaatc     3660
catcatccga gtgcatgctt agaaatgtgt cagttcgtct tgctcagcag atatctgatg     3720
aggcttcaag atatatgcct gatatttgtg taattagagc tatacaaaaa attatctggg     3780
catcaggatg tgggtcgtta cagctagtat ttagcccaaa tgaagaaatc actaaaattt     3840
atgagaagac caatgcaggc aatgagccag acttggaaga cgaacaggtt tgctgtgaag     3900
cattggaagt gatgacctta tgttttgcct tgattccaac agcccttagat gctcttagta     3960 aagaaaaggc ttggcagaca ttcatcattg acttactatt gcactgtcac agcaaaactg     4020
ttcgtcaggt ggcacaggag cagttctttt taatgtgcac cagatgttgc atgggacacc     4080
```

```
ggcctctact tttcttcatt actctactct ttactgtttt ggggagcaca gcaagagaga   4140
gagctaaaca ctcaggcgac tactttactc ttttaagaca ccttcttaat tacgcttaca   4200
atagtaatat taatgtaccc aatgctgaag ttcttttcaa taatgaaatt gattggctta   4260
aaagaattag ggatgatgtt aaagaacag gagaaacggg tattgaagag acgatcttag    4320
agggccacct tggagtgaca aaggagttac tggccttca aacttctgag aaaaaatttc    4380
atattggttg tgaaaaagga ggtgctaatc tcattaaaga attaattgat gatttcatat   4440
ttcctgcatc caatgtttac ctacagtata tgagaaatgg agagcttcca gctgaacagg   4500
ctattccggt ctgtggttca ccacctacaa ttaatgctgg ttttgaatta cttgtagcat   4560
tagctgttgg ctgtgtgagg aatctcaaac aaatagtaga ttctttgact gaatgtatt    4620 acattggcac agcaataact acttgtgaag cacttactga gtgggaatat ctgccacctg   4680
ttggaccccg cccacccaaa ggattcgtgg ggctgaaaaa tgccggtgct acttgttaca   4740
tgaattctgt gattcagcaa ctctacatga ttccttccat taggaacggt attcttgcca   4800
ttgaaggcac aggtagtgat gtagatgatg atatgtctgg ggatgagaag caggacaatg   4860
agagcaatgt tgatcccagg gatgatgtat ttggatatcc tcaacaattt gaagataaac   4920
cagcattaag taaaactgaa gatagaaaag agtacaacat tggtgtccta agacaccttc   4980
aggtcatctt tggtcattta gctgcttctc gactgcaata ctatgtgccc agaggatttt   5040
ggaaacagtt caggctttgg ggtgagcctg ttaatctgcg tgaacaacac gatgctttag   5100 aatttttaa ttcattggtg gatagtttag atgaagcttt aaaagcttta ggacatccag    5160
ctatgctaag taaagtctta ggaggttcct tgctgatca gaagatctgc caaggctgcc    5220
cacataggta cgaatgtgaa gaatctttta cgaccctaaa cgtagacatt agaaatcacc   5280
aaaatcttct tgattctttg gaacagtatg tcaaaggaga tttactagaa ggtgcaaatg   5340
catatcattg tgaaaaatgc aataaaaagg ttgataccgt aaagcgcttg ctgattaaaa   5400
aattacctcc tgttcttgct atacaactaa agcgatttga ctatgactgg gaaagagaat   5460
gtgcaatcaa gttcaatgat tattttgaat ttcctcgaga gctggacatg gaaccttaca   5520
cagttgcagg tgtcgcaaag ctggaagggg ataatgtaaa cccagagagt cagttgatac   5580
aacagagtga gcagtctgaa agtgagacag caggaagcac aaaatacaga cttgtgggtg   5640
tgctcgtaca cagtggtcaa gcgagtgggg ggcattatta ttcttacatc atccaaagga   5700
atggtggaga tggtgagaga aatcgctggt ataaatttga tgatggtgat gtaacagaat   5760
gtaaaatgga tgatgacgaa gaaatgaaaa accagtgttt tggtggagag tacatgggag   5820
aagtgtttga tcacatgatg aagcgtatgt catacaggcg ccagaaaagg tggtggaatg   5880
cttatatacc tttttatgaa cgaatggaca caatagacca agatgatgag ttgataagat   5940
atatatcaga gcttgctatc accaccagac ctcatcagat tattatgcca tcagccattg   6000
agagaagtgt acggaaacag aacgtacaat tcatgcataa ccgaatgcag tacagtatgg   6060
agtattttca gttatgaaa aaactgctta catgtaatgg cgtttactta aaccctcctc    6120
ccgggcaaga tcacctgttg cctgaagcag aagaaatcac tatgatcagt attcaacttg   6180
ctgctaggtt cctctttact acaggatttc acacaaagaa agtagtccgt ggctctgcca   6240
gtgattggta tgatgcattg tgtattctcc ttcgtcacag caagaatgta cgttttggt    6300 ttgctcataa cgtccttttt aatgtttcaa atcgcttctc cgaataccnt ctggagtgcc   6360
ctagtgcaga agtgagggt gcgtttgcaa aacttatagt ctttattgca cattttttcct   6420
```

-continued

```
tgcaagatgg gccatgtcct tcaccttttg cctctcctgg accttctagt caggcttatg        6480
acaacttaag cttgagtgat cacttactaa gagcagtact aaatctcttg agaagggaag        6540
tttcagagca tgggcgtcat ttacagcagt atttcaacct gtttgtaatg tatgccaatt        6600
taggtgtggc agagaagaca cagcttctga aattgagtgt acctgctact tttatgcttg        6660
tgtctttaga tgaaggtcca ggtcctccaa tcaaatacca gtatgctgaa ttaggcaaat        6720
tatactcagt agtgtcacag ctgatccgct gttgcaatgt ctcttcaaga atgcagtctt        6780
caatcaatgg taatcctcct cttcccaatc cttttggtga tcctaattta tcacaaccta        6840
taatgccaat tcagcagaat gtggcagaca ttttatttgt gagaacaagt tatgtgaaga        6900
aaatcattga agactgcagt aattcagagg aaaccgtcaa attgcttcgt ttttgctgct        6960
gggagaatcc tcagttctca tctactgtcc tcagtgaact tctctggcag gttgcatatt        7020
cctatcccta tgaactgcgg ccctatttgg atctgctttt gcaaatctta ctgattgagg        7080
actcctggca aactcacaga attcataatg cactgaaagg aattccagat gaccgagatg        7140
ggctgtttga cacaatccag cgctctaaga atcactatca aaaagagca taccagtgta        7200 taaaatgtat ggtagctcta tttagtaact gtcctgttgc ttaccaaatc ctgcagggca        7260
atggagatct taaagaaag tggacctggg cagtggaatg gcttgagat gaacttgaaa         7320 gaagaccata tactggcaat cctcagtaca cttacaacaa ttggtctccc ccagtgcaaa        7380
gcaatgaaac gtccaatggt tatttcttgg agagatcaca tagtgctagg atgacacttg        7440
caaaagcttg tgaactctgt ccagaggagg agccagatga ccaagatgct ccagatgaac        7500
atgagtcgcc tccacctgaa gatgccccat tgtaccccca ttcacctgga tctcagtatc        7560
aacagaataa ccatgtgcat ggacagccat atacaggccc agcagcacat cacatgaaca        7620
accctcagag aactggccaa cgagcacaag aaaattatga aggcagtgaa gaagtatccc        7680
cacctcaaac caaggatcaa tgaaatgcac ataattaact ggttccatca agactgtgca        7740
cccaggcctt acagtccaac cttttctgt gtctggctaa tatttaaaac tagaaaaact        7800
attcctaatc aacatggagt ggagagttta ttcactgtct tatctgcaga aatttgctgt        7860
caatatataa cccgcctgca gtggaaagtg tatagtgttt tgtaataaat ggcctgatgc        7920
taatgtgtaa atggcaaagg tgtatatagt atattaatgt tgactgttaa ttcttaagca        7980 agaaacttt ttcttgatga gactcacaga tctacacaaa ctacaaaagt taattttctg        8040
ttacacccac tgcactctta accagtgttg ctgcctcatg gcagtggatc agctcc            8096
```

<210> SEQ ID NO 34
<211> LENGTH: 10091
<212> TYPE: DNA
<213> ORGANISM: Human

<400> SEQUENCE: 34

```
gaagtgacat gttggcatgg gcccaattct gctggtcctt tagtatacaa aaaaataaa           60 ggtttaccag tatgtcacta catgcagatt tatggattgt acagaaaatt ggtgattccc         120
aaatttcact gtgcatcaaa ataatcgatg gaactttaaa gactaaagat ttctagaccc        180
caccccaggc ccgatgattg agaatatcta gaggggaccc aagaatccat atatttaagt        240
gccccaccca caacaatgac ctttaagcag gtagtttgca tttgggaacc actgctacag        300
gttactagtg ggacaaccag ttaggagcat aagtttgaac attttacagt ttgtcacctg        360
tgatagctta tcacctgtga tataaccaga atccaatta agattgctat ctctctgtaa         420
tctgtttgca atttaggtgt taattttttt gaaagttcag aaaaaagtag acaaaacaga         480
```

-continued

```
aaagaaatca agtacaacta cataatgaca aaaaacgtat tacacttgta ttaaacttca    540
aaactggaga ataaaggtgc aatataacat gaaaataatt aaatgctaag tgaaataata    600
tcaaatgtag ttgaccctga agaaaatgca gtagtgaggg atccctaacc tgtgggccct    660
ccaggaatta ctgttgaatg gtcttgagaa tccactggaa aagaccaagc attgttacct    720
gaataattga actttgttta tttctccata tttttgcagt ggtaattcca ttataaaacc    780
taatgaaaca atgttttat agatggtgtg gaaagacttt tctgggctca gaggtgaaac    840
tgacccttgt gtatcagcag catttctgac tgactgagag agtgtagtga ttaacagagt    900
tgtgatgtta gttaagaaac ttagatttgc cattgtagct tttctaccaa ttagcagatt    960
gtttaactca ctgaaattgt aaagtggtag acgtggactt agtcattact gggcagctta   1020
tgaattgtat tcatttactc atgatgtaaa aatggttagt ctccactttt aaggctctag   1080
ttctagtggc taaataggta cttatttata cagtatgata actgctgtat taaaatacat   1140
gtctcaaatg tggaatagta gaagaggtga agaaaatcat agtttgaggt agaatactgt   1200
ttgctggtct taaaaactgt ggtattttgg tgattccata aattaggtca gatacttcca   1260
ctggagggaa acagtttaaa ggatatatgt gatactatta atagaatgag gaagacacac   1320
cagatattta ggagggaatt agcgagcttg aaactaagag ctggtttgaa tgagactggg   1380
tcataagtga tttcaagtac cagattaagg cactgagatt ttatttttaa gcactgaagt   1440 cagattttt cctttaaaa gaaggattc atgatgaaat ctgctttttg ttttgcagag   1500
agcttggaga taattctggt ggctgtgtgg agtatgtgtt ggaggtatta aattttcaca   1560
gtatatataa ggcagcaatt gataggcctt tcacagattc ttctgataac tacataaaga   1620
gacaaaaaaa agaaaaaaga gcaaagatct gtgctgtgtc aagtatgaca gccatcactc   1680
atggctctcc agtaggaggg aacgacagcc agggccaggt tcttgatggc cagtctcagc   1740
atctcttcca acagaaccag acttcatcac ctgattcttc caatgagaat tccgtagcaa   1800
ctcctcctcc agaggaacaa gggcaaggtg atgccccacc acagcatgaa gatgaagagc   1860
ctgcatttcc acatactgag ctggcaaacc tggatgacat gatcaacagg cctcgatggg   1920
tggttcctgt tttgccaaaa ggggaattag aagtgctttt agaagctgct attgatctta   1980
gtgtaaaagg ccttgatgtt aaaagtgaag catgccaacg ttttttttcga gatggactaa   2040 caatatcttt cactaaaatt cttatggatg aggctgtgag tggctggaag tttgaaattc   2100
atagatgtat tattaacaat actcatcgcc tagtggagct ttgtgtggcc aagttgtccc   2160
aagattggtt tccacttcta gaacttctcg ccatggcctt aaatcctcac tgcaagtttc   2220
atatctacaa tggtacacgt ccgtgtgaat taatttcctc aaatgctcag ttgcctgaag   2280
atgaattatt tgctcgttct tcagatcctc gatcaccaaa aggttggcta gtggatctca   2340
tcaataaatt tggcacatta aatgggttcc agattttgca tgatcgtttt tttaatggat   2400
cagcattaaa tattcaaata attgcagctc ttattaaacc atttggacaa tgctatgagt   2460
ttctcagtca acatacactg aaaaagtact tcattccagt tatagaaatg gttccacatt   2520
tattggaaaa cttaactgat gaagaactga aaaaggaggc aaagaatgaa gccaaaaatg   2580 atgcccttc aatgattatt aaatctttga agaacttagc ttcaagaatt tcaggacaag   2640
atgagactat aaaaaatttg gaatttttta ggttaaagat gatactcaga ttgttgcaaa   2700
tttcctcttt taatggaaag atgaatgcac tgaatgaaat aaataaggtt atatctagtg   2760
tatcatatta tactcatcgg catagtaatc ctgaggagga agaatggctg acagctgagc   2820
```

-continued

```
gaatggcaga atggatacag caaaataata tcttatccat agtcttgcaa gacagtcttc    2880
atcaaccaca atatgtagaa aagctagaga aaattcttcg ttttgtgatt aaagaaaagg    2940
ctcttacatt acaggacctt gataatatct gggcagcaca ggcaggaaaa catgaagcca    3000
ttgtgaagaa tgtacatgat ctgctagcaa agttggcttg ggattttct cctggacaac     3060 ttgatcatct ttttgattgc tttaaggcaa gttggacaaa tgcaagtaaa aagcaacgtg    3120
aaaagctcct tgagttgata cgccgtcttg cagaagatga taaagatggt gtgatggcac    3180
acaaagtgtt gaaccttctt tggaacctgg ctcagagtga tgatgtgcct gtatacatca    3240
tggaccttgc tcttagtgcc cacataaaaa tactagatta tagttgtgcc caggatcgag    3300
atgcacagaa gatccagtgg atagatcact ttatagaaga acttcgcaca aatgacaagt    3360
gggtaattcc tgctctgaaa caaataagag aaatttgtag tttgtttggt gaagcatctc    3420
aaaatttgag tcaaactcag cgaagtcccc acatatttta tcgccatgat ttaatcaacc    3480
agcttcaaca aaatcatgct ttagttactt tggtagcaga aaaccttgca acctacatga    3540
atagcatcag attgtatgct ggagatcatg aagactatga tccacaaaca gtgaggcttg    3600
gaagtcgata cagtcatgtt caagaagttc aagaacgact aaacttcctt agatttttag    3660
tgaaggatgg ccaactgtgg ctctgtgctc ctcaggcaaa acaaatatgg aagtgcttag    3720
cagaaaatgc agtttatctt tgtgatcgtg aagcctgttt taagtggtat tccaagttaa    3780
tgggggatga accagacttg gatcctgata ttaataagga cttctttgaa agtaatgtac    3840
ttcagcttga tccttccctt ttaactgaaa atggaatgaa atgctttgaa agattttca    3900 aagctgtcaa ttgtcgagaa aggaaactaa tagcaaaaag aagatcctat atgatggatg    3960
atttggaatt aattggacta gactaccttt ggagggttgt gattcagagt agtgacgaga    4020
ttgctaacag agctatagat cttcttaaag agatatacac aaaccttggc ccaagattaa    4080
aagccaatca ggtggttatc catgaagact tcattcagtc ttgctttgat cgtttaaaag    4140
catcatatga tacactgtgt gtttttgatg gtgacaaaaa cagcattaat tgtgcaagac    4200
aagaagccat tcgaatggtt agagtattaa ctgttataaa agagtacatt aatgaatgtg    4260
acagtgatta tcacaaggaa agaatgattc tacctatgtc gagagcattt cgtggcaaac    4320
acctctctct tatagttcgg tttccaaacc agggcagaca ggttgatgag ttggatatat    4380
ggtctcatac gaatgacaca attggttcag tacggcgatg tattgttaat cgtattaaag    4440
ccaatgtagc ccacaaaaaa attgaacttt tgtgggtgg tgagctgata gattctgaag    4500
atgacagaaa gctaattgga caattaaact taaaagataa atctctaatt acagccaaac    4560
ttacacaaat aaatttcaat atgccatcaa gtcctgataq ctcttccgat tcctcaactg    4620
catctcctgg aaaccaccgt aatcattaca atgatggtcc caatctagag gtggaaagtt    4680
gtttgcctgg ggtgataatg tcagtgcatc ccagatacat ctctttcctt tggcaagttg    4740
cagacttagg tagcaacctg aatatgccac ctcttagaga tggagcaaga gtacttatga    4800
aacttatgcc accagataga acagctgtag aaaaattacg agctgttttgt ttggaccatg    4860 caaaacttgg agaaggcaaa cttagtccac cccttgactc tcttttcttt ggtccttctg    4920
cctcccaagt tctataccta acagaggtag tttatgcctt gttaatgcct gctggtgtgc    4980
ctctaactga tgggtcctct gactttcaag ttcacttctt gaaaagtggt ggcttacctc    5040
ttgtactgag tatgctaata agaaataact tcttgccaaa tacagatatg gaaactcgaa    5100
ggggtgctta tttaaatgct cttaaaatag ccaaactgtt gttaactgcg attggctatg    5160
gccatgttcg agctgtagca gaagcttgtc agccagttgt agatggtaca gaccccataa    5220
```

-continued

```
cacagattaa ccaagttact catgatcaag cagtggtgct acaaagtgcc cttcagagca    5280
ttcctaatcc ctcatccgag tgcgtactta gaaatgagtc catacttctt gctcaggaaa    5340
tatctaatga ggcttcaaga tatatgcctg atatttgtgt aattagggct atacagaaaa    5400
ttatctgggc atcagcatgt ggggcattag gactagtttt tagcccaaat gaagaaataa    5460
ctaaaattta tcagatgacc accaatggaa gcataagctg ggaggtggaa gatgaacaag    5520
tttgctgtga agcactggaa gtgatgacct tatgttttgc tttacttcca acagcgttgg    5580
atgcacttag taaagaaaaa gcctggcaga ccttcatcat tgacttatta ttgcactgtc    5640
caagcaaaac tgttcgtcag ttggcacagg agcagttctt tttaatgtgc accagatgtt    5700
gcatgggaca caggcctctg cttttcttca ttactttact ctttaccata ctggggagca    5760
cagcaagaga aagggtaaa tattcaggtg attatttcac acttttacgg caccttctca    5820
attatgctta caatggcaat attaacatac ccaatgctga agttcttctt gtcagtgaaa    5880
ttgattggct caaaggatt agggataatg ttaaaacac aggtgaaaca ggtgtcgaag    5940
agccaatact ggaaggccac cttggggtaa caaaagagtt attggccttt caaacttctg    6000
agaaaaagta tcactttggt tgtgaaaaag gaggtgctaa tctcattaaa gaattaattg    6060
atgatttcat ctttcccgca tccaaagttt acctgcagta tttaagaagt ggagaactac    6120
cagctgagca ggctattcca gtctgtagtt caccgttac catcaatgcc ggttttgagc    6180
tacttgtagc attagctatt ggctgtgtga ggaatctcaa acagatagta gactgtttga    6240
ctgaaatgta ttacatgggc acagcaatta ctacttgtga agcacttact gagtgggaat    6300 atctgcccccc tgttggaccc cgcccaccaa aaggatttgt gggactcaaa aatgctggtg    6360
ctacgtgtta catgaactct gtgatccagc agctatacat gattccttct atcaggaaca    6420
gtattcttgc aattgaaggc acaggtagtg atttacacga tgatatgttc ggggatgaga    6480
agcaggacag tgagagtaat gttgatcccc gagatgatgt atttggatat cctcatcaat    6540
ttgaagacaa gccagcatta agtaagacag aagataggaa agagtataat attggtgtcc    6600
taagacacct tcaggtcatc tttggtcatt tagctgcttc ccaactacaa tactatgtac    6660
ccagaggatt ttggaaacag ttcaggcttt ggggtgaacc tgttaatctc cgtgaacaac    6720
atgatgcctt agagtttttt aattctttgg tggatagttt agatgaagct ttaaaagctt    6780
taggacaccc ggctatacta agtaaagtcc taggaggctc cttgctgat cagaagatct    6840 gccaaggctg cccacatagg tatgaatgtg aagaatcttt tacaactttg aatgtggata    6900
ttagaaatca tcaaaatctt cttgactctt tggaacagta tatcaaagga gatttattgg    6960
aaggtgcaaa tgcatatcat tgtgaaaaat gtgataaaaa ggttgacaca gtaaagcgcc    7020
tgctaattaa aaaattgcct cgggttcttg ctatccaact caaacgattt gactatgact    7080
gggaaagaga atgtgcaatt aaattcaatg attattttga atttcctcga gagctggata    7140
tgggacctta cacagtagca ggtgttgcaa acctggaaag ggataatgta aactcagaaa    7200
atgagttgat tgaacagaaa gagcagtctg acaatgaaac tgcaggaggc acaaagtaca    7260
gacttgtagg agtgcttgta cacagtggtc aagcaagcgg tgggcattat tattcttaca    7320
tcattcaaag gaatggtaaa gatgatcaga cagatcactg gtataaattt gatgatggag    7380
atgtaacaga atgcaaaatg gatgatgatg aagaaatgaa aaatcagtgt tttggtggag    7440
agtacatggg agaagtatt gatcacatga tgaagcgcat gtcatatagg cgacagaaga    7500
ggtggtggaa tgcttacata ctttttttatg aacaaatgga tatgatagat gaagatgatg    7560
```

-continued

```
agatgataag atacatatca gagctaacta ttgcaagacc ccatcagatc attatgtcac    7620
cagccattga gagaagtgta cggaaacaaa atgtgaaatt tatgcataac cgattgcaat    7680
atagtttaga gtattttcag tttgtgaaaa aactgcttac atgtaatggt gtttatttaa    7740
accctgctcc agggcaggat tatttgttgc ctgaagcaga agaaattact atgattagta    7800
ttcagcttgc tgctagattc ctctttacca ctggatttca caccaagaaa atagttcgtg    7860
gtcctgccag tgactggtat gatgcactgt gcgttcttct ccgtcacagc aaaaatgtag    7920 gttttttggtt tactcataat gtccttttta atgtatcaaa tcgcttctct gaataccttc    7980
tggagtgccc tagtgcagaa gtgagggggtg catttgcaaa acttatagtg tttattgcac    8040
acttttcctt gcaagatggg tcttgtcctt ctccttttgc atctccagga ccttctagtc    8100
aggcatgtga taacttgagc ttgagtgacc acttactaag agccacacta aatctcttga    8160
gaagggaagt ttcagagcat ggacatcatt tacagcaata ttttaattttg tttgtaatgt    8220 atgccaattt aggtgtggca gaaaaaacac agcttctgaa attgaatgta cctgctacct    8280
ttatgcttgt gtctttagac gaaggaccag gtcctccaat caaatatcag tatgctgaat    8340
taggcaagtt atattcagta gtgtctcagc tgattcgttg ttgcaatgtg tcatcaacaa    8400
tgcagtcttc aatcaatggt aatcccctc tccccaatcc tttcggtgac cttaatttat    8460
cacagcctat aatgccaatt cagcagaatg tgttagacat tttatttgtg agaacaagtt    8520
atgtgaagaa aattattgaa gactgcagta actcagagga taccatcaaa ttacttcgct    8580
tttgctcttg ggagaatcct cagttctcat ctactgtcct cagcgaactt ctctggcagg    8640
ttgcatattc atatacctat gaacttcggc catatttaga tctacttttc caaattttac    8700
tgattgagga ctcctggcag actcacagaa ttcataatgc acttaaagga attccagatg    8760
acagagatgg gctgttcgat acaatacagc gctcgaagaa tcactatcaa aaacgagcat    8820
atcagtgcat aaaatgtatg gtagctctat ttagcagttg tcctgttgct taccagatct    8880
tacagggtaa cggagatctt aaaagaaaat ggacctgggc agtggaatgg ctaggagatg    8940
aacttgaaag aagaccatat actggcaatc ctcagtatag ttacaacaat tggtctcctc    9000
cagtacaaag caatgaaaca gcaaatggtt atttcttaga aagatcacat agtgctagga    9060
tgacacttgc aaaagcttgt gaactctgtc cagaagagga gccagatgac caggatgccc    9120
cagatgagca tgagccctct ccatcagaag atgccccatt atatcctcat tcacctgcct    9180
ctcagtatca acagaataat catgtacatg gacagccata tacaggacca gcagcacatc    9240
acttgaacaa ccctcagaaa acaggccaac gaacacaaga aaattatgaa ggcaatgaag    9300
aagtatcctc acctcagatg aaggatcagt gaaaagcaat aattaactgc ttcctttatg    9360
actatgcact aaggtcttat agtccaaact ttctctgtgt ctggctagta ttgaaaacta    9420
gataaactgc tccaaaccaa catggagtaa agagcatatt cactggttta tttgcagtaa    9480
tttgcaattt gtcagtgtat aagacacatg cagggtgaag tgtacagagt tttgtaacaa    9540
atgactggtc ctaatctgta aatgagaaag gtatatatac tatgttaatg tctgactgtt    9600
aattcttaag caagaaactt tttttgatga aaacaagtca gatctacaca gtcacacaat    9660 tatttttgt tgtgttcact acattgtgca attgatattg cctgctttga gcagtttggt    9720
caacttacca acttcccccc aaaaaaggga acataaaaga gcccatcttt gtcagtttac    9780
accaatagtt tcttgttaat ccttcttttcc tggatatata aggctggtgg taacttttga    9840
attatatggt tgatgtggaa aattggcagt gtaacatttc tagatactt tcattacctt    9900 tttattctgg tatataggct aaccacttta aagctattct tatgctgtaa cagttagcat    9960
```

```
ggcttcacac tgtttgtgta gccaagagga cagaattaca tgaatgacag tgcccagagt    10020
gacagctgta tattgctcag agcttttatt tcttatacct agaataaata taaatggggg    10080
gaaaaaaaaa a                                                         10091
```

<210> SEQ ID NO 35
<211> LENGTH: 2547
<212> TYPE: PRT
<213> ORGANISM: Human

<400> SEQUENCE: 35

```
Met Thr Ala Thr Thr Arg Gly Ser Pro Val Gly Gly Asn Asp Asn Gln
 1               5                  10                  15

Gly Gln Ala Pro Asp Gly Gln Ser Leu Pro Pro Leu Gln Gln Asn Gln
            20                  25                  30

Thr Ser Ser Pro Asp Ser Ser Asn Glu Asn Ser Pro Ala Thr Pro Pro
        35                  40                  45

Asp Glu Gln Gly Gln Gly Asp Ala Pro Pro Gln Leu Glu Asp Glu Glu
    50                  55                  60

Pro Ala Phe Pro His Thr Asp Leu Ala Lys Leu Asp Asp Met Ile Asn
65                  70                  75                  80

Arg Pro Arg Trp Val Val Pro Val Leu Pro Lys Gly Glu Leu Glu Val
                85                  90                  95

Leu Leu Glu Ala Ala Ile Asp Leu Ser Lys Lys Gly Leu Asp Val Lys
            100                 105                 110

Ser Glu Ala Cys Gln Arg Phe Phe Arg Asp Gly Leu Thr Ile Ser Phe
        115                 120                 125

Thr Lys Ile Leu Thr Asp Glu Ala Val Ser Gly Trp Lys Phe Glu Ile
    130                 135                 140

His Arg Cys Leu Val Glu Leu Cys Val Ala Lys Leu Ser Gln Asp Trp
145                 150                 155                 160

Phe Pro Leu Leu Glu Leu Leu Ala Met Ala Leu Asn Pro His Cys Lys
                165                 170                 175

Phe His Ile Tyr Asn Gly Thr Arg Pro Cys Glu Ser Val Ser Ser Ser
            180                 185                 190

Val Gln Leu Pro Glu Asp Glu Leu Phe Ala Arg Ser Pro Asp Pro Arg
        195                 200                 205

Ser Pro Lys Gly Trp Leu Val Asp Leu Leu Asn Lys Phe Gly Thr Leu
    210                 215                 220

Asn Gly Phe Gln Ile Leu His Asp Arg Phe Ile Asn Gly Ser Ala Leu
225                 230                 235                 240

Asn Val Gln Ile Ile Ala Ala Leu Ile Lys Pro Phe Gly Gln Cys Tyr
                245                 250                 255

Glu Phe Leu Thr Leu His Thr Val Lys Lys Tyr Phe Leu Pro Ile Ile
            260                 265                 270

Glu Met Val Pro Gln Phe Leu Glu Asn Leu Thr Asp Glu Glu Leu Lys
        275                 280                 285

Lys Glu Ala Lys Asn Glu Ala Lys Asn Asp Ala Leu Ser Met Ile Ile
    290                 295                 300

Lys Ser Leu Lys Asn Leu Ala Ser Arg Val Pro Gly Gln Glu Glu Thr
305                 310                 315                 320

Val Lys Asn Leu Glu Ile Phe Arg Leu Lys Met Ile Leu Arg Leu Leu
                325                 330                 335

Gln Ile Ser Ser Phe Asn Gly Lys Met Asn Ala Leu Asn Glu Val Asn
```

```
                    340                 345                 350
Lys Val Ile Ser Ser Val Ser Tyr Tyr Thr His Arg His Gly Asn Pro
                355                 360                 365
Glu Glu Glu Glu Trp Leu Thr Ala Glu Arg Met Ala Glu Trp Ile Gln
            370                 375                 380
Gln Asn Asn Ile Leu Ser Ile Val Leu Arg Asp Ser Leu His Gln Pro
385                 390                 395                 400
Gln Tyr Val Glu Lys Leu Glu Lys Ile Leu Arg Phe Val Ile Lys Glu
                405                 410                 415
Lys Ala Leu Thr Leu Gln Asp Leu Asp Asn Ile Trp Ala Ala Gln Ala
                420                 425                 430
Gly Lys His Glu Ala Ile Val Lys Asn Val His Asp Leu Leu Ala Lys
                435                 440                 445
Leu Ala Trp Asp Phe Ser Pro Glu Gln Leu Asp His Pro Phe Asp Cys
450                 455                 460
Phe Lys Ala Ser Arg Thr Asn Ala Ser Lys Lys Gln Arg Glu Lys Leu
465                 470                 475                 480
Leu Glu Leu Ile Arg Arg Leu Ala Glu Asp Asp Lys Asp Gly Val Met
                485                 490                 495
Ala His Arg Val Leu Asn Leu Leu Trp Asn Leu Ala His Ser Asp Asp
                500                 505                 510
Val Pro Val Asp Ile Met Asp Leu Ala Leu Ser Ala His Ile Lys Ile
                515                 520                 525
Leu Asp Tyr Ser Cys Ser Gln Asp Arg Asp Thr Gln Lys Ile Gln Trp
                530                 535                 540
Ile Asp Arg Phe Ile Glu Glu Leu Arg Thr Asn Asp Lys Trp Val Ile
545                 550                 555                 560
Pro Ala Leu Lys Gln Ile Arg Glu Ile Cys Ser Leu Phe Gly Glu Ala
                565                 570                 575
Pro Gln Asn Leu Ser Gln Thr Gln Arg Ser Pro His Val Phe Tyr Arg
                580                 585                 590
His Asp Leu Ile Asn Gln Leu Gln His Asn His Ala Leu Val Thr Leu
                595                 600                 605
Val Ala Glu Asn Leu Val Thr Tyr Met Glu Ser Met Arg Leu Tyr Ala
                610                 615                 620
Arg Asp His Glu Asp Tyr Asp Pro Gln Thr Val Arg Leu Gly Ser Arg
625                 630                 635                 640
Tyr Ser His Val Gln Glu Val Gln Glu Arg Leu Asn Phe Leu Arg Phe
                645                 650                 655
Leu Leu Lys Asp Gly Gln Leu Trp Leu Cys Ala Pro Gln Ala Lys Gln
                660                 665                 670
Ile Trp Lys Cys Leu Ala Glu Asn Ala Val Tyr Leu Cys Asp Arg Glu
                675                 680                 685
Ala Cys Phe Lys Trp Tyr Ser Lys Leu Met Gly Asp Glu Pro Asp Leu
                690                 695                 700
Asp Pro Asp Ile Asn Lys Asp Phe Phe Glu Ser Asn Val Leu Gln Leu
705                 710                 715                 720
Asp Pro Ser Leu Leu Thr Glu Asn Gly Met Lys Cys Phe Glu Arg Phe
                725                 730                 735
Phe Lys Ala Val Asn Cys Arg Glu Gly Lys Leu Val Ala Lys Arg Arg
                740                 745                 750
Ala Tyr Met Met Asp Asp Leu Glu Leu Ile Gly Leu Asp Tyr Leu Trp
                755                 760                 765
```

-continued

```
Arg Val Val Ile Gln Ser Asn Asp Ile Ala Ser Arg Ala Ile Asp
    770                 775                 780
Leu Leu Lys Glu Ile Tyr Thr Asn Leu Gly Pro Arg Leu Gln Val Asn
785                 790                 795                 800
Gln Val Val Ile His Glu Asp Phe Ile Gln Ser Cys Phe Asp Arg Leu
                805                 810                 815
Lys Ala Ser Tyr Asp Thr Leu Cys Val Leu Asp Gly Asp Lys Asp Ser
                820                 825                 830
Val Asn Cys Ala Arg Gln Glu Ala Val Arg Met Val Arg Val Leu Thr
                835                 840                 845
Val Leu Arg Glu Tyr Ile Asn Glu Cys Asp Ser Asp Tyr His Glu Glu
            850                 855                 860
Arg Thr Ile Leu Pro Met Ser Arg Ala Phe Arg Gly Lys His Leu Ser
865                 870                 875                 880
Phe Val Val Arg Phe Pro Asn Gln Gly Arg Gln Val Asp Asp Leu Glu
                885                 890                 895
Val Trp Ser His Thr Asn Asp Thr Ile Gly Ser Val Arg Arg Cys Ile
                900                 905                 910
Leu Asn Arg Ile Lys Ala Asn Val Ala His Thr Lys Ile Glu Leu Phe
            915                 920                 925
Val Gly Gly Glu Leu Ile Asp Pro Ala Asp Arg Lys Leu Ile Gly
930                 935                 940
Gln Leu Asn Leu Lys Asp Lys Ser Leu Ile Thr Ala Lys Leu Thr Gln
945                 950                 955                 960
Ile Ser Ser Asn Met Pro Ser Ser Pro Asp Ser Ser Ser Asp Ser Ser
                965                 970                 975
Thr Gly Ser Pro Gly Asn His Gly Asn His Tyr Ser Asp Gly Pro Asn
            980                 985                 990
Pro Glu Val Glu Ser Cys Leu Pro Gly Val Ile Met Ser Leu His Pro
            995                 1000                1005
Arg Tyr Ile Ser Phe Leu Trp Gln Val Ala Asp Leu Gly Ser Ser Leu
    1010                1015                1020
Asn Met Pro Pro Leu Arg Asp Gly Ala Arg Val Leu Met Lys Leu Met
1025                1030                1035                1040
Pro Pro Asp Ser Thr Thr Ile Glu Lys Leu Arg Ala Ile Cys Leu Asp
            1045                1050                1055
His Ala Lys Leu Gly Glu Ser Ser Leu Ser Pro Ser Leu Asp Ser Leu
            1060                1065                1070
Phe Phe Gly Pro Ser Ala Ser Gln Val Leu Tyr Leu Thr Glu Val Val
        1075                1080                1085
Tyr Ala Leu Leu Met Pro Ala Gly Ala Pro Leu Ala Asp Asp Ser Ser
    1090                1095                1100
Asp Phe Gln Phe His Phe Leu Lys Ser Gly Gly Leu Pro Leu Val Leu
1105                1110                1115                1120
Ser Met Leu Thr Arg Asn Asn Phe Leu Pro Asn Ala Asp Met Glu Thr
                1125                1130                1135
Arg Arg Gly Ala Tyr Leu Asn Ala Leu Lys Ile Ala Lys Leu Leu Leu
                1140                1145                1150
Thr Ala Ile Gly Tyr Gly His Val Arg Ala Val Ala Glu Ala Cys Gln
            1155                1160                1165
Pro Gly Val Glu Gly Val Asn Pro Met Thr Gln Ile Asn Gln Val Thr
    1170                1175                1180
```

-continued

```
His Asp Gln Ala Val Val Leu Gln Ser Ala Leu Gln Ser Ile Pro Asn
1185                1190                1195                1200

Pro Ser Ser Glu Cys Met Leu Arg Asn Val Ser Val Arg Leu Ala Gln
            1205                1210                1215

Gln Ile Ser Asp Glu Ala Ser Arg Tyr Met Pro Asp Ile Cys Val Ile
            1220                1225                1230

Arg Ala Ile Gln Lys Ile Ile Trp Ala Ser Gly Cys Gly Ser Leu Gln
            1235                1240                1245

Leu Val Phe Ser Pro Asn Glu Glu Ile Thr Lys Ile Tyr Glu Lys Thr
            1250                1255                1260

Asn Ala Gly Asn Glu Pro Asp Leu Glu Asp Glu Gln Val Cys Cys Glu
1265                1270                1275                1280

Ala Leu Glu Val Met Thr Leu Cys Phe Ala Leu Ile Pro Thr Ala Leu
                1285                1290                1295

Asp Ala Leu Ser Lys Glu Lys Ala Trp Gln Thr Phe Ile Ile Asp Leu
                1300                1305                1310

Leu Leu His Cys His Ser Lys Thr Val Arg Gln Val Ala Gln Glu Gln
                1315                1320                1325

Phe Phe Leu Met Cys Thr Arg Cys Cys Met Gly His Arg Pro Leu Leu
            1330                1335                1340

Phe Phe Ile Thr Leu Leu Phe Thr Val Leu Gly Ser Thr Ala Arg Glu
1345                1350                1355                1360

Arg Ala Lys His Ser Gly Asp Tyr Phe Thr Leu Leu Arg His Leu Leu
            1365                1370                1375

Asn Tyr Ala Tyr Asn Ser Asn Ile Asn Val Pro Asn Ala Glu Val Leu
            1380                1385                1390

Phe Asn Asn Glu Ile Asp Trp Leu Lys Arg Ile Arg Asp Asp Val Lys
            1395                1400                1405

Arg Thr Gly Glu Thr Gly Ile Glu Glu Thr Ile Leu Glu Gly His Leu
            1410                1415                1420

Gly Val Thr Lys Glu Leu Leu Ala Phe Gln Thr Ser Glu Lys Lys Phe
1425                1430                1435                1440

His Ile Gly Cys Glu Lys Gly Gly Ala Asn Leu Ile Lys Glu Leu Ile
                1445                1450                1455

Asp Asp Phe Ile Phe Pro Ala Ser Asn Val Tyr Leu Gln Tyr Met Arg
            1460                1465                1470

Asn Gly Glu Leu Pro Ala Glu Gln Ala Ile Pro Val Cys Gly Ser Pro
            1475                1480                1485

Pro Thr Ile Asn Ala Gly Phe Glu Leu Leu Val Ala Leu Ala Val Gly
            1490                1495                1500

Cys Val Arg Asn Leu Lys Gln Ile Val Asp Ser Leu Thr Glu Met Tyr
1505                1510                1515                1520

Tyr Ile Gly Thr Ala Ile Thr Thr Cys Glu Ala Leu Thr Glu Trp Glu
                1525                1530                1535

Tyr Leu Pro Pro Val Gly Pro Arg Pro Pro Lys Gly Phe Val Gly Leu
            1540                1545                1550

Lys Asn Ala Gly Ala Thr Cys Tyr Met Asn Ser Val Ile Gln Gln Leu
            1555                1560                1565

Tyr Met Ile Pro Ser Ile Arg Asn Gly Ile Leu Ala Ile Glu Gly Thr
            1570                1575                1580

Gly Ser Asp Val Asp Asp Asp Met Ser Gly Asp Glu Lys Gln Asp Asn
1585                1590                1595                1600

Glu Ser Asn Val Asp Pro Arg Asp Asp Val Phe Gly Tyr Pro Gln Gln
```

-continued

```
                    1605                1610                1615
Phe Glu Asp Lys Pro Ala Leu Ser Lys Thr Glu Asp Arg Lys Glu Tyr
                1620                1625                1630

Asn Ile Gly Val Leu Arg His Leu Gln Val Ile Phe Gly His Leu Ala
            1635                1640                1645

Ala Ser Arg Leu Gln Tyr Tyr Val Pro Arg Gly Phe Trp Lys Gln Phe
        1650                1655                1660

Arg Leu Trp Gly Glu Pro Val Asn Leu Arg Glu Gln His Asp Ala Leu
1665                1670                1675                1680

Glu Phe Phe Asn Ser Leu Val Asp Ser Leu Asp Glu Ala Leu Lys Ala
                1685                1690                1695

Leu Gly His Pro Ala Met Leu Ser Lys Val Leu Gly Gly Ser Phe Ala
            1700                1705                1710

Asp Gln Lys Ile Cys Gln Gly Cys Pro His Arg Tyr Glu Cys Glu Glu
        1715                1720                1725

Ser Phe Thr Thr Leu Asn Val Asp Ile Arg Asn His Gln Asn Leu Leu
    1730                1735                1740

Asp Ser Leu Glu Gln Tyr Val Lys Gly Asp Leu Leu Glu Gly Ala Asn
1745                1750                1755                1760

Ala Tyr His Cys Glu Lys Cys Asn Lys Lys Val Asp Thr Val Lys Arg
                1765                1770                1775

Leu Leu Ile Lys Lys Leu Pro Pro Val Leu Ala Ile Gln Leu Lys Arg
            1780                1785                1790

Phe Asp Tyr Asp Trp Glu Arg Glu Cys Ala Ile Lys Phe Asn Asp Tyr
        1795                1800                1805

Phe Glu Phe Pro Arg Glu Leu Asp Met Glu Pro Tyr Thr Val Ala Gly
    1810                1815                1820

Val Ala Lys Leu Glu Gly Asp Asn Val Asn Pro Glu Ser Gln Leu Ile
1825                1830                1835                1840

Gln Gln Ser Glu Gln Ser Glu Ser Gly Thr Ala Gly Ser Thr Lys Tyr
                1845                1850                1855

Arg Leu Val Gly Val Leu Val His Ser Gly Gln Ala Ser Gly Gly His
            1860                1865                1870

Tyr Tyr Ser Tyr Ile Ile Gln Arg Asn Gly Gly Asp Gly Glu Arg Asn
        1875                1880                1885

Arg Trp Tyr Lys Phe Asp Asp Gly Asp Val Thr Glu Cys Lys Met Asp
    1890                1895                1900

Asp Asp Glu Glu Met Lys Asn Gln Cys Phe Gly Gly Glu Tyr Met Gly
1905                1910                1915                1920

Glu Val Phe Asp His Met Met Lys Arg Met Ser Tyr Arg Arg Gln Lys
                1925                1930                1935

Arg Trp Trp Asn Ala Tyr Ile Pro Phe Tyr Glu Arg Met Asp Thr Ile
            1940                1945                1950

Asp Gln Asp Asp Glu Leu Ile Arg Tyr Ile Ser Glu Leu Ala Ile Thr
        1955                1960                1965

Thr Arg Pro His Gln Ile Ile Met Pro Ser Ala Ile Glu Arg Ser Val
    1970                1975                1980

Arg Lys Gln Asn Val Gln Phe Met His Asn Arg Met Gln Tyr Ser Met
1985                1990                1995                2000

Glu Tyr Phe Gln Phe Met Lys Lys Leu Leu Thr Cys Asn Gly Val Tyr
                2005                2010                2015

Leu Asn Pro Pro Pro Gly Gln Asp His Leu Leu Pro Glu Ala Glu Glu
            2020                2025                2030
```

```
Ile Thr Met Ile Ser Ile Gln Leu Ala Ala Arg Phe Leu Phe Thr Thr
        2035                2040                2045

Gly Phe His Thr Lys Lys Val Val Arg Gly Ser Ala Ser Asp Trp Tyr
        2050                2055                2060

Asp Ala Leu Cys Ile Leu Leu Arg His Ser Lys Asn Val Arg Phe Trp
2065                2070                2075                2080

Phe Ala His Asn Val Leu Phe Asn Val Ser Asn Arg Phe Ser Glu Tyr
            2085                2090                2095

Leu Leu Glu Cys Pro Ser Ala Glu Val Arg Gly Ala Phe Ala Lys Leu
                2100                2105                2110

Ile Val Phe Ile Ala His Phe Ser Leu Gln Asp Gly Pro Cys Pro Ser
            2115                2120                2125

Pro Phe Ala Ser Pro Gly Pro Ser Ser Gln Ala Tyr Asp Asn Leu Ser
2130                2135                2140

Leu Ser Asp His Leu Leu Arg Ala Val Leu Asn Leu Leu Arg Arg Glu
2145                2150                2155                2160

Val Ser Glu His Gly Arg His Leu Gln Gln Tyr Phe Asn Leu Phe Val
            2165                2170                2175

Met Tyr Ala Asn Leu Gly Val Ala Glu Lys Thr Gln Leu Leu Lys Leu
            2180                2185                2190

Ser Val Pro Ala Thr Phe Met Leu Val Ser Leu Asp Glu Gly Pro Gly
            2195                2200                2205

Pro Pro Ile Lys Tyr Gln Tyr Ala Glu Leu Gly Lys Leu Tyr Ser Val
            2210                2215                2220

Val Ser Gln Leu Ile Arg Cys Cys Asn Val Ser Ser Arg Met Gln Ser
2225                2230                2235                2240

Ser Ile Asn Gly Asn Pro Pro Leu Pro Asn Pro Phe Gly Asp Pro Asn
            2245                2250                2255

Leu Ser Gln Pro Ile Met Pro Ile Gln Gln Asn Val Ala Asp Ile Leu
            2260                2265                2270

Phe Val Arg Thr Ser Tyr Val Lys Lys Ile Ile Glu Asp Cys Ser Asn
            2275                2280                2285

Ser Glu Glu Thr Val Lys Leu Leu Arg Phe Cys Cys Trp Glu Asn Pro
2290                2295                2300

Gln Phe Ser Ser Thr Val Leu Ser Glu Leu Leu Trp Gln Val Ala Tyr
2305                2310                2315                2320

Ser Tyr Pro Tyr Glu Leu Arg Pro Tyr Leu Asp Leu Leu Leu Gln Ile
            2325                2330                2335

Leu Leu Ile Glu Asp Ser Trp Gln Thr His Arg Ile His Asn Ala Leu
            2340                2345                2350

Lys Gly Ile Pro Asp Asp Arg Asp Gly Leu Phe Asp Thr Ile Gln Arg
            2355                2360                2365

Ser Lys Asn His Tyr Gln Lys Arg Ala Tyr Gln Cys Ile Lys Cys Met
            2370                2375                2380

Val Ala Leu Phe Ser Asn Cys Pro Val Ala Tyr Gln Ile Leu Gln Gly
2385                2390                2395                2400

Asn Gly Asp Leu Lys Arg Lys Trp Thr Trp Ala Val Glu Trp Leu Gly
                2405                2410                2415

Asp Glu Leu Glu Arg Arg Pro Tyr Thr Gly Asn Pro Gln Tyr Thr Tyr
            2420                2425                2430

Asn Asn Trp Ser Pro Pro Val Gln Ser Asn Glu Thr Ser Asn Gly Tyr
            2435                2440                2445
```

```
Phe Leu Glu Arg Ser His Ser Ala Arg Met Thr Leu Ala Lys Ala Cys
    2450                2455                2460

Glu Leu Cys Pro Glu Glu Pro Asp Asp Gln Asp Ala Pro Asp Glu
2465            2470                2475                2480

His Glu Ser Pro Pro Pro Glu Asp Ala Pro Leu Tyr Pro His Ser Pro
                2485                2490                2495

Gly Ser Gln Tyr Gln Gln Asn Asn His Val His Gly Pro Tyr Thr
            2500                2505                2510

Gly Pro Ala Ala His His Met Asn Asn Pro Gln Arg Thr Gly Gln Arg
            2515                2520                2525

Ala Gln Glu Asn Tyr Glu Gly Ser Glu Glu Val Ser Pro Pro Gln Thr
            2530                2535                2540

Lys Asp Gln
2545

<210> SEQ ID NO 36
<211> LENGTH: 2555
<212> TYPE: PRT
<213> ORGANISM: Human

<400> SEQUENCE: 36

Met Thr Ala Ile Thr His Gly Ser Pro Val Gly Gly Asn Asp Ser Gln
1               5                   10                  15

Gly Gln Val Leu Asp Gly Gln Ser Gln His Leu Phe Gln Gln Asn Gln
            20                  25                  30

Thr Ser Ser Pro Asp Ser Ser Asn Glu Asn Ser Val Ala Thr Pro Pro
        35                  40                  45

Pro Glu Glu Gln Gly Gln Gly Asp Ala Pro Pro Gln His Glu Asp Glu
50                  55                  60

Glu Pro Ala Phe Pro His Thr Glu Leu Ala Asn Leu Asp Asp Met Ile
65                  70                  75                  80

Asn Arg Pro Arg Trp Val Pro Val Leu Pro Lys Gly Glu Leu Glu
                    85                  90                  95

Val Leu Leu Glu Ala Ala Ile Asp Leu Ser Val Lys Gly Leu Asp Val
                100                 105                 110

Lys Ser Glu Ala Cys Gln Arg Phe Phe Arg Asp Gly Leu Thr Ile Ser
            115                 120                 125

Phe Thr Lys Ile Leu Met Asp Glu Ala Val Ser Gly Trp Lys Phe Glu
130                 135                 140

Ile His Arg Cys Ile Ile Asn Asn Thr His Arg Leu Val Glu Leu Cys
145                 150                 155                 160

Val Ala Lys Leu Ser Gln Asp Trp Phe Pro Leu Leu Glu Leu Leu Ala
                165                 170                 175

Met Ala Leu Asn Pro His Cys Lys Phe His Ile Tyr Asn Gly Thr Arg
                180                 185                 190

Pro Cys Glu Leu Ile Ser Ser Asn Ala Gln Leu Pro Glu Asp Glu Leu
            195                 200                 205

Phe Ala Arg Ser Ser Asp Pro Arg Ser Pro Lys Gly Trp Leu Val Asp
210                 215                 220

Leu Ile Asn Lys Phe Gly Thr Leu Asn Gly Phe Gln Ile Leu His Asp
225                 230                 235                 240

Arg Phe Phe Asn Gly Ser Ala Leu Asn Ile Gln Ile Ile Ala Ala Leu
                245                 250                 255

Ile Lys Pro Phe Gly Gln Cys Tyr Glu Phe Leu Ser Gln His Thr Leu
                260                 265                 270
```

-continued

```
Lys Lys Tyr Phe Ile Pro Val Ile Glu Met Val Pro His Leu Leu Glu
            275                 280                 285
Asn Leu Thr Asp Glu Glu Leu Lys Lys Glu Ala Lys Asn Glu Ala Lys
            290                 295                 300
Asn Asp Ala Leu Ser Met Ile Ile Lys Ser Leu Lys Asn Leu Ala Ser
305                 310                 315                 320
Arg Ile Ser Gly Gln Asp Glu Thr Ile Lys Asn Leu Glu Ile Phe Arg
                325                 330                 335
Leu Lys Met Ile Leu Arg Leu Leu Gln Ile Ser Ser Phe Asn Gly Lys
            340                 345                 350
Met Asn Ala Leu Asn Glu Ile Asn Lys Val Ile Ser Ser Val Ser Tyr
            355                 360                 365
Tyr Thr His Arg His Ser Asn Pro Glu Glu Glu Trp Leu Thr Ala
            370                 375                 380
Glu Arg Met Ala Glu Trp Ile Gln Gln Asn Asn Ile Leu Ser Ile Val
385                 390                 395                 400
Leu Gln Asp Ser Leu His Gln Pro Gln Tyr Val Glu Lys Leu Glu Lys
                405                 410                 415
Ile Leu Arg Phe Val Ile Lys Glu Lys Ala Leu Thr Leu Gln Asp Leu
            420                 425                 430
Asp Asn Ile Trp Ala Ala Gln Ala Gly Lys His Glu Ala Ile Val Lys
            435                 440                 445
Asn Val His Asp Leu Leu Ala Lys Leu Ala Trp Asp Phe Ser Pro Gly
            450                 455                 460
Gln Leu Asp His Leu Phe Asp Cys Phe Lys Ala Ser Trp Thr Asn Ala
465                 470                 475                 480
Ser Lys Lys Gln Arg Glu Lys Leu Leu Glu Leu Ile Arg Arg Leu Ala
                485                 490                 495
Glu Asp Asp Lys Asp Gly Val Met Ala His Lys Val Leu Asn Leu Leu
            500                 505                 510
Trp Asn Leu Ala Gln Ser Asp Asp Val Pro Val Tyr Ile Met Asp Leu
            515                 520                 525
Ala Leu Ser Ala His Ile Lys Ile Leu Asp Tyr Ser Cys Ala Gln Asp
            530                 535                 540
Arg Asp Ala Gln Lys Ile Gln Trp Ile Asp His Phe Ile Glu Glu Leu
545                 550                 555                 560
Arg Thr Asn Asp Lys Trp Val Ile Pro Ala Leu Lys Gln Ile Arg Glu
                565                 570                 575
Ile Cys Ser Leu Phe Gly Glu Ala Ser Gln Asn Leu Ser Gln Thr Gln
            580                 585                 590
Arg Ser Pro His Ile Phe Tyr Arg His Asp Leu Ile Asn Gln Leu Gln
            595                 600                 605
Gln Asn His Ala Leu Val Thr Leu Val Ala Glu Asn Leu Ala Thr Tyr
            610                 615                 620
Met Asn Ser Ile Arg Leu Tyr Ala Gly Asp His Glu Asp Tyr Asp Pro
625                 630                 635                 640
Gln Thr Val Arg Leu Gly Ser Arg Tyr Ser His Val Gln Glu Val Gln
                645                 650                 655
Glu Arg Leu Asn Phe Leu Arg Phe Leu Val Lys Asp Gly Gln Leu Trp
            660                 665                 670
Leu Cys Ala Pro Gln Ala Lys Gln Ile Trp Lys Cys Leu Ala Glu Asn
            675                 680                 685
```

-continued

```
Ala Val Tyr Leu Cys Asp Arg Glu Ala Cys Phe Lys Trp Tyr Ser Lys
    690                 695                 700
Leu Met Gly Asp Glu Pro Asp Leu Asp Pro Asp Ile Asn Lys Asp Phe
705                 710                 715                 720
Phe Glu Ser Asn Val Leu Gln Leu Asp Pro Ser Leu Leu Thr Glu Asn
                725                 730                 735
Gly Met Lys Cys Phe Glu Arg Phe Phe Lys Ala Val Asn Cys Arg Glu
            740                 745                 750
Arg Lys Leu Ile Ala Lys Arg Ser Tyr Met Met Asp Asp Leu Glu
        755                 760                 765
Leu Ile Gly Leu Asp Tyr Leu Trp Arg Val Val Ile Gln Ser Ser Asp
    770                 775                 780
Glu Ile Ala Asn Arg Ala Ile Asp Leu Leu Lys Glu Ile Tyr Thr Asn
785                 790                 795                 800
Leu Gly Pro Arg Leu Lys Ala Asn Gln Val Val Ile His Glu Asp Phe
                805                 810                 815
Ile Gln Ser Cys Phe Asp Arg Leu Lys Ala Ser Tyr Asp Thr Leu Cys
            820                 825                 830
Val Phe Asp Gly Asp Lys Asn Ser Ile Asn Cys Ala Arg Gln Glu Ala
        835                 840                 845
Ile Arg Met Val Arg Val Leu Thr Val Ile Lys Glu Tyr Ile Asn Glu
    850                 855                 860
Cys Asp Ser Asp Tyr His Lys Glu Arg Met Ile Leu Pro Met Ser Arg
865                 870                 875                 880
Ala Phe Arg Gly Lys His Leu Ser Leu Ile Val Arg Phe Pro Asn Gln
                885                 890                 895
Gly Arg Gln Val Asp Glu Leu Asp Ile Trp Ser His Thr Asn Asp Thr
            900                 905                 910
Ile Gly Ser Val Arg Arg Cys Ile Val Asn Arg Ile Lys Ala Asn Val
        915                 920                 925
Ala His Lys Lys Ile Glu Leu Phe Val Gly Gly Glu Leu Ile Asp Ser
    930                 935                 940
Glu Asp Asp Arg Lys Leu Ile Gly Gln Leu Asn Leu Lys Asp Lys Ser
945                 950                 955                 960
Leu Ile Thr Ala Lys Leu Thr Gln Ile Asn Phe Asn Met Pro Ser Ser
                965                 970                 975
Pro Asp Ser Ser Ser Asp Ser Ser Thr Ala Ser Pro Gly Asn His Arg
            980                 985                 990
Asn His Tyr Asn Asp Gly Pro Asn Leu Glu Val Glu Ser Cys Leu Pro
        995                 1000                1005
Gly Val Ile Met Ser Val His Pro Arg Tyr Ile Ser Phe Leu Trp Gln
    1010                1015                1020
Val Ala Asp Leu Gly Ser Asn Leu Asn Met Pro Pro Leu Arg Asp Gly
1025                1030                1035                1040
Ala Arg Val Leu Met Lys Leu Met Pro Pro Asp Arg Thr Ala Val Glu
                1045                1050                1055
Lys Leu Arg Ala Val Cys Leu Asp His Ala Lys Leu Gly Glu Gly Lys
            1060                1065                1070
Leu Ser Pro Pro Leu Asp Ser Leu Phe Phe Gly Pro Ser Ala Ser Gln
        1075                1080                1085
Val Leu Tyr Leu Thr Glu Val Val Tyr Ala Leu Leu Met Pro Ala Gly
    1090                1095                1100
Val Pro Leu Thr Asp Gly Ser Ser Asp Phe Gln Val His Phe Leu Lys
```

-continued

```
                   1105                1110                1115                1120
Ser Gly Gly Leu Pro Leu Val Leu Ser Met Leu Ile Arg Asn Asn Phe
                       1125                1130                1135
Leu Pro Asn Thr Asp Met Glu Thr Arg Arg Gly Ala Tyr Leu Asn Ala
                       1140                1145                1150
Leu Lys Ile Ala Lys Leu Leu Leu Thr Ala Ile Gly Tyr Gly His Val
                       1155                1160                1165
Arg Ala Val Ala Glu Ala Cys Gln Pro Val Val Asp Gly Thr Asp Pro
                       1170                1175                1180
Ile Thr Gln Ile Asn Gln Val Thr His Asp Gln Ala Val Val Leu Gln
1185                1190                1195                1200
Ser Ala Leu Gln Ser Ile Pro Asn Pro Ser Ser Glu Cys Val Leu Arg
                       1205                1210                1215
Asn Glu Ser Ile Leu Leu Ala Gln Glu Ile Ser Asn Glu Ala Ser Arg
                       1220                1225                1230
Tyr Met Pro Asp Ile Cys Val Ile Arg Ala Ile Gln Lys Ile Ile Trp
                       1235                1240                1245
Ala Ser Ala Cys Gly Ala Leu Gly Leu Val Phe Ser Pro Asn Glu Glu
                       1250                1255                1260
Ile Thr Lys Ile Tyr Gln Met Thr Thr Asn Gly Ser Asn Lys Leu Glu
1265                1270                1275                1280
Val Glu Asp Glu Gln Val Cys Cys Glu Ala Leu Glu Val Met Thr Leu
                       1285                1290                1295
Cys Phe Ala Leu Leu Pro Thr Ala Leu Asp Ala Leu Ser Lys Glu Lys
                       1300                1305                1310
Ala Trp Gln Thr Phe Ile Ile Asp Leu Leu Leu His Cys Pro Ser Lys
                       1315                1320                1325
Thr Val Arg Gln Leu Ala Gln Glu Gln Phe Phe Leu Met Cys Thr Arg
                       1330                1335                1340
Cys Cys Met Gly His Arg Pro Leu Leu Phe Phe Ile Thr Leu Leu Phe
1345                1350                1355                1360
Thr Ile Leu Gly Ser Thr Ala Arg Glu Lys Gly Lys Tyr Ser Gly Asp
                       1365                1370                1375
Tyr Phe Thr Leu Leu Arg His Leu Leu Asn Tyr Ala Tyr Asn Gly Asn
                       1380                1385                1390
Ile Asn Ile Pro Asn Ala Glu Val Leu Leu Val Ser Glu Ile Asp Trp
                       1395                1400                1405
Leu Lys Arg Ile Arg Asp Asn Val Lys Asn Thr Gly Glu Thr Gly Val
                       1410                1415                1420
Glu Glu Pro Ile Leu Glu Gly His Leu Gly Val Thr Lys Glu Leu Leu
1425                1430                1435                1440
Ala Phe Gln Thr Ser Glu Lys Lys Tyr His Phe Gly Cys Glu Lys Gly
                       1445                1450                1455
Gly Ala Asn Leu Ile Lys Glu Leu Ile Asp Asp Phe Ile Phe Pro Ala
                       1460                1465                1470
Ser Lys Val Tyr Leu Gln Tyr Leu Arg Ser Gly Glu Leu Pro Ala Glu
                       1475                1480                1485
Gln Ala Ile Pro Val Cys Ser Ser Pro Val Thr Ile Asn Ala Gly Phe
                       1490                1495                1500
Glu Leu Leu Val Ala Leu Ala Ile Gly Cys Val Arg Asn Leu Lys Gln
1505                1510                1515                1520
Ile Val Asp Cys Leu Thr Glu Met Tyr Tyr Met Gly Thr Ala Ile Thr
                       1525                1530                1535
```

-continued

Thr Cys Glu Ala Leu Thr Glu Trp Glu Tyr Leu Pro Pro Val Gly Pro
                1540                1545                1550

Arg Pro Pro Lys Gly Phe Val Gly Leu Lys Asn Ala Gly Ala Thr Cys
                1555                1560                1565

Tyr Met Asn Ser Val Ile Gln Gln Leu Tyr Met Ile Pro Ser Ile Arg
                1570                1575                1580

Asn Ser Ile Leu Ala Ile Glu Gly Thr Gly Ser Asp Leu His Asp Asp
1585                1590                1595                1600

Met Phe Gly Asp Glu Lys Gln Asp Ser Glu Ser Asn Val Asp Pro Arg
                1605                1610                1615

Asp Asp Val Phe Gly Tyr Pro His Gln Phe Glu Asp Lys Pro Ala Leu
                1620                1625                1630

Ser Lys Thr Glu Asp Arg Lys Glu Tyr Asn Ile Gly Val Leu Arg His
                1635                1640                1645

Leu Gln Val Ile Phe Gly His Leu Ala Ala Ser Gln Leu Gln Tyr Tyr
                1650                1655                1660

Val Pro Arg Gly Phe Trp Lys Gln Phe Arg Leu Trp Gly Glu Pro Val
1665                1670                1675                1680

Asn Leu Arg Glu Gln His Asp Ala Leu Glu Phe Phe Asn Ser Leu Val
                1685                1690                1695

Asp Ser Leu Asp Glu Ala Leu Lys Ala Leu Gly His Pro Ala Ile Leu
                1700                1705                1710

Ser Lys Val Leu Gly Gly Ser Phe Ala Asp Gln Lys Ile Cys Gln Gly
                1715                1720                1725

Cys Pro His Arg Tyr Glu Cys Glu Glu Ser Phe Thr Thr Leu Asn Val
                1730                1735                1740

Asp Ile Arg Asn His Gln Asn Leu Leu Asp Ser Leu Glu Gln Tyr Ile
1745                1750                1755                1760

Lys Gly Asp Leu Leu Glu Gly Ala Asn Ala Tyr His Cys Glu Lys Cys
                1765                1770                1775

Asp Lys Lys Val Asp Thr Val Lys Arg Leu Leu Ile Lys Lys Leu Pro
                1780                1785                1790

Arg Val Leu Ala Ile Gln Leu Lys Arg Phe Asp Tyr Asp Trp Glu Arg
                1795                1800                1805

Glu Cys Ala Ile Lys Phe Asn Asp Tyr Phe Glu Phe Pro Arg Glu Leu
                1810                1815                1820

Asp Met Gly Pro Tyr Thr Val Ala Gly Val Ala Asn Leu Glu Arg Asp
1825                1830                1835                1840

Asn Val Asn Ser Glu Asn Glu Leu Ile Glu Gln Lys Glu Gln Ser Asp
                1845                1850                1855

Asn Glu Thr Ala Gly Gly Thr Lys Tyr Arg Leu Val Gly Val Leu Val
                1860                1865                1870

His Ser Gly Gln Ala Ser Gly Gly His Tyr Tyr Ser Tyr Ile Ile Gln
                1875                1880                1885

Arg Asn Gly Lys Asp Asp Gln Thr Asp His Trp Tyr Lys Phe Asp Asp
                1890                1895                1900

Gly Asp Val Thr Glu Cys Lys Met Asp Asp Glu Glu Met Lys Asn
1905                1910                1915                1920

Gln Cys Phe Gly Gly Glu Tyr Met Gly Glu Val Phe Asp His Met Met
                1925                1930                1935

Lys Arg Met Ser Tyr Arg Arg Gln Lys Arg Trp Trp Asn Ala Tyr Ile
                1940                1945                1950

-continued

```
Leu Phe Tyr Glu Gln Met Asp Met Ile Asp Glu Asp Glu Met Ile
        1955                1960                1965

Arg Tyr Ile Ser Glu Leu Thr Ile Ala Arg Pro His Gln Ile Ile Met
    1970                1975                1980

Ser Pro Ala Ile Glu Arg Ser Val Arg Lys Gln Asn Val Lys Phe Met
1985                1990                1995                2000

His Asn Arg Leu Gln Tyr Ser Leu Glu Tyr Phe Gln Phe Val Lys Lys
                2005                2010                2015

Leu Leu Thr Cys Asn Gly Val Tyr Leu Asn Pro Ala Pro Gly Gln Asp
                2020                2025                2030

Tyr Leu Leu Pro Glu Ala Glu Ile Thr Met Ile Ser Ile Gln Leu
                2035                2040                2045

Ala Ala Arg Phe Leu Phe Thr Thr Gly Phe His Thr Lys Lys Ile Val
    2050                2055                2060

Arg Gly Pro Ala Ser Asp Trp Tyr Asp Ala Leu Cys Val Leu Leu Arg
2065                2070                2075                2080

His Ser Lys Asn Val Gly Phe Trp Phe Thr His Asn Val Leu Phe Asn
                2085                2090                2095

Val Ser Asn Arg Phe Ser Glu Tyr Leu Leu Glu Cys Pro Ser Ala Glu
                2100                2105                2110

Val Arg Gly Ala Phe Ala Lys Leu Ile Val Phe Ile Ala His Phe Ser
    2115                2120                2125

Leu Gln Asp Gly Ser Cys Pro Ser Pro Phe Ala Ser Pro Gly Pro Ser
    2130                2135                2140

Ser Gln Ala Cys Asp Asn Leu Ser Leu Ser Asp His Leu Leu Arg Ala
2145                2150                2155                2160

Thr Leu Asn Leu Leu Arg Arg Glu Val Ser Glu His Gly His His Leu
                2165                2170                2175

Gln Gln Tyr Phe Asn Leu Phe Val Met Tyr Ala Asn Leu Gly Val Ala
                2180                2185                2190

Glu Lys Thr Gln Leu Leu Lys Leu Asn Val Pro Ala Thr Phe Met Leu
                2195                2200                2205

Val Ser Leu Asp Glu Gly Pro Gly Pro Pro Ile Lys Tyr Gln Tyr Ala
    2210                2215                2220

Glu Leu Gly Lys Leu Tyr Ser Val Val Ser Gln Leu Ile Arg Cys Cys
2225                2230                2235                2240

Asn Val Ser Ser Thr Met Gln Ser Ser Ile Asn Gly Asn Pro Pro Leu
                2245                2250                2255

Pro Asn Pro Phe Gly Asp Leu Asn Leu Ser Gln Pro Ile Met Pro Ile
                2260                2265                2270

Gln Gln Asn Val Leu Asp Ile Leu Phe Val Arg Thr Ser Tyr Val Lys
                2275                2280                2285

Lys Ile Ile Glu Asp Cys Ser Asn Ser Glu Asp Thr Ile Lys Leu Leu
    2290                2295                2300

Arg Phe Cys Ser Trp Glu Asn Pro Gln Phe Ser Ser Thr Val Leu Ser
2305                2310                2315                2320

Glu Leu Leu Trp Gln Val Ala Tyr Ser Tyr Thr Tyr Glu Leu Arg Pro
                2325                2330                2335

Tyr Leu Asp Leu Leu Phe Gln Ile Leu Leu Ile Glu Asp Ser Trp Gln
                2340                2345                2350

Thr His Arg Ile His Asn Ala Leu Lys Gly Ile Pro Asp Asp Arg Asp
    2355                2360                2365

Gly Leu Phe Asp Thr Ile Gln Arg Ser Lys Asn His Tyr Gln Lys Arg
```

```
                    2370                2375                2380
Ala Tyr Gln Cys Ile Lys Cys Met Val Ala Leu Phe Ser Ser Cys Pro
2385                2390                2395                2400

Val Ala Tyr Gln Ile Leu Gln Gly Asn Gly Asp Leu Lys Arg Lys Trp
                2405                2410                2415

Thr Trp Ala Val Glu Trp Leu Gly Asp Glu Leu Glu Arg Arg Pro Tyr
            2420                2425                2430

Thr Gly Asn Pro Gln Tyr Ser Tyr Asn Asn Trp Ser Pro Pro Val Gln
        2435                2440                2445

Ser Asn Glu Thr Ala Asn Gly Tyr Phe Leu Glu Arg Ser His Ser Ala
    2450                2455                2460

Arg Met Thr Leu Ala Lys Ala Cys Glu Leu Cys Pro Glu Glu Pro
2465                2470                2475                2480

Asp Asp Gln Asp Ala Pro Asp Glu His Glu Pro Ser Pro Ser Glu Asp
                2485                2490                2495

Ala Pro Leu Tyr Pro His Ser Pro Ala Ser Gln Tyr Gln Gln Asn Asn
                2500                2505                2510

His Val His Gly Gln Pro Tyr Thr Gly Pro Ala Ala His His Leu Asn
        2515                2520                2525

Asn Pro Gln Lys Thr Gly Gln Arg Thr Gln Glu Asn Tyr Glu Gly Asn
        2530                2535                2540

Glu Glu Val Ser Ser Pro Gln Met Lys Asp Gln
2545                2550                2555

<210> SEQ ID NO 37
<211> LENGTH: 2328
<212> TYPE: DNA
<213> ORGANISM: Human

<400> SEQUENCE: 37
ctgtggattt agctactctc acctgaggct actgagcaag ttgtcatgca ccatgagaca      60
aagcccaagc tgtcccacca ggcagtaagt atggagaggt tcaggcacat ggcatagctg     120
ctatttcgca caattttcac tacaccagtg gtgacaaaat agaagaggtt catccataca     180
cagaacctgg tgaagagctg gaggcagaaa gaagtgtcta tgtggagacg caactgaaac     240
aaaggtggca cagcaactgt tccaatcccg tgtctttcct catggcttcc caggagtttg     300
aggttgaagc tattgttgac aaaagacagg ataaaaatgg gaatacacag tatttggttc     360
ggtggaaagg ttatgacaaa caggatgaca cttgggaacc agagcagcac ctcatgaact     420
gtgaaaaatg tgtacatgat tttaatagac gacagactga aaaacagaaa aaactgacat     480
ggactacaac cagtagaatt ttttcaaaca atgccagaag aagaacttcc agatctacaa     540
aagcaaacta ttctaagaac tctcctaaaa cgccagtgac tgataaacac cacaggtcca     600
aaaaccgcaa gttatttgct gccagcaaga acgttaggaa aaaggcagct tcaattctct     660
ccgacacaaa gaatatggag ataataaatt caactattga gacccttgca cctgacagcc     720
cctttgacca caaaactgtg agtggctttc agaaacttga gaaactggac cctattgcag     780
cagatcagca ggacacggtg gtcttcaagg tgacagaagg gaaactcctc cgggacccct     840
tgtcacgtcc tggtgcagaa cagactggaa tacagaacaa gactcagata cacccactaa     900
tgtcgcagat gtctggctca gttactgctt ctatggccac aggttcagct acccgaaagg     960
gtatagtggt attaatagac ccattagcag ccaatgggac aacagacatg catacctcag    1020
ttccaagagt gaaaggtggg caaagaaata ttactgatga cagcagagac cagcctttta    1080
```

-continued

```
tcaagaagat gcacttcacc ataaggctaa cagaaagtgc cagcacatac agagacattg    1140
tagtgaagaa agaggatgga ttcacccaga tagtgctatc aactagatcg acagaaaaaa    1200
atgcactgaa tacagaagta attaaagaaa tagttaatgc tctgaatagc gctgctgcag    1260
atgacagcaa gctcgtgctg ttcagtgcag ctggaagtgt cttttgctgc ggtcttgatt    1320
ttgggtactt tgtgaagcac ttaaggaata acagaaacac agcaagcctt gaatggtgg     1380 acaccatcaa gaactttgtg aatactttta ttcaatttaa aaagcctatt gttgtatcag    1440
tcaatggccc tgcgattgga ctaggtgcat ccatcctgcc tctttgtgat ctcgtgtggg    1500
ctaatgaaaa ggcttggttc caaccccctt atacgacctt tggacagagt ccagatggct    1560
gttcttctat tacattcccc aaaatgatgg gtaaagcatc tgccaatgaa atgttaattg    1620
ctgggcgaaa gctgacagca agggaggcat gcgccaaagg cctggtctct caggtatttt    1680
tgactggaac tttcacccaa gaggttatga ttcaaattaa ggagcttgcc tcatacaatc    1740
caattgtact ggaagaatgt aaggccctcg ttcgctgtaa tattaagttg gagttggaac    1800
aggccaatga gagagagtgt gaggtgctga ggaagatctg gagctcagcc caagggatag    1860
aatccatgtt aaaaatacct ctgttgggat ataaagcagc cttccctccc agaaagacac    1920
agaatgatca gagatggtgc ccttgacttt atagtggcac aaacgcttca gagacacaca    1980
attataagag acttatcttt tagcataaat acttatggct caaaatccac tgacgatcat    2040
tctcctaaac tgaacacatg actagaattg gtggtgagat atcgcttgat tttcttttcc    2100
tttataaatg tctagttctt acccagttaa caaaagaaaa ctttatcgct ctaaagtaaa    2160
acttgtaaca ccacattagt gaattatgga atgattttgg tggaaatatc caggttctaa    2220
tgtgtggaat gtgcagattt aggttacttt agtgtatgtt ctagttaata agttaaaatt    2280
ctggacacat tattaaaggc agaaacttct ttcaaagcaa aaaaaaaa               2328
```

<210> SEQ ID NO 38
<211> LENGTH: 1964
<212> TYPE: DNA
<213> ORGANISM: Human

<400> SEQUENCE: 38

```
gtaacaggca ggaagaaagc tttctgtact acaccagagg gttggggctg tggatttagc     60
tactctcacc tgaggctact gagcaagctg tcatgcacca tgagacaaag cccaagctgt    120
cccaccaggc agtaagtgtg gagaggttca ggcacatggc atagctgcta tttcgcacaa    180
ttttcactac accagtggtg accaaataga agaggttcat ccatacacag aacctggtga    240
agagctggag gcagaaagaa gtgtctatgt ggagacgcaa ctgaaacaaa ggtggcacag    300
caactgttcc aatcccgtgt ctttcctcat ggcttcccag gagtttgagg ttgaagctat    360
tgttgacaaa agacaggata aaaatgggaa tacacagtat ttggttcggt ggaaaggtta    420
tgacaaacag gatgacactt gggaaccaga gcagcacctc atgaactgtg aaaaatgtgt    480
acatgatttt aatagacgac agactgaaaa acagaaaaaa ctgacatgga ctacaaccag    540
tagaattttt tcaaacaatg ccagaagaag aacttccaga tctacaaaag caaactattc    600
taagaactct cctaaaactc cagtgactga taaacaccac aggtccaaaa actgcaagtt    660
atttgctgcc agcaagaacg ttaggagaaa ggcagcttca actctctccg acacaaagaa    720
tatggagata taaattcaa ctattgagac ccttgcacct gacagcccct ttgaccacaa    780
gaaaactgtg agtggctttc agaaacttga gaaactggac cctattgcag cagatcagca    840
ggacacggtg gtcttcaagg tgacagaagg gaaactcctc cgggaccctt tgtcacatcc    900
```

```
tggtgcagaa cagactggaa tacagaacaa gactcagatg cacccactaa tgtcgcagat    960
gtctggctca gttactgctt ctatggccac aggttcagct acccgaaagg gtatagtggt   1020
attaatagac ccattagcag ccaatgggac aacagacatg catacctcag ttccaagagt   1080
gaaaggtggg caaagaaata ttactgatga cagcagaggc cagccttttta tcaagaagat   1140 gcacttcacc ataaggctaa cagaaagtgc catcacatac agagacattg tagtgaagaa   1200
agaggatgga ttcacccaga tagtgctatc aactagatcg acagaaaaaa atgcactgaa   1260
tacagaagta attaaagaaa tggttaatgc tctgaatagc gctgctgcag atgacagcaa   1320
gctcgtgctg ttcagtgcag ctggaagtgt cttttgctgc ggtcttgatt ttgggtactt   1380
tgtgaggcac ttaaggaatg acagaaacac agcaagcctt gaaatggtgg acaccatcaa   1440
gaactttgtg aatacttttta ttcaatttaa aaagcctatt gttgtatcag tcaatggccc   1500
tgccattgga ctaggtgcat ccatcctgcc tctttgtgat ctcgtgtggg ctaatgaaaa   1560
ggcttggttc caaaccccctt atcgaccctt tggacagagt ccagatggct gttcttctat   1620
tacattcccc aaaatgatgg gtaaagcatc tgccaatgaa atgttaattg ctgggcgaaa   1680
gctgacagca cgggaggcat gcgccaaagg cctggtctct caggtatttt tgactggaac   1740
tttcacccaa gaggttatga ttcaaattaa ggagcttgcc tcatacaatg caattgtact   1800
ggaagaatgt aaggccctcg ttcgctgtaa tattaagttg gagttggaac aggccaatga   1860
gagagagtgt gaggtgctga ggaagatctg gagctcagcc caaggatag aatccatgtt    1920 aaagtatgtt gaaataaaa ttgatgagtt ttaaaaaaaa aaaa                      1964
```

<210> SEQ ID NO 39
<211> LENGTH: 554
<212> TYPE: PRT
<213> ORGANISM: Human

<400> SEQUENCE: 39

```
Met Ala Ser Gln Glu Phe Glu Val Glu Ala Ile Val Asp Lys Arg Gln
 1               5                  10                  15

Asp Lys Asn Gly Asn Thr Gln Tyr Leu Val Arg Trp Lys Gly Tyr Asp
             20                  25                  30

Lys Gln Asp Asp Thr Trp Glu Pro Glu Gln His Leu Met Asn Cys Glu
         35                  40                  45

Lys Cys Val His Asp Phe Asn Arg Arg Gln Thr Glu Lys Gln Lys Lys
     50                  55                  60

Leu Thr Trp Thr Thr Thr Ser Arg Ile Phe Ser Asn Asn Ala Arg Arg
 65                  70                  75                  80

Arg Thr Ser Arg Ser Thr Lys Ala Asn Tyr Ser Lys Asn Ser Pro Lys
                 85                  90                  95

Thr Pro Val Thr Asp Lys His His Arg Ser Lys Asn Arg Lys Leu Phe
            100                 105                 110

Ala Ala Ser Lys Asn Val Arg Arg Lys Ala Ala Ser Ile Leu Ser Asp
        115                 120                 125

Thr Lys Asn Met Glu Ile Ile Asn Ser Thr Ile Glu Thr Leu Ala Pro
    130                 135                 140

Asp Ser Pro Phe Asp His Lys Thr Val Ser Gly Phe Gln Lys Leu Glu
145                 150                 155                 160

Lys Leu Asp Pro Ile Ala Ala Asp Gln Gln Asp Thr Val Val Phe Lys
                165                 170                 175

Val Thr Glu Gly Lys Leu Leu Arg Asp Pro Leu Ser Arg Pro Gly Ala
```

|                 |     | 180 |     |     |     | 185 |     |     |     | 190 |     |     |     |
|---|---|---|---|---|---|---|---|---|---|---|---|---|---|

Glu Gln Thr Gly Ile Gln Asn Lys Thr Gln Ile His Pro Leu Met Ser
                195                   200                205

Gln Met Ser Gly Ser Val Thr Ala Ser Met Ala Thr Gly Ser Ala Thr
210                 215                   220

Arg Lys Gly Ile Val Leu Ile Asp Pro Leu Ala Ala Asn Gly Thr
225              230             235           240

Thr Asp Met His Thr Ser Val Pro Arg Val Lys Gly Gln Arg Asn
           245             250             255

Ile Thr Asp Asp Ser Arg Asp Gln Pro Phe Ile Lys Lys Met His Phe
        260               265             270

Thr Ile Arg Leu Thr Glu Ser Ala Ser Thr Tyr Arg Asp Ile Val Val
        275               280             285

Lys Lys Glu Asp Gly Phe Thr Gln Ile Val Leu Ser Thr Arg Ser Thr
290                 295             300

Glu Lys Asn Ala Leu Asn Thr Glu Val Ile Lys Glu Ile Val Asn Ala
305                 310             315           320

Leu Asn Ser Ala Ala Ala Asp Asp Ser Lys Leu Val Leu Phe Ser Ala
        325               330             335

Ala Gly Ser Val Phe Cys Cys Gly Leu Asp Phe Gly Tyr Phe Val Lys
        340               345             350

His Leu Arg Asn Asn Arg Asn Thr Ala Ser Leu Glu Met Val Asp Thr
        355               360             365

Ile Lys Asn Phe Val Asn Thr Phe Ile Gln Phe Lys Lys Pro Ile Val
370                 375             380

Val Ser Val Asn Gly Pro Ala Ile Gly Leu Gly Ala Ser Ile Leu Pro
385                 390             395           400

Leu Cys Asp Leu Val Trp Ala Asn Glu Lys Ala Trp Phe Gln Thr Pro
           405             410             415

Tyr Thr Thr Phe Gly Gln Ser Pro Asp Gly Cys Ser Ser Ile Thr Phe
           420             425             430

Pro Lys Met Met Gly Lys Ala Ser Ala Asn Glu Met Leu Ile Ala Gly
           435             440             445

Arg Lys Leu Thr Ala Arg Glu Ala Cys Ala Lys Gly Leu Val Ser Gln
450                 455             460

Val Phe Leu Thr Gly Thr Phe Thr Gln Glu Val Met Ile Gln Ile Lys
465                 470             475           480

Glu Leu Ala Ser Tyr Asn Pro Ile Val Leu Glu Glu Cys Lys Ala Leu
           485             490             495

Val Arg Cys Asn Ile Lys Leu Glu Leu Glu Gln Ala Asn Glu Arg Glu
        500               505             510

Cys Glu Val Leu Arg Lys Ile Trp Ser Ser Ala Gln Gly Ile Glu Ser
        515               520             525

Met Leu Lys Ile Pro Leu Leu Gly Tyr Lys Ala Ala Phe Pro Pro Arg
530                 535             540

Lys Thr Gln Asn Asp Gln Arg Trp Cys Pro
545                 550

```
<210> SEQ ID NO 40
<211> LENGTH: 541
<212> TYPE: PRT
<213> ORGANISM: Human

<400> SEQUENCE: 40
```

-continued

```
Met Ala Ser Gln Glu Phe Glu Val Ala Ile Val Asp Lys Arg Gln
 1               5                  10                  15

Asp Lys Asn Gly Asn Thr Gln Tyr Leu Val Arg Trp Lys Gly Tyr Asp
             20                  25                  30

Lys Gln Asp Asp Thr Trp Glu Pro Glu Gln His Leu Met Asn Cys Glu
         35                  40                  45

Lys Cys Val His Asp Phe Asn Arg Arg Gln Thr Glu Lys Gln Lys Lys
 50                  55                  60

Leu Thr Trp Thr Thr Thr Ser Arg Ile Phe Ser Asn Asn Ala Arg Arg
 65                  70                  75                  80

Arg Thr Ser Arg Ser Thr Lys Ala Asn Tyr Ser Lys Asn Ser Pro Lys
                 85                  90                  95

Thr Pro Val Thr Asp Lys His His Arg Ser Lys Asn Cys Lys Leu Phe
                100                 105                 110

Ala Ala Ser Lys Asn Val Arg Arg Lys Ala Ala Ser Thr Leu Ser Asp
             115                 120                 125

Thr Lys Asn Met Glu Ile Ile Asn Ser Thr Ile Glu Thr Leu Ala Pro
         130                 135                 140

Asp Ser Pro Phe Asp His Lys Lys Thr Val Ser Gly Phe Gln Lys Leu
145                 150                 155                 160

Glu Lys Leu Asp Pro Ile Ala Ala Asp Gln Gln Asp Thr Val Val Phe
                165                 170                 175

Lys Val Thr Glu Gly Lys Leu Leu Arg Asp Pro Leu Ser His Pro Gly
             180                 185                 190

Ala Glu Gln Thr Gly Ile Gln Asn Lys Thr Gln Met His Pro Leu Met
         195                 200                 205

Ser Gln Met Ser Gly Ser Val Thr Ala Ser Met Ala Thr Gly Ser Ala
     210                 215                 220

Thr Arg Lys Gly Ile Val Val Leu Ile Asp Pro Leu Ala Ala Asn Gly
225                 230                 235                 240

Thr Thr Asp Met His Thr Ser Val Pro Arg Val Lys Gly Gly Gln Arg
                245                 250                 255

Asn Ile Thr Asp Asp Ser Arg Gly Gln Pro Phe Ile Lys Lys Met His
             260                 265                 270

Phe Thr Ile Arg Leu Thr Glu Ser Ala Ile Thr Tyr Arg Asp Ile Val
         275                 280                 285

Val Lys Lys Glu Asp Gly Phe Thr Gln Ile Val Leu Ser Thr Arg Ser
     290                 295                 300

Thr Glu Lys Asn Ala Leu Asn Thr Glu Val Ile Lys Glu Met Val Asn
305                 310                 315                 320

Ala Leu Asn Ser Ala Ala Ala Asp Asp Ser Lys Leu Val Leu Phe Ser
                325                 330                 335

Ala Ala Gly Ser Val Phe Cys Cys Gly Leu Asp Phe Gly Tyr Phe Val
             340                 345                 350

Arg His Leu Arg Asn Asp Arg Asn Thr Ala Ser Leu Glu Met Val Asp
         355                 360                 365

Thr Ile Lys Asn Phe Val Asn Thr Phe Ile Gln Phe Lys Lys Pro Ile
     370                 375                 380

Val Val Ser Val Asn Gly Pro Ala Ile Gly Leu Gly Ala Ser Ile Leu
385                 390                 395                 400

Pro Leu Cys Asp Leu Val Trp Ala Asn Glu Lys Ala Trp Phe Gln Thr
                405                 410                 415

Pro Tyr Thr Thr Phe Gly Gln Ser Pro Asp Gly Cys Ser Ser Ile Thr
```

―continued

```
                420                 425                 430
        Phe Pro Lys Met Met Gly Lys Ala Ser Ala Asn Glu Met Leu Ile Ala
                435                 440                 445

Gly Arg Lys Leu Thr Ala Arg Glu Ala Cys Ala Lys Gly Leu Val Ser
            450                 455                 460

Gln Val Phe Leu Thr Gly Thr Phe Thr Gln Glu Val Met Ile Gln Ile
        465                 470                 475                 480

Lys Glu Leu Ala Ser Tyr Asn Ala Ile Val Leu Glu Cys Lys Ala
                        485                 490                 495

Leu Val Arg Cys Asn Ile Lys Leu Glu Leu Gln Ala Asn Glu Arg
                    500                 505                 510

Glu Cys Glu Val Leu Arg Lys Ile Trp Ser Ser Ala Gln Gly Ile Glu
            515                 520                 525

Ser Met Leu Lys Tyr Val Glu Asn Lys Ile Asp Glu Phe
            530                 535                 540

<210> SEQ ID NO 41
<211> LENGTH: 552
<212> TYPE: DNA
<213> ORGANISM: Human
<220> FEATURE:
<221> NAME/KEY: CDS
<222> LOCATION: (73)...(358)

<400> SEQUENCE: 41
gagaggggta tacacaggga ggccaggcag cctggagtta gtcgaccgtt gcgagacgtt      60
gagctgcggc ag atg agt cca aag ccg aga gcc tcg gga cct ccg gcc aag     111
              Met Ser Pro Lys Pro Arg Ala Ser Gly Pro Pro Ala Lys
                1               5                  10 gcc aag gag aca gga aag agg aag tcc tcc tct cag ccg agc ccc agt       159
Ala Lys Glu Thr Gly Lys Arg Lys Ser Ser Ser Gln Pro Ser Pro Ser
 15                  20                  25 ggc ccg aag aag aag act acc aag gtg gcc gag aag gga gaa gca gtt       207
Gly Pro Lys Lys Lys Thr Thr Lys Val Ala Glu Lys Gly Glu Ala Val
 30                  35                  40                  45 cgt gga ggg aga cgc ggg aag aaa ggg gct gcg aca aag atg gcg gcc       255
Arg Gly Gly Arg Arg Gly Lys Lys Gly Ala Ala Thr Lys Met Ala Ala
                 50                  55                  60 gtg acg gca cct gag gcg gag agc ggg cca gcg gca ccc ggc ccc agc       303
Val Thr Ala Pro Glu Ala Glu Ser Gly Pro Ala Ala Pro Gly Pro Ser
             65                  70                  75 gac cag ccc agc cag gag ctc cct cag cac gag ctg ccg ccg gag gag       351
Asp Gln Pro Ser Gln Glu Leu Pro Gln His Glu Leu Pro Pro Glu Glu
         80                  85                  90 cca gtg a gcgaggggac ccagcacgac cccctgagtc aggagagcga gctggaggaa      408
Pro Val
     95 ccactgagta aggggcgccc atctactccc ctatctccct gagcagcaac taagtttagg     468 cccagctgcc agacctcaga gatctcacca gcaggtgct tcccatgttg atgacaataa      528 aatgaatgtg ttgcaaaaaa aaaa                                            552

<210> SEQ ID NO 42
<211> LENGTH: 95
<212> TYPE: PRT
<213> ORGANISM: Human

<400> SEQUENCE: 42

Met Ser Pro Lys Pro Arg Ala Ser Gly Pro Pro Ala Lys Ala Lys Glu
```

```
            1               5                   10                  15
        Thr Gly Lys Arg Lys Ser Ser Gln Pro Ser Pro Ser Gly Pro Lys
                        20                  25                  30
        Lys Lys Thr Thr Lys Val Ala Glu Lys Gly Glu Ala Val Arg Gly Gly
                    35                  40                  45
        Arg Arg Gly Lys Lys Gly Ala Ala Thr Lys Met Ala Ala Val Thr Ala
                50                  55                  60
        Pro Glu Ala Glu Ser Gly Pro Ala Ala Pro Gly Pro Ser Asp Gln Pro
        65                  70                  75                  80
        Ser Gln Glu Leu Pro Gln His Glu Leu Pro Pro Glu Glu Pro Val
                        85                  90                  95

<210> SEQ ID NO 43
<211> LENGTH: 1212
<212> TYPE: DNA
<213> ORGANISM: Human
<220> FEATURE:
<221> NAME/KEY: CDS
<222> LOCATION: (333)...(561)

<400> SEQUENCE: 43
aatatctcag gacccaggac catgtgatat gggcccaaca cctggatgat gttactcttc      60
tgcctaggtc atgcgtaaag agggaattag gcatattgc ttggcccagt cccgtaatga     120
tatgactctc ctgcttgtgc cagagccaca gaagtgtgct tggtgacata atctttgagg    180
ctgtcacatc accaagatta tattgtatca ctggaccagc ataaagctga cacttctgac    240
tatgcccagc cttcaaataa tactacactg tataattggc tcaacaccca ggtgatattg    300
ttccatttac ctgagaccag ataaaaagcc ta atg atg acg ctt gtc ccc aga      353
                                   Met Met Thr Leu Val Pro Arg
                                    1               5 gcc agg aca cgt gca gga cag gat cat tac tct cat ccc tgc ccc aga      401
Ala Arg Thr Arg Ala Gly Gln Asp His Tyr Ser His Pro Cys Pro Arg
        10                  15                  20 ttt tca cag gtg ctg ctt aca gag ggc atc atg aca tat tgc ttg aca      449
Phe Ser Gln Val Leu Leu Thr Glu Gly Ile Met Thr Tyr Cys Leu Thr
    25                  30                  35 aag aac cta agt gat gtt aat att ctg cat agg ttg cta aaa aat ggg      497
Lys Asn Leu Ser Asp Val Asn Ile Leu His Arg Leu Leu Lys Asn Gly
40                  45                  50                  55 aat gtg aga aat acc ttg ctt cag tcc aaa gtg ggc ttg ctg aca tat      545
Asn Val Arg Asn Thr Leu Leu Gln Ser Lys Val Gly Leu Leu Thr Tyr
                60                  65                  70 tat gtg aaa ctg tac c cgggtgaagt gactcttctg actaggccca gcatacaaat    601
Tyr Val Lys Leu Tyr
            75 gagattatgc tgtatcactg gctcagtgtc gaagcccaga tcacagaagt aattgtgcca    661 tatgtggaac aagcagctaa gcaatagata acatccatcg tggctctgcc ttcaaaggga    721 aattttacat atgtcactgg gaccatcacc cagatgatgt cctgcccact aaaagaattg    781 tgacataacg ctgactgcaa aaactgggta atgcaactct cctctttatt ctggagtctg    841 ccaaaacaag ggattatcac atattgcgga gtccagcacc caggtaaaat tttgtcatat    901 acccagcttc agataccatg caatgataca actatcatac ctggacccaa agaggagaga    961 tattttgatt ctcattgcca ttcttatggc cacaagcaaa gtaatggttc tcatagtggt   1021 ataaagttca cacagtatta tgacactccc agcgtatcat agaaaatgtg agtagtacaa   1081 tgagtgttat aacagggaac agcaaaccaa tgctattgtg attattggat tcacacccag   1141
```

```
ctgacgcgac tatcattctc tcacaagaac agaacctgca aataaagtac taaatctcac    1201
caaaaaaaaa a                                                         1212
```

<210> SEQ ID NO 44
<211> LENGTH: 76
<212> TYPE: PRT
<213> ORGANISM: Human

<400> SEQUENCE: 44

```
Met Met Thr Leu Val Pro Arg Ala Arg Thr Arg Ala Gly Gln Asp His
 1               5                  10                  15

Tyr Ser His Pro Cys Pro Arg Phe Ser Gln Val Leu Thr Glu Gly
             20                  25                  30

Ile Met Thr Tyr Cys Leu Thr Lys Asn Leu Ser Asp Val Asn Ile Leu
             35                  40                  45

His Arg Leu Leu Lys Asn Gly Asn Val Arg Asn Thr Leu Leu Gln Ser
         50                  55                  60

Lys Val Gly Leu Leu Thr Tyr Tyr Val Lys Leu Tyr
65                   70                  75
```

<210> SEQ ID NO 45
<211> LENGTH: 1588
<212> TYPE: DNA
<213> ORGANISM: Human
<220> FEATURE:
<221> NAME/KEY: CDS
<222> LOCATION: (664)...(1051)

<400> SEQUENCE: 45

```
attaaaaact tctgataaaa ttacctaagt acacacaaac aaaaacatgc ccacacaaat    60
cacttaattt ctaaaacttt taattttct gcttctctag taccttgtat tccatcacac    120
agcaaaatct ggcagctcca cttccagaat ttacttgaac tccacagctt atttccgatt    180
tcctgttatc accagagtct aaaacacagt ttatattgca ttcacctcct attttacacc    240
gtaatttcct actttacact ctaactttat ataaaaaaga aactaccttt tcaagatcta    300
attcacgcaa ttttatttgt tcttaattga gacttctttc taggtgctgt cacaccttgt    360
aacgtcagat acaaatgtct ctatccaatt tcatgagttc cagttatttt attttaaggg    420
aatgtgtata tacatttata aatttgtgta tgtgtgtatt cacttattct ttattttata    480
tgttttgcat gcatatattc actaaatccc tgataataga aagataacaa atctttttt    540 ttctttcttt tttgtatgta aattattttc cgaaggaggt gggttgggag aaatatatct    600
taacttggca agtttaaaag agaaagtggc cattactaat gaaaattatt ctctagcatt    660
ttc atg ttt atc ttt aat agc att gct gat gac ata ttc cct ctt atc    708
    Met Phe Ile Phe Asn Ser Ile Ala Asp Asp Ile Phe Pro Leu Ile
     1               5                  10                  15 agt tgt gta ggt gcc att cac tgc aat ata ctg gcc atc cgc act ggc    756
Ser Cys Val Gly Ala Ile His Cys Asn Ile Leu Ala Ile Arg Thr Gly
             20                  25                  30 aac gac ttt gct gcc att aag cta cag gta ata aaa ttg atc tat ctc    804
Asn Asp Phe Ala Ala Ile Lys Leu Gln Val Ile Lys Leu Ile Tyr Leu
         35                  40                  45 atg ata tgg cat tcg ttg gtg att atc tca cct gta gtg act ctg gca    852
Met Ile Trp His Ser Leu Val Ile Ile Ser Pro Val Val Thr Leu Ala
     50                  55                  60 ttc ttc cct gca tct ctg aaa cag ggg agc tta cac ttt cta tta atc    900
Phe Phe Pro Ala Ser Leu Lys Gln Gly Ser Leu His Phe Leu Leu Ile
 65                  70                  75
```

```
ata tat ttt gta tta ttg ttg aca cca tgg ctg gag ttt tcg aaa agt      948
Ile Tyr Phe Val Leu Leu Leu Thr Pro Trp Leu Glu Phe Ser Lys Ser
 80              85                  90                  95 gga act cat ctt cct agc aac aca aaa ata att cca gca tgg tgg gta      996
Gly Thr His Leu Pro Ser Asn Thr Lys Ile Ile Pro Ala Trp Trp Val
                100                 105                 110 agt atg gat gct tat ctt aat cat gct agt ata tgc tgc cat caa ttc     1044
Ser Met Asp Ala Tyr Leu Asn His Ala Ser Ile Cys Cys His Gln Phe
                115                 120                 125 tcc tgc t tgtcagcagt gaaactgcag ctgtcaaatg aggaattgat aagagacacg    1101
Ser Cys aggtgggaca tacaatccta cactacagat ttcagttttt agaaaatgtg ataataatat   1161
tgatatttag tttctttgga gggaacgttt taccgaagtg ttgtgactca ataattgccg   1221
tgtagttcat caaaacctac atattagcct ttggctttaa gctccgcttc tgtcagtatt   1281
tgcaaccaag gtggtcgggc aaagtattgc caggagatac tgaaaatcat ccagaagcac   1341
tgtgatattg tgtaagcatc tggagaaaat tcagttaaaa gaataaaagt aagcagctga   1401
ggaattacta tcactcatgg agaagggtag gatattttca ataagtgagt atgcaatatc   1461
catatatact ttcacagaac aaagagtaaa gaggctgagt gtgactttat aaagatactc   1521
atgaaaaata taaacaacaa aaccttggaa gtagtttcta ataaaattga tttttctaaa   1581
aaaaaaa                                                             1588

<210> SEQ ID NO 46
<211> LENGTH: 129
<212> TYPE: PRT
<213> ORGANISM: Human

<400> SEQUENCE: 46

Met Phe Ile Phe Asn Ser Ile Ala Asp Asp Ile Phe Pro Leu Ile Ser
 1               5                  10                  15

Cys Val Gly Ala Ile His Cys Asn Ile Leu Ala Ile Arg Thr Gly Asn
                20                  25                  30

Asp Phe Ala Ala Ile Lys Leu Gln Val Ile Lys Leu Ile Tyr Leu Met
            35                  40                  45

Ile Trp His Ser Leu Val Ile Ile Ser Pro Val Thr Leu Ala Phe
 50                  55                  60

Phe Pro Ala Ser Leu Lys Gln Gly Ser Leu His Phe Leu Leu Ile Ile
 65                  70                  75                  80

Tyr Phe Val Leu Leu Leu Thr Pro Trp Leu Glu Phe Ser Lys Ser Gly
                85                  90                  95

Thr His Leu Pro Ser Asn Thr Lys Ile Ile Pro Ala Trp Trp Val Ser
                100                 105                 110

Met Asp Ala Tyr Leu Asn His Ala Ser Ile Cys Cys His Gln Phe Ser
            115                 120                 125

Cys

<210> SEQ ID NO 47
<211> LENGTH: 1248
<212> TYPE: DNA
<213> ORGANISM: Human
<220> FEATURE:
<221> NAME/KEY: CDS
<222> LOCATION: (183)...(834)

<400> SEQUENCE: 47
```

| | |
|---|---:|
| aagaagagga gcacaccaca ccagaaacag acatcttgca gtgtttcact gtctcaacct | 60 |
| tatctgcaca gtccgaggtc agtctgagag agcttctgag agacccagga tgaagggatg | 120 |
| cagtgaggtc aagagcccaa ccttctttca ctgacaccca cctctaagga ctcagaagag | 180 |

| | | |
|---|---|---:|
| ac atg aat aaa atg ggc ctc aac aat ccc aag aag aac cac tca agg<br>   Met Asn Lys Met Gly Leu Asn Asn Pro Lys Lys Asn His Ser Arg<br>    1               5                    10                  15 | | 227 |
| aca atg gga gcc act ggg ctt ggc ttc cta ctt ccc tgg aaa caa gac<br>Thr Met Gly Ala Thr Gly Leu Gly Phe Leu Leu Pro Trp Lys Gln Asp<br>                   20                       25                       30 | | 275 |
| aat ttg aat ggc act gac tgc cag gga tgc aat att tta tac ttc tct<br>Asn Leu Asn Gly Thr Asp Cys Gln Gly Cys Asn Ile Leu Tyr Phe Ser<br>                   35                       40                       45 | | 323 |
| gag act acg ggg agc atg tgt tct gaa ctt tcc ctg aac aga ggt ctt<br>Glu Thr Thr Gly Ser Met Cys Ser Glu Leu Ser Leu Asn Arg Gly Leu<br>           50                       55                       60 | | 371 |
| gag gcc aga agg aag aag gat ctt aaa gac tca ttt ctc tgg aga tat<br>Glu Ala Arg Arg Lys Lys Asp Leu Lys Asp Ser Phe Leu Trp Arg Tyr<br> 65                     70                       75 | | 419 |
| ggg aag gtt ggc tgt atc tca ctt cca ctt cgt gag atg acc gcc tgg<br>Gly Lys Val Gly Cys Ile Ser Leu Pro Leu Arg Glu Met Thr Ala Trp<br>80                   85                       90                       95 | | 467 |
| att aac cca ccc caa att tca gag att ttc caa ggc tac cac cag agg<br>Ile Asn Pro Pro Gln Ile Ser Glu Ile Phe Gln Gly Tyr His Gln Arg<br>                  100                     105                    110 | | 515 |
| gtg cac gga gct gat gca ctg agc ctg caa acc aac tct ctg aga agc<br>Val His Gly Ala Asp Ala Leu Ser Leu Gln Thr Asn Ser Leu Arg Ser<br>             115                     120                    125 | | 563 |
| agg tta tct tca cag tgc ctc gga cag agc ttc ctt ctc agg aca ctc<br>Arg Leu Ser Ser Gln Cys Leu Gly Gln Ser Phe Leu Leu Arg Thr Leu<br>       130                     135                    140 | | 611 |
| gag aga gcc gtg gtt tca ggg cac ttg ggg aca tct gtg gcc acg ttc<br>Glu Arg Ala Val Val Ser Gly His Leu Gly Thr Ser Val Ala Thr Phe<br>145                      150                     155 | | 659 |
| atg aag aag act aag cct act tca tct cag gac ccg ccc aag agt ggc<br>Met Lys Lys Thr Lys Pro Thr Ser Ser Gln Asp Pro Pro Lys Ser Gly<br>160                     165                     170                 175 | | 707 |
| cgc ggc ttt ggg aca cct gcg gtc ggg tcc acc atg agg ata aaa cct<br>Arg Gly Phe Gly Thr Pro Ala Val Gly Ser Thr Met Arg Ile Lys Pro<br>             180                     185                    190 | | 755 |
| cct tct ctt ctg gac atg tcc agg agt ggc cgt tgc tac aag tca cct<br>Pro Ser Leu Leu Asp Met Ser Arg Ser Gly Arg Cys Tyr Lys Ser Pro<br>       195                     200                    205 | | 803 |
| ggt gct acg acc agg gtg aga ata aag acg t ctcctcagga ccctcccagg<br>Gly Ala Thr Thr Arg Val Arg Ile Lys Thr<br>             210                     215 | | 854 |

| | |
|---|---:|
| agagtacatg gcattgagac atctggcggc caagtgagga aaagacaccc tgtctgcagc | 914 |
| acccagaact gaggaggggc actgccctgg gccttacttc ccagccctgg cctccaattc | 974 |
| tgaccttaca aaagtgtccc ttgagtgagg cagtgaccac gcattgtcac agctaccaaa | 1034 |
| gtgtggtttg cagatgatct gggcttgttt ctggcagaga ttctggtaca gagaaggag | 1094 |
| aggcgttgag tggaaccacg atgggctgag gccaggggag acatcacaac ctccaacaac | 1154 |
| actttttttc atgctttaat aaatcatttt tcttagagaa ctaaagtagt tgaaacaata | 1214 |
| tagaaacatt ttttaagtag gcataaaaaa aaaa | 1248 |

<210> SEQ ID NO 48
<211> LENGTH: 217

<212> TYPE: PRT
<213> ORGANISM: Human

<400> SEQUENCE: 48

Met Asn Lys Met Gly Leu Asn Asn Pro Lys Lys Asn His Ser Arg Thr
 1               5                  10                  15

Met Gly Ala Thr Gly Leu Gly Phe Leu Leu Pro Trp Lys Gln Asp Asn
             20                  25                  30

Leu Asn Gly Thr Asp Cys Gln Gly Cys Asn Ile Leu Tyr Phe Ser Glu
         35                  40                  45

Thr Thr Gly Ser Met Cys Ser Glu Leu Ser Leu Asn Arg Gly Leu Glu
     50                  55                  60

Ala Arg Arg Lys Lys Asp Leu Lys Asp Ser Phe Leu Trp Arg Tyr Gly
 65                  70                  75                  80

Lys Val Gly Cys Ile Ser Leu Pro Leu Arg Glu Met Thr Ala Trp Ile
                 85                  90                  95

Asn Pro Pro Gln Ile Ser Glu Ile Phe Gln Gly Tyr His Gln Arg Val
            100                 105                 110

His Gly Ala Asp Ala Leu Ser Leu Gln Thr Asn Ser Leu Arg Ser Arg
        115                 120                 125

Leu Ser Ser Gln Cys Leu Gly Gln Ser Phe Leu Leu Arg Thr Leu Glu
    130                 135                 140

Arg Ala Val Val Ser Gly His Leu Gly Thr Ser Val Ala Thr Phe Met
145                 150                 155                 160

Lys Lys Thr Lys Pro Thr Ser Ser Gln Asp Pro Pro Lys Ser Gly Arg
                165                 170                 175

Gly Phe Gly Thr Pro Ala Val Gly Ser Thr Met Arg Ile Lys Pro Pro
            180                 185                 190

Ser Leu Leu Asp Met Ser Arg Ser Gly Arg Cys Tyr Lys Ser Pro Gly
        195                 200                 205

Ala Thr Thr Arg Val Arg Ile Lys Thr
    210                 215

<210> SEQ ID NO 49
<211> LENGTH: 920
<212> TYPE: DNA
<213> ORGANISM: Human

<400> SEQUENCE: 49
tgtctgtcag agctgtcagc ctgcttaagc agagtaaaat ggtacaggca gtgcagcctg      60
gtagcgagaa aaaaggctgc ctgtgaaatc ccactgtggg accataagtg gggacctcag     120
ggcccctcca tggcatctcc atggccatgt catgctggag aaggaggcgt ttcaagaatg     180
tgagctgatc gctggaaact gctcatctga ctccagtctc aaaagaggct atgtgcaaga     240
atcgggtgaa gttgtgagac cccatccacc cctcacaaga ttgtatcccc accctgtctg     300
accttactgc tgctcaaact atctgtccaa ggatgaaaac ccaggacaaa ggaggagtaa     360
ccctcatgat gtgaagcacg tgttcacctg tgaatataac ctgaggatca tgagactatc     420
tgtggatttc acagagaaga cagacgagaa gacaccgctg acacttctcc acggaggtct     480 cctttttccac caagatgcag atgcttcttg caaggactat cctgtgaatc ccacagagaa     540
gacaggtgtg gttccaatgc cggtgcacct ccagggaatt ctccttctct accaagctcc     600
aggccttctg ccatgatcat gagactattt gtggatttca cagagaagat aggtgaaggt     660
acagcatggc atccaccct caccagaggg gtatccccac ccctatctga ccttattacc     720

```
ttattgctgt tcaaagtctc tatcccagac tgaaatccca agacaatgga gaagttcccc      780
ctgatgatgt gaagcaccaa ctcctctggg aatcaaattc gaggtaaatt taataggccc      840
ggtagagatg aatgatagtg tctctccttg gattggctga agacaatta aacactggta       900 tatttctgtt aaaaaaaaaa                                                  920

<210> SEQ ID NO 50
<211> LENGTH: 3177
<212> TYPE: DNA
<213> ORGANISM: Human

<400> SEQUENCE: 50
aggcttgcca tcaccacaga tggcctctga gacactgttt gaaccacatc tgcacctgtg       60
agaggccagt ttgaggtatg agaacactgt ttcaatttgg acttgccttt gtcttggttc      120
ctgcttttcc cagatggcac ctacccaacc caggatgaat gagtgcagag aggtcaagtg      180
ccaggccatc ttttgctgac accctttttct ggtatttcag gtataagtcc atcatccaaa     240
gactgctcaa catctcacca gaatatattt caatcctcat ggggcatgat tctttcacaa      300 aaccccttc aggaatggag tcagaagagt agttccaga gacaacctca cagtcttgga        360
acggctctgc ctcccatgtg atctgaccat ggagatggca tataagggcc ctaagtttga      420
gacttttagg gtactgcaat gcgttatcac aggcagcctt tatcctgata ccaagccagc      480
tctgcctgta ccatttttcct ctgcttaggc aggctgacag ccctgacacc ctggtgctcc     540
agtttgagtc actatatgtg gatgtgctag tcttgggggca atggacctga gctgtgagct     600
gtagctagtg tcacaatgaa tgccagcttt gctagtaaca attcccttg gcttggtaga       660 gaagggacc tctgtggagg tacaatggtg gtgcactgtc acctgtcttc tctgtgggat       720
ccatgggaca gttccatgat cctaggagag ggtagatgtg agccagcctg aagaaatgtc      780
aagcagagcc ccaggaatga agcacaaaat cactacagat ccaaaaggat ctgcagaatt      840
tgtcaggcct gcctagacat tgtaggggtt agtcttattg aaatgtgtcc cactgtaatt     900
tccaacttca gccttcctgt gttcccagca gtttctctct cccaggtggg gctttctgca      960
gaatgacaca gcctcagaag ctactgggct gtgtgttact gtgggagtgt tgcgagtgtt     1020
ggatgtcagc atgtgtgtgt ggctttgtgt gtgtgtgtag gtgtctgtgt gtgtgtatgt     1080
aaatgaattc tgtggatcag gaatcagcaa tgactagtta agctgtctgt gaccagccgg     1140
gttccccatc gtctgccccct gccaaaaaaa caggtactct tctacaaaga agaggagagc   1200
accacaccca agaacagaca tctcccagtg ttgcattata aagcagccaa cccacagaca     1260
ctagcactct ggtctgcata gcccctttaa tttacctaga attcagttcc cagccaagta     1320
ggtgcttcat gtcctgaggg tgcaatcctc catcatcttg agatttcatg ctggtacaga     1380
gagtgtgaca gcaataaggt cagatagggg tgagtataca acctggtgaa gggtggatgg     1440
ggtcccgtac cttcaccagc aaaaagggtg aaaatagatg acacagaatg tgcttccaac     1500
tccatcccca cattcccata attgcaaaat cagtcaacaa catggcctgg tgtttaggtg     1560
ggagtactcc aacctgcagg aagaatttgg agtgcaaatt gtggccaatc tggaaaactc     1620
ctggtttgag ggtttaaata cctgtagtca aatggaagtg gaatagattg atgctgggtg    1680
ggttgtggcc tccacatttg tgtcctcttt tactgacttc cattgtcctc attggtgtag    1740
ggcttcctgg atctggctca acatcttcca cactaaactc ttccctgttc acagaagacc    1800
atcataaaaa tgcattgtag aggccctgca aggaccagga tgaagggaga cagtgaggtc    1860
aagagcccag ccatctttca ctgacaccca cttctggggtt ctcaggctgg ctgacaggtc   1920
```

```
tgacagccca tcacgaaagc ctgcatactc ttagacacaa ggactgagct atgggctcca    1980
gctagcatca caatgaaggc caccattgcc tagggataag tccctgtgac tttgtggata    2040
agaactccgt ggagccaatc caaggagaga cactatcatt catctctacc gggcctatta    2100
aatttacctc gaatttgatt cccagaggag ttggtgcttc acatcatcag ggggaacttc    2160
tccattgtct tgggatttca gtctgggata gagactttga acagcaataa gtttccttgg    2220
tctggctcaa cgtcttctaa actcaacatt ccccagttca tggaaaatga tcctcatggg    2280
attctattgt aaaagctgca tgattcctgg agaatgtttt attgtcctgg agtcaaccca    2340
aaaatcaaca ctaccagtca tgttgcagag ctccttgaat taaccttgaa ttcagtttcc    2400
agctgagcag ctgcttcacg ttgtgagggg gcaatcctcc atcatcctgg gatttcattc    2460
tgggacacag agtttgagca gcaataaggc tgggtccaca ttgcccctca acagcattag    2520
tggacatgat tgtcagactt gcaatttccg cagacacctt ctgtgaacat ttttcaacat    2580
catctacatg agtgagagac ccgttcgaca tgtaagaata ctgcttgact ttggacctgc    2640
ctttgtcgtg gttcctgcct ttctcataga tcccctgcca ggcccaggat gataggaggc    2700
aatgaagtca agggccgagc ccattcatt gaaagctgac tctgggtct cggtataat     2760 tccatcacat aaaatcccct caacaactca ccagactata ttccaatctc catgaaacct    2820
gattcttgca cacagcctct ttcaggaatg gagtcagaag agcagtcttc agagaccacc    2880
tcagtttgga aaagcctcct ccttcagtgg ttcccagcca tggagtcatc gtgaaggggc    2940
tccatggtca ataattttac ggtactgcac ttggttatca cagacagact ttttcatgat    3000
agcatgccat ctctgtctat atcattttcc tctgcttagg caggctgaca actctgacag    3060
ccaggggccc gaatctacct ggcaaatgtg catgctctac tctcagtgca aaaggcctgt    3120
ttgggagttc tgactagtgt cacaataaat gccgccattg cctagtgaaa aaaaaaa     3177
```

<210> SEQ ID NO 51
<211> LENGTH: 20
<212> TYPE: DNA
<213> ORGANISM: Human

<400> SEQUENCE: 51
cattcggttt taccagccag                                                  20

<210> SEQ ID NO 52
<211> LENGTH: 20
<212> TYPE: DNA
<213> ORGANISM: Human

<400> SEQUENCE: 52
cagtgactcg aggttcaatg                                                  20

<210> SEQ ID NO 53
<211> LENGTH: 24
<212> TYPE: DNA
<213> ORGANISM: Human

<400> SEQUENCE: 53
gcatcataat atggatctag tagg                                             24

<210> SEQ ID NO 54
<211> LENGTH: 21
<212> TYPE: DNA
<213> ORGANISM: Human

```
<400> SEQUENCE: 54
ggagatactg aatagcatag c                                              21

<210> SEQ ID NO 55
<211> LENGTH: 20
<212> TYPE: DNA
<213> ORGANISM: Human

<400> SEQUENCE: 55
caaagacctg ctgacaatgg                                                20

<210> SEQ ID NO 56
<211> LENGTH: 37
<212> TYPE: DNA
<213> ORGANISM: Human

<400> SEQUENCE: 56
ctccgctaag tctttcacca agacctgctg acaatgg                             37

<210> SEQ ID NO 57
<211> LENGTH: 19
<212> TYPE: DNA
<213> ORGANISM: Human

<400> SEQUENCE: 57
ctctgtagcc agcctcttc                                                 19

<210> SEQ ID NO 58
<211> LENGTH: 20
<212> TYPE: DNA
<213> ORGANISM: Human

<400> SEQUENCE: 58
gactcctttc tggcggttac                                                20

<210> SEQ ID NO 59
<211> LENGTH: 22
<212> TYPE: DNA
<213> ORGANISM: Human

<400> SEQUENCE: 59
gagcccatct ttgtcagttt ac                                             22

<210> SEQ ID NO 60
<211> LENGTH: 22
<212> TYPE: DNA
<213> ORGANISM: Human

<400> SEQUENCE: 60
ctgccaattt tccacatcaa cc                                             22

<210> SEQ ID NO 61
<211> LENGTH: 19
<212> TYPE: DNA
<213> ORGANISM: Human

<400> SEQUENCE: 61
ggctcaaaat ccactgacg                                                 19

<210> SEQ ID NO 62
<211> LENGTH: 19
<212> TYPE: DNA
<213> ORGANISM: Human
```

-continued

<400> SEQUENCE: 62
caagcgatat ctcaccacc                                      19

<210> SEQ ID NO 63
<211> LENGTH: 20
<212> TYPE: DNA
<213> ORGANISM: Human

<400> SEQUENCE: 63
ctccctgagc agcaactaag                                     20

<210> SEQ ID NO 64
<211> LENGTH: 20
<212> TYPE: DNA
<213> ORGANISM: Human

<400> SEQUENCE: 64
gtcatcaaca tgggaagcac                                     20

<210> SEQ ID NO 65
<211> LENGTH: 19
<212> TYPE: DNA
<213> ORGANISM: Human

<400> SEQUENCE: 65
ccaggaccat gtgatatgg                                      19

<210> SEQ ID NO 66
<211> LENGTH: 24
<212> TYPE: DNA
<213> ORGANISM: Human

<400> SEQUENCE: 66
ctaattccct ctttacgcat gacc                                24

<210> SEQ ID NO 67
<211> LENGTH: 20
<212> TYPE: DNA
<213> ORGANISM: Human

<400> SEQUENCE: 67
cactcatgga gaagggtagg                                     20

<210> SEQ ID NO 68
<211> LENGTH: 20
<212> TYPE: DNA
<213> ORGANISM: Human

<400> SEQUENCE: 68
gtcacactca gcctctttac                                     20

<210> SEQ ID NO 69
<211> LENGTH: 20
<212> TYPE: DNA
<213> ORGANISM: Human

<400> SEQUENCE: 69
gagcacacca caccagaaac                                     20

<210> SEQ ID NO 70
<211> LENGTH: 20
<212> TYPE: DNA

```
<213> ORGANISM: Human

<400> SEQUENCE: 70
ctcagactga cctcggactg                                              20

<210> SEQ ID NO 71
<211> LENGTH: 21
<212> TYPE: DNA
<213> ORGANISM: Human

<400> SEQUENCE: 71
ctctgggaat caaattcgag g                                            21

<210> SEQ ID NO 72
<211> LENGTH: 20
<212> TYPE: DNA
<213> ORGANISM: Human

<400> SEQUENCE: 72
gtctttcagc caatccaagg                                              20

<210> SEQ ID NO 73
<211> LENGTH: 19
<212> TYPE: DNA
<213> ORGANISM: Human

<400> SEQUENCE: 73
gacaactctg acagccagg                                               19

<210> SEQ ID NO 74
<211> LENGTH: 19
<212> TYPE: DNA
<213> ORGANISM: Human

<400> SEQUENCE: 74
gtcagaactc ccaaacagg                                               19

<210> SEQ ID NO 75
<211> LENGTH: 21
<212> TYPE: DNA
<213> ORGANISM: Human

<400> SEQUENCE: 75
ctacatgcag atgacatggt g                                            21

<210> SEQ ID NO 76
<211> LENGTH: 18
<212> TYPE: DNA
<213> ORGANISM: Human

<400> SEQUENCE: 76
ggccaaggtg cataggtg                                                18

<210> SEQ ID NO 77
<211> LENGTH: 20
<212> TYPE: DNA
<213> ORGANISM: Human

<400> SEQUENCE: 77
catgttccct gtagcacatc                                              20

<210> SEQ ID NO 78
<211> LENGTH: 24
```

```
<212> TYPE: DNA
<213> ORGANISM: Human

<400> SEQUENCE: 78
cgtttccatt acttccattt cctg                                              24

<210> SEQ ID NO 79
<211> LENGTH: 18
<212> TYPE: DNA
<213> ORGANISM: Human

<400> SEQUENCE: 79
cccgcccttt catcatcc                                                     18

<210> SEQ ID NO 80
<211> LENGTH: 19
<212> TYPE: DNA
<213> ORGANISM: Human

<400> SEQUENCE: 80
gctccccaaa gtagccttc                                                    19

<210> SEQ ID NO 81
<211> LENGTH: 19
<212> TYPE: DNA
<213> ORGANISM: Human

<400> SEQUENCE: 81
cacgaggcgc catttgctg                                                    19

<210> SEQ ID NO 82
<211> LENGTH: 19
<212> TYPE: DNA
<213> ORGANISM: Human

<400> SEQUENCE: 82
ctggaggcca ggcaacgtg                                                    19

<210> SEQ ID NO 83
<211> LENGTH: 18
<212> TYPE: DNA
<213> ORGANISM: Human

<400> SEQUENCE: 83
cctccacctg aagatgcc                                                     18

<210> SEQ ID NO 84
<211> LENGTH: 19
<212> TYPE: DNA
<213> ORGANISM: Human

<400> SEQUENCE: 84
ctgagatcca ggtgaatgg                                                    19

<210> SEQ ID NO 85
<211> LENGTH: 2945
<212> TYPE: DNA
<213> ORGANISM: Human

<400> SEQUENCE: 85
ggagagagga cctatttcta cctaaggaca ttcccggaag gcaatgggtt tcaaacaata       60
tcctgaagag actcatctcg gggaactaag caggtggtaa tcagagaaca cagagccccc      120
```

-continued

```
ggaagaattt tatggcattt caggcaagcc acaggccagc ctggggaaaa agcaggaaga     180
aaaactggca atacgagggc ccaacccaaa agttattcct gaagagaaac aacgtgtcag     240
caccagatgg gccttcagac cccagcatct ccgcgagcag tgagcaaagc ggggcacagc     300
agcctcccgg tttacaggtt gaaaggattg ttgacaaaag gaaaaataaa aagggaaga     360 cagagtattt ggttcggtgg aaaggctatg acagcgagga cgacacttgg gagccggaac     420
agcacctcgt gaactgtgag gaatacatcc acgacttcaa cagacgccac acggagaagc     480
agaaggagag cacattgacc agaacaaaca ggacctctcc caacaatgct aggaaacaaa     540
tctccagatc caccaacagc aacttttcta agacctctcc taaggcactc gtgattggga     600
aagaccacga atccaaaaac agccagctgt ttgctgccag ccagaagttc aggaagaaca     660
cagctccatc tctctccagc cggaagaaca tggacctagc gaagtcaggt atcaagatcc     720
tcgtgcctaa aagccccgtt aagagcagga ccgcagtgga cggctttcag agcgagagcc     780
ctgagaaact ggaccccgtc gagcagggtc aggaggacac agtggcaccc gaagtggcag     840
cggaaaagcc ggtcggagct ttattgggcc ccggtgccga gagggccagg atggggagca     900
ggcccaggat acacccacta gtgcctcagg tgcccggccc tgtgactgca gccatggcca     960
caggcttagc tgttaacggg aaaggtacat ctccgttcat ggatgcatta acagccaatg    1020
ggacaaccaa catacagaca tctgttacag gagtgactgc cagcaaaagg aaatttattg    1080
acgacagaag agaccagcct tttgacaagc gattgcgttt cagcgtgagg caaacagaaa    1140
gtgcctacag atacagagat attgtggtca ggaagcagga tggcttcacc cacatcttgt    1200
tatccacaaa gtcctcagag aataactcac taaatccaga ggtaatgaga gaagtccaga    1260
gtgctctgag cacggccgct gccgatgaca gcaagctggt actgctcagc gccgttggca    1320
gcgtcttctg ttgtggactt gactttattt attttatacg acgtctgaca gatgacagga    1380
aaagagaaag cactaaaatg gcagaagcta tcagaaactt cgtgaatact ttcattcaat    1440
ttaagaagcc cattattgta gcagtcaatg gcccagccat tggtctagga gcatctatat    1500
tgcctctttg cgatgtggtt tgggctaatg aaaaggcttg gtttcaaaca ccctatacca    1560
ccttcggaca gagtccagat ggctgttcta ccgttatgtt tcccaagata atgggaggag    1620
catctgcaaa cgagatgctg ctcagtggac ggaagctgac agcgcaggag gcgtgtggca    1680
agggcctggt ctcccaggtg ttttggcccg ggacgttcac tcaggaagtg atggttcgca    1740
ttaaggagct tgcctcgtgc aatccagttg tgcttgagga atccaaagcc ctcgtgcgct    1800
gcaacatgaa gatggagctg gagcaggcca acgagaggga gtgtgaggtg ctgaagaaaa    1860 tctgggctc ggcccagggg atggactcca tgttaaagta cttgcagagg aagatcgatg    1920
agttctgagt gtcgggctgc ccactggtga caccgggatc gggctgagca ggagaacatc    1980
accggctcca gttcccctga tccattctca cagcctgaaa caagctcacc cgtagcttac    2040
gcttggaagc aggactggga acatccacgc tatttattat cgaggagttt taaagtactg    2100
taactttaaa ataaataact acaaagcttc tttgtcvaaa cgtcattatt ttatacttat    2160
atacacgcag gtgtaaaagt ataaaggtga gcactagact gctcttagaa gctctaattt    2220
ttgttttctt tggctagtac tgtataaaaa acagaattgt gttttattgg ttttggatga    2280
cagaaaagtc tggaataatg tttgtttttcc tcatttcttc cttctagaac acagaatcta    2340 aggggggtgtt agccagcctc gcctccctgc cccacgtaga gacacagagt gatgtgaggc    2400 gttggcttttt tctccaagaa ggtacagata cctcagattc gggaaactca aaatcaaaag    2460
acttagcttc taggataaat acttctgatg aaaaatccgc tgaggagcat accccaaacc    2520
```

```
agacatatgc ttaggattca tgctgagata tcaattggtt tccccttctt tttaaaatac    2580
gtccagttct tacccagtta acatgaagaa accactgtct ctagaagaaa gcttgttttg    2640
cagtattagt gaatcactga atagcttaag tatgactatc taagttataa gttagtcttt    2700
agtgggtttt aaatagtttt tctgacccct ctgaaaaata actacataag tgcttcttgt    2760
tgctgggtga gaaatactac tttatagaca gttttggttt tctgtttgca gatatgattg    2820
atgtatttca ccaaaataaa atatttttat gtttataaag tgtaattttt aggttcactt    2880
agaatatatt ttatttaata agttaaaatt cttttggcac actattaaat gcaaaaactc    2940
ctttc                                                                2945

<210> SEQ ID NO 86
<211> LENGTH: 2983
<212> TYPE: DNA
<213> ORGANISM: Human

<400> SEQUENCE: 86
ctttgaggtg gtttagcatc ccacttgttc cttgaggaca tctgttccta cctaagagca      60
ctcacctgag atgctcaaag gtccagaaga aacacttctc gggtgacaaa gcaggtggtg     120
accagagaac agaggccccc caaaatttt atggcattca aggcaaagca cagccaaccc      180
ggagggaaag caagagtcca gcctggaaat acatagccca acccgaaggt tatctctgaa     240
ggaaaacaat gggcataggc aatagccagc ctaattcaca ggaagcccag ctctgcacac     300
ttccagagaa agctgaacaa cctactgatg ataacacctg ccagcaaaat aatgtggttc     360
ctgcaacagt ctcagaaccc gatcaagcgt cccctgcaat tcaagacgcg gagactcagg    420
tggaaagtat cgttgacaaa aggaaaaaca agaaagggaa gacagaatat ctggtgcggt     480
ggaaaggcta tgacagtgag gatgacacgt gggagcctga gcagcacctg gtgaactgtg    540
aggaatacat ccatgacttc aaccggcgcc acaacgagag gcaaaaggaa ggtagcctgg     600
ctcgtgccag cagagcctcc cccagcaacg cccggaagca gatttccagg tccacccaca    660
gcactctctc caagaccaac tccaaagcac ttgtggtagg caaagatcat gagtccaaaa     720
gcagccagct gttggctgcc agccagaagt tcaggaaaaa cccagcccca tctcttgcaa     780
accgcaagaa catggacctc gccaagtcag ggatcaaaat tctcgtgcct aagagccccg     840
ttaagggcag gacctcggtt gatggctttc aggggggagag ccccgagaag ctggaccctg    900
tggatcaggg tgccgaggac actgtagccc cagaggtgac tgcagagaag cccactgggg    960
ctttgctggg ccctggtgcg gagcgagcca ggatggggag caggcccga atacatccac     1020 tagtgcctca ggtttctggc cccgtgactg ctgccatggc cacaggctta gctgttaatg    1080
gaaaaggtac atctccattc atggatgcgc tagcagccaa cggaacagtc accatacaga    1140
catccgtaac aggagtgaca gccgggaaaa ggaaattat tgacgacaga agagaccaac    1200
cttttgacaa gcggttgcgt ttcagtgtga ggcagacaga gagtgcctac agatacagag     1260
atattgtcgt caggaagcaa gatggcttca cccacatctt gttatccaca aaatcgtcag    1320
agaataactc actaaaccca gaggtgatga agaagtrca gagcgccctg agcacagctg    1380
cagccgacga cagcaagctg gttctgctca gcgccgtggg cagcgtcttc tgctgtggtc    1440
tggactttat ttattttatt cggcgcctca cagatgaccg aaagagagaa agcactaaaa    1500
tggcagacgc tatcagaaac ttcgtgaata ctttcattca gtttaagaag cctattattg    1560
tagctgttaa tggcccagcc attggactag gagcatccat attgcctctt tgtgatgtgg    1620
```

```
tttgggctaa cgaaaaggct tggtttcaaa caccctatac caccttcgga cagagtccag    1680
atggctgctc taccgttatg tttcccaaga ttatgggagg agcatctgcg aatgaaatgc    1740
tgttcagtgg gcggaagttg acggcacagg aggcctgtgg caagggtctg gtctcccagg    1800
tgttttggcc aggaaccttc acacaggaag tcatggttcg aatcaaggag ctggcttcat    1860
gtaacccagt tgtcctggag gaatccaaag ccctggtgcg ctgcaatatg aagatggagc    1920
tagagcaggc caatgagaga gaatgtgaag tgctgaagaa gatctggggc tccgcccagg    1980
gcatggactc catgttaaag tacttacaga ggaaaatcga tgagttctga tgggcaggct    2040
gagcaggaca tcggtggctc ccacttgcta cgtcgtcctg cagtggctcg tgcttggagg    2100
cagaactgga aacatccgag ctatttattg ccgcggagtt tttaagtact gtaactttaa    2160
aataaataca aagcttcttt gtctaagcgt ctttatttta tactcatgta tacacaagta    2220
taaaaatgta attgagcact aggctgctct tggaagctct aattttcttg taagctagtt    2280
gtggattttt gttttgtttt tgtttttaaa aggaattatg ttttcatttt gggtgacaga    2340
agagtttgaa ataatgtttg ttttactctt ttttttttc cttaaatcta gatcacagac    2400
cctcaaaatt actagccagc cttctccccc tccctctact gaaacatgta gaaatactta    2460
aacatgttcc tgcctctagg ggggaggggg aggtgtgagt acctcaatgc tgaaaacagt    2520
tctgatcaaa cttaagacca acctggtaaa aaaagcatca ctgatggaaa atcccaccca    2580 cggggggcgtg ggtttctgct gaaatgcccg ccgctctacc tttcttactg tcccattctt    2640
acccagccac cgtgaagagc ccagtgtctg gaggaaagca ggtggtccag tgtctgtgag    2700
tcactccgta gctcgagtgt tacttgctaa gttatgaatt agcattagtg ggtttaaata    2760 gttttttctga ccctttttga aaaataacta cataagtact ccttgtggct gggtgagaaa    2820
tactactttg catagttttg tttgtctatc tgcagatatg attgctgtat tacaccaaaa    2880 gtattttta tgtttataaa gtgtaattttt taggttcact tagaatatat tttatttaat    2940
ttaaaattct cttggcacac tattaaatac gtaaactcct ttc                      2983

<210> SEQ ID NO 87
<211> LENGTH: 542
<212> TYPE: DNA
<213> ORGANISM: Human

<400> SEQUENCE: 87
gttgcgagac gttgagctgc ggaagatgag tccaaagccg agagcctcgg gacctccggc     60
caaggccacg gaggcaggaa agaggaagtc ctcctctcag ccgagcccca gtgacccgaa    120
gaagaagact accaaggtgg ccgagaaggg aaaagcagtt cgtagaggga gacgcgggaa    180 gaaagggct gcgacaaaga tggcggccgt gacggcacct gaggcggaga gcgggccagc    240
ggcacccggc cccagcgacc agcccagcca ggagctccct cagcacgagc tgccgccgga    300
ggagccagtg agcgagggga cccagcacga ccccccgagt caggaggccg agctggagga    360
accactgagt caggagagcg aggtggaaga accactgact gtgtggatgg ccagcttttc    420
ccctgtctcc gagagcagcg actaagttca ggcccagccg ccagacctca gagatctcac    480
cagcggggtg cttgccattc tgaagataat aaaatgaatg tgttgcaaat tgaaaaaaaa    540
aa                                                                  542

<210> SEQ ID NO 88
<211> LENGTH: 703
<212> TYPE: DNA
<213> ORGANISM: Human
```

```
<400> SEQUENCE: 88
cggaagatga gtccaaagcc gagagcctcg ggacctccgg ccaaggccac ggaggcagga        60
aagaggaagt cctcctctca gccgagcccc agtgacccga agaagaagac taccaaggtg      120
gccaagaagg gaaaagcagt tcgtagaggg agacgcggga agaaaggggc tgcgacaaag      180
atggcggccg tgacggcacc tgaggcggag agcgggccag cggcacccgg ccccagcgac      240
cagcccagcc aggagctccc tcagcacgag ctgccgccgg aggagccagt gagcgagggg      300
acccagcacg acccccctgag tcaggaggcc gagctggagg aaccactgag tcaggagagc      360
gaggtggaag aaccactgag tcaggagagc caggtggagg aaccactgag tcaggagagc      420
gaggtggagg aaccgctgag tcaggagagc caggtggaag aaccactgag tcaggagagc      480
gaggtggagg aaccactgag tcaggagagc caggtggagg aaccactgag tcaggagagc      540
gagatggaag aactaccgag tgtgtagacg gccagctact cccctatctc cgagagcagc      600
gactaagttc aggcccagcc gccagacctc agagatctca ccagcggggt gcttgccatt      660
ctgaagataa taaaatgaat gtgttgcaaa ttgaaaaaaa aaa                        703

<210> SEQ ID NO 89
<211> LENGTH: 9439
<212> TYPE: DNA
<213> ORGANISM: Human

<400> SEQUENCE: 89
cgttgcgaga cgttgagctg cggaagatga gtccaaagcc gagagcctcg ggacctccgg       60
ccaaggccac ggaggcagga aagaggaagt cctcctctca gccgagcccc agtgacccga      120
agaagaagac taccaaggtg gccaagaagg gaaaagcagt tcgtagaggg agacgcggga      180
agaaaggggc tgcgacaaag atggcggccg tgacggcacc tgaggcggag agcgggccag      240
cggcacccgg ccccagcgac cagcccagcc aggagctccc tcagcacgag ctgccgccgg      300
aggagccagt gagcgagggg acccagcacg acccccctgag tcaggaggcc gagctggagg      360
aaccactgag tcaggagagc gaggtggaag aaccactgag tcaggagagc caggtggagg      420
aaccactgag tcaggagagc gaggtggaag aaccactgag tcaggagagc caggtggagg      480
aaccactgag tcaggagagc gaggtggagg aaccactgag tcaggagagc caggtggagg      540
aaccactgag tcaggagagc gagatggaag aaccactgag tcaggagagc caggtggagg      600
aaccaccgag tcaggagagc gagatggaag aactaccgag tgtgtagacg gccaagtact      660
cccctatctc cgagagcagc gactaagttc aggcccagcc gccagacctc agagatctca      720
ccagcggggt gcttgccatt ctgaagataa taaaatgaat gtgttgcaaa ttgaaaaaaa      780
aaacattcgg ttttaccagc cagcagtgac tcgaggttca atggcatcat aatatggatc      840
tagtagggga gatactgaat agcatagcca aagacctgct gacaatggct ccgctaagtc      900
tttcaccaag acctgctgac aatggctctg tagccagcct cttcgactcc tttctggcgg      960
ttacgagccc atctttgtca gtttacctgc caattttcca catcaaccgg ctcaaaatcc     1020
actgacgcaa gcgatatctc accaccctcc ctgagcagca actaaggtca tcaacatggg     1080
aagcacccag gaccatgtga tatggctaat tccctctttta cgcatgaccc actcatggag     1140
aagggtaggg tcacactcag cctctttacg agcacaccac accagaaacc tcagactgac     1200
ctcggactgc tctgggaatc aaattcgagg gtctttcagc caatccaagg gacaactctg     1260
acagccaggg tcagaactcc caaacaggct acatgcagat gacatggtgg gccaaggtgc     1320
```

```
ataggtgcat gttccctgta gcacatccgt ttccattact tccatttcct gcccgccctt   1380
tcatcatccg ctccccaaag tagccttcca cgaggcgcca tttgctgctg gaggccaggc   1440
aacgtgcctc cacctgaaga tgccctgaga tccaggtgaa tggggagaga ggacctattt   1500
ctacctaagg acattcccgg aaggcaatgg gtttcaaaca atatcctgaa gagactcatc   1560
tcggggaact aagcaggtgg taatcagaga acacagagcc cccggaagaa ttttatggca   1620
tttcaggcaa gccacaggcc agcctgggga aaaagcagga agaaaaactg gcaatacgag   1680
ggcccaaccc aaaagttatt cctgaagaga acaacgtgt cagcaccaga tgggccttca    1740
gaccccagca tctccgcgag cagtgagcaa agcggggcac agcagcctcc cggtttacag   1800
gttgaaagga ttgttgacaa aaggaaaaat aaaaagggga agacagagta tttggttcgg   1860
tggaaaggct atgacagcga ggacgacact tgggagccgg aacagcacct cgtgaactgt   1920
gaggaataca tccacgactt caacagacgc cacacggaga agcagaagga gagcacattg   1980
accagaacaa acaggacctc tcccaacaat gctaggaaac aaatctccag atccaccaac   2040
agcaactttt ctaagacctc tcctaaggca ctcgtgattg ggaaagacca cgaatccaaa   2100
aacagccagc tgtttgctgc cagccagaag ttcaggaaga acacagctcc atctctctcc   2160
agccggaaga acatggacct agcgaagtca ggtatcaaga tcctcgtgcc taaaagcccc   2220
gttaagagca ggaccgcagt ggacggcttt cagagcgaga gccctgagaa actggacccc   2280
gtcgagcagg gtcaggagga cacagtggca cccgaagtgg cagcggaaaa gccggtcgga   2340
gctttattgg gccccggtgc cgagagggcc aggatgggga gcaggcccag gatacaccca   2400
ctagtgcctc aggtgcccgg ccctgtgact gcagccatgg ccacaggctt agctgttaac   2460
gggaaaggta catctccgtt catggatgca ttaacagcca atgggacaac caacatacag   2520
acatctgtta caggagtgac tgccagcaaa aggaaattta ttgacgacag aagagaccag   2580 cctttttgaca agcgattgcg tttcagcgtg aggcaaacag aaagtgccta cagatacaga   2640
gatattgtgg tcaggaagca ggatggcttc acccacatct tgttatccac aaagtcctca   2700
gagaataact cactaaatcc agaggtaatg agagaagtcc agagtgctct gagcacggcc   2760
gctgccgatg acagcaagct ggtactgctc agcgccgttg gcagcgtctt ctgttgtgga   2820
cttgacttta tttattttat acgacgtctg acagatgaca ggaaaagaga aagcactaaa   2880
atggcagaag ctatcagaaa cttcgtgaat actttcattc aatttaagaa gcccattatt   2940
gtagcagtca atgcccagc cattggtcta ggagcatcta tattgcctct ttgcgatgtg    3000
gtttgggcta atgaaaaggc ttggtttcaa acaccctata ccaccttcgg acagagtcca   3060
gatggctgtt ctaccgttat gtttcccaag ataatgggag gagcatctgc aaacgagatg   3120
ctgctcagtg gacggaagct gacagcgcag gaggcgtgtg gcaagggcct ggtctcccag   3180
gtgttttggc ccgggacgtt cactcaggaa gtgatggttc gcattaagga gcttgcctcg   3240
tgcaatccag ttgtgcttga ggaatccaaa gccctcgtgc gctgcaacat gaagatggag   3300
ctggagcagg ccaacgagag ggagtgtgag gtgctgaaga aaatctgggg ctcggcccag   3360
gggatggact ccatgttaaa gtacttgcag aggaagatcg atgagttctg agtgtcgggc   3420
tgcccactgg tgcaccgggg atcgggctga gcaggagaac atcaccggct ccagttcccc   3480
tgatccattc tcacagcctg aaacaagctc acccgtagct tacgcttgga agcaggactg   3540
ggaacatcca cgctatttat tatcgaggag ttttaaagta ctgtaacttt aaaataaata   3600
actacaaagc ttctttgtcv aaacgtcatt attttatact tatatacacg caggtgtaaa   3660
agtataaagg tgagcactag actgctctta gaagctctaa ttttttgtttt ctttggctag   3720
```

```
tactgtataa aaaacagaat tgtgtttat tggttttgga tgacagaaaa gtctggaata    3780
atgtttgttt tcctcatttc ttccttctag aacacagaat ctaagggggt gttagccagc    3840
ctcgcctccc tgccccacgt agagacacag agtgatgtga ggcgttggct ttttctccaa    3900
gaaggtacag atacctcaga ttcgggaaac tcaaaatcaa aagacttagc ttctaggata    3960
aatacttctg atgaaaaatc cgctgaggag catacccaa accagacata tgcttaggat    4020
tcatgctgag atatcaattg gtttccctt cttttaaaa tacgtccagt tcttacccag    4080
ttaacatgaa gaaaccactg tctctagaag aaagcttgtt ttgcagtatt agtgaatcac    4140
tgaatagctt aagtatgact atctaagtta taagttagtc tttagtgggt tttaaatagt    4200
ttttctgacc cttctgaaaa ataactacat aagtgcttct tgttgctggg tgagaaatac    4260
tactttatag acagttttgg ttttctgttt gcagatatga ttgatgtatt tcaccaaaat    4320
aaaatatttt tatgtttata aagtgtaatt tttaggttca cttagaatat attttattta    4380
ataagttaaa attcttttgg cacactatta aatgcaaaaa ctcctttcct ttgaggtggt    4440
ttagcatccc acttgttcct tgaggacatc tgttcctacc taagagcact cacctgagat    4500
gctcaaaggt ccagaagaaa cacttctcgg gtgacaaagc aggtggtgac cagagaacag    4560
aggcccccca aaattttat ggcattcaag gcaaagcaca gccaacccgg agggaaagca    4620
agagtccagc ctggaaatac atagcccaac ccgaaggtta tctctgaagg aaaacaatgg    4680
gcataggcaa tagccagcct aattcacagg aagcccagct ctgcacactt ccagagaaag    4740
ctgaacaacc tactgatgat aacacctgcc agcaaaataa tgtggttcct gcaacagtct    4800
cagaacccga tcaagcgtcc cctgcaattc aagacgcgga gactcaggtg gaaagtatcg    4860
ttgacaaaag gaaaaacaag aaagggaaga cagaatatct ggtgcggtgg aaaggctatg    4920
acagtgagga tgacacgtgg gagcctgagc agcacctggt gaactgtgag gaatacatcc    4980
atgacttcaa ccggcgccac aacgagaggc aaaaggaagg tagcctggct cgtgccagca    5040
gagcctcccc cagcaacgcc cggaagcaga tttccaggtc cacccacagc actctctcca    5100
agaccaactc caaagcactt gtggtaggca agatcatga gtccaaaagc agccagctgt    5160
tggctgccag ccagaagttc aggaaaaacc cagccccatc tcttgcaaac cgcaagaaca    5220
tggacctcgc caagtcaggg atcaaaattc tcgtgcctaa gagccccgtt aagggcagga    5280
cctcggttga tggctttcag ggggagagcc ccgagaagct ggaccctgtg gatcagggtg    5340
ccgaggacac tgtagcccca gaggtgactg cagagaagcc cactggggct ttgctgggcc    5400
ctggtgcgga gcgagccagg atggggagca ggccccgaat acatccacta gtgcctcagg    5460
tttctggccc cgtgactgct gccatggcca caggcttagc tgttaatgga aaaggtacat    5520
ctccattcat ggatgcgcta gcagccaacg gaacagtcac catacagaca tccgtaacag    5580
gagtgacagc cgggaaaagg aaatttattg acgacagaag agaccaacct tttgacaagc    5640
ggttgcgttt cagtgtgagg cagacagaga gtgcctacag atacagagat attgtcgtca    5700
ggaagcaaga tggcttcacc cacatcttgt tatccacaaa atcgtcagag ataactcac    5760 taaacccaga ggtgatgaaa gaagtrcaga gcgccctgag cacagctgca gccgacgaca    5820
gcaagctggt tctgctcagc gccgtgggca gcgtcttctg ctgtggtctg gactttattt    5880
attttattcg gcgcctcaca gatgaccgaa agagagaaag cactaaaatg gcagacgcta    5940
tcagaaactt cgtgaatact ttcattcagt ttaagaagcc tattattgta gctgttaatg    6000
gcccagccat tggactagga gcatccatat tgcctctttg tgatgtggtt tgggctaacg    6060
```

-continued

```
aaaaggcttg gtttcaaaca ccctatacca ccttcggaca gagtccagat ggctgctcta    6120
ccgttatgtt tcccaagatt atgggaggag catctgcgaa tgaaatgctg ttcagtgggc    6180
ggaagttgac ggcacaggag gcctgtggca agggtctggt ctcccaggtg ttttggccag    6240
gaaccttcac acaggaagtc atggttcgaa tcaaggagct ggcttcatgt aacccagttg    6300
tcctggagga atccaaagcc ctggtgcgct gcaatatgaa gatggagcta gagcaggcca    6360
atgagagaga atgtgaagtg ctgaagaaga tctggggctc cgcccagggc atggactcca    6420
tgttaaagta cttacagagg aaaatcgatg agttctgatg gcaggctga gcaggacatc     6480
ggtggctccc acttgctacg tcgtcctgca gtggctcgtg cttggaggca gaactggaaa    6540
catccgagct atttattgcc gcggagtttt taagtactgt aactttaaaa taaatacaaa    6600
gcttctttgt ctaagcgtct ttattttata ctcatgtata cacaagtata aaaatgtaat    6660
tgagcactag gctgctcttg gaagctctaa ttttcttgta agctagttgt ggattttgt     6720
tttgttttg ttttaaaag gaattatgtt ttcattttgg gtgacagaag agtttgaaat      6780
aatgtttgtt ttactctttt tttttttcct taaatctaga tcacagaccc tcaaaattac    6840
tagccagcct tctcccctc cctctactga aacatgtaga aatacttaaa catgttcctg     6900
cctctagggg ggaggggag gtgtgagtac ctcaatgctg aaaacagttc tgatcaaact     6960
taagaccaac ctggtaaaaa aagcatcact gatggaaaat cccacccacg ggggcgtggg    7020
tttctgctga aatgcccgcc gctctacctt tcttactgtc ccattcttac ccagccaccg    7080
tgaagagccc agtgtctgga ggaaagcagg tggtccagtg tctgtgagtc actccgtagc    7140
tcgagtgtta cttgctaagt tatgaattag cattagtggg tttaaatagt ttttctgacc    7200
cttttgaaa aataactaca taagtactcc ttgtggctgg gtgagaaata ctactttgca     7260
tagttttgtt tgtctatctg cagatatgat tgctgtatta caccaaaagt atttttatg     7320
tttataaagt gtaattttta ggttcactta gaatatattt tatttaattt aaaattctct    7380
tggcacacta ttaaatacgt aaactccttt cgttgcgaga cgttgagctg cggaagatga    7440
gtccaaagcc gagagcctcg ggacctccgg ccaaggccac ggaggcagga aagaggaagt    7500
cctcctctca gccgagcccc agtgacccga agaagaagac taccaaggtg gccgagaagg    7560
gaaaagcagt tcgtagaggg agacgcggga agaaggggc tgcgacaaag atggcggccg    7620
tgacggcacc tgaggcggag agcgggccag cggcacccgg ccccagcgac cagcccagcc    7680
aggagctccc tcagcacgag ctgccgccgg aggagccagt gagcgagggg acccagcacg    7740
acccccgag tcaggaggcc gagctggagg aaccactgag tcaggagagc gaggtggaag     7800
aaccactgac tgtgtggatg gccagctttt cccctgtctc cgagagcagc gactaagttc    7860
aggcccagcc gccagacctc agagatctca ccagcggggt gcttgccatt ctgaagataa    7920
taaaatgaat gtgttgcaaa ttgaaaaaaa aaacggaaga tgagtccaaa gccgagagcc    7980
tcgggacctc cggccaaggc cacggaggca ggaaagagga agtcctcctc tcagccgagc    8040
cccagtgacc cgaagaagaa gactaccaag gtggccaaga agggaaaagc agttcgtaga    8100
gggagacgcg ggaagaaagg ggctgcgaca agatggcgg ccgtgacggc acctgaggcg     8160
gagagcgggc cagcggcacc cggccccagc gaccagccca gccaggagct ccctcagcac    8220
gagctgccgc cggaggagcc agtgagcgag gggacccagc acgacccccct gagtcaggag    8280
gccgagctgg aggaaccact gagtcaggag agcgaggtgg aagaaccact gagtcaggag    8340
agccaggtgg aggaaccact gagtcaggag agcgaggtgg aggaaccgct gagtcaggag    8400
agccaggtgg aagaaccact gagtcaggag agcgaggtgg aggaaccact gagtcaggag    8460
```

```
agccaggtgg aggaaccact gagtcaggag agcgagatgg aagaactacc gagtgtgtag      8520
acggccagct actcccctat ctccgagagc agcgactaag ttcaggccca gccgccagac      8580
ctcagagatc tcaccagcgg ggtgcttgcc attctgaaga taataaaatg aatgtgttgc      8640
aaattgaaaa aaaaaacgtt gcgagacgtt gagctgcgga agatgagtcc aaagccgaga      8700
gcctcgggac ctccggccaa ggccacgagg cgaggaaaga ggaagtcctc ctctcagccg      8760
agccccagtg acccgaagaa gaagactacc aaggtggcca agaagggaaa agcagttcgt      8820
agagggagac gcgggaagaa aggggctgcg acaaagatgg cggccgtgac ggcacctgag      8880
gcggagagcg ggccagcggc acccggcccc agcgaccagc ccagccagga gctccctcag      8940
cacgagctgc cgccggagga gccagtgagc gaggggaccc agcacgaccc cctgagtcag      9000
gaggccgagc tggaggaacc actgagtcag gagagcgagg tggaagaacc actgagtcag      9060
gagagccagg tggaggaacc actgagtcag gagagcgagg tggaagaacc actgagtcag      9120
gagagccagg tggaggaacc actgagtcag gagagcgagg tggaggaacc actgagtcag      9180
gagagccagg tggaggaacc actgagtcag gagagcgaga tggaagaacc actgagtcag      9240
gagagccagg tggaggaacc accgagtcag gagagcgaga tggaagaact accgagtgtg      9300
tagacggcca agtactcccc tatctccgag agcagcgact aagttcaggc ccagccgcca      9360
gacctcagag atctcaccag cggggtgctt gccattctga agataataaa atgaatgtgt      9420
tgcaaattga aaaaaaaaa                                                   9439

<210> SEQ ID NO 90
<211> LENGTH: 2319
<212> TYPE: DNA
<213> ORGANISM: Human

<400> SEQUENCE: 90
ccagtgtaag agttccgcta ttcggtctca cacctacagt ggactacccg attttttcgct      60 tctcttcagg gatgagtcat gtggtggtga aaaatgaccc tgaactggac cagcagcttg      120
ctaatctgga cctgaactct gaaaaacaga gtggaggagc aagtacagcg agcaaagggc      180
gctatatacc tcctcactta aggaacaaag aagcatctaa aggattccat gataaagaca      240
gttcaggttg gagttgcagc aaagataagg atgcatatag cagttttggg tctcgagatt      300
ctagaggaaa gcctggttat ttcagtgaac gtggaagtgg atcaagggga agatttgatg      360
atcgtggacg gagtgactat gatggtattg gcaatcgtga aagacctggc tttggcagat      420
ttgaacggag tggacatagt cgttggtgtg acagtcagt tgaagatgat tggtcaaaac      480
cacttccacc aagtgaacgc ttggagcaag aactgttttc tggaggaaac acggggatta      540
actttgagaa atatgatgat ataccagtag aggcaaccgg cagtaactgt cctccacata      600
ttgagaattt tagcgatatt gacatgggag aaattatcat ggggaacatt gaacttactc      660
gctatactcg tcctactcca gtgcaaaaac atgccattcc tattattaag ggaaaaagag      720
acttagtggc ttgtgcccaa acaggatctg gaaaactgc agcatttctt ttacccatac      780
tgagtcagat atatacagat ggtccaggag aagctttgaa ggctgtgaag gaaaatggaa      840
ggtatgggcg ccgcaaacaa tatccaatat ccttggtttt agcccaaca agagaattgg      900 ctgtacagat ctatgaggaa gccagaaaat ttcctaccg atctagagtt cgtccttgtg      960
tagtttatgg tggtgctgat attggtcagc agattcggga cttagaacgt ggatgccact      1020
tgttagtagc cactccagga cgtctagtgg atatgatgga aagaggaaag attggattag      1080
```

```
acttctgcaa gtacttagtg ttggatgaag ctgataggat gctggatatg ggatttgaac    1140
ctcagatacg tcgtatagtt gaacaagata ctatgccacc aaaggggcgtt cgtcacacca    1200 tgatgtttag tgctactttt cctaaggaaa tacagatgct tgctcgtgac ttttttggatg   1260 aatatatctt tttggctgta ggcagagtag gctctacctc tgagaacatc acacagaaag    1320
tagtttgggt ggaagactta gataaacggt catttctact ggacatttta ggtgcaacag    1380
ggagtgattc acttacttta gtgtttgtgg agaccaaaaa gggagcagat tccctggagg    1440
atttcttata ccatgaagga tatgcttgta ctagtattca tggagaccgg tcacagagag    1500
atcgagagga ggcccttcac cagtttcgct caggaaaaag cccaattcta gtggctacag    1560
ctgtggcagc acgaggacta gacatttcaa atgtgagaca tgttatcaat tttgatttgc    1620
caagtgatat tgaagaatat gtgcatcgta ttggccgtac aggacgtgta ggaaacctgg    1680
gccttgccac ctcattcttt aatgaaaaaa atatgaatat tacaaaggat ttgttggatc    1740
ttcttgtaga agctaaacaa gaagtgcctt cttggttgga aaatatggct tatgaacacc    1800
actacaaggg tggcagtcgt ggacgatcta aaagtaatag attcagtgga ggatttggtg    1860
ccagagacta tcgacaaagt agtggttcca gcagttccgg ctttggtgct agtcgcggaa    1920
gcagcagccg cagtggtgga ggtggttacg gcgacagcag aggatttggt ggaggtggct    1980
atggaggctt ctacaatagt gatggatatg gaggaaatta taactcccag ggggttgact    2040
ggtggggcaa ctgaatctgc tttgcagcaa agtcaccctt acaaagaagc taatatggaa    2100
accacatgta acttagccag actatattgt gtagcttcaa gaacttgcag tacattacca    2160
gctgtgattc tcctgataat tcaagggagc tcaaagtcac aagaagaaaa atgaaaggaa    2220
aaaacagcag ccctattcag aaattggttt gaagatgtaa ttgctctagt ttggattaaa    2280
ctcttcccct cctgctttag tgccacccca aaaaaaaa                            2319
```

```
<210> SEQ ID NO 91
<211> LENGTH: 660
<212> TYPE: PRT
<213> ORGANISM: Human

<400> SEQUENCE: 91

Met Ser His Val Val Lys Asn Asp Pro Glu Leu Asp Gln Gln Leu
 1               5                  10                  15

Ala Asn Leu Asp Leu Asn Ser Glu Lys Gln Ser Gly Gly Ala Ser Thr
            20                  25                  30

Ala Ser Lys Gly Arg Tyr Ile Pro Pro His Leu Arg Asn Lys Glu Ala
        35                  40                  45

Ser Lys Gly Phe His Asp Lys Asp Ser Ser Gly Trp Ser Cys Ser Lys
    50                  55                  60

Asp Lys Asp Ala Tyr Ser Ser Phe Gly Ser Arg Asp Ser Arg Gly Lys
65                  70                  75                  80

Pro Gly Tyr Phe Ser Glu Arg Gly Ser Gly Ser Arg Gly Arg Phe Asp
                85                  90                  95

Asp Arg Gly Arg Ser Asp Tyr Asp Gly Ile Gly Asn Arg Glu Arg Pro
            100                 105                 110

Gly Phe Gly Arg Phe Glu Arg Ser Gly His Ser Arg Trp Cys Asp Lys
        115                 120                 125

Ser Val Glu Asp Asp Trp Ser Lys Pro Leu Pro Pro Ser Glu Arg Leu
    130                 135                 140

Glu Gln Glu Leu Phe Ser Gly Gly Asn Thr Gly Ile Asn Phe Glu Lys
145                 150                 155                 160
```

```
Tyr Asp Asp Ile Pro Val Glu Ala Thr Gly Ser Asn Cys Pro Pro His
            165                 170                 175
Ile Glu Asn Phe Ser Asp Ile Asp Met Gly Glu Ile Ile Met Gly Asn
            180                 185                 190
Ile Glu Leu Thr Arg Tyr Thr Arg Pro Thr Pro Val Gln Lys His Ala
            195                 200                 205
Ile Pro Ile Ile Lys Gly Lys Arg Asp Leu Val Ala Cys Ala Gln Thr
            210                 215                 220
Gly Ser Gly Lys Thr Ala Ala Phe Leu Leu Pro Ile Leu Ser Gln Ile
225                 230                 235                 240
Tyr Thr Asp Gly Pro Gly Glu Ala Leu Lys Ala Val Lys Glu Asn Gly
            245                 250                 255
Arg Tyr Gly Arg Arg Lys Gln Tyr Pro Ile Ser Leu Val Leu Ala Pro
            260                 265                 270
Thr Arg Glu Leu Ala Val Gln Ile Tyr Glu Glu Ala Arg Lys Phe Ser
            275                 280                 285
Tyr Arg Ser Arg Val Arg Pro Cys Val Val Tyr Gly Gly Ala Asp Ile
            290                 295                 300
Gly Gln Gln Ile Arg Asp Leu Glu Arg Gly Cys His Leu Leu Val Ala
305                 310                 315                 320
Thr Pro Gly Arg Leu Val Asp Met Met Glu Arg Gly Lys Ile Gly Leu
            325                 330                 335
Asp Phe Cys Lys Tyr Leu Val Leu Asp Glu Ala Asp Arg Met Leu Asp
            340                 345                 350
Met Gly Phe Glu Pro Gln Ile Arg Arg Ile Val Glu Gln Asp Thr Met
            355                 360                 365
Pro Pro Lys Gly Val Arg His Thr Met Met Phe Ser Ala Thr Phe Pro
            370                 375                 380
Lys Glu Ile Gln Met Leu Ala Arg Asp Phe Leu Asp Glu Tyr Ile Phe
385                 390                 395                 400
Leu Ala Val Gly Arg Val Gly Ser Thr Ser Glu Asn Ile Thr Gln Lys
            405                 410                 415
Val Val Trp Val Glu Asp Leu Asp Lys Arg Ser Phe Leu Leu Asp Ile
            420                 425                 430
Leu Gly Ala Thr Gly Ser Asp Ser Leu Thr Leu Val Phe Val Glu Thr
            435                 440                 445
Lys Lys Gly Ala Asp Ser Leu Glu Asp Phe Leu Tyr His Glu Gly Tyr
            450                 455                 460
Ala Cys Thr Ser Ile His Gly Asp Arg Ser Gln Arg Asp Arg Glu Glu
465                 470                 475                 480
Ala Leu His Gln Phe Arg Ser Gly Lys Ser Pro Ile Leu Val Ala Thr
            485                 490                 495
Ala Val Ala Ala Arg Gly Leu Asp Ile Ser Asn Val Arg His Val Ile
            500                 505                 510
Asn Phe Asp Leu Pro Ser Asp Ile Glu Glu Tyr Val His Arg Ile Gly
            515                 520                 525
Arg Thr Gly Arg Val Gly Asn Leu Gly Leu Ala Thr Ser Phe Phe Asn
            530                 535                 540
Glu Lys Asn Met Asn Ile Thr Lys Asp Leu Leu Asp Leu Leu Val Glu
545                 550                 555                 560
Ala Lys Gln Glu Val Pro Ser Trp Leu Glu Asn Met Ala Tyr Glu His
            565                 570                 575
```

-continued

```
His Tyr Lys Gly Gly Ser Arg Gly Arg Ser Lys Ser Asn Arg Phe Ser
            580                 585                 590

Gly Gly Phe Gly Ala Arg Asp Tyr Arg Gln Ser Ser Gly Ser Ser Ser
            595                 600                 605

Ser Gly Phe Gly Ala Ser Arg Gly Ser Ser Ser Arg Ser Gly Gly Gly
            610                 615                 620

Gly Tyr Gly Asp Ser Arg Gly Phe Gly Gly Gly Tyr Gly Gly Phe
625                 630                 635                 640

Tyr Asn Ser Asp Gly Tyr Gly Gly Asn Tyr Asn Ser Gln Gly Val Asp
                645                 650                 655

Trp Trp Gly Asn
            660
```

GENES IN THE NON-RECOMBINING REGION OF THE Y CHROMOSOME

RELATED APPLICATIONS

This application claims the benefit of U.S. Provisional Application No. 60/041,877, filed Apr. 11, 1997, entitled "Genes in the Non-Recombining Region of the Y Chromosome" by Bruce T. Lahn and David C. Page. The entire teachings of the above referenced application is expressly incorporated herein by reference.

GOVERNMENT SUPPORT

The invention described herein was made in whole or in part with government support under Grant Number HG00257 awarded by the National Institutes of Health. The United States Government has certain rights in the invention.

BACKGROUND OF THE INVENTION

The human Y chromosome is distinguished from all other nuclear chromosomes by four characteristics: the absence of recombination, its presence in males only, its common ancestry and persistent meiotic relationship with the X chromosome, and the tendency of its genes to degenerate during evolution (J. J. Bull, *Evolution of Sex Determining Mechanisms* (Benjamin Cummings, Menlo Park, Calif., 1983); J. A. Graves, *Annu. Rev. Genet.* 30:233 (1996); B. Charlesworth, *Curr. Biol.* 6:149 (1996); W. R. Rice, *BioScience,* 46, 331 (1996)). To be precise, these distinctive characteristics apply only to the non-recombining portion or region of the Y chromosome (NRY), which comprises 95% of the human Y chromosome. The remaining 5% of the chromosome is composed of two pseudoautosomal regions that maintain sequence identity with the X chromosome by meiotic recombination (H. J. Cooke et al., *Nature* 317:687 (1985); M. C. Simmler et al., *Nature* 317:692 (1985); D. Freije et al., *Science* 258:1784 (1992); G. A. Rappold, *Hum. Genet.* 92:315 (1993)). Given the NRY's peculiar characteristics, one might expect its gene content to be idiosyncratic. Since discovery of the Y chromosome in 1923, its gene content has been the subject of speculation. By the middle of this century, while studies of human pedigrees had identified many traits exhibiting autosomal or X-linked inheritance, no convincing cases of Y-linked inheritance could be found (T. S. Painter, *J. Exp. Zool.* (1923); C. Stern, *Am. J. Hum. Genet.* 9:147 (1957)). As a result, consensus began to emerge that the Y chromosome carried few, if any, genes. In 1959, reports of XO females and XXY males established the existence of a sex-determining gene on the human Y chromosome (P. A. Jacobs et al. *Nature* 183:302 (1959); C. E. Ford et al., *Lancet,* i:711 (1959)), but this was perceived as a special case on a generally desolate chromosome. Opionions began to change only during the past decade, when eight NRY transcription units (or families of closely related transcription units) were identified, most during regionally focused, positional closing experiments (D. C. Page et al., *Cell* 51:1091 (1987); A. H. Sinclair et al., *Nature* 346:240–244 (1990); J. Arnemann et al., *Genomics* 11: 108 (1991); E. C. Salido et al., *Am. J. Hum. Genet.* 50:303 (1992); E. M. Fisher et al., *Cell* 63:1205 (1990); K. Ma et al., *Cell* 75:1287 (1993); A. I. Agulnik et al., *Hum. Mol. Genet.* 3:879 (1994); R. Reijo et al., *Nat. Genet.* 10:383 (1995)). It was not known if there were more genes in the NRY.

SUMMARY OF THE INVENTION

A systematic search of the non-recombining region of the human Y chromosome (NRY) has identified 12 novel genes of gene families. All 12 novel genes, and six of eight NRY genes or families previously isolated by less systematic means, fall into two classes. The first class of genes exists, in one copy and is expressed in many organs; they have functional X homologs that escape X inactivation, as predicted for genes involved in Turner (XO) syndrome. The second class consists of Y-chromosomal gene families expressed specifically in testes, and may account for infertility among men with Y deletions.

The genes described herein, portions of the genes and DNA which hybridizes to genes or gene portions described are useful in diagnostic methods, such as a method to identify individuals in whom all or a portion of a gene or genes of the NRY is missing or altered. For example, Y chromosomal DNA from males with a known condition, such as infertility or reduced sperm count, can be assessed, using the gene(s) described herein, or characteristic portions thereof, to determine whether their DNA lacks some or all of the gene(s) described herein or contains an altered gene(s) (e.g., a gene in which there is a deletion, substitution, addition or mutation, compared to the sequences presented herein). Y chromosomal DNA (e.g., from a male with reduced sperm count or viability) can be assessed, using DNA described herein or DNA which hybridizes to DNA described herein, to determine whether the condition is associated with or caused by the occurrence of the gene or the gene alteration. For example, the presence or absence of all or a portion of a gene or genes shown to be necessary for fertility or adequate sperm count can be assessed, using DNA which hybridizes to the gene or genes of interest to determine the basis for their infertility or reduced sperm count. In one embodiment, the occurrence of one or more Y-specific genes or a characteristic portion of one or more Y-specific genes is assessed in Y chromosomal DNA. In another embodiment, deletion or alteration of one of the testis-specific (Y-specific) genes described is assessed, such as by a hybridization method in which DNA which hybridizes to one of the Y-specific genes described herein or a characteristic portion thereof is used to assess a DNA sample obtained from a male who has a reduced sperm count. Lack of hybridization of the Y-specific DNA used to DNA in the sample indicates that the gene is not present in sample DNA or is present in an altered form which does not hybridize to Y-specific DNA of the present invention. In another embodiment, an X-homologous gene or genes present on the NRY can be used to determine whether the gene is present in an individual or if it occurs in an altered form in the individual. Using known methods, such as hybridization methods, X or Y chromosomal DNA from an individual can be assessed for the presence or absence of one or more of the X-homologous genes or a characteristic portion of one or more X-homologous genes. X or Y chromosomal DNA can also be assessed for the presence or absence of an altered form of one or more of the X-homologous genes described. In the present methods, DNA can be analyzed for the occurrence of Y-specific DNA, X-homologous genes or both. For example, a "battery" or group of DNA probes (sequences) can be used to analyze sample DNA; the probes can include Y-specific DNA probes (e.g., DNA which hybridizes to a Y-specific gene), X-homologous gene probes (e.g., DNA which hybridizes to an X-homologous gene) or both types of probes. DNA described herein is also useful as primers in an amplification method, such as PCR, useful for identifying and amplifying Y-specific DNA or X-homologous genes in a sample (e.g., Y chromosomal DNA). Further, proteins or peptides encoded by the DNA described herein, such as proteins or peptides encoded by an X-homologous gene or proteins or peptides encoded by testis-specific DNA (a testis-specific gene), can be assessed in samples. This can be carried out, for example, using antibodies which recognize proteins or peptides of the present invention (proteins or peptides encoded by DNA described herein).

BRIEF DESCRIPTION OF THE DRAWINGS

FIGS. 2A–2E show the amino acid sequence alignments of the chromodomain (SEQ ID NO.: 1–6) and putative catalytic domain (SEQ ID NO.: 7–12) of human CDY genes with their respective homologs. Amino acid identities are indicated by boxing and for each protein, the first and last amino acid residues are numbered (with respect to the initiator methionine) and the total length of the protein is indicated. Chromodomain: SEQ ID NO.: 1, CDY (human); SEQ ID NO.: 2, HP1 (Drosophila); SEQ ID NO.: 3, Polycomb (Drosophila); SEQ ID NO.: 4, CHD1 (Drosophila); SEQ ID NO.: 5, Su(var) 3–9 (Drosophila; SEQ ID NO.: 6, PDD1 (Tetrahymena); Covalent modification domain: SEQ ID NO.: 7, CDY (human); SEQ ID NO.: 8, Enoyl-CoA Hydratase (Human); SEQ ID NO.: 9, 4-CBA-CoA dehalogenase (Arthrobacter) SEQ ID NO.: 10, Carnitine Racemase (*E. coli*); SEQ ID NO.: 11, Crotonase (C. acetobutylicum); SEQ ID NO.: 12, Naphthoate synthase (*E. coli*).

Figure 3A:
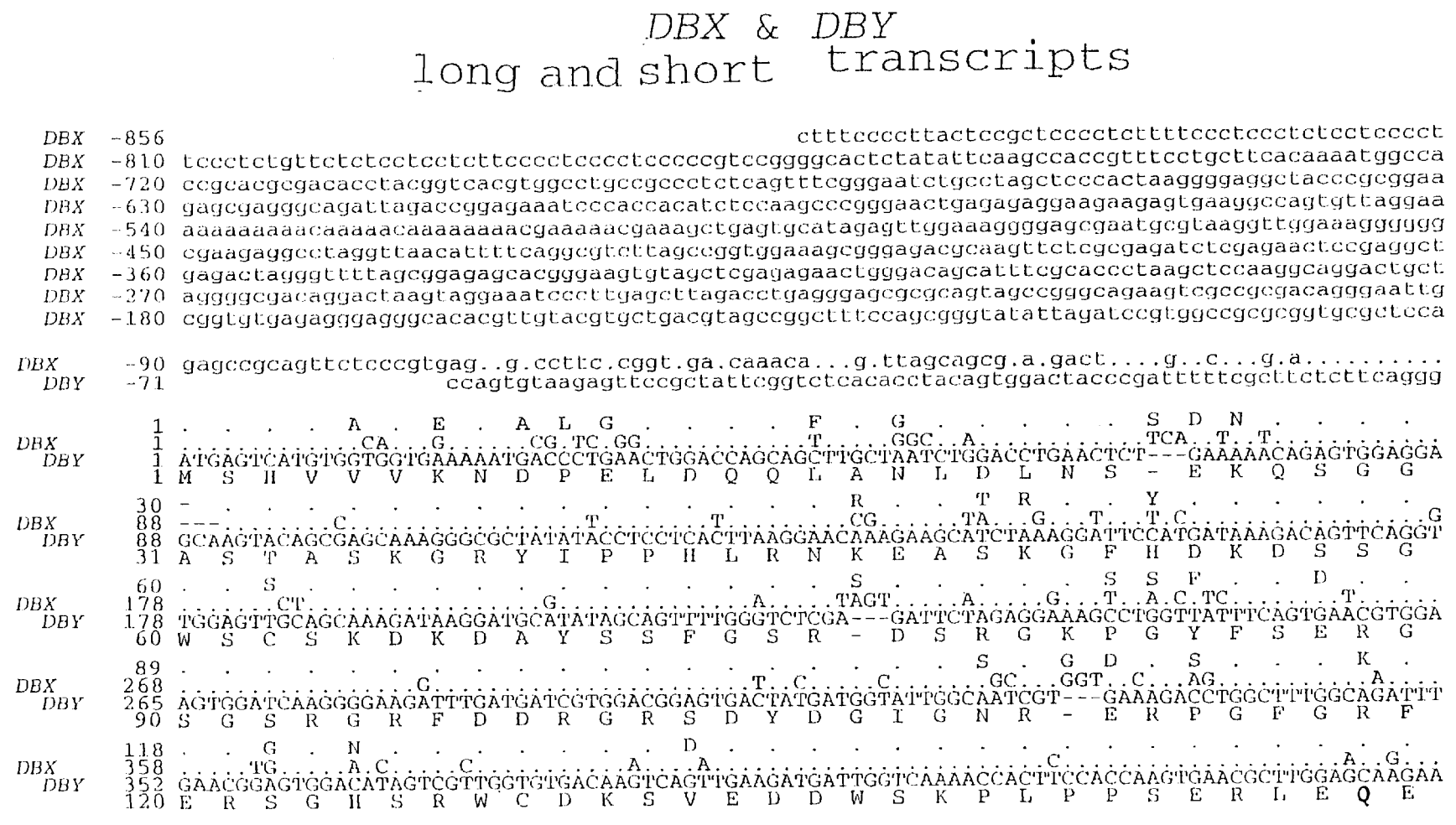
Figure 3B:
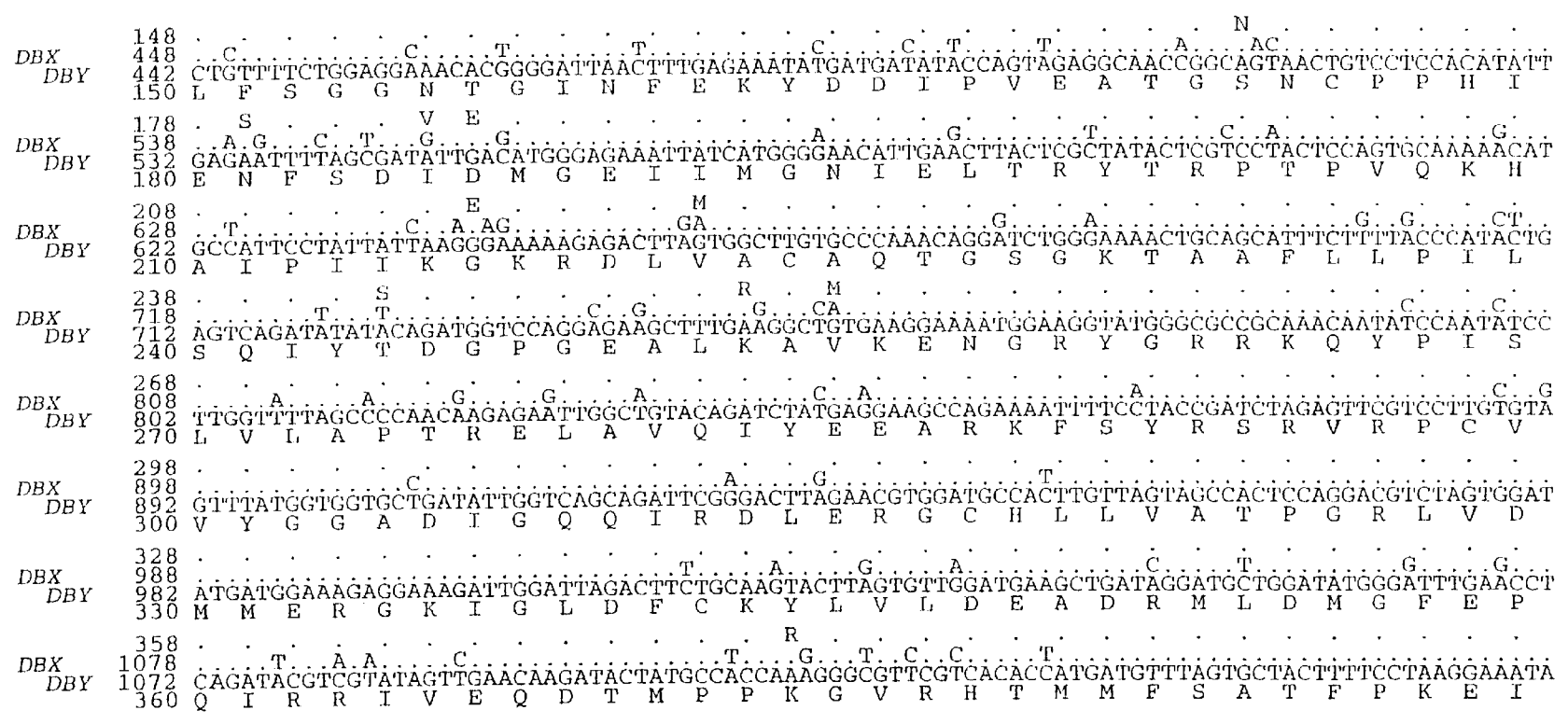
Figure 3C:
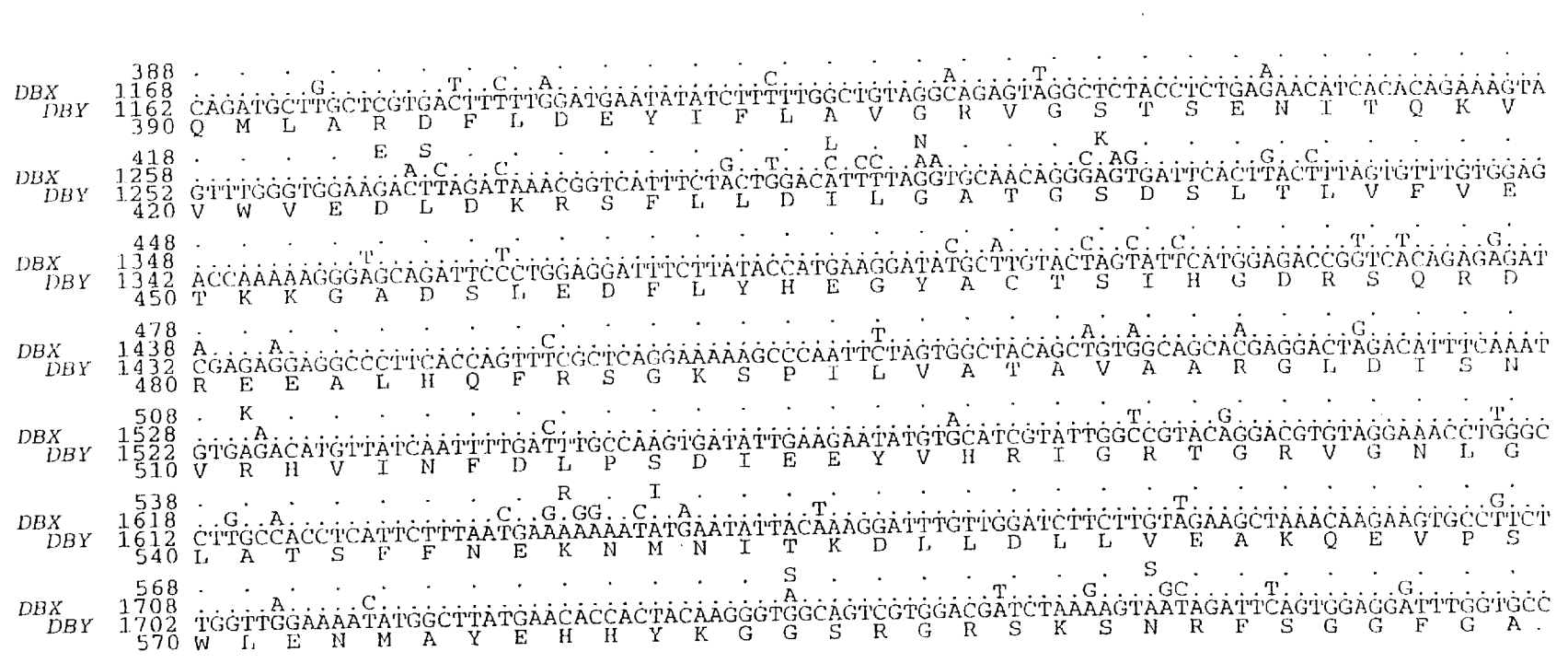
Figure 3F:
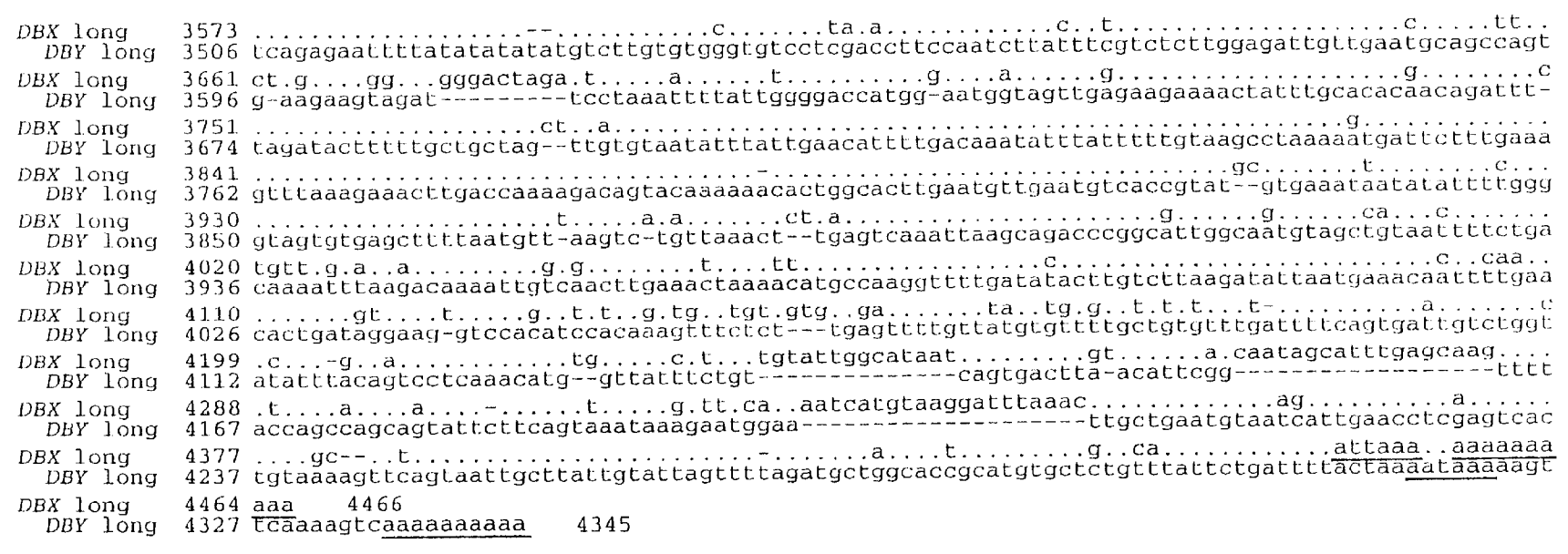

FIGS. 3A–3F are the nucleic acid sequence of DBX (long and short transcipts, SEQ ID NO: 13 and SEQ ID NO: 14, respectively) and the encoded amino acid sequences (SEQ ID NO: 15 and SEQ ID NO.: 16, respectively), DBY (long and short transcripts SEQ ID NO.: 17 and SEQ ID NO.: 90 respectively) and the encoded amino acid sequence (SEQ ID NO: 18 and SEQ ID NO.: 91 respectively). Dots in the DBX DNA and protein sequences indicate that the nucleic acids or amino acid residues are the same as those represented for DBY; dashes indicate a missing nucleic acid or amino acid residue.

Figure 4B:
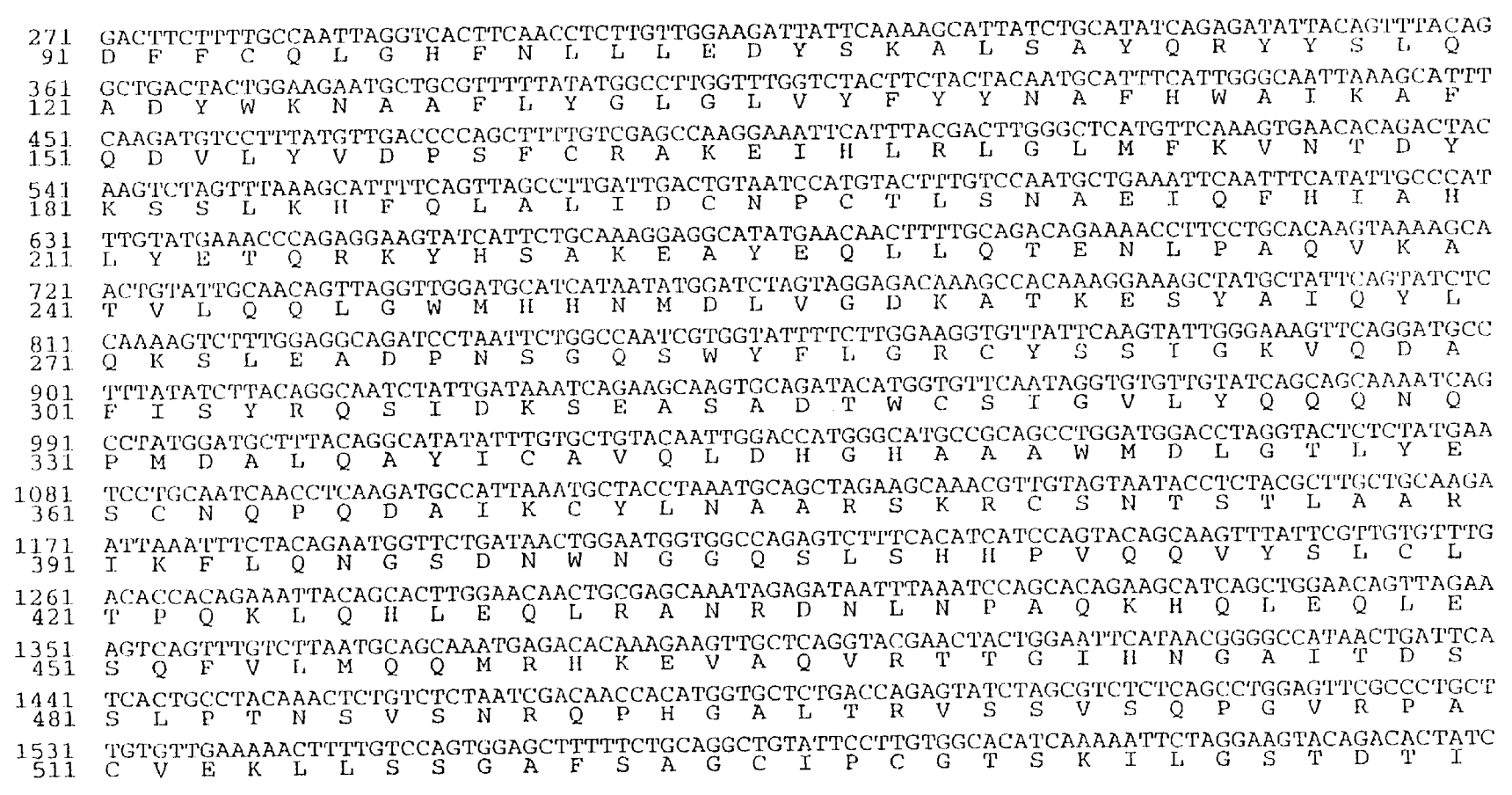
Figure 4C:
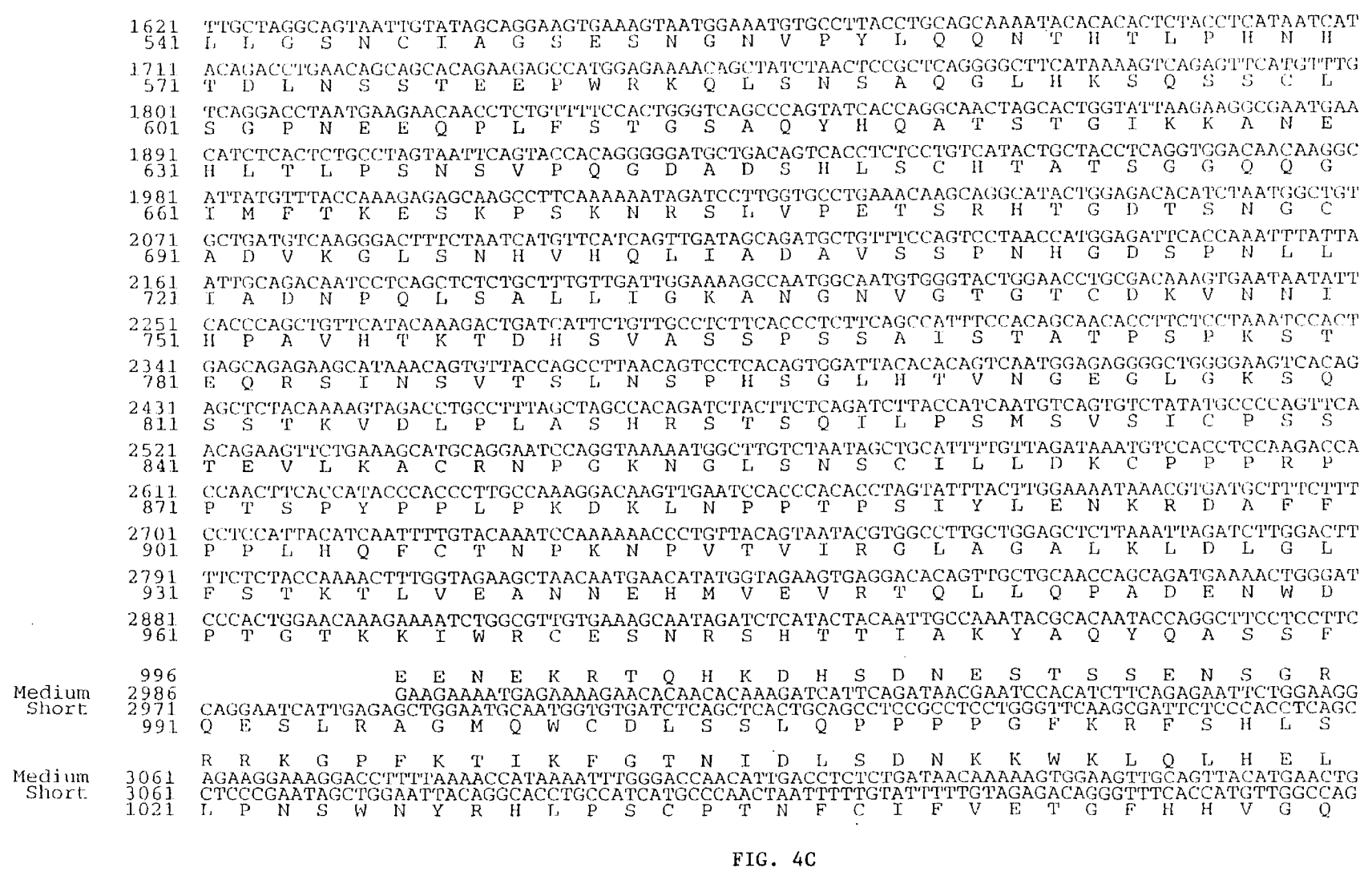
Figure 4E:
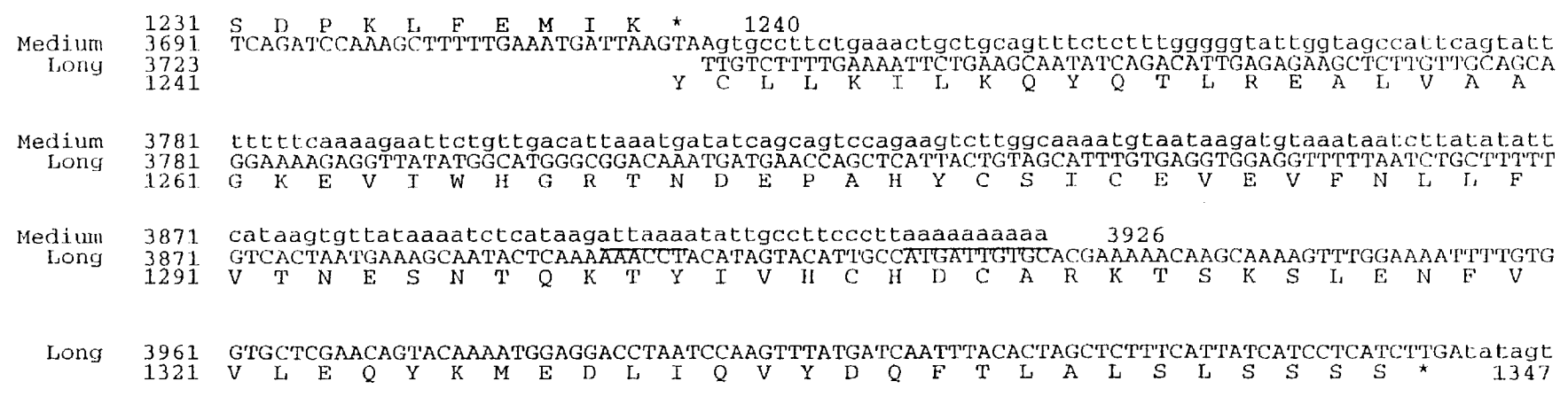

FIGS. 4A–4F present the nuclei acid sequences for three forms of TPRY (short, medium and long, SEQ ID NO: 19, SEQ ID NO: 20 and SEQ ID NO: 21, respectively) and the encoded amino acid sequences for the short, medium and long forms (SEQ ID NO: 22, SEQ ID NO.: 23 and SEQ ID NO: 24, respectively).

Figure 5:
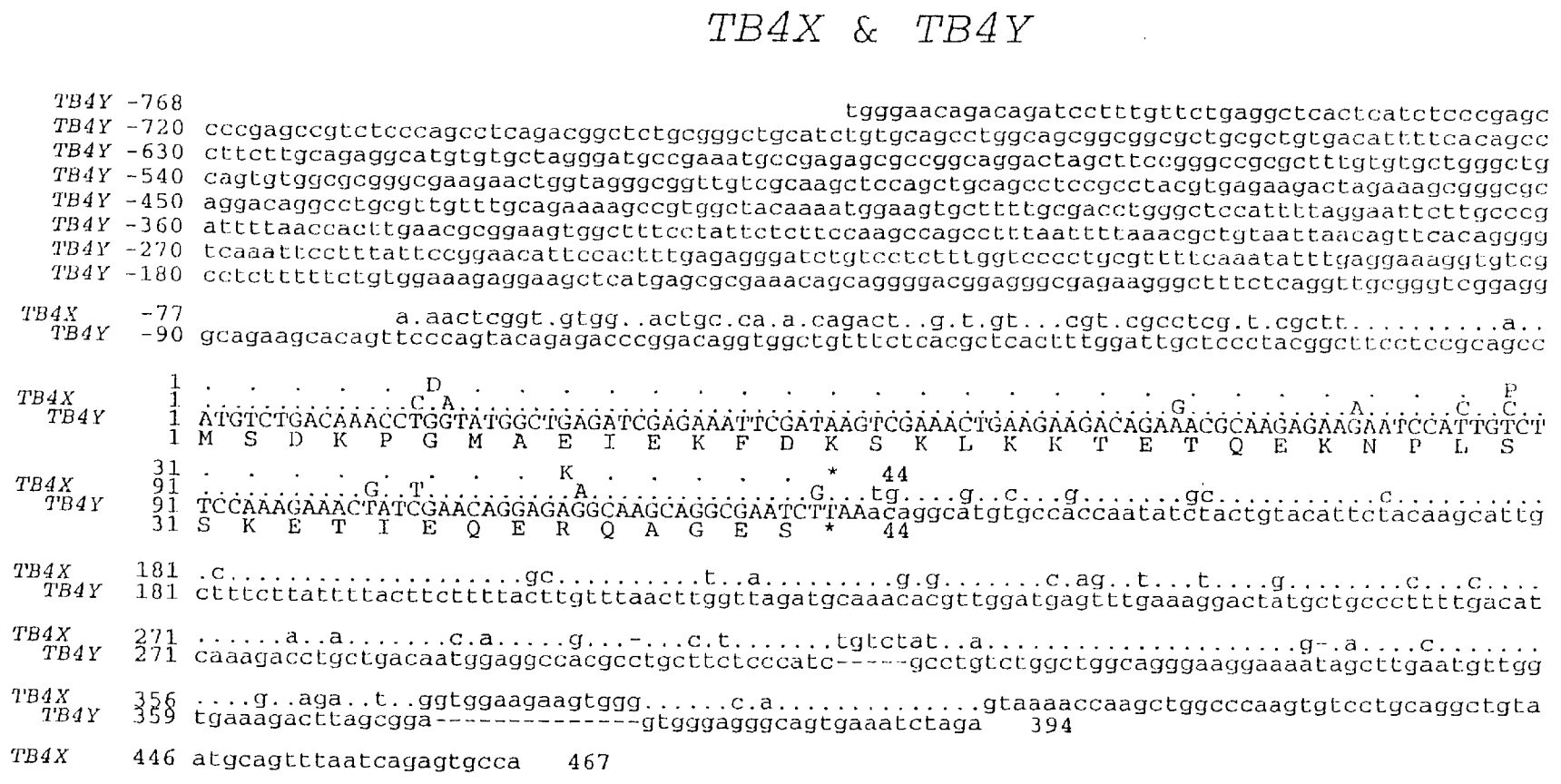

FIG. 5 presents the nucleic acid sequences of TB4X (SEQ ID NO: 25) and TB4Y (SEQ ID NO: 26) and the encoded amino acid sequences (SEQ ID NO: 27 and SEQ ID NO: 28, respectively). Dots in the TB4X DNA and protein sequences indicate that the nucleic acids or amino acid residues are the same as those represented for TB4Y.

Figure 6B:
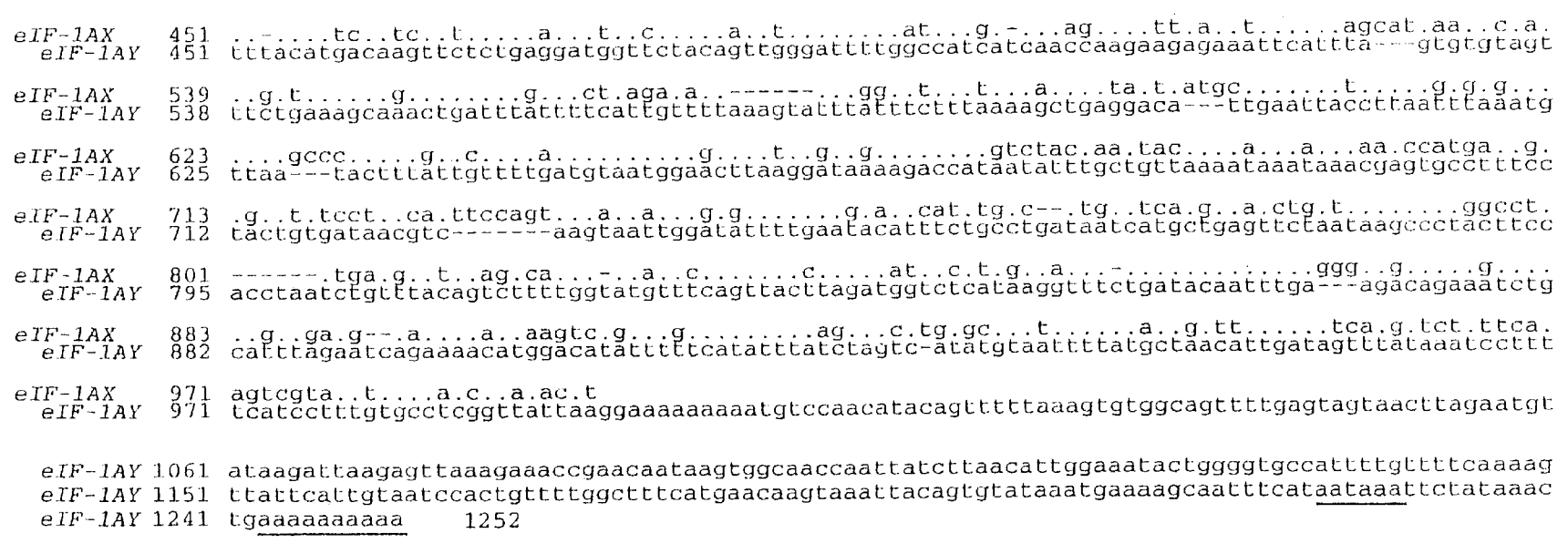

FIGS. 6A and 6B represent the nucleic acid sequences of EIF1AX (SEQ ID NO: 29) and EIF1AY (SEQ ID NO: 30) and the encoded amino acid sequences (SEQ ID NO: 31 and SEQ ID NO: 32, respectively).

Figure 7B:
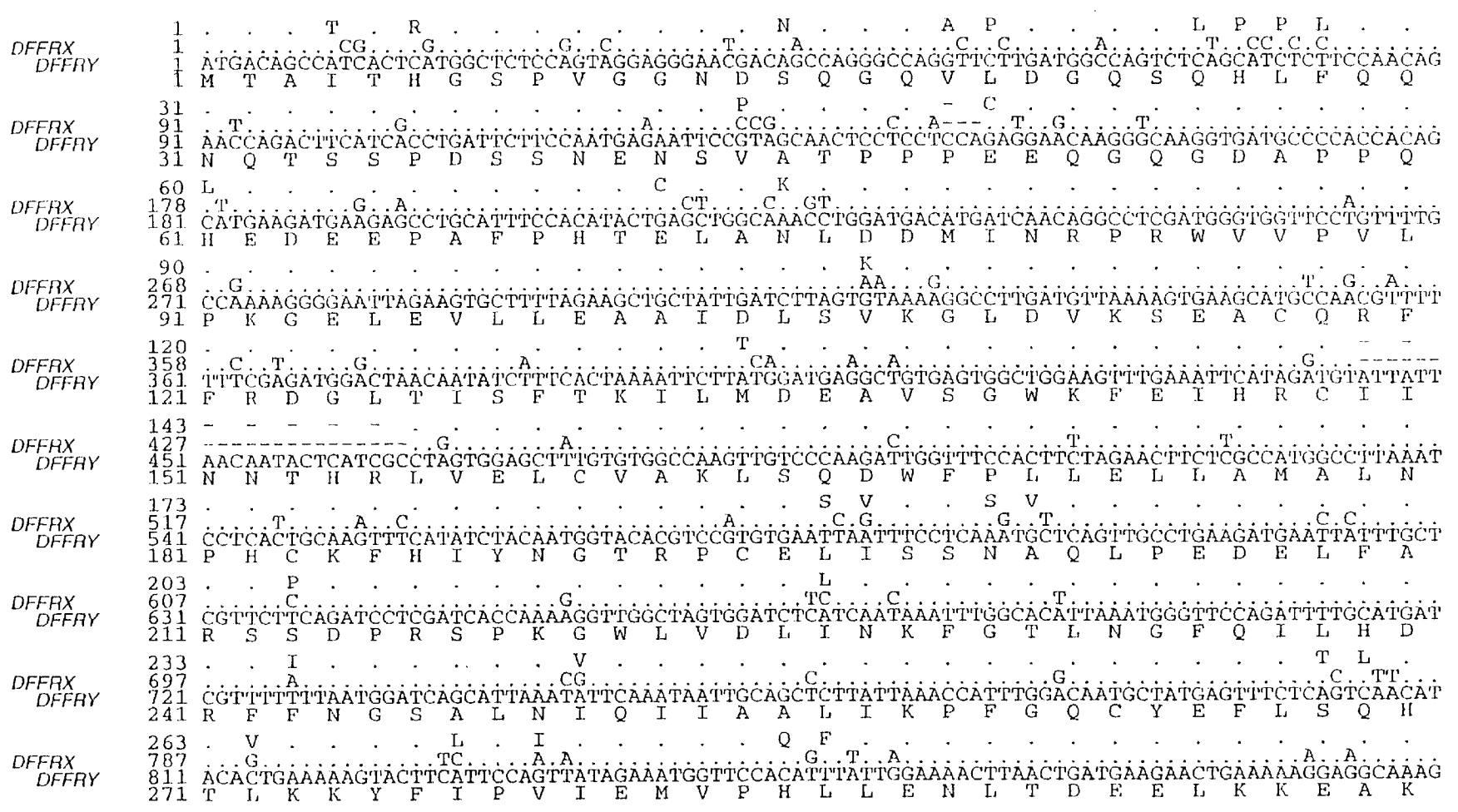
Figure 7C:
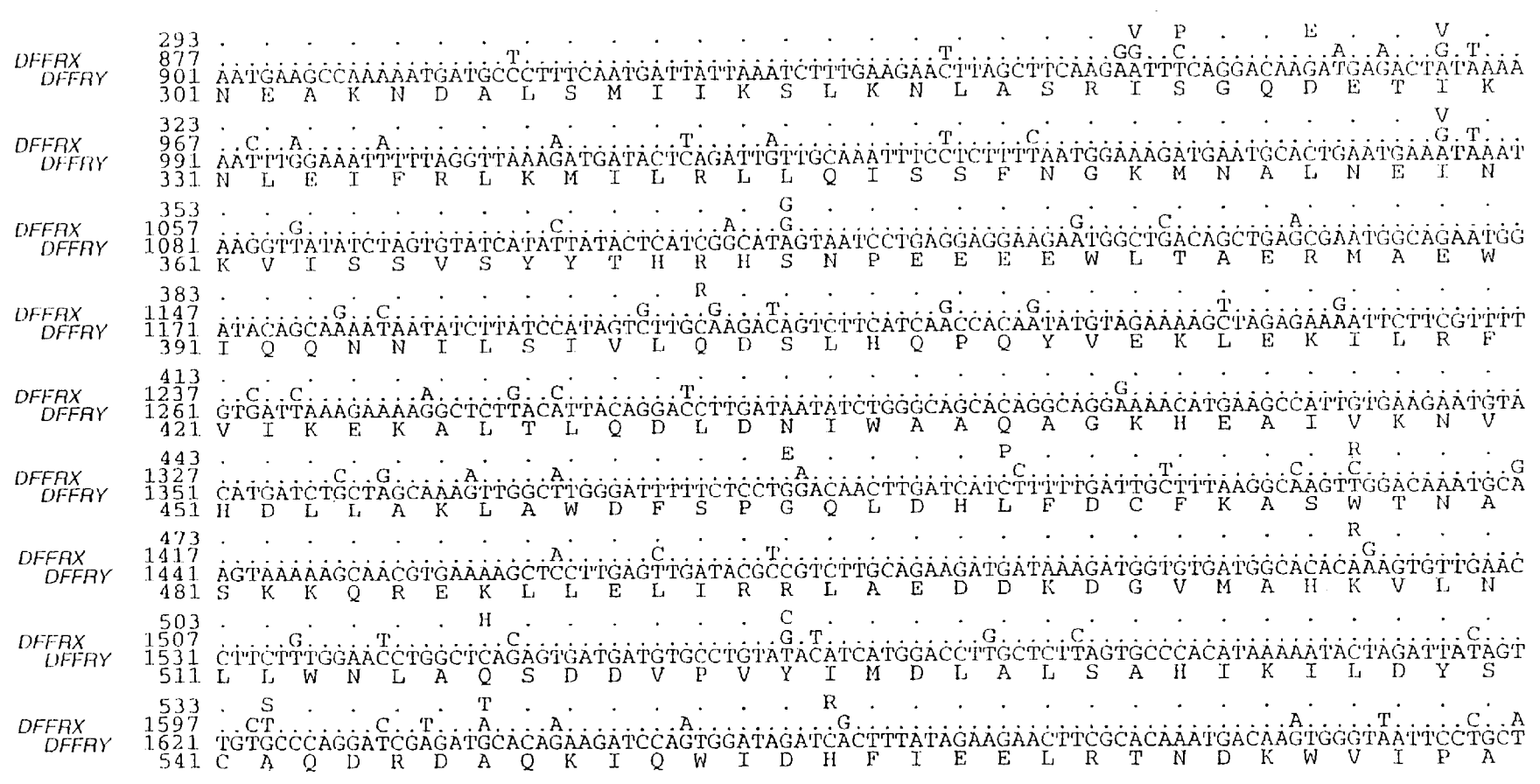
Figure 7D:
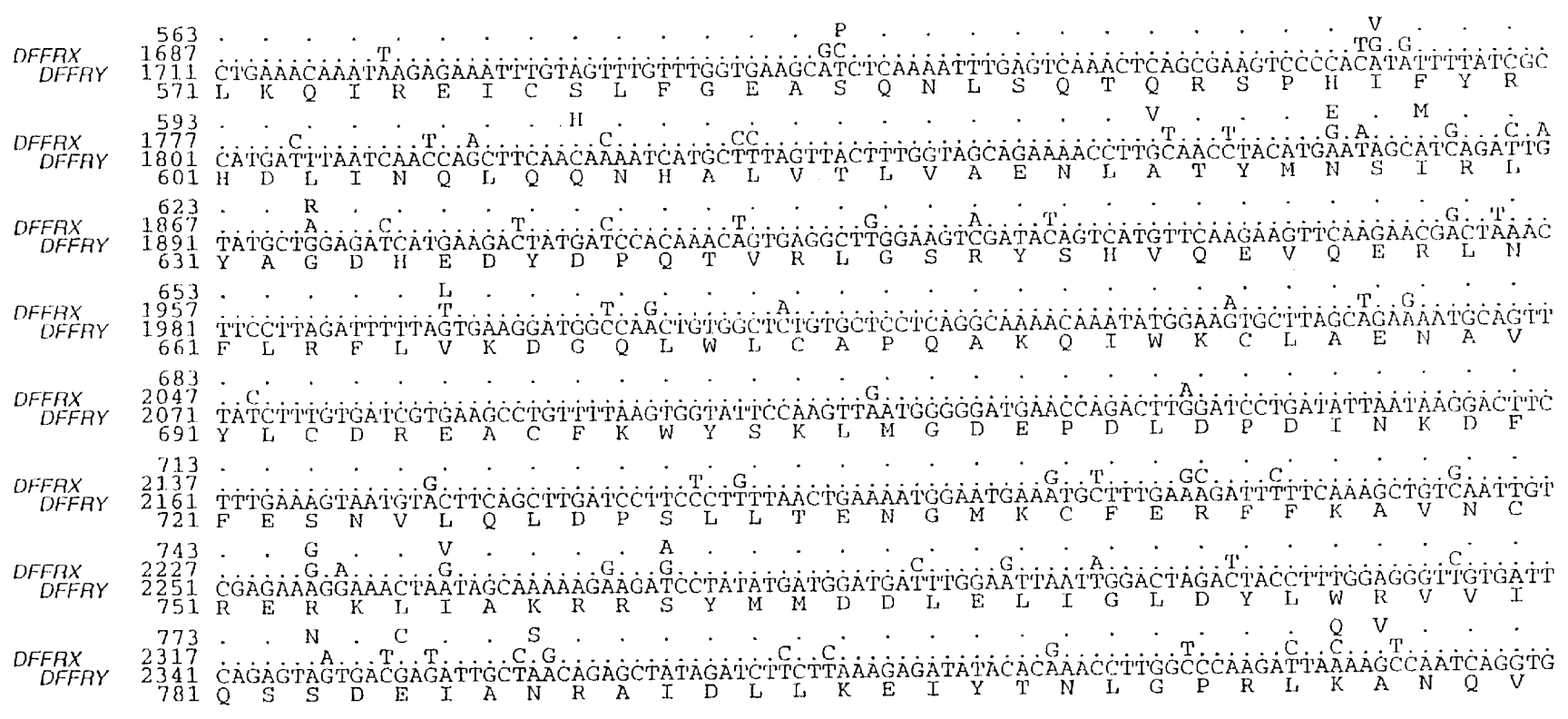
Figure 7E:
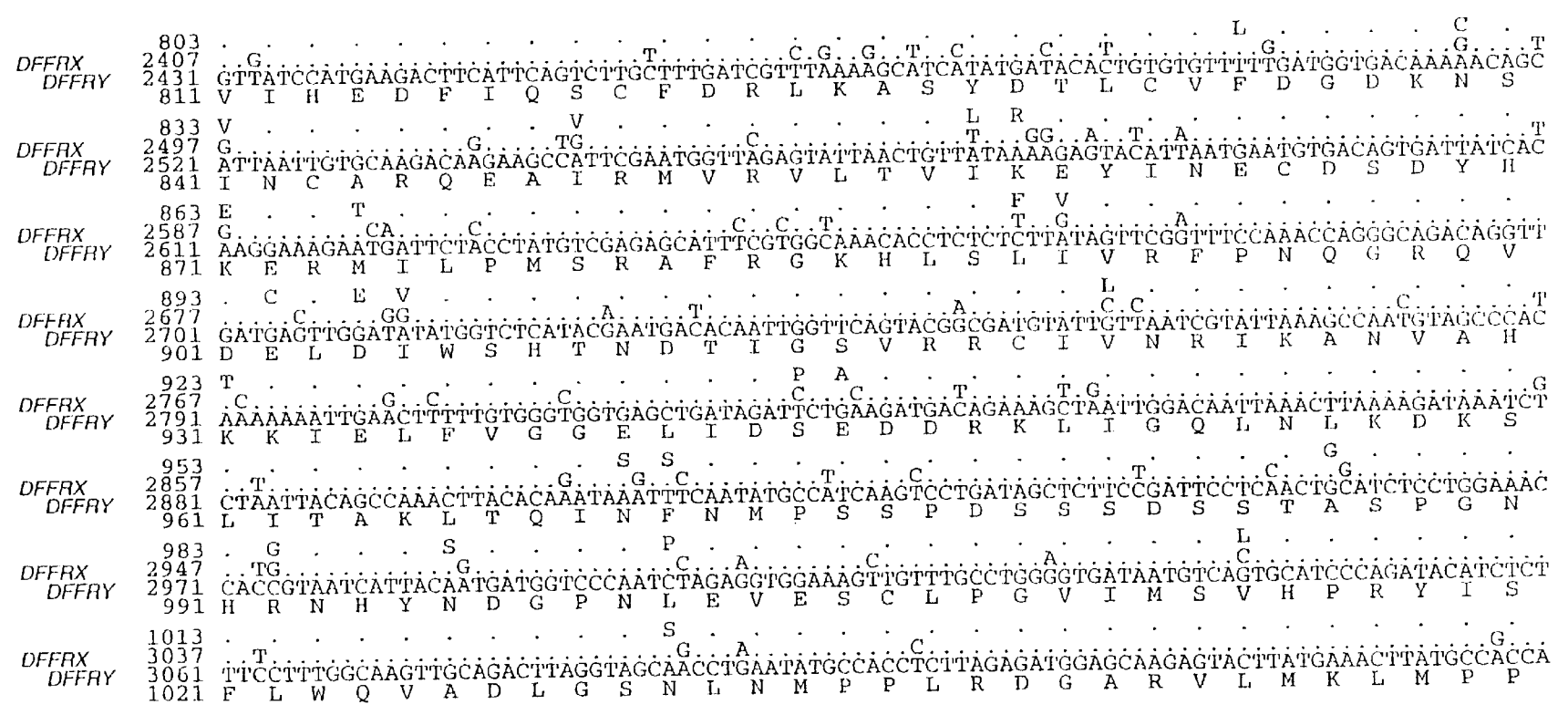
Figure 7F:
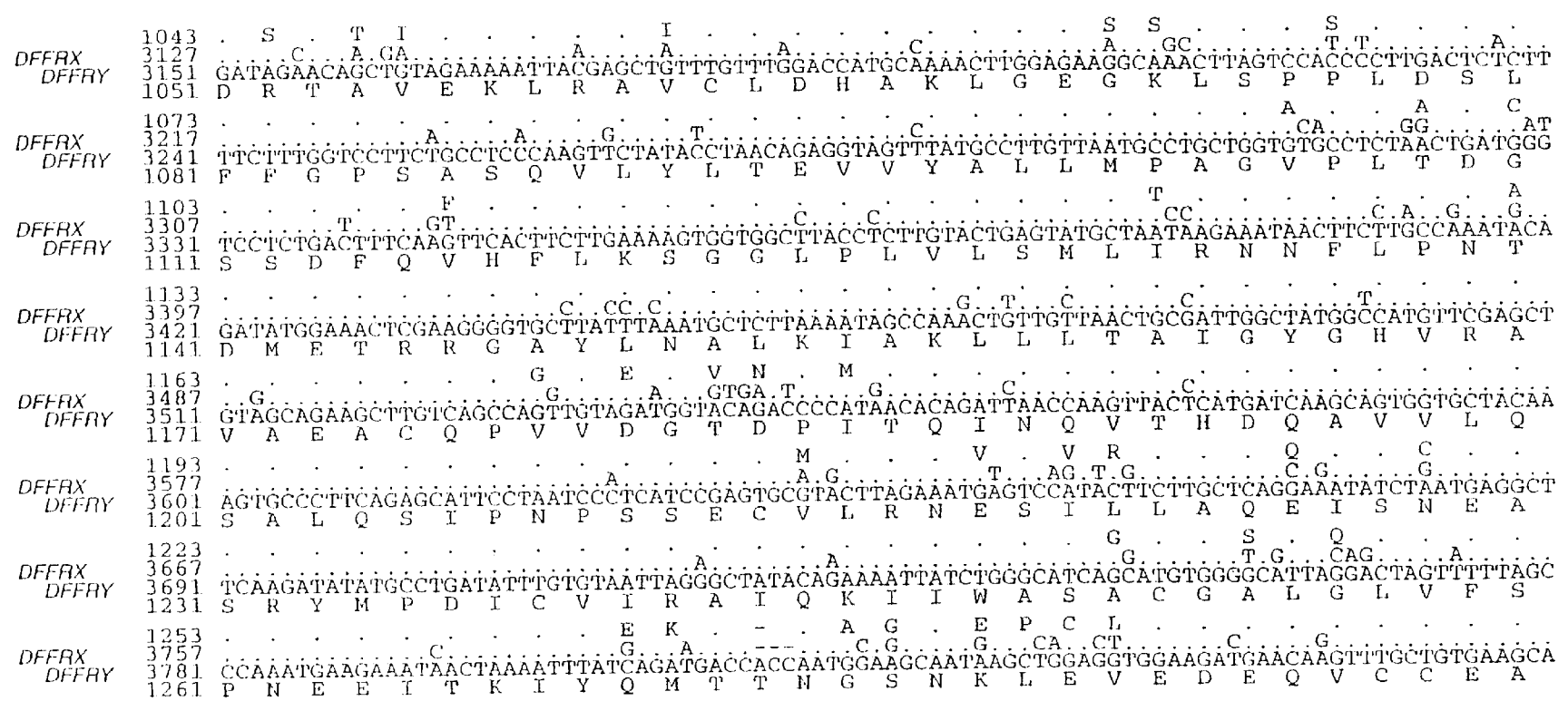
Figure 7G:
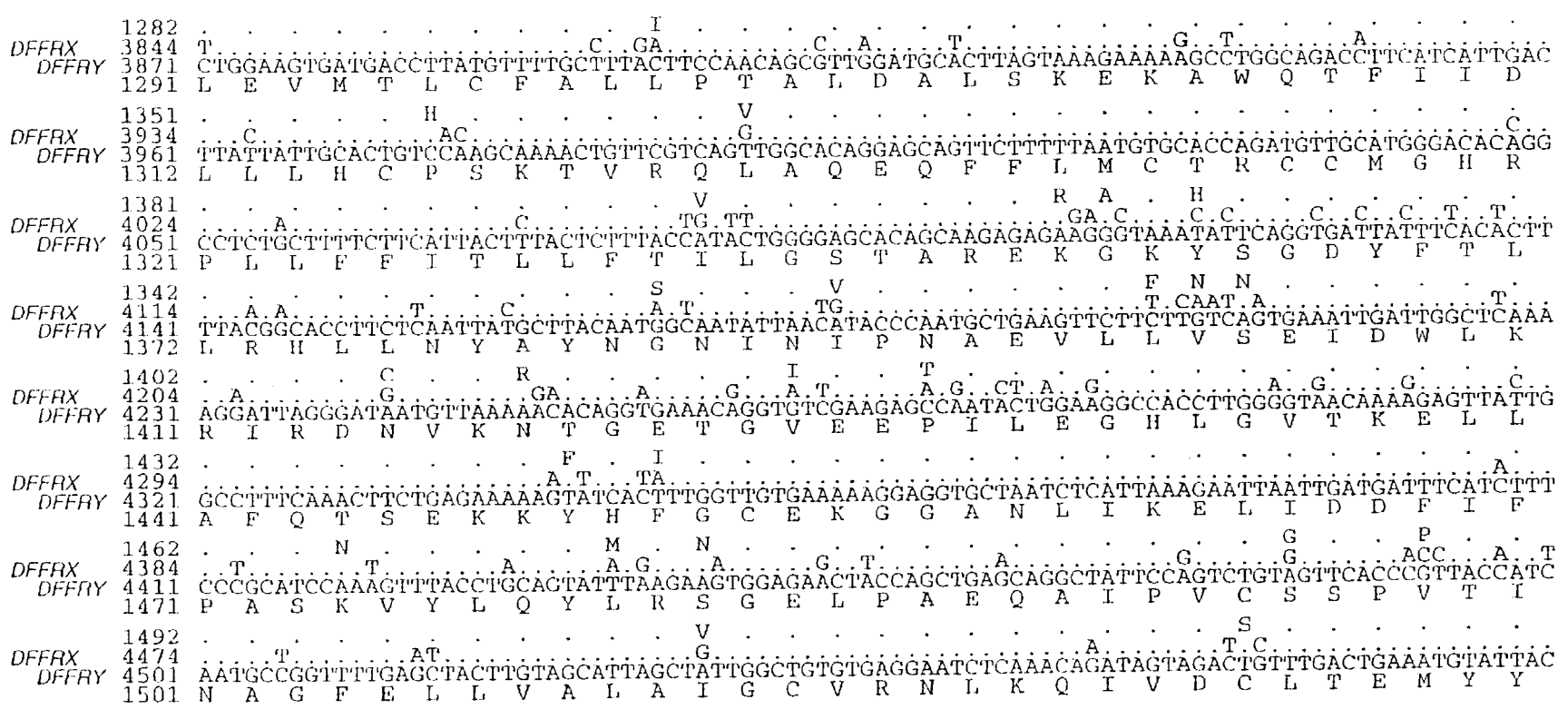
Figure 7H:
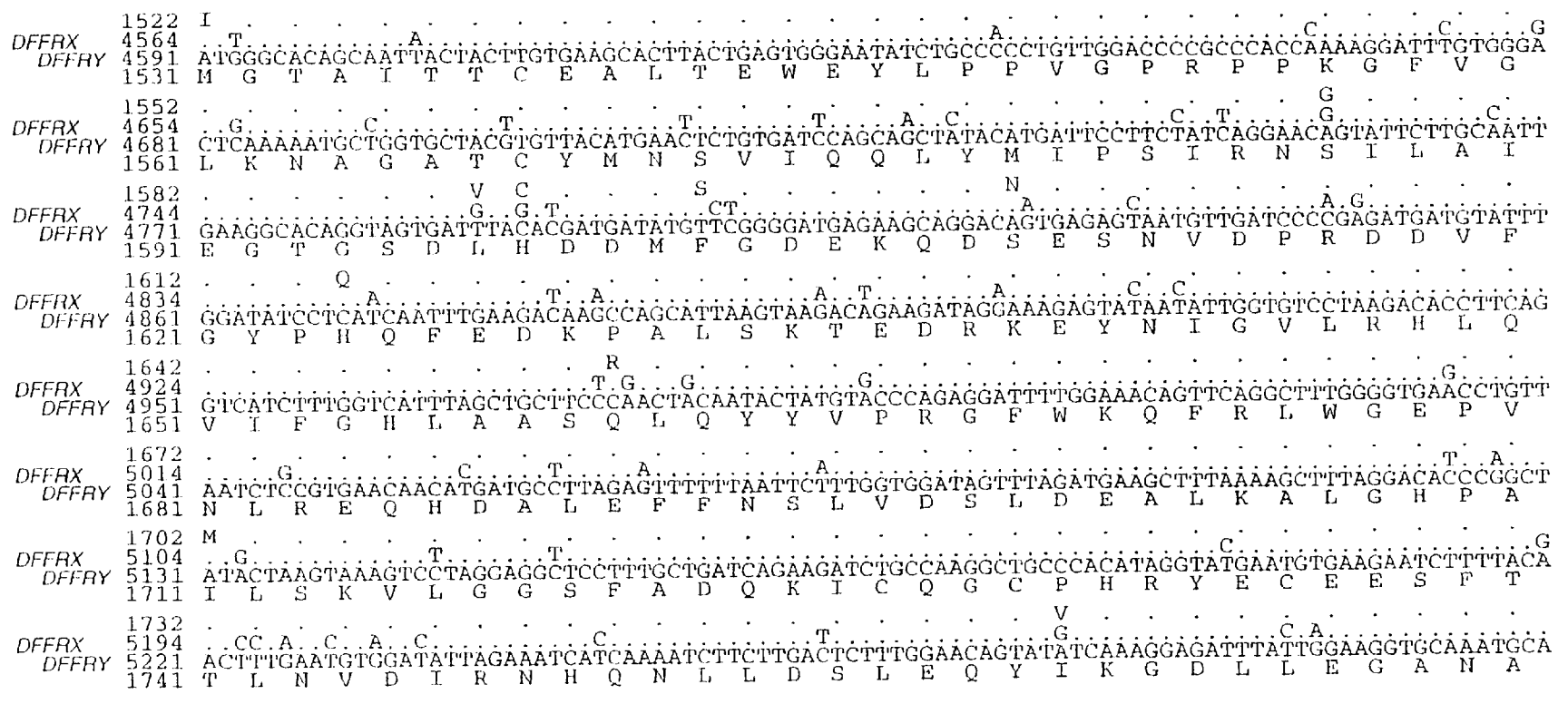
Figure 7J:
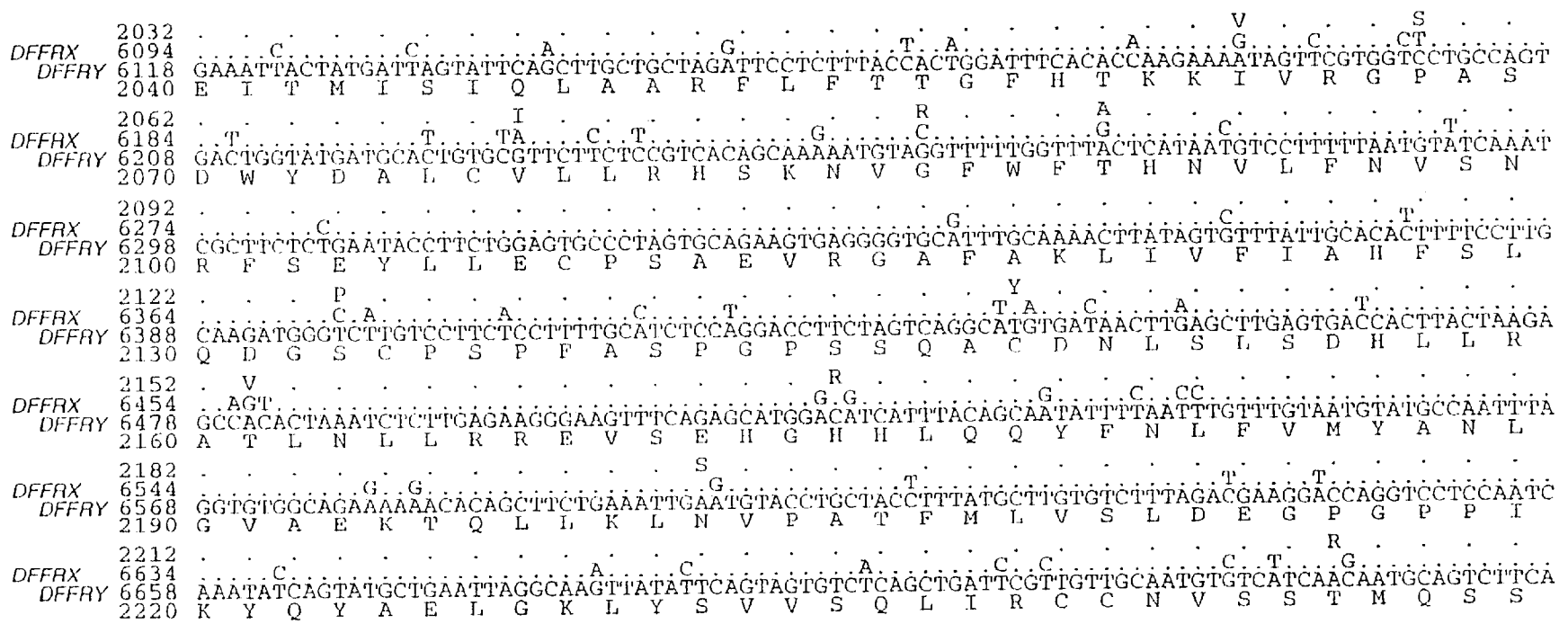
Figure 7K:
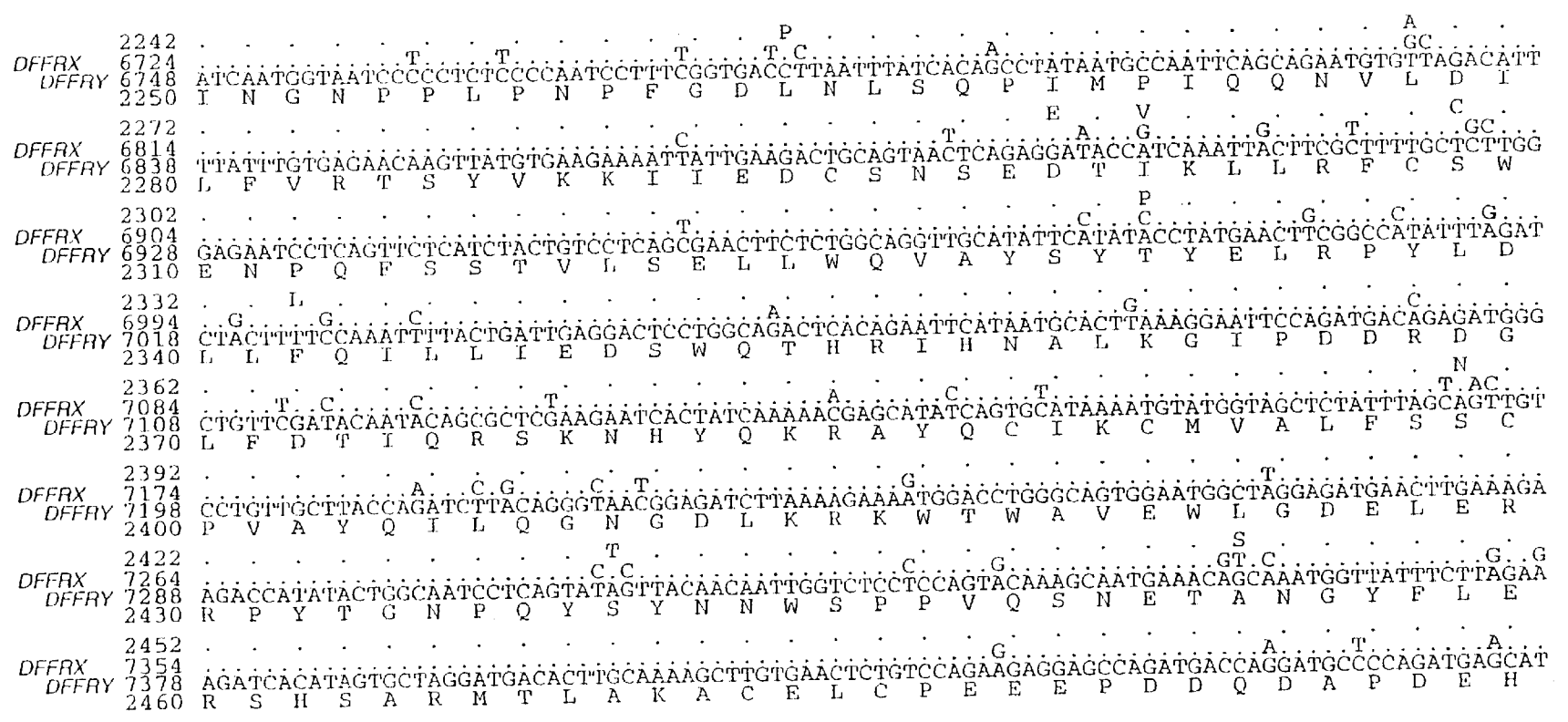

FIGS. 7A–7L represent the nucleic acid sequences of DFFRX (SEQ ID NO: 33) and DFFRY (SEQ ID NO: 34) and the encoded amino acid sequences (SEQ ID NO: 35 and SEQ ID NO: 36, respectively).

Figure 8A:
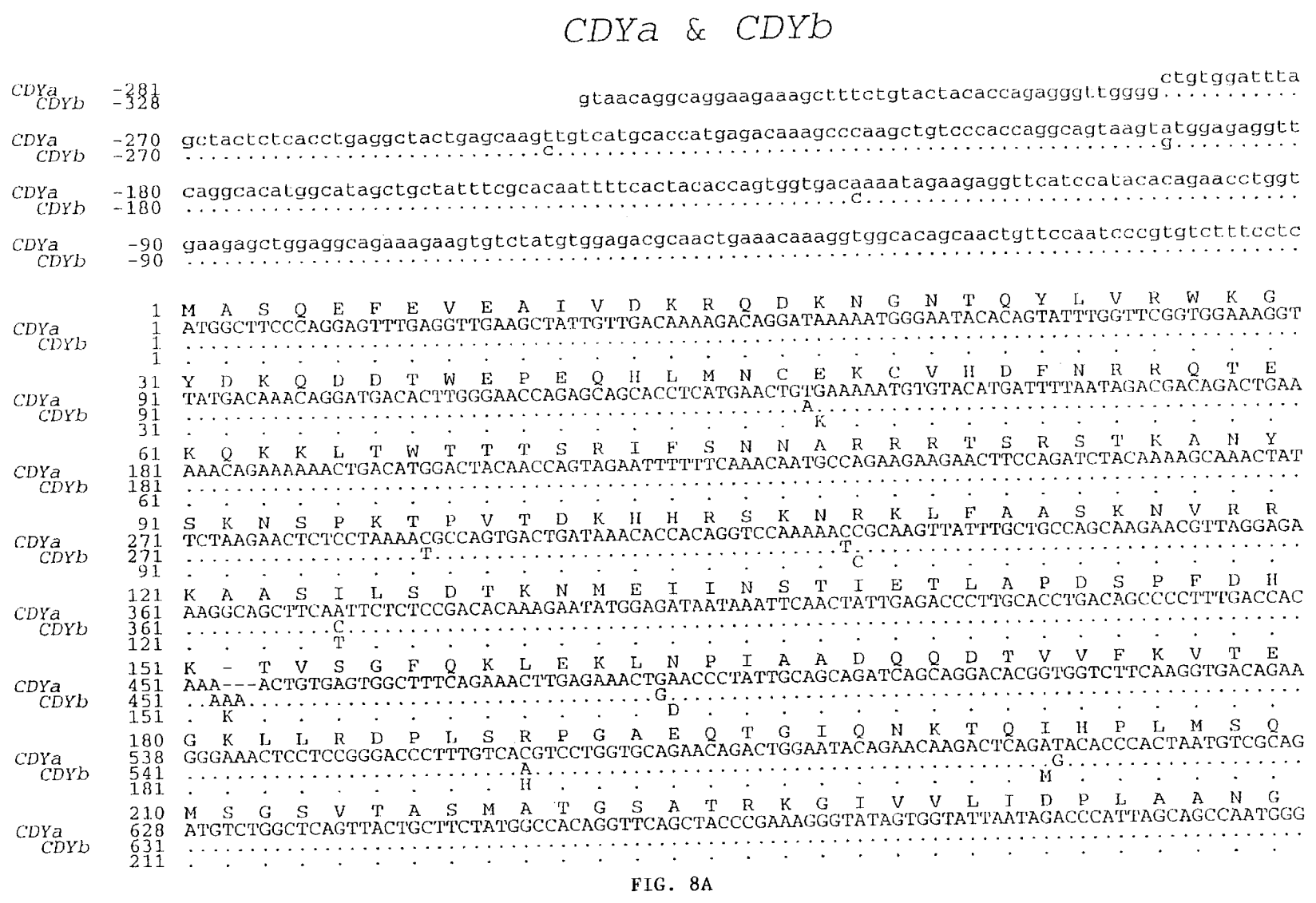
Figure 8B:
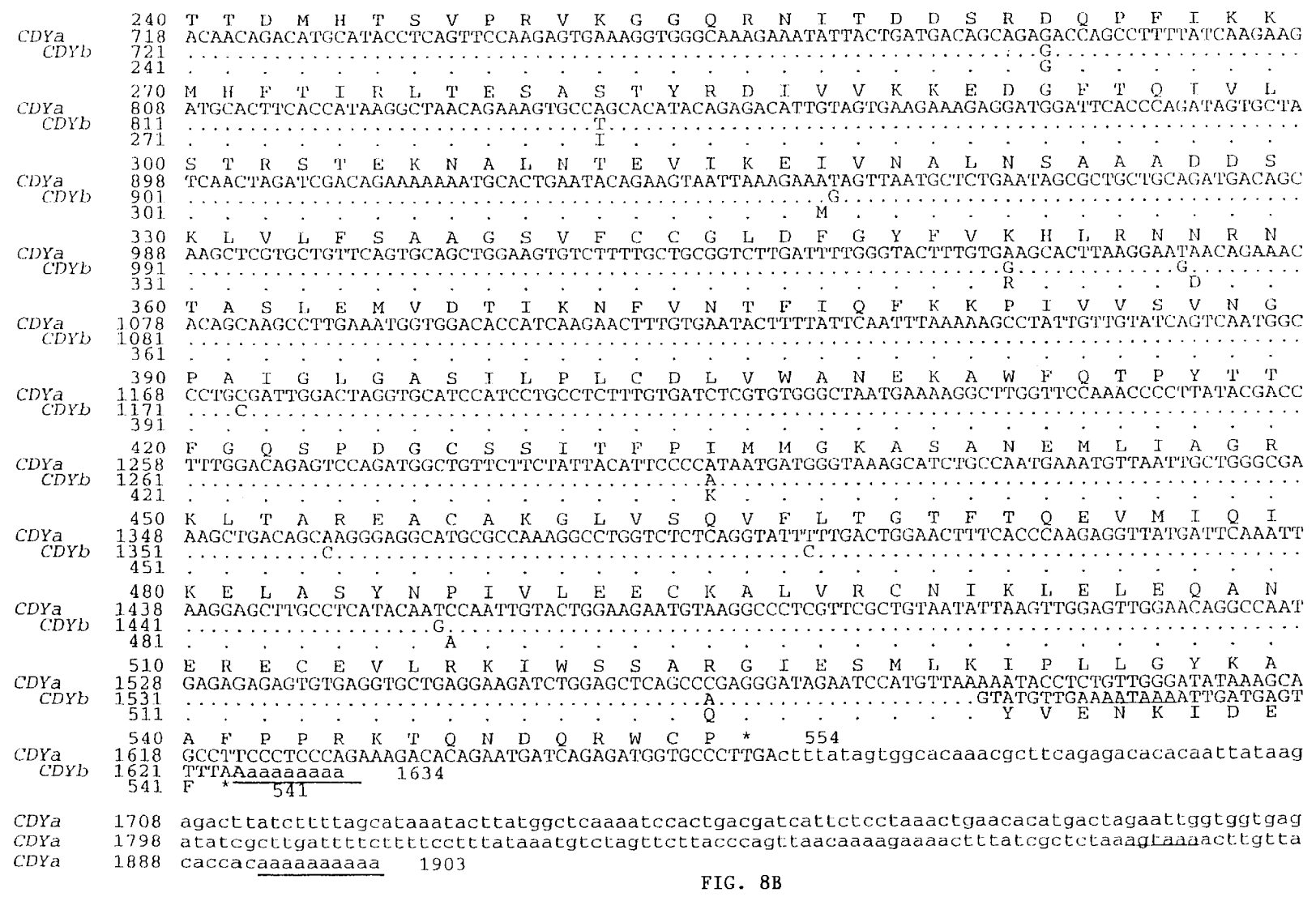

FIGS. 8A and 8B represent the nucleic acid sequences of CDYa (SEQ ID NO: 37) and CDYb (SEQ ID NO: 38) and the encoded amino acid sequences (SEQ ID NO: 39 and SEQ ID NO: 40, respectively).

FIG. 9 represents the nucleic acid sequences of BPY1 (SEQ ID NO: 41) and the encoded amino acid sequence (SEQ ID NO: 42).

FIG. 10 represents the nucleic acid sequence of BPY2 (SEQ ID NO: 43) and the encoded amino acid sequence (SEQ ID NO: 44).

FIG. 11 represents the nucleic acid sequences of XKRY (SEQ ID NO: 45) and the encoded amino acid sequence (SEQ ID NO: 46).

FIG. 12 represents the nucleic acid sequences of PTPRY (SEQ ID NO: 47) and the encoded amino acid sequence (SEQ ID NO: 48).

FIG. 13 is the nucleic acid sequence of TTY1 (SEQ ID NO: 49).

FIG. 14 is the nucleic acid sequence of TTY2 (SEQ ID NO: 50).

FIGS. 15A–15C show the nucleic acid sequence of the human CDY Like (CDYL) (SEQ ID NO: 85) gene, which is the human autosomal homolog of CDY, located on chromosome 6p and expressed ubiquitously.

FIGS. 16A–16C show the nucleic acid sequence of the mouse Cdyl (CDY like) gene (SEQ ID NO.: 86), which is the mouse ortholog of human CDYL, located on chromosome 13 and expressed predominantly in the testis. A longer transcript of the gene is ubiquitously expressed.

FIGS. 17A–17C show the nucleic acid sequences of human Variably Charged Protein family members VCP2r (SEQ ID NO.: 87), VCP8r (SEQ ID NO.: 88) and VCP10r (SEQ ID NO.: 89), respectively, which are expressed in the testis and highly polymorphic.

DETAILED DESCRIPTION OF THE INVENTION

Y chromosome genes, classed as genes having X homologues and testis-specific (Y-specific) genes, are the subject of the invention described herein, as are DNA which hybridize to (are complementary to) all or characteristic portions of the Y chromosome genes, the encoded products (e.g., proteins, peptides, glycoproteins), antibodies and methods of diagnosis or treatment in which the genes, complementary DNA, encoded proteins or antibodies are used. As described herein, fragments that hybridized to Y chromosomal DNA were selected and then their nucleotide sequences determined. It was expected that these sequence fragments would represent a redundant sampling of a much smaller set of genes. Computer analysis revealed that 577 fragments corresponded to known Y genes, including seven of eight NRY genes and all eight pseudoautosomal genes previously reported. These findings suggested that the 2539 sequence fragments represented the great majority of all Y-chromosomal genes. After further analysis, both to eliminate human repetitive sequences and to assemble overlapping fragments into contigs, 912 novel and non-overlapping sequences were hybridized to Southern blots of human genomic DNAs. 308 sequences that detected at least one prominent male-specific fragment were judged likely to derive from the NRY, and for each work was carried out to isolate cDNA clones from a human testis library, as described in Example 1. Nucleotide sequencing of cDNA clones, and rescreening of libraries as necessary, yielded full-length cDNA sequences for ten novel NRY genes or families, and partial cDNA sequences for two additional ones (Table and FIGS. 1–14).

TABLE

12 Novel Genes or Families in the NRY

| Gene Symbol | Gene Name | Tissue Expression | Multi-copy on Y | x homolog | Escape x Inactivation |
|---|---|---|---|---|---|
| DBY | Dead Box Y | ubiquitous | | DBX | yes |
| TB4Y | Thymosin β4, Y isoform | ubiquitous | | TB4X | yes |
| EIF1AY | Translation Initiation Factor 1A, Y isoform | ubiquitous | | EIF1AX | yes |
| TPRY | TPR motif Y | ubiquitous | | TPRX | yes |
| DFFRY | Drosophila Fat Facets Related Y | ubiquitous | | DFFRX | yes |
| CDY | Chromodomain Y | testis | yes | | |
| BPY1 | Basic Protein Y 1 | testis | yes | | |
| BPY2 | Basic Protein Y 2 | testis | yes | | |
| XKRY | XK Related Y | testis | yes | | |
| PTPRY | Protein-Tyrosine Phosphatase Related Y | testis | yes | | |
| TTY1 | Testis Transcript Y 1 | testis | yes | | |
| TTY2 | Testis Transcript Y 2 | testis | yes | | |

Figure 1A:
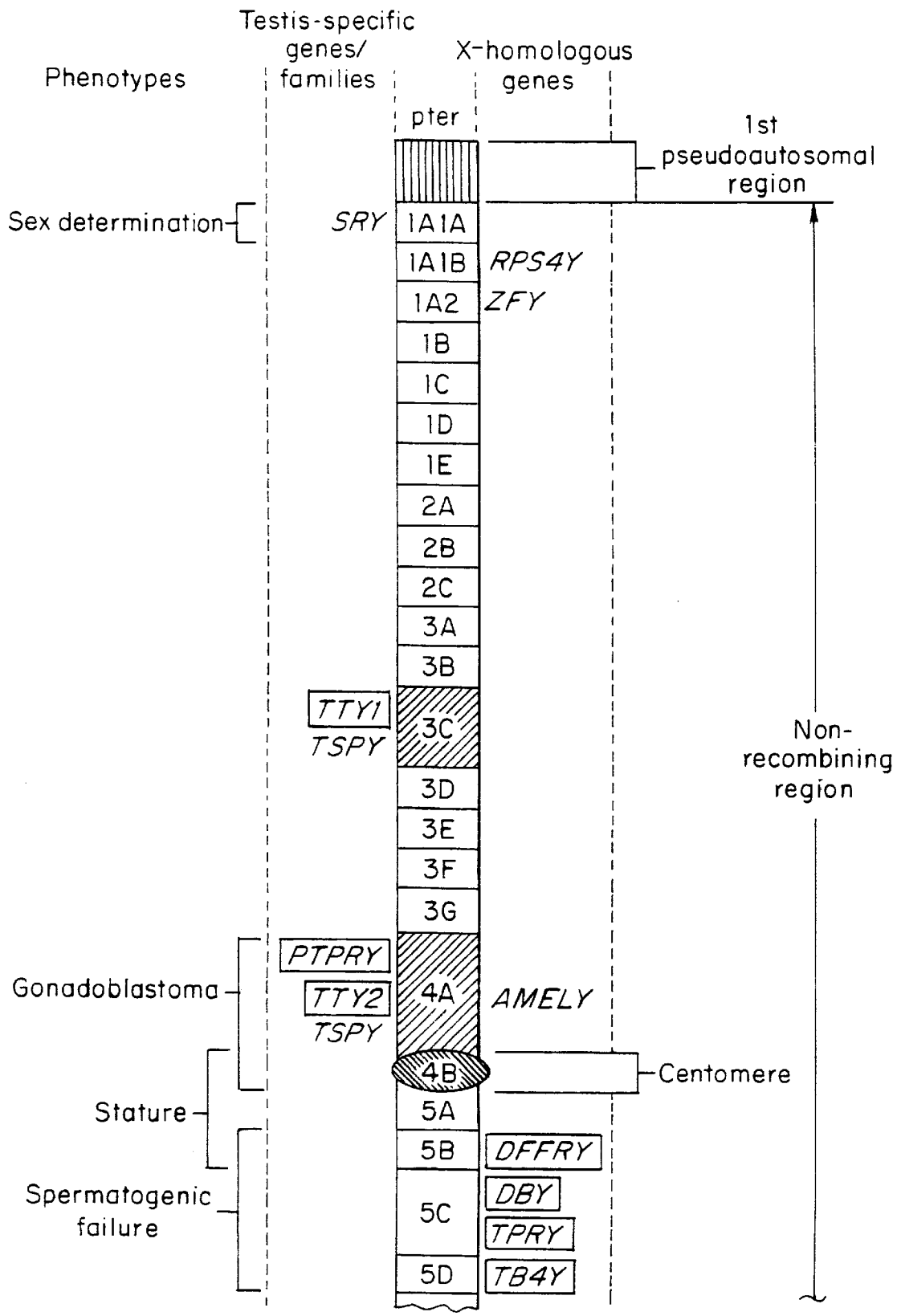
FIGS. 1A and 1B are a gene map of the non-recombining region of the Y chromosome.
Figure 1B:
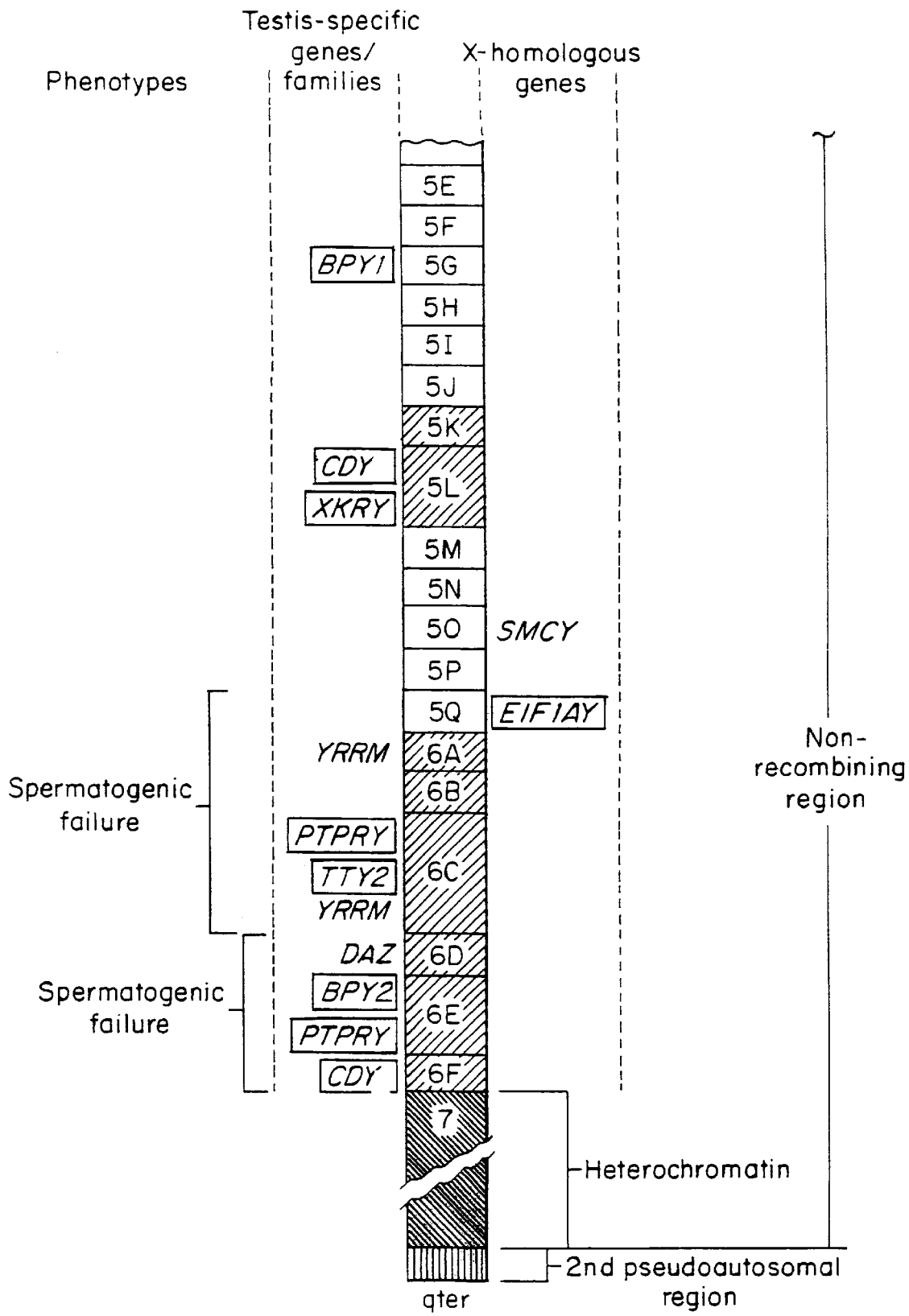
Figure 2B:
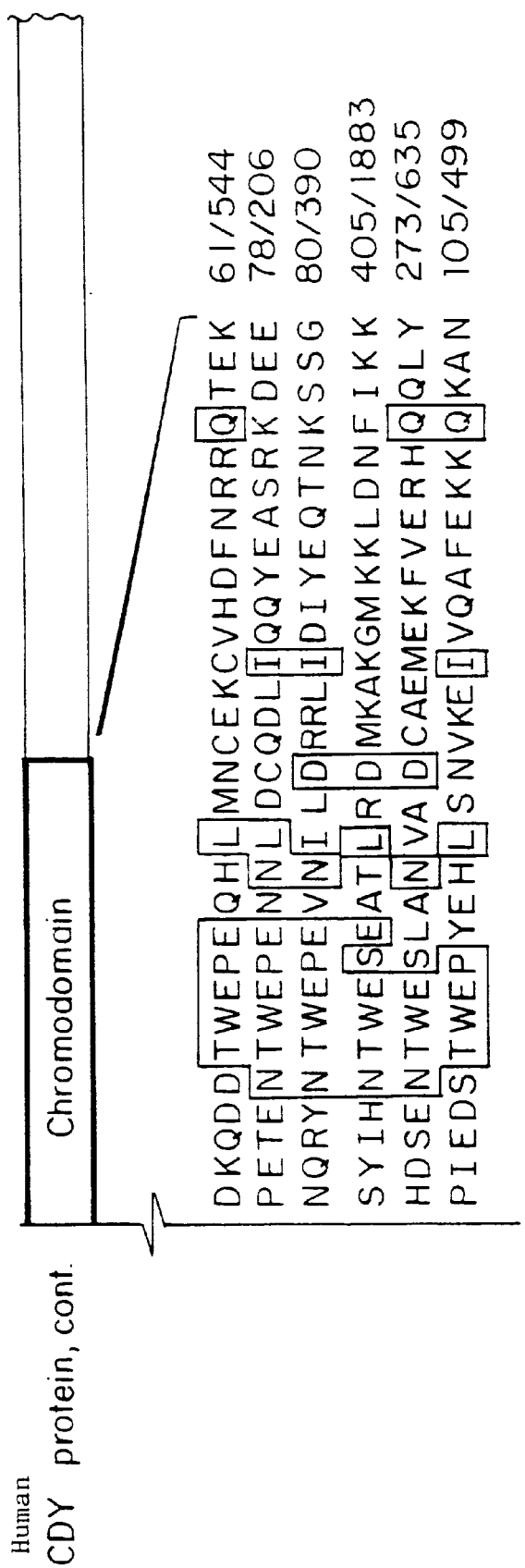
Figure 2E:
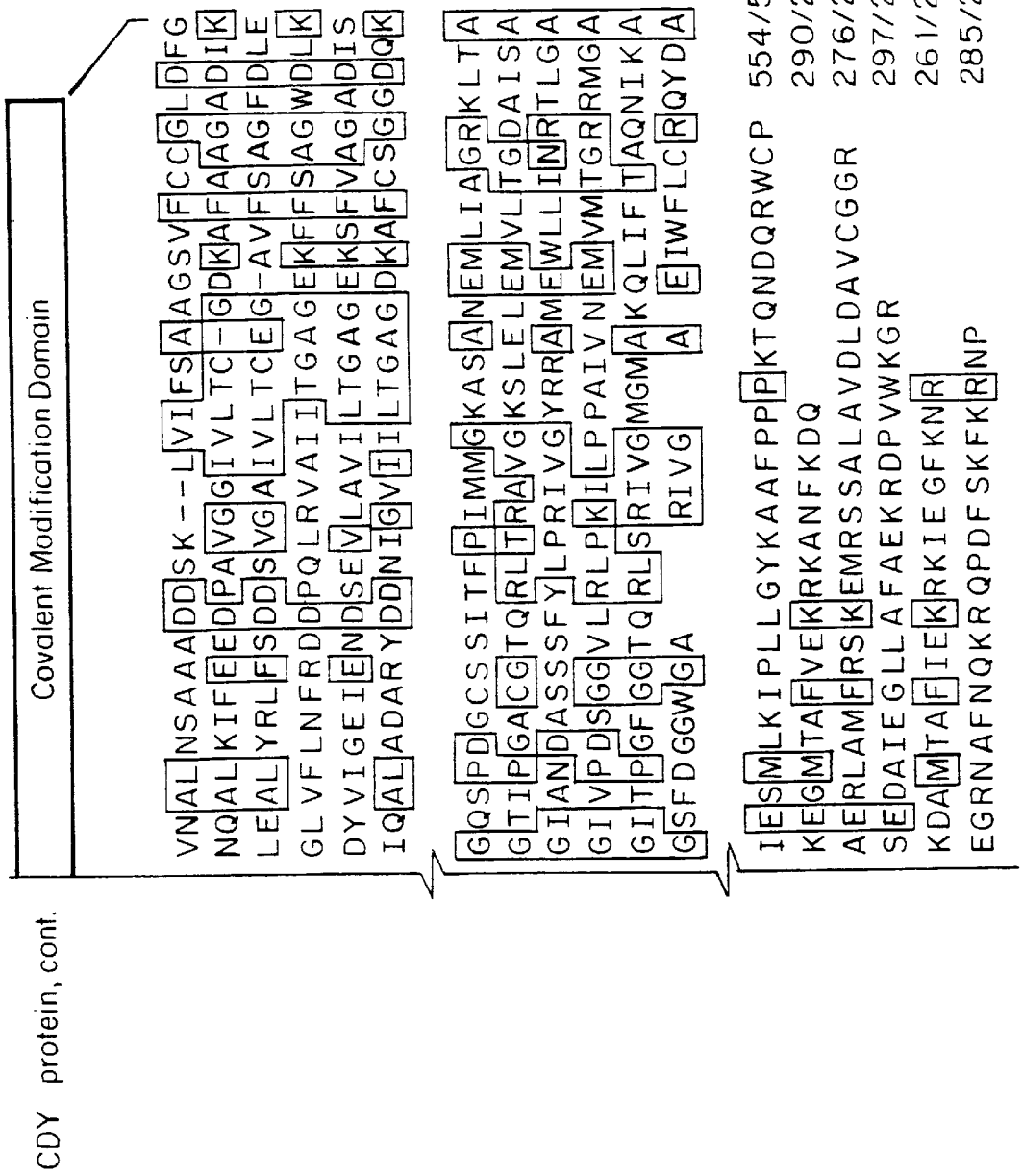

All 12 novel genes were localized on the Y chromosome, as described in Example 2. FIGS. 1A–1B are a gene map of NRY. As shown, the Y chromosome consists of a large non-recombining region (NRY; euchromatin plus heterochromatin) flanked by pseudoautosomal regions (pter, short arm telomere; qter, long arm telomere). The NRY is divided into 43 ordered intervals (1A1A through 7) which are defined by naturally occurring deletions (D. Vollrath, et al., Science 258:52 (1992)). Listed immediately above the Y chromosome in FIGS. 1A–1B are nine NRY genes with functional X homologs; novel genes are boxed. Indicated immediately below the Y chromosome are 11 testis-specific genes or families, some with multiple locations. It is likely that some testis-specific families have members in additional deletion intervals; the locations indicated are representative, but are not necessarily exhaustive. At the bottom of FIGS. 1A–1B are shown NRY regions implicated, by deletion mapping, in sex determination, germ cell tumorigenesis (gonadoblastoma), stature, and spermatogenic failure (K. Ma et al., Cell 75:1287 (1993); R. Reijo et al., Nat. Genet. 10:383 (1995); P. H. Vogt et al., Hum. Mol. Genet. 5:933 (1996); J. L. Pryor et al., New England J. Med. 336:534 (1997); K. Tsuchiya et al., Am. J. Hum. Genet. 57:1400 (1995); P. Salo et al., Hum. Genet. 95:283 (1995)). Euchromatic regions that are made up, at least partially, of Y-specific repeats are drawn in grey. AMELY, which appears to fall within such a repeat-containing region, is actually located in a sub-region of 4A that is not repetitive.

Expression of the 12 novel genes was assessed in diverse human tissues, by Northern blotting. Autoradiograms were produced by hybridizing $^{32}$P-labeled cDNA probes to Northern blots of poly(A)$^+$ RNAs (2 µg/lane) from human tissues (Clontech, Palo Alto, Calif.). Probes employed were cDNA clones, full-length (most genes) or partial (DBY, nucleotides 1476–2319 of GenBank AF000985; TPRY, nucleotides 861–1768 of GenBank AF000996; DFFRY, nucleotides 8604–9878 of GenBank AF000986). Blots were hybridized at 65° C. in Church's buffer (0.5 M Na$_2$PO$_4$ at pH7.5, with 7% SDS), and washed at 65° C. in 1×SSC and 0.1% SDS. DBY, TB4Y, EIF1AY and DFFRY probes cross-hybridize to transcripts derived from their X homologs. For all five X-homologous genes (DBY, TPRY, TB4Y, EIF1AY and DFFRY), expression was tested and confirmed in three male tissues (brain, prostate and testis) by RT-PCR using Y-specific primers.

The novel genes encode an assortment of proteins and are dispersed throughout the euchromatic portions of the NRY. Nonetheless, all 12 genes fall into two discrete classes: 1) X-homologous genes and 2) testis-specific, Y-specific gene families (Table).

The X-homologous genes share the following characteristics: each has a homolog on the X chromosome encoding an extremely similar but nonidentical protein isoform, each is expressed in a wide range of human tissues (is not testis-specific), each appears to exist in a single copy on the NRY. There are five novel representatives of this X-homologous class:

1. DBY encodes a novel "DEAD box" protein, perhaps an RNA helicase involved in translation initiation (P. Linder, et al., Nature, 337, 121 (1989); R. -Y. Chuang, P. L. Weaver, Z. Liu, T. -H. Chang, Science, 275, 1468 (1997)). The DBY protein is 91% identical to DBX, encoded by a homologous gene on the human X chromosome.

2. TPRY encodes a novel protein containing 10 tandem "TPR" motifs, a protein-protein interaction domain found in the products of the yeast SSN6/CYC8, CDC16, and CDC23 genes, among others (R. S. Sikorski, M. S. Boguski, M. Goebl, P. Hieter, Cell, 60, 307 (1990); D. Tzamarias, K. Struhl, Genes Dev, 9, 821 (1995)). Differential splicing may generate TPRY isoforms that differ at their carboxy termini. The amino terminal portion of the TPRY protein is 83% identical to TPRX, encoded by an homologous gene on the X chromosome.

3. TB4Y encodes a 44 amino acid protein that differs at only three residues from thymosin β$_4$, which functions in actin sequestration (H. Gondo, et al., J. Immunol. 139:3840 (1987); D. Safer, M. Elzinga, V. T. Nachmias, J Biol Chem, 266, 4029 (1991)), and we found is located on the X. It is proposed that the X-linked gene encoding thymosin β$_4$ be called TB4X.

4. EIF1AY encodes a Y-linked isoform of translation initiation factor 1A (eIF-1A) (T. E. Dever, et al., J Biol Chem, 269, 3212 (1994); J. W. Hershey, Annu. Rev. Biochem. 60, 717 (1991)), which we discovered is located on the X. It is proposed that the X-linked gene encoding eIF-1A be called EIF1AX. The amino acid sequences of the X and Y-encoded proteins are 97% identical.

5. DFFRY encodes a Y-linked isoform of DFFRX, a recently described X-linked protein. A Y-linked homolog was detected previously, but had been thought to be a pseudogene. The human DFFRX and DFFRY proteins, which are 91% identical, are homologous to the Drosophila fat-facets gene product, a deubiquinating enzyme required for eye development and oogenesis (M. H. Jones, et al., Hum Mol Genet 5, 1695 (1996); J. A. Fischer-Vize, G. M. Rubin, R. Lehmann, *Development*, 116, 985 (1992); Y. Huang, R. T. Baker, J. A. Fischer-Vize, *Science*, 270, 1828 (1995)).

The second group of novel NRY genes, the testis-specific, Y-specific gene families, share a very different set of characteristics: each appears to be expressed specifically in testes and each appears to exist in multiple copies on the NRY, as judged by I) the number and intensity of hybridizing fragments on genomic Southern blots or ii) multiple map locations on the Y. We report five novel testis-specific, Y-specific gene families with full-length cDNA sequences:

1. The CDY family encodes proteins with an amino-terminal "chromodomain," a chromatin binding motif (T. C. James, S. C. Elgin, *Mol Cell Biol*, 6, 3862 (1986); B. Tschiersch, et al., *EMBO J*, 13, 3822 (1944); R. Paro, D. S. Hogness, *Proc Natl Acad Sci U.S.A.*, 88, 263 (1991); D. G. Stokes, K. D. Tartof, R. P. Perry, *Proc. Natl Acad Sci U.S.A.*, 93, 7137 (1996); M. T. Madireddi, et al., *Cell*, 87, 75 (1996)) (FIGS. 3A–3F). The carboxy-terminal half shows striking amino acid similarity, over a region of more than 200 residues, to nearly the full length of several enzymes, both prokaryotic and eukaryotic (M. Kanazawa, et al., *Enzyme Protein*, 47, 9 (1993); A. Schmitz, K. H. Gartemann, J. Fiedler, E. Grund, R. Eichenlaub, *Appl. Environ. Microbiol.* 258, 4068 (1992); Z. L. Boynton, G. N. Bennet, F. B. Rudolph, *J Bacteriol*, 178, 3015 (1996); V. Sharma, K. Suvarna, R. Meganathan, M. E. Hudspeth, *J Bacteriol*, 174, 5057 (1992); P. M. Palosaari, et al., *J Biol Chem*, 266, 10750 (1991)). The reactions catalyzed by these homologs are diverse, but in each case the substrate contains cofactor A (CoA) attached to a carbonyl group, and an alkoxide intermediate is formed. The unprecedented combination of a chromodomain and a putative CoA-substrate enzyme in a single polypeptide suggests that, in vivo, CDY proteins may catalyze covalent modification of DNA or chromosomal proteins, perhaps during spermatogenesis.

2. The BPY1 genes encode a basic protein, 125 residues long, with little sequence similarity to known proteins. The encoded protein is rich in serine, lysine, arginine, and proline and has a pI of 9.4. Southern blotting studies revealed homologous sequences on the human X chromosome, but screening of cDNA libraries has failed to yield X-derived clones.

3. The BPY2 genes encode a second basic protein, 106 residues in length, without obvious sequence similarity to BPY1 or other known proteins. The pI of BPY2 is 10.0.

4. The XKRY genes encode a protein with sequence similarity to XK, a putative membrane transport protein defective in McLeod syndrome (M. Ho, et al., *Cell*, 77, 869 (1994)).

5. The PTPRY genes encode a protein with weak homology to a putative protein-tyrosine phosphatase (PTPase) in the mouse (W. Hendriks, et al., *J Cell Biochem*, 59, 418 (1995)). Two additional families of testis-specific transcription units, referred to as TTY1 and TTY2, have been identified. The sequences represented in FIGS. 14 and 15A–15C are being assessed for open reading frames.

It appears that conventional single-copy genes, commonplace elsewhere in the genome, are quite uncommon in the NRY. Indeed, the two classes of NRY genes suggested by the systematic search described herein accommodate not only the 12 genes reported here, but also six of eight previously identified NRY genes. SRY, a Y-specific gene that triggers the male pathway of sexual differentiation, is expressed in testes, and exists in only one copy in the NRY. AMELY, which has an X-linked homolog AMELX, is expressed only in the developing tooth bud. The X inactivation status of AMELX is unknown.

Also described herein are five additional genes and their sequences (FIGS. 15A–5C, 16A–16C, 17A–17C): human CDY Like (CDYL), which is the human homolog of CDY; it is on chromosome 6p and expressed ubiquitously; mouse Cdyl (CDY like), which is the mouse ortholog of human CDYL; it is on chromosome 13 and expressed predominantly in testis and also has a longer transcript that is expressed ubiquitously; and human VCP (Variably Charged Protein) family, which is a family of genes on the X chromosome that are homologous to BPYI, expressed in the testis and highly polymorphic. Human CDY, human CDYL and mouse Cdyl have been shown to be histone acetyltransferases by in vitro assays. Human CDY is a candidate for the Azoospermia Factor (AZF) because it is within the AZFc region that is commonly deleted in infertile men. Chemicals that block the enzymatic activity of any of these genes are candidate male contraceptives.

Inhibitors of the enzymatic activity of these genes, such as the human CDY gene, can be identified through an in vitro assay. For example, the protein encoded by one of the genes (e.g., CDY-encoded protein) can be produced, such as by recombinant means (e.g., in bacterial cells containing a vector or plasmid which includes the gene to be expressed), and obtained. The effect of a candidate inhibitor (drug) on the enzymatic activity of the protein can be assessed by combining the candidate inhibitor with the protein, a substrate of its enzymatic activity (e.g., histones) acetyl CoA (e.g., radiolabelled acetyl CoA) and other assay components (e.g., an appropriate physiological solution or buffer), to produce a combination. The combination is maintained under conditions under which the enzymatic activity of the protein is maintained and appropriate for the protein to act upon/interact with its substrate (e.g., for the CDY gene to retain its histone acetyltransferase activity). As a result, the substrate is acted upon by the protein if the candidate inhibitor does not inhibit the protein and the protein acts upon the substrate. If the substrate is not acted upon by the protein, this is an indication that the candidate inhibitor is an inhibitor of the protein. For example, if a histone acetyltransferase, such as CDY-encoded protein is inhibited by a candidate inhibitor, its histone acetyltransferase activity will be blocked. If radiolabelled acetyl CoA is used, transfer of the radiolabelled acetyl group to the enzyme substrate (histones) is inhibited (will not occur or will occur to a lesser extent than occurs in the absence of the candidate inhibitor). Whether transfer occurs can be assessed by determining the location of radiolabelled acetyl groups from acetyl CoA. If the histone substrates are not radiolabelled or are radiolabelled to a lesser extent in the presence of a candidate inhibitor (than in its absence), the candidate inhibitor is an inhibitor of the protein. Inhibitors identified in this way can be further assessed in additional in vitro assays or in in vivo assays (e.g., in an appropriate animal model).

To interpret the observation that these X-homologous and multi-copy, testis-specific groups account for 18 to 20 known NRY genes or families, we postulate that the NRY's evolution was dominated by two strategies. The first strategy favors conservation of certain existing genes and the second favors the acquisition of a class of novel genes: 1) The X-homologous genes probably reflect the common ancestry of the X and Y chromosomes, and selective pressures to maintain comparable expression of genes in males and females. 2) The abundance of testis-specific families may have resulted from the NRY's selectively retaining and amplifying genes that enhance male reproductive fitness.

1) Dosage compensation and X-Y homology. Experts agree that the mammalian X and Y chromosomes evolved from autosomes, with nearly all ancestral gene functions deteriorating on the non-recombining portion of the emerging Y chromosome while being maintained on the nascent X chromosome (J. J. Bull, *Evolution of Sex Determining Mechanisms* (Benjamin Cummings, Menlo Park, Calif., 1983); J. A. Graves, *Annu. Rev. Genet.* 30:233 (1996); B. Charlesworth, *Curr. Biol.* 6:149 (1996); W. R. Rice, *BioScience* 46:331 (1996)). Functional degeneration of the NRY would result in females having two, but males only one, copy of many genes, creating the need for a mechanism to equalize X-linked gene expression in the sexes. In mammals, a predominant solution to this problem is provided by X inactivation, the transcriptional silencing of one X chromosome in females.

However, the findings on X-homologous NRY genes described herein, combined with previous studies, illustrate the importance in human evolution of an alternative solution: preservation of homologous genes on both the NRY and the X chromosome, with both male and female cells expressing two copies of such genes. A critical prediction of this model is that, in female cells, the X homologs should escape X inactivation. This is the case for all widely expressed X-linked genes with known NRY homologs, including the X homologs of five novel NRY genes reported here (E. M. Fisher, et al., *Cell* 63:1205 (1990); A. I. Agulnik et al., *Hum. Mol. Genet.* 3:879 (1994); M. H. Jones et al., *Hum. Mol. Genet.* 5:1695 (1996); J. A. Fischer-Vize et al., *Development* 116:985 (1992); Y. Huang et al., *Science* 270:1828 (1995); A. Schneider-Gädicke et al., *Cell* 57:1247 (1989)). A second prediction of this model is that the human X and Y encoded proteins should be functionally interchangeable even though the nucleotide sequence of their corresponding genes are considerably diverged. Indeed, each of the eight known X-NRY gene pairs encode closely related isoforms, with 83 to 97% amino acid identity throughout their lengths; functional interchangeability has been demonstrated in the one case tested to date (M. Watanabe et al., *Nat. Genet.* 4:268 (1993)).

Turner syndrome is classically associated with an XO sex chromosome constitution. In 1965, Ferguson-Smith postulated that the Turner phenotype might be due to inadequate expression of X-Y common genes that escape X inactivation (M. A. Ferguson-Smith, *J. Med. Genet.* 2:142 (1965)). These "Turner genes" have yet to be identified with certainty. However, there now exists a substantial collection of X-homologous NRY genes (FIGS. 1A–1B) which can be assessed for genes which contribute to or are responsible for the Turner phenotype. The potential role of RPS4Y and RPS4X in Turner syndrome is controversial (E. M. Fisher et al., *Cell* 63:1205 (1990); W. Just et al., *Hum. Genet.* 89:240 (1992)). At least one Turner gene maps to the Xp-Yp pseudoautosomal region (T. Ogata et al., *J. Med. Genet.* 30:918 (1993)). Seven of the eight X-NRY gene pairs appear to be ubiquitously expressed, and at least three encode housekeeping proteins: an essential ribosomal protein (RPS4), an essential translation initiation factor (eIF-1A), and a modulator of actin polymerization (thymosin β4). Perhaps some features of the XO phenotype (e.g., poor fetal viability) reflect inadequate expression of such housekeeping functions.

2) Male fitness and Y-specific, testis-specific genes. As first appreciated by R. A. Fisher, animal genomes may contain genes or alleles that enhance male reproductive fitness but are inconsequential or detrimental with respect to female fitness (R. A. Fisher, *Biol. Rev.* 6:345 (1931)). As Fisher recognized, selective pressures would tend to favor the accumulation of such genes in male-specific regions of genomes. Of course, male reproductive fitness depends critically on sperm production, the central task of the adult testis. Since the NRY is the only male-specific portion of the mammalian genome, it should have a unique tendency to accumulate male-benefit genes during evolution.

These principles are illustrated by several gene families on the human NRY. De novo deletions of the DAZ gene cluster on the human Y chromosome are associated with severe spermatogenic defects (R. Reijo et al., *Nat. Genet.* 10:383 (1995)), and in Drosophila the DAZ homolog boule is required for spermatogenesis (C. G. Eberhart et al., *Nature* 381:783 (1996)). The DAZ gene cluster on the human Y chromosome arose, during primate evolution, by transposition and amplification of an autosomal gene. Likewise, two other testis-specific NRY gene families—YRRM and TSPY—may also be the result of the Y chromosome's having acquired and amplified autosomal genes (R. Saxena et al., *Nat. Genet.* 14:292 (1996); M. L. Delbridge et al., *Nat. Genet.* 15:131 (1997). It is possible that the selective advantage conferred by the NRY's retaining and amplifying male fertility factors (from throughout the genome) accounts for the multitude of testis-specific gene families there. This may have been the preeminent force in shaping the NRY's gene repertoire, as it appears that the great majority of NRY transcription units are members of such testis-specific families. In the NRY, each of the testis-specific gene families has multiple members, 20 to 40 copies in the case of TSPY (E. Manz et al., *Genomics* 17: 726 (1993)), and perhaps as many as 20 copies in the case of YRRM (K. Ma et al., *Cell* 75:1287 (1993)). All together, the various Y-specific gene families may include as many as several hundred genes or copies. Though it is not known how many of these are functional, it seems likely that Y-specific, testis-specific gene families comprise the great majority of NRY transcription units.

Recent genetic studies underscore the importance of the human Y chromosome in fertility. Many men with spermatogenic failure, but who are otherwise healthy, have deletions of portions of the NRY (K. Ma et al., *Cell* 75: 1287 (1993); R. Reijo et al., *Nat. Genet.* 10:383 (1995); P. H. Vogt et al., *Hum. Mol. Genet.* 5:933 (1996); J. L. Pryor et al., *New England J. Med.* 336:534 (1997)). These findings suggested the existence of NRY genes that play critical roles in male germ cell development but are not required elsewhere in the body. Previous deletion mapping studies have implicated four regions of the NRY in either spermatogenic failure or germ cell tumorigenesis, and in each of these four regions we now report novel candidate genes expressed specifically, or most abundantly, in testes (FIGS. 1A–1B). As shown in FIGS. 1A–1B, the region implicated in gonadoblastoma, stature and spermatogenic failure all contain novel candidate genes. Two of the three regions implicated in spermatogenic failure each contain one or more novel testis-specific genes. The third region implicated in spermatogenic failure (intervals 5B–5D) contains two X-homologous genes, DBY and EIF1AY, with abundant, testis-specific transcripts in addition to higher-molecular-weight, ubiquitous transcripts.

While X-homologous and testis-specific genes are somewhat intermingled within the NRY, clustering is evident (FIGS. 1A–1B). The geographic distribution of the two classes correlates quite well with previously identified sequence domains within the euchromatic NRY (D. Vollrath et al., *Science* 258:52 (1992); S. Foote et al., *Science* 258:60 (1992)). Ten of the 11 known testis-specific families map to previously identified regions of Y-specific repetitive sequences. The only exception is BPY1, which crosshybridizes to the X chromosome and maps to a previously recognized region of X homology. Indeed, one or more testis-specific gene families are found in nearly all known regions of euchromatic Y repeats (FIGS. 1A–1B). Ironically, it had been widely assumed that these regions consisted of "junk" DNA, partly on theoretical grounds (B. Charlesworth, *Science* 251:1030 (1991); E. Seboun et al., *Cold Spring Harb. Symp. Quant. Biol.* 1:237 (1986)). To the contrary, the results presented here argue that these Y-specific repetitive regions contain the great majority of the NRY's transcription units (The only exception is BPY1, which cross-hybridizes to the X chromosome and maps to a previously recognized region of X homology). These regions may be the result of rampant gene amplification during mammalian evolution. By contrast, none of the eight X-homologous genes map to the Y-repeat regions; all eight map to regions previously identified as consisting largely of single-copy (or in some cases X-homologous) sequences. It is possible that, early in mammalian evolution, these regions of the NRY shared extensive sequence identity with the nascent X chromosome. The stage is now set for systematic evolutionary, biochemical and cell biological studies of the NRY, an idiosyncratic segment of the human genome.

The present invention relates to isolated DNA and genes, present on (which occur on) the Y chromosome, whose sequences are provided herein, as well as characteristic portions of the DNA. It relates to additional nucleic acid/ nucleotide sequences which are not identical to the sequences presented herein but include substitutions or differences; DNA which includes substitutions or differences and encodes the same amino acid sequence as a DNA whose sequence is provided herein or includes substitutions which do not alter the ability of a DNA probe or primer which hybridizes to DNA whose sequence is presented herein to hybridize to the DNA containing the substitutions or differences. It further relates to DNA which encodes a protein or peptide whose sequence is presented herein. The present invention also includes the complements of the DNA sequences presented herein, DNA which hybridizes under stringent (high stringency) conditions to the DNA whose sequences are presented and to RNA transcripts. The invention further relates to encoded proteins, peptides and other products (e.g., glycoproteins) and antibodies which are raised against or bind to proteins or peptides whose amino acid sequences are presented herein or are encoded by DNA whose sequences are provided. As used herein, the term isolated DNA which occurs on the non-recombining region of the human Y chromosome refers to DNA which has been obtained or removed from the human Y chromosome or DNA, produced by any means (e.g., recombinant techniques, synthetic methods), which has the sequence of such Y chromosome DNA. For example, isolated testis-specific DNA or isolated testis-specific DNA which occurs on the non-recombining region of the human Y chromosome is DNA which has been obtained or removed from the non-recombining region of the human Y chromosome or which has the sequence of such DNA and has been obtained or produced by any means.

Thus, this invention has application to several areas. It may be used diagnostically to identify males with reduced sperm count in whom a gene has been deleted or altered. It may also be used therapeutically in gene therapy treatments to remedy fertility disorders associated with deletion or alteration of a gene described. In one embodiment of a gene therapy method, a gene described herein, or a gene portion which encodes a functional protein, is introduced into a man whose sperm count is reduced and in whom the gene is expressed and the encoded protein replaces the protein normally produced or enhances the quantity produced. The present invention may also be useful in designing or identifying agents which function as a male contraceptive by inducing reduced sperm count. This invention also has application as a research tool, as the nucleotide sequences described herein have been localized to regions of the Y chromosome.

The present invention includes nucleotide sequences described herein, and their complements, which are useful as hybridization probes or primers for an amplification method, such as polymerase chain reaction (PCR), to show the presence, absence or disruption of the gene of the present invention. Probes and primers can have all or a portion of the nucleotide sequence (nucleic acid sequence) of a gene described herein or all or a portion of its complement. For example, sequences shown in the Figures or Example 2 (SEQ ID NOS.: 1–84), as well as the complements thereof, can be used. The probes and primers can be any length, provided that they are of sufficient length and appropriate composition (appropriate nucleotide sequence) to hybridize to all or an identifying or characteristic portion of the gene described or to a disrupted form of the gene, and remain hybridized under the conditions use. Useful probes include, but are not limited to, nucleotide sequences which distinguish between a gene described herein and an altered form of that gene shown to be associated with reduced sperm count (azoospermia, oligospermia). Generally, the probe will be at least 7 nucleotides, while the upper limit is the length of the gene itself, e.g., up to about 40,000 nucleotides in length. Probes can be, for example, 10 to 14 nucleotides or longer (e.g., 20, 30, 50, 100, 250 nucleotides or any other useful length); the length of a specific probe will be determined by the assay in which it is used.

In one embodiment, the present invention is a method of diagnosing or aiding in the diagnosis of reduced sperm count associated with deletion or alteration of a gene described herein. Any man may be assessed with this method of diagnosis. In general, the man will have been at least preliminarily assessed, by another method, as having a reduced sperm count. By combining nucleic acid probes derived either from the isolated native sequence or cDNA sequence of the gene, or from appropriate primers, with the DNA from a sample to be assessed, under conditions suitable for hybridization of the probes with unaltered complementary nucleotide sequences in the sample but not with altered complementary nucleotide sequences, it can be determined whether the man possesses the intact gene. If the gene is unaltered, it may be concluded that the alteration of the gene is not responsible for the reduced sperm count. This invention may also be used in a similar method wherein the hybridization conditions are such that the probes will hybridize only with altered DNA and not with unaltered sequences. The hybridized DNA can also be isolated and sequenced to determine the precise nature of the alteration associated with the reduced sperm count. DNA assessed by the present method can be obtained from a variety of tissues and body fluids, such as blood or semen. In one embodiment, the above methods are carried out on DNA obtained from a blood sample.

The invention also provides expression vectors containing a nucleotide (nucleic acid) sequence described herein, which is operably linked to at least one regulatory sequence. "Operably linked" is intended to mean that the nucleotide sequence is linked to a regulatory sequence in a manner which allows expression of the nucleotide sequence. The term "regulatory sequence" included promoters, enhancers, and other expression control elements (see, e.g., Goeddel, *Gene Expression Technology: Methods in Enzymology* 185, Academic Press, San Diego, Calif. (1990)). It should be understood that the design of the expression vector may depend on such factors as the choice of the host cell to be transformed and/or the protein or peptide desired to be expressed. For instance, the peptides of the present invention can be produced by ligating the cloned gene, or a portion thereof, into a vector suitable for expression in either prokaryotic cells, eukaryotic cells or both (see, for example, Broach, et al., *Experimental Manipulation of Gene Expression,* ed. M, Inouye (Academic Press, 1983) p. 83; *Molecular Cloning: A Laboratory Manual,* 2nd Ed., ed. Sambrook et al. (Cold Spring Harbor Laboratory Press, 1989) Chapters 16 and 17).

Prokaryotic and eukaryotic host cells transfected by the described vectors are also provided by this invention. For instance, cells which can be transfected with the vectors of the present invention include, but are not limited to, bacterial cells such as *E. coli,* insect cells (baculovirus), yeast and mammalian cells, such as Chinese hamster ovary cells (CHO).

Thus, a nucleotide sequence described herein can be used to produce a recombinant form of the protein via microbial or eukaryotic cellular processes. Production of a recombinant form of the protein can be carried out using known techniques, such as by ligating the oligonucleotide sequence into a DNA or RNA construct, such as an expression vector, and transforming or transfecting the construct into host cells, either eukaryotic (yeast, avian, insect or mammalian) or prokaryotic (bacterial cells). Similar procedures, or modifications thereof, can be employed to prepare recombinant proteins according to the present invention by microbial means or tissue-culture technology.

The present invention also pertains to pharmaceutical compositions comprising the proteins and peptides described herein. For instance, the peptides or proteins of the present invention can be formulated with a physiologically acceptable medium to prepare a pharmaceutical composition. The particular physiological medium may include, but is not limited to, water, buffered saline, polyols (e.g., glycerol, propylene glycol, liquid polethylene glycol) and dextrose solutions. The optimum concentration of the active ingredient(s) in the chosen medium can be determined empirically, according to procedures well known to medicinal chemists, and will depend on the ultimate pharmaceutical formulation desired. Methods of introduction of exogenous polypeptides at the site of treatment include, but are not limited to, intradermal, intramuscular, intraperitoneal, intravenous, subcutaneous, oral and intranasal. Other suitable methods of introduction can also include rechargeable or biodegradable devices and slow release polymeric devices. The pharmaceutical compositions of this invention can also be administered as part of a combinatorial therapy with other agents.

This invention also has utility in methods of treating disorders of reduced sperm count associated with deletion or alternation of a gene described herein. These genes may be used in a method of gene therapy, whereby the gene or a gene portion encoding a functional protein is inserted into cells in which the functional protein is expressed and from which it is generally secreted to remedy the deficiency caused by the defect in the native gene.

The present invention is also related to antibodies which bind a protein or peptide encoded by all or a portion of a gene of the present invention, as well as antibodies which bind the protein or peptide encoded by all or a portion of a disrupted form of the gene. For instance, polyclonal and monoclonal antibodies which bind to the described polypeptide or protein are within the scope of the invention. A mammal, such as a mouse, hamster or rabbit, can be immunized with an immunogenic form of the protein or peptide (an antigenic fragment of the protein or peptide which is capable of eliciting an antibody response). Techniques for conferring immunogenicity on a protein or peptide include conjugation to carriers or other techniques are well known in the art. The protein or peptide can be administered in the presence of an adjuvant. The progress of immunization can be monitored by detection of antibody titers in plasma or serum. Standard ELISA or other immunoassays can be used with the immunogen as antigen to assess the levels of antibody.

Following immunization, anti-peptide antisera can be obtained, and if desired, polyclonal antibodies can be isolated from the serum. Monoclonal antibodies can be isolated from the serum. Monoclonal antibodies can also be produced by standard techniques which are well known in the art (Koehler and Milstein, *Nature* 256: 495–497 (19775); Kozbar et al., *Immunology Today* 4: 72 (1983); and Cole et al., *Monoclonal Antibodies and Cancer Therapy,* Alan R. Liss, Inc., pp. 77–96 (1985)). Such antibodies are useful as diagnostics for the intact or disrupted gene and also as research tools for identifying either the intact or disrupted gene.

The present invention is illustrated by the following examples, which are not intended to be limiting in any way.

EXAMPLE 1

Isolation of cDNA Clones from Human Testis Library

"cDNA selection" (M. Lovett et al., *Proc. Natl. Acad. Sci. USA* 88:9628 (1991)) was carried out using bulk cDNA prepared from human adult tests (Clontech, Palo Alto, Calif.) and, as selector, a cosmid library prepared from flow-sorted Y chromosomes (Lawrence Livermore National Laboratory: LL0YNC03). A total of 3600 random cosmids providing nearly five-fold coverage of the 30-Mb euchromatic region, were used to generate 150 pools of selector DNA. Using each of the 150 selector pools, we carried out four successive rounds of cDNA selection, followed by two rounds of subtraction with human COT-1 DNA (Gibco BRL, Gaithersburg, Md.) to remove highly repetitive sequences. A plasmid library was prepared from each of the 150 resulting pools of selected cDNA fragments, and 24 clones from each library were sequenced from one end. Of the 3600 sequences generated, about 600 were of poor technical quality and about 500 were found to derive from cloning vector or *E. coli* host, leaving 2539 sequences for further analysis. Of the 2539 sequence fragments, 536 corresponded to previously reported NRY genes (487 to TSPY, 15 to YRRM, 14 to RPS4Y, 9 to SMCY, 5 to DAZ, 3 to SRY, 3 to ZFY) and 41 corresponded to previously reported pseudoautosomal genes (15 to XR7, 11 to CSF2RA, 4 to IL3RA, 3 to ASMT, 3 to IL9R, 2 to ANT3, 2 to MIC2, 1 to SYBL1). Electronic analysis of the roughly 2000 remaining sequences revealed that about 200 contained known repetitive elements, and these were not pursued. By electronically identifying redundancies and sequence overlaps, the remaining sequences were reduced to 1093 sequence contigs. Sequences representing these 1093 contigs were individually hybridized to dot-blotted yeast genomic DNAs of 60 YACs comprising most of the Y's euchromatic region (S. Foote et al., *Science* 258:60 (1992)). 181 sequences that hybridized to the great majority of the YACs were judged likely to contain highly repeated elements and were not pursued, leaving 912 sequences for further analysis. The 912 sequences were individually hybridized to Southern blots of R1-digested human 46,XX female and 49,XYYYY male (L. Sirota et al., *Clin. Genet.* 19:87 (1981) genomic DNAs. Blots were hybridized at 65° C. in Church's buffer (0.5 M Na$_i$PO$_4$ at pH7.5, with 7% SDS), and washed at 65° C. in 1× SSC and 0.1% SDS, with 832 hybridizations yielding interpretable results. Many sequences appeared to contain highly repeated elements common to males and females, or failed to detect an unambiguously Y-specific restriction fragment, and these were not pursued. By contrast, 308 sequences hybridized to at least one prominent fragment present in 49,XYYYY but absent in 46,XX, suggesting that these sequences derived from the NRY. Each of these 308 sequences was individually used to screen, by hybridization, about 2 million plaques from a 1 phage library of human adult testis cDNA (Clontech, Palo Alto, Calif.).

EXAMPLE 2

Localization of 12 Novel Genes on the Y Chromosome

Genes were localized on a previously reported NRY deletion map by testing with PCR for their presence or absence in individuals carrying partial Y chromosomes (D. Vollrath et al., *Science* 258:52 (1992). Most genes were localized to a single deletion interval. Some genes could not be unambiguously placed because copies exist in multiple locations in the NRY. In such cases, genes were localized by PCR testing of YACs encompassing the NRY's euchromatic region (S. Foote et al., *Science* 258:60 (1992)). X homologs of Y genes were mapped onto the X by PCR testing a panel of human/rodent somatic hybrid cell lines (Research Genetics, Huntsville, Ala.). All PCR assays consists of 30 cycles of the following conditions: 1 min denaturing at 94° C., 45 sec annealing at 60° C., and 45 sec extension at 72° C. TB4X primers were designed from an unreported intron. TPRX primers were designed from unreported cDNA sequence. All other primers were designed from cDNA sequences as submitted to Genbank. PCR primers were as follows:

| GENE | LEFT PRIMER | RIGHT PRIMER |
|---|---|---|
| DBY | CATTCGGTTTTACCAGCCAG (SEQ ID NO.: 51) | CAGTGACTCGAGGTTCAATG (SEQ ID NO.: 52) |
| TPRY | GCATCATAATATGGATCTAGTAGG (SEQ ID NO.: 53) | GGAGATACTGAATAGCATAGC (SEQ ID NO.: 54) |
| TB4Y | CAAAGACCTGCTGACAATGG (SEQ ID NO.: 55) | CTCCGCTAAGTCTTTCACC (SEQ ID NO.: 56) |
| EIF1AY | CTCTGTAGCCAGCCTCTTC (SEQ ID NO.: 57) | GACTCCTTTCTGGCGGTTAC (SEQ ID NO.: 58) |
| DFFRY | GAGCCCATCTTTGTCAGTTTAC (SEQ ID NO.: 59) | CTGCCAATTTTCCACATCAACC (SEQ ID NO.: 60) |
| CDY | GGCTCAAAATCCACTGACG (SEQ ID NO.: 61) | CAAGCGATATCTCACCACC (SEQ ID NO.: 62) |
| BPY1 | CTCCCTGAGCAGCAACTAAG (SEQ ID NO.: 63) | GTCATCAACATGGGAAGCAC (SEQ ID NO.: 64) |
| BPY2 | CCAGGACCATGTGATATGG (SEQ ID NO.: 65) | CTAATTCCCTCTTTACGCATGACC (SEQ ID NO.: 66) |
| XKRY | CACTCATGGAGAAGGGTAGG (SEQ ID NO.: 67) | GTCACACTCAGCCTCTTTAC (SEQ ID NO.: 68) |
| PTPRY | GAGCACACCACACCAGAAAC (SEQ ID NO.: 69) | CTCAGACTGACCTCGGACTG (SEQ ID NO.: 70) |
| TTY1 | CTCTGGGAATCAAATTCGAGG (SEQ ID NO.: 71) | GTCTTTCAGCCAATCCAAGG (SEQ ID NO.: 72) |
| TTY2 | GACAACTCTGACAGCCAGG (SEQ ID NO.: 73) | GTCAGAACTCCCAAACAGG (SEQ ID NO.: 74) |
| DBX | CTACATGCAGATGACATGGTG (SEQ ID NO.: 75) | GGCCAAGGTGCATAGGTG (SEQ ID NO.: 76) |
| TPRX | CATGTTCCCTGTAGCACATC (SEQ ID NO.: 77) | CGTTTCCATTACTTCCATTTCCTG (SEQ ID NO.: 78) |
| TB4X | CCCGCCCTTTCATCATCC (SEQ ID NO.: 79) | GCTCCCCAAAGTAGCCTTC (SEQ ID NO.: 80) |
| EIF1AX | CACGAGGCGCCATTTGCTG (SEQ ID NO.: 81) | CTGGAGGCCAGGCAACGTG (SEQ ID NO.: 82) |
| DFFRX | CCTCCACCTGAAGATGCC (SEQ ID NO.: 83) | CTGAGATCCAGGTGAATGG (SEQ ID NO.: 84) |

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:

1. An isolated testis-specific DNA which encodes SEQ ID NO: 39, or the complement thereof.

2. An isolated testis-specific DNA comprising SEQ ID NO: 37 or the complement thereof.

3. An isolated nucleotide sequence which specifically hybridizes to a nucleic acid that encodes SEQ ID NO: 39 at 65° C. in 1× SSC and 0.1% SDS.

4. An isolated nucleotide sequence which specifically hybridizes to a nucleic acid that comprises SEQ ID NO: 37 at 65° C. in 1× SSC and 0.1% SDS.

* * * * *